US009724408B2

(12) United States Patent
Dubensky, Jr. et al.

(10) Patent No.: US 9,724,408 B2
(45) Date of Patent: Aug. 8, 2017

(54) COMPOSITIONS AND METHODS FOR ACTIVATING STIMULATOR OF INTERFERON GENE-DEPENDENT SIGNALLING

(71) Applicants: ADURO BIOTECH, INC., Berkeley, CA (US); THE REGENTS OF THE UNIVERSITY OF CALIFORNIA, Oakland, CA (US)

(72) Inventors: Thomas W. Dubensky, Jr., Piedmont, CA (US); David B. Kanne, Corte Madera, CA (US); Meredith Lai Ling Leong, Oakland, CA (US); Edward Emile Lemmens, Walnut Creek, CA (US); Laura H. Glickman, Oakland, CA (US); Russell E. Vance, Albany, CA (US)

(73) Assignees: ADURO BIOTECH, INC., Berkeley, CA (US); THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 14/280,667

(22) Filed: May 18, 2014

(65) Prior Publication Data
US 2015/0056224 A1    Feb. 26, 2015

Related U.S. Application Data

(60) Provisional application No. 61/825,005, filed on May 18, 2013, provisional application No. 61/902,125, filed on Nov. 8, 2013.

(51) Int. Cl.
| | | |
|---|---|---|
| *A61K 39/00* | (2006.01) | |
| *A61K 39/38* | (2006.01) | |
| *A01N 43/04* | (2006.01) | |
| *A61K 31/70* | (2006.01) | |
| *C07H 21/00* | (2006.01) | |
| *A61K 39/39* | (2006.01) | |
| *A61K 31/7084* | (2006.01) | |
| *A61K 45/06* | (2006.01) | |
| *C07H 21/02* | (2006.01) | |

(52) U.S. Cl.
CPC .......... *A61K 39/39* (2013.01); *A61K 31/7084* (2013.01); *A61K 45/06* (2013.01); *C07H 21/02* (2013.01); *A61K 2039/55511* (2013.01); *A61K 2039/55561* (2013.01)

(58) Field of Classification Search
CPC .. C07D 473/00; A61K 31/7084; A61K 39/39; A61K 45/06; A61K 2039/55511; A61K 2039/55561

See application file for complete search history.

(56) References Cited

U.S. PATENT DOCUMENTS

| | | | |
|---|---|---|---|
| 5,547,941 A | 8/1996 | Battistini et al. | |
| 5,637,483 A | 6/1997 | Dranoff et al. | |
| 5,698,432 A | 12/1997 | Oxford | |
| 5,904,920 A | 5/1999 | Dranoff et al. | |
| 5,985,290 A | 11/1999 | Jaffee et al. | |
| 6,033,674 A | 3/2000 | Jaffee et al. | |
| 6,090,611 A | 7/2000 | Covacci et al. | |
| 6,277,368 B1 | 8/2001 | Hiserodt et al. | |
| 6,350,445 B1 | 2/2002 | Jaffee et al. | |
| 6,464,973 B1 | 10/2002 | Levitsky et al. | |
| 6,558,670 B1 | 5/2003 | Friede et al. | |
| 6,780,429 B1 | 8/2004 | Matsuyama et al. | |
| 7,569,555 B2 | 8/2009 | Karaolis | |
| 7,592,326 B2 | 9/2009 | Karaolis | |
| 7,709,458 B2 | 5/2010 | Karaolis et al. | |
| 8,012,469 B2 | 9/2011 | Levitsky et al. | |
| 8,283,328 B2 * | 10/2012 | Krieg ..................... | A61K 31/70 514/44 R |
| 8,304,396 B2 * | 11/2012 | Krieg ..................... | A61K 31/70 424/184.1 |
| 8,367,716 B2 * | 2/2013 | Karaolis ....................... | 514/440 |
| 8,450,293 B2 | 5/2013 | Jones et al. | |
| 9,061,048 B2 | 6/2015 | Portnoy et al. | |
| 2001/0041682 A1 | 11/2001 | Stutts et al. | |

(Continued)

FOREIGN PATENT DOCUMENTS

| | | |
|---|---|---|
| WO | 2005030186 A2 | 4/2005 |
| WO | 2005039535 A1 | 5/2005 |

(Continued)

OTHER PUBLICATIONS (R) Patel et al., Filing receipt plus Specification minus claims for U.S. Appl. No. 61/817,269, filed Apr. 29, 2013.*
(S) Patel et al., Filing receipt minus Specification plus claims for U.S. Appl. No. 61/817,269, filed Apr. 29, 2013.*
Abutaily et al., Cadherins, catenins and APC in pleural malignant mesothelioma. J Pathol. Nov. 2003;201(3):355-362.
Adler-Moore et al., Characterization of the murine Th2 response to immunization with liposomal M2e influenza vaccine. Vaccine. Jun. 15, 2011;29(27):4460-4468.
Ahmed et al., Assessing the Safety of Adjuvanted Vaccines. Sci Transl Med. Jul. 27, 2011;3(93):93rv2.

(Continued)

*Primary Examiner* — Lawrence E Crane
(74) *Attorney, Agent, or Firm* — Acuity Law Group, P.C.; Michael Whittaker

(57) ABSTRACT

The present invention provides highly active cyclic-dinucleotide (CDN) immune stimulators that activate DCs via a recently discovered cytoplasmic receptor known as STING (Stimulator of Interferon Genes). In particular, the CDNs of the present invention are provided in the form of a composition comprising one or more cyclic purine dinucleotides induce STING-dependent type I interferon production, wherein the cyclic purine dinucleotides present in the composition are substantially pure 2',5',2',5' and 2',5',3',5' CDNs, and preferably Rp,Rp stereoisomers thereof.

6 Claims, 38 Drawing Sheets

(56) References Cited

U.S. PATENT DOCUMENTS

| | | |
|---|---|---|
| 2002/0140414 A1 | 10/2002 | Sohn et al. |
| 2002/0150588 A1 | 10/2002 | Allison et al. |
| 2003/0003092 A1 | 1/2003 | Krissansen et al. |
| 2003/0138413 A1 | 7/2003 | Vicari et al. |
| 2005/0281783 A1 | 12/2005 | Kinch et al. |
| 2006/0040887 A1 | 2/2006 | Karaolis |
| 2006/0286549 A1 | 12/2006 | Sohn et al. |
| 2007/0059683 A1 | 3/2007 | Barber et al. |
| 2007/0224210 A1 | 9/2007 | Krieg et al. |
| 2007/0244059 A1 | 10/2007 | Karaolis |
| 2007/0281897 A1 | 12/2007 | Karaolis |
| 2008/0076778 A1 | 3/2008 | Ossovskaya et al. |
| 2008/0286296 A1 | 11/2008 | Ebensen et al. |
| 2010/0150946 A1 | 6/2010 | Jooss et al. |
| 2010/0310602 A1 | 12/2010 | Reed et al. |
| 2011/0081674 A1 | 4/2011 | Han et al. |
| 2011/0262485 A1 | 10/2011 | Barber |
| 2011/0287948 A1 | 11/2011 | Suresh et al. |
| 2012/0041057 A1 | 2/2012 | Jones et al. |
| 2012/0164107 A1 | 6/2012 | Portnoy et al. |
| 2012/0178710 A1 | 7/2012 | Jones et al. |
| 2014/0155345 A1 | 6/2014 | Jones et al. |
| 2014/0205653 A1 | 7/2014 | Dubensky et al. |
| 2014/0329889 A1 | 11/2014 | Vance et al. |
| 2014/0341976 A1 | 11/2014 | Dubensky et al. |
| 2015/0056224 A1 | 2/2015 | Dubensky et al. |
| 2016/0068560 A1 | 3/2016 | Patel et al. |
| 2016/0210400 A1 | 7/2016 | Patel et al. |

FOREIGN PATENT DOCUMENTS

| | | | |
|---|---|---|---|
| WO | 2005087238 A2 | 9/2005 | |
| WO | 2005089777 A1 | 9/2005 | |
| WO | 2007054279 A2 | 5/2007 | |
| WO | 2007064945 A2 | 6/2007 | |
| WO | 2009133560 A1 | 11/2009 | |
| WO | 2010017248 A2 | 2/2010 | |
| WO | 2010067262 A1 | 6/2010 | |
| WO | 2010104883 A1 | 9/2010 | |
| WO | 2011003025 A1 | 1/2011 | |
| WO | 2011136828 A1 | 11/2011 | |
| WO | 2011139769 A2 | 11/2011 | |
| WO | 2012068360 A1 | 5/2012 | |
| WO | 2012088155 A1 | 6/2012 | |
| WO | 2012139209 A1 | 10/2012 | |
| WO | 2013086331 A1 | 6/2013 | |
| WO | 2013166000 A1 | 11/2013 | |
| WO | 2013185052 A1 | 12/2013 | |
| WO | 2014093936 A1 | 6/2014 | |
| WO | 2014099824 A1 | 6/2014 | |
| WO | 2014179335 A1 | 11/2014 | |
| WO | 2014179760 A1 | 11/2014 | |
| WO | 2014189805 A1 | 11/2014 | |
| WO | 2014189806 A1 | 11/2014 | |
| WO | WO 2014/179335 A1 * | 11/2014 | |
| WO | 2015017652 A1 | 2/2015 | |
| WO | 2015061294 A2 | 4/2015 | |
| WO | 2015074145 A1 | 5/2015 | |
| WO | 2015077354 A1 | 5/2015 | |
| WO | 2015108595 A1 | 7/2015 | |
| WO | 2015185565 A1 | 12/2015 | |

OTHER PUBLICATIONS

Ahn et al., All CVB Serotypes and Clinical Isolates Induce Irreversible Cytopathic Effects in Primary Cardiomyocytes. J Med Virol. Feb. 2005;75(2):290-294.

Altwein and Luboldt, Prognostic Factors for Carcinoma of the Prostate. Urol Int. 1999:63(1):62-71.

Alvarez-Lafuente et al., Human parvovirus B19, varicella zoster virus, and human herpes virus 6 in temporal artery biopsy specimens of patients with giant cell arteritis: analysis with quantitative real time polymerase chain reaction. Ann Rheum Dis. May 2005;64(5):780-782.

Andersen and thor Straten, Survivin—a universal tumor antigen. Histol Histopathol. Apr. 2002;17(2):669-675.

Argani et al., Discovery of New Markers of Cancer through Serial Analysis of Gene Expression Prostate Stem Cell Antigen is Overexpressed in Pancreatic Adenocarcinoma. Cancer Res. Jun. 1, 2001;61(11):4320-4324.

Arora et al., Identification of Differentially Expressed Genes in Oral Squamous Cell Carcinoma. Mol Carcinog. Feb. 2005;42(2):97-108.

Attoui et al., Comparative sequence analysis of American, European and Asian isolates of viruses in the genus Coltivirus. J Gen Virol. Oct. 1998;79 ( Pt 10):2481-2489.

Badovinac et al., Accelerated CD8+ T-cell memory and prime-boost response after dendritic-cell vaccination. Nat Med. Jul. 2005;11(7):748-756.

Bahjat et al., Cytosolic Entry Controls CD8+-T-Cell Potency during Bacterial Infection. Infect Immun. Nov. 2006;74 (11):6387-6397.

Bahjat et al., Suppression of Cell-Mediated Immunity following Recognition of Phagosome-Confined Bacteria. PLoS Pathog. Sep. 2009;5(9):e1000568.

Bala et al., PLGA Nanoparticles in Drug Delivery: The State of the Art. Crit Rev Ther Drug Carrier Syst. 2004;21 (5):387-422.

Baldwin et al., The Importance of Adjuvant Formulation in the Development of a Tuberculosis Vaccine. J Immunol. Mar. 1, 2012;188(5):2189-2197.

Barbanti-Brodano et al., Simian virus 40 infection in humans and association with human diseases: results and hypotheses. Virology. Jan. 5, 2004;318(1):1-9.

Barber, Cytoplasmic DNA innate immune pathways. Immunol Rev. Sep. 2011;243(1):99-108.

Barber, STING-dependent signaling. Nat Immunol. Sep. 20, 2011;12(10):929-930.

Barthold et al., Infectivity, disease patterns, and serologic profiles of reovirus serotypes 1, 2, and 3 in infant and weanling mice. Lab Anim Sci. Oct. 1993;43(5):425-430.

Baurain et al., High Frequency of Autologous Anti-Melanoma CTL Directed Against an Antigen Generated by a Point Mutation in a New Helicase Gene. J Immunol. Jun. 1, 2000;164(11):6057-6066.

Bevanger et al., Competitive Enzyme Immunoassay for Antibodies to a 43,000-Molecular-Weight Francisella tularensis Outer Membrane Protein for the Diagnosis of Tularemia. J Clin Microbiol. May 1989;27(5):922-926.

Bhigjee et al., Sequence of the env gene of some KwaZulu-Natal, South African strains of HTLV type I. AIDS Res Hum Retroviruses. Sep. 1, 1999;15(13):1229-1233.

Biagini et al., Simultaneous measurement of specific serum IgG responses to five select agents. Anal Bioanal Chem. Jun. 2005;382(4):1027-1034.

Bondurant et al., Definition of an Immunogenic RegionWithin the OvarianTumor Antigen Stratum Corneum Chymotryptic Enzyme. Clin Cancer Res. May 1, 2005;11(9):3446-3454.

Brezniceanu et al., HMGB1 inhibits cell death in yeast and mammalian cells and is abundantly expressed in human breast carcinoma. FASEB J. Jul. 2003;17(10):1295-1297.

Brian and Baric, Coronavirus Genome Structure and Replication. Curr Top Microbiol Immunol. 2005;287:1-30.

Brinkmann et al., Novel Genes in the PAGE and GAGE Family of Tumor Antigens Found by Homology Walking in the dbEST Database. Cancer Res. Apr. 1, 1999;59(7):1445-1448.

Bronte et al., Genetic Vaccination with "Self" Tyrosinase-related Protein 2 Causes Melanoma Eradication but not Vitiligo. Cancer Res. Jan. 15, 2000;60(2):253-258.

Brown et al., Complete Genomic Sequencing Shows that Polioviruses and Members of Human Enterovirus Species C are Closely Related in the Noncapsid Coding Region. J Virol. Aug. 2003;77(16):8973-8984.

Brown, Variants of B19. Dev Biol (Basel). 2004;118:71-77.

Burdette and Vance, STING and the innate immune response to nucleic acids in the cytosol. Nat Immunol. Jan. 2013;14(1):19-26.

Burdette et al., STING is a direct innate immune sensor of cyclic di-GMP. Nature. Sep. 25, 2011:478(7370):515-518 doi:10.1038/nature10429.

(56) References Cited

OTHER PUBLICATIONS

Capdepont et al., New Insights in HTLV-I Phylogeny by Sequencing and Analyzing the Entire Envelope Gene. AIDS Res Hum Retroviruses. Jan. 2005;21(1):28-42.
Capurro et al., Glypican-3: A Novel Serum and Histochemical Marker for Hepatocellular Carcinoma. Gastroenterology. Jul. 2003;125(1):89-97.
Carbone et al., New developments about the association of SV40 with human mesothelioma. Oncogene. Aug. 11, 2003;22(33):5173-5180.
Chan et al., In Situ Hybridization Study of PSP94 (Prostatic Secretory Protein of 94 Amino Acids) Expression in Human Prostates. Prostate. Oct. 1, 1999;41(2):99-109.
Chang et al., A Phase I Trial of Tumor Lysate-Pulsed Dendritic Cells in the Treatment of Advanced Cancer. Clin Cancer Res. Apr. 2002;8(4):1021-1032.
Chen et al., Immunodominant CD41 responses identified in a patient vaccinated with full-length NY-ESO-1 formulated with ISCOMATRIX adjuvant. Proc Natl Acad Sci USA. Jun. 22, 2004;101(25):9363-9368.
Chern et al., Glycoprotein B Subtyping of Cytomegalovirus (CMV) in the Vitreous of Patients with AIDS and CMV Retinitis. J Infect Dis. Oct. 1998;178(4):1149-1153.
Chiari et al., Two Antigens Recognized by Autologous Cytolytic T Lymphocytes on a Melanoma Result from a Single Point Mutation in an Essential Housekeeping Gene. Cancer Res. Nov. 15, 1999;59(22):5785-5792.
Christiansen et al., Polarity of Prostate Specific Membrane Antigen, Prostate Stem Cell Antigen, and Prostate Specific Antigen in Prostate Tissue and in a Cultured Epithelial Cell Line. Prostate. Apr. 1, 2003;55(1):9-19.
Clifton et al., A chlamydial type III translocated protein is tyrosine-phosphorylated at the site of entry and associated with recruitment of actin. Proc Natl Acad Sci USA. Jul. 6, 2004;101(27):10166-10171.
Clinton et al., A Comparative Study of Four Serological Tumor Markers for the Detection of Breast Cancer. Biomed Sci Instrum. 2003;39:408-414.
Cobaleda et al., A primitive hematopoietic cell is the target for the leukemic transformation in human Philadelphia-positive acute lymphoblastic leukemia. Blood. Feb. 1, 2000;95(3):1007-1013.
Codrington et al., Analysis of ETV6/AML1 abnormalities in acute lymphoblastic leukaemia: incidence, alternative spliced forms and minimal residual disease value. Br J Haematol. Dec. 2000;111(4):1071-1079.
Coffman et al., Vaccine adjuvants: putting innate immunity to work. Immunity. Oct. 29, 2010;33(4):492-503.
International Search Report and Written Opinion issued in PCT/US2013/075189 dated Mar. 11, 2014.
Suzuki et al., Identification of Natural Antigenic Peptides of a Human Gastric Signet Ring Cell Carcinoma Recognized by HLA-A31-Restricted Cytotoxic T Lymphocytes. J Immunol. Sep. 1, 1999;163(5):2783-2791.
Takahashi et al., 707-AP Peptide Recognized by Human Antibody Induces Human Leukocyte Antigen A2-Restricted Cytotoxic T Lymphocyte Killing of Melanoma. Clin Cancer Res. Aug. 1997;3(8):1363-1370.
Tamayo et al., Roles of Cyclic Diguanylate in the Regulation of Bacterial Pathogenesis. Annu Rev Microbiol. 2007;61:131-148.
Tamura et al., Identification of Cyclophilin B-derived Peptides Capable of Inducing Histocompatibility Leukocyte Antigen-A2-restricted and Tumor-specific Cytotoxic T Lymphocytes. Jpn J Cancer Res. Jul. 2001;92(7):762-767.
Tanaka et al., Expression of Tumor-Rejection Antigens in Gynecologic Cancers. Jpn J Cancer Res. Nov. 2000;91 (11):1177-1184.
Tannapfel et al., BRAF Gene Mutations are Rare Events in Gastroenteropancreatic Neuroendocrine Tumors. Am J Clin Pathol. Feb. 2005;123(2):256-2601.
Treurnicht et al., HHV-8 subtypes in South Africa: identification of a case suggesting a novel B variant. J Med Virol. Feb. 2002;66(2):235-240.
Trimble et al., Comparison of the CD8+ T cell responses and antitumor effects generated by DNA vaccine administered through gene gun, biojector, and syringe. Vaccine. Sep. 8, 2003;21(25-26):4036-4042.
Tsang et al., Phenotypic Stability of a Cytotoxic T-Cell Line Directed Against an Immunodominant Epitope of Human Carcinoembryonic Antigen. Clin Cancer Res. Dec. 1997;3(12 Pt 1):2439-2449.
Tsuruma et al., Phase I clinical study of anti-apoptosis protein, survivin-derived peptide vaccine therapy for patients with advanced or recurrent colorectal cancer. J Transl Med. Jun. 13, 2004;2(1):19 (11 pages).
Vallejo et al., Nucleotide Sequence and Restriction Fragment-Length Polymorphism Analysis of Human T-Cell Lymphotropic Virus Type II (HTLV-II) in Southern Europe: Evidence for the HTLV-IIa and HTLV-IIb Subtypes. J Acquir Immune Defic Syndr Hum Retrovirol. Dec. 1, 1996;13(4):384-391.
Van Erp et al., Application of a sol particle immunoassay to the determination of affinity constants of monoclonal antibodies. J Immunoassay. 1991;12(3):425-443.
Vance et al., Patterns of Pathogenesis: Discrimination of Pathogenic and Nonpathogenic Microbes by the Innate Immune System. Cell Host Microbe. Jul. 23, 2009;6(1):10-21.
Vandamme et al., African Origin of Human T-Lymphotropic Virus Type 2 (HTLV-2) Supported by a Potential New HTLV-2d Subtype in Congolese Bambuti Efe Pygmies. J Virol. May 1998;72(5):4327-4340.
Virok et al., Chlamydial Infection Induces Pathobiotype-Specific Protein Tyrosine Phosphorylation in Epithelial Cells. Infect Immun. Apr. 2005;73(4):1939-1946.
Von Lindern et al., The Translocation (6;9), Associated with a Specific Subtype of Acute Myeloid Leukemia, Results in the Fusion of Two Genes, dek and can, and the Expression of a Chimeric, Leukemia-Specific dek-can mRNA. Mol Cell Biol. Apr. 1992;12(4):1687-1697.
Waltregny et al., Screening of histone deacetylases (HDAC) expression in human prostate cancer reveals distinct class I HDAC profiles between epithelial and stromal cells. Eur J Histochem. Jul.-Sep. 2004;48(3):273-290.
Wang et al., Alterations of APC, c-met, and p53 Genes in Tumor Tissue and Serum of Patients with Gastric Cancers. J Surg Res. Aug. 2004;120(2):242-248.
Wang et al., Identification of a Novel Major Histocompatibility Complex Class II-restricted Tumor Antigen Resulting from a Chromosomal Rearrangement Recognized by CD4+ T Cells. J Exp Med. May 17, 1999;189(10):1659-1668.
Wentworth et al., An Influenza A (H1N1) Virus, Closely Related to Swine Influenza Virus, Responsible for a Fatal Case of Human Influenza. J Virol. Apr. 1994;68(4):2051-2058.
Wille-Reece et al., Immunization with HIV-1 Gag Protein Conjugated to a TLR7/8 Agonist Results in the Generation of HIV-1 Gag-Specific Th1 and CD8+ T Cell Responses. J Immunol. Jun. 15, 2005;174(12):7676-7683.
Wille-Reece et al., Toll-like receptor agonists influence the magnitude and quality of memory T cell responses after prime-boost immunization in nonhuman primates. J Exp Med. May 15, 2006;203(5):1249-1258.
Wilson et al., Simplified conjugation chemistry for coupling peptides to F(ab') fragments: autologous red cell agglutination assay for HIV-1 antibodies. J Immunol Methods. Oct. 14, 1994;175(2):267-273.
Witte et al., Innate Immune Pathways Triggered by Listeria monocytogenes and Their Role in the Induction of Cell-Mediated Immunity. Adv Immunol. 2012;113:135-156.
Woodward et al., c-di-AMP secreted by intracellular Listeria monocytogenes activates a host type I interferon response. Science. Jun. 25, 2010;328(5986):1703-1705.
Coler et al. Development and Characterization of Synthetic Glucopyranosyl Lipid Adjuvant System as a Vaccine Adjuvant. PLoS One. Jan. 26, 2011;6(1):e16333.

(56) References Cited

OTHER PUBLICATIONS

Coughlin et al., Orally Bioavailable Anti-HBV Dinucleotide Acyloxyalkyl Prodrugs. Bioorg Med Chem Lett. Mar. 1, 2010;20(5):1783-1786.

Creighton et al., Mechanisms and catalysts of disulfide bond formation in proteins. Trends Biotechnol. Jan. 1995;13(1):18-23.

Crimmins et al., Listeria monocytogenes multidrug resistance transporters activate a cytosolic surveillance pathway of innate immunity. Proc Natl Acad Sci U S A. Jul. 22, 2008;105(29):10191-10196.

Dalerba et al., MAGE, BAGE and GAGE gene expression in human rhabdomyosarcomas. Int J Cancer. Jul. 1, 2001;93(1):85-90.

Damasus-Awatai and Freeman-Wang, Human papilloma virus and cervical screening. Curr Opin Obstet Gynecol. Dec. 2003;15(6):473-477.

Das et al., Evaluation of a Western Equine Encephalitis recombinant E1 protein for protective immunity and diagnostics. Antiviral Res. Nov. 2004;64(2):85-92.

Davies et al., Characterisation of a recombinant Fv fragment of anti-MUC1 antibody HMFG1. Cancer Lett. Jul. 29, 1994;82(2):179-184.

Davies et al., Coordinated Regulation of Accessory Genetic Elements Produces Cyclic Di-Nucleotides for V. cholerae Virulence. Cell. Apr. 13, 2012;149(2):358-370.

De Backer et al., Characterization of the GAGE Genes That are Expressed in Various Human Cancers and in Normal Testis. Cancer Res. Jul. 1, 1999;59(13):3157-3165.

de Villiers et al., Classification of papillomaviruses. Virology. Jun. 20, 2004;324(1):17-24.

Demidenko and Blagosklonny, Flavopiridol Induces p53 via Initial Inhibition of Mdm2 and P21 and, Independently of p53, Sensitizes Apoptosis-Reluctant Cells to Tumor Necrosis Factor. Cancer Res. May 15, 2004;64(10):3653-3660.

Desmet and Ishii, Nucleic acid sensing at the interface between innate and adaptive immunity in vaccination. Nat Rev Immunol. Jun. 22, 2012;12(7):479-491.

Dessureault et al., A phase-I Trial Using a Universal GM-CSF-producing and CD40L-expressing Bystander Cell Line (GM.CD40L) in the Formulation of Autologous Tumor Cell-based Vaccines for Cancer Patients with Stage IV disease. Ann Surg Oncol. Feb. 2007;14(2):869-884.

Diner et al., The Innate Immune DNA Sensor cGAS Produces a Noncanonical Cyclic Dinucleotide that Activates Human STING. Cell Rep. May 30, 2013;3(5)1355-1361.

Disis and Cheever, HER-2/Neu Protein: A Target for Antigen-Specific Immunotherapy of Human Cancer. Adv Cancer Res. 1997;71:343-371.

Disis et al., Humoral Epitope-Spreading Following Immunization with a HER-2/neu Peptide Based Vaccine in Cancer Patients. J Clin Immunol. Sep. 2004;24(5):571-578.

Dosaka-Akita et al., Expression of N-Acetylglucosaminyltransferase V is Associated with Prognosis and Histology in Non-Small Cell Lung Cancers. Clin Cancer Res. Mar. 1, 2004;10(5):1773-1779.

Dubensky and Reed, Adjuvants for cancer vaccines. Semin Immunol. Jun. 2010;22(3):155-161.

Duxbury et al., CEACAM6 as a novel target for indirect type 1 immunotoxin-based therapy in pancreatic adenocarcinoma. Biochem Biophys Res Commun. May 7, 2004;317(3):837-843.

Eager and Nemunaitis, GM-CSF Gene-Transduced Tumor Vaccines. Mol Ther. Jul. 2005;12(1):18-27.

Ebensen et al., Bis-(3',5')-cyclic dimeric adenosine monophosphate: Strong Th1/Th2/Th17 promoting mucosal adjuvant. Vaccine. Jul. 18, 2011;29(32):5210-5220.

Ebensen et al., The bacterial second messenger cyclic diGMP exhibits potent adjuvant properties. Vaccine. Feb. 9, 2007;25(8):1464-1469.

Ebensen et al., The Bacterial Second Messenger cdiGMP Exhibits Promising Activity as a Mucosal Adjuvant. Clin Vaccine Immunol. Aug. 2007;14(8):952-958.

Einstein et al., Comparison of the immunogenicity and safety of Cervarix and Gardasil human papillomavirus (HPV) cervical cancer vaccines in healthy women aged 18-45 years. Hum Vaccin. Oct. 2009;5(10):705-719.

Elgh et al., Serological Diagnosis of Hantavirus Infections by an Enzyme-Linked Immunosorbent Assay Based on Detection of Immunoglobulin G and M Responses to Recombinant Nucleocapsid Proteins of Five Viral Serotypes. J Clin Microbiol. May 1997;35(5):1122-1130.

Engels et al., Serologic Evidence for Exposure to Simian Virus 40 in North American Zoo Workers. J Infect Dis. Dec. 15, 2004;190(12):2065-2069.

Enjoji et al., RCAS1, a Useful Serum Marker to Predict the Recurrence of Cancer: Two Cases of Cholangiocarcinoma and Pancreatic Cancer. Dig Dis Sci. Oct. 2004;49(10):1654-1656.

Ericson et al., Expression of Cyclin-Dependent Kinase 6, but not Cyclin-Dependent Kinase 4, Alters Morphology of Cultured Mouse Astrocytes. Mol Cancer Res. Jul. 2003;1(9):654-664.

Estrada-Franco et al., Venezuelan Equine Encephalitis Virus, Southern Mexico. Emerg Infect Dis. Dec. 2004;10 (12):2113-2121.

Fang et al., Expression of Dnmt1, demethylase, MeCP2 and methylation of tumor-related genes in human gastric cancer. World J Gastroenterol. Dec. 1, 2004;10(23):3394-3398.

Faure et al., Inducible Hsp70 as Target of Anticancer Immunotherapy: Identification of HLA-A*0201-Restricted Epitopes. Int J Cancer. Mar. 1, 2004;108(6):863-870.

Fleishhauer et al., The DAM Gene Family Encodes a New Group of Tumor-specific Antigens Recognized by Human Leukocyte Antigen Al-restricted Cytotoxic T Lymphocytes. Cancer Res. Jul. 15, 1998;58(14):2969-2972.

Fong et al., Altered peptide ligand vaccination with Flt3 ligand expanded dendritic cells for tumor immunotherapy. Proc Natl Acad Sci U S A. Jul. 17, 2001;98(15):8809-8814.

Fuessel et al., Multiple tumor marker analyses (PSA, hK2, PSCA, trp-p8) in primary prostate cancers using quantitative RT-PCR. Int J Oncol. Jul. 2003;23(1):221-228.

Fujii et al., The VesiVax system: a method for rapid vaccine development. Front Biosci. Jan. 1, 2008;13:1968-1980.

Gaffney et al., One-Flask Syntheses of c-di-GMP and the [Rp,Rp] and [Rp,Sp] Thiophosphate Analogues. Org Lett. Jul. 16, 2010;12(14):3269-3271.

Gambus et al., Epitope mapping of a mouse monoclonal anti-MUC2 antibody suggests the existence of an immunodominant region in the COOH terminus of the MUC2 tandem-repeat sequence. Int J Cancer. Jan. 3, 1995;60 (1):146-148.

Gao et al., Cyclic [G(20,50)pA(30,50)p] is the Metazoan Second Messenger Produced by DNA-Activated Cyclic GMP-AMP Synthase. Cell. May 23, 2013;153(5):1094-1107.

Gao et al., Structure-Function Analysis of STING Activation by c[G(2',5')pA(3',5')p] and Targeting by Antiviral DMXAA. Cell. Aug. 15, 2013;154(4):748-762.

Geisbert and Jahrling, Differentiation of filoviruses by electron microscopy. Virus Res. Dec. 1995;39(2-3):129-150.

Ghazizadeh et al., Role of cdk4, p16INK4, and Rb Expression in the Prognosis of Bronchioloalveolar Carcinomas. Respiration. Jan.-Feb. 2005;72(1):68-73.

Gilliam et al., A phase II study of G17DT in gastric carcinoma. Eur J Surg Oncol. Jun. 2004;30(5):536-543.

Gonzalez et al., A comparative sequence analysis to revise the current taxonomy of the family Coronaviridae. Arch Virol. Nov. 2003;148(11):2207-2235.

Good et al., Development and regulation of cell-mediated immune responses to the blood stages of malaria: implications for vaccine research. Annu Rev Immunol. 2005;23:69-99.

Good et al., The immunological challenge to developing a vaccine to the blood stages of malaria parasites. Immunol Rev. Oct. 2004;201:254-267.

Grajkowski et al., Convenient Synthesis of a Propargylated Cyclic (3'-5') Diguanylic Acid and its "Click" Conjugation to a Biotinylated Azide. Bioconjug Chem. Nov. 17, 2010;21(11):2147-2152.

(56) References Cited

OTHER PUBLICATIONS

Grimm et al., Mouse alpha-fetoprotein-specific DNA-based immunotherapy of hepatocellular carcinoma leads to tumor regression in mice. Gastroenterology. Oct. 2000;119(4):1104-1112.
Groh et al., Efficient cross-priming of tumor antigen-specific T cells by dendritic cells sensitized with diverse anti-MICA opsonized tumor cells. Proc Natl Acad Sci USA. May 3, 2005;102(18):6461-6466.
Gueguen et al., An Antigen Recognized by Autologous CTLs on a Human Bladder Carcinoma. J Immunol. Jun. 15, 1998;160(12):6188-6194.
Shivapurkar et al., Presence of Simian Virus 40 DNA Sequences in Human Lymphoid and Hematopoietic Malignancies and Their Relationship to Aberrant Promoter Methylation of Multiple Genes. Cancer Res. Jun. 1, 2004;64(11):3757-3760.
Siegel et al., Induction of antitumour immunity using survivin peptide-pulsed dendritic cells in a murine lymphoma model. Br J Haematol. Sep. 2003;122(6):911-914.
Simon et al., Cervical response to vaccination against HPV16 E7 in case of severe dysplasia. Eur J Obstet Gynecol Reprod Biol. Aug. 15, 2003;109(2):219-223.
Singh et al., Non-replicating adenovirus vectors expressing avian influenza virus hemagglutinin and nucleocapsid proteins induce chicken specific effector, memory and effector memory CD8(+) T lymphocytes. Virology. Sep. 15, 2010;405(1):62-69.
Sjolander et al., Serological divergence of Dobrava and Saaremaa hantaviruses: evidence for two distinct serotypes. Epidemiol Infect. Feb. 2002;128(1):99-103.
Skoberne et al., KBMA Listeria monocytogenes is an effective vector for DC-mediated induction of antitumor immunity. J Clin Invest. Dec. 2008;118(12):3990-4001.
Slager et al., Induction of CAMEL/NY-ESO-ORF2-specific CD8+ T cells upon stimulation with dendritic cells infected with a modified Ad5 vector expressing a chimeric Ad5/35 fiber. Cancer Gene Ther. Mar. 2004;11(3):227-236.
Small et al., Immunotherapy of Hormone-Refractory Prostate Cancer With Antigen-Loaded Dendritic Cells. J Clin Oncol. Dec. 1, 2000;18(23):3894-3903.
Smits et al., Phylogenetic and Evolutionary Relationships among Torovirus Field Variants: Evidence for Multiple Intertypic Recombination Events. J Virol. Sep. 2003;77(17):9567-9577.
Sofia et al., Nucleoside, Nucleotide, and Non-Nucleoside Inhibitors of Hepatitis C Virus NS5B RNA—Dependent RNA—Polymerase. J Med Chem. Mar. 22, 2012;55(6):2481-2531.
Sofia, Nucleotide prodrugs for HCV Therapy. Antivir Chem Chemother. Aug. 23, 2011;22(1):23-49.
Stams et al., Expression Levels of TEL, AML1, and the Fusion ProductsTEL-AML1 and AML1-TEL versus Drug Sensitivity and Clinical Outcome in t(12;21)-Positive Pediatric Acute Lymphoblastic Leukemia. Clin Cancer Res. Apr. 15, 2005;11(8):2974-2980.
Steffens et al., Immunohistochemical analysis of tumor antigen saturation following injection of monoclonal antibody G250. Anticancer Res. Mar.-Apr. 1999;19(2A):1197-1200.
Stirnadel et al., Assessment of different sources of variation in the antibody responses to specific malaria antigens in children in Papua New Guinea. Int J Epidemiol. Jun. 2000;29(3):579-586.
Stolier et al., Initial experience with surgical treatment planning in the newly diagnosed breast cancer patient at high risk for BRCA-1 or BRCA-2 mutation. Breast J. Nov.-Dec. 2004;10(6):475-480.
Studahl et al., Herpesvirus DNA Detection in Cerebral Spinal Fluid: Differences in Clinical Presentation between Alpha-, Beta-, and Gamma-Herpesviruses. Scand J Infect Dis. 2000;32(3):237-248.
Sun et al., Cyclic GMP-AMP Synthase is a Cytosolic DNA Sensor That Activates the Type I Interferon Pathway. Science. Feb. 15, 2013;339(6121):786-791.
Gulmann et al., Adenomatous Polyposis Coli Gene, beta-Catenin, and E-Cadherin Expression in Proximal and Distal Gastric Cancers and Precursor Lesions. Appl Immunohistochem Mol Morphol. Sep. 2003;11(3):230-237.

Gupta et al., Refolding, purification, and crystallization of apical membrane antigen 1 from Plasmodium falciparum. Protein Expr Purif. May 2005;41(1):186-198.
Haddad et al., Novel antigen identification method for discovery of protective malaria antigens by rapid testing of DNA vaccines encoding exons from the parasite genome. Infect Immun. Mar. 2004;72(3):1594-1602.
Hakansson et al., Establishment and phenotypic characterization of human U937 cells with inducible P210 BCR/ABL expression reveals upregulation of CEACAM1 (CD66a). (2004) Leukemia 18:538-547.
Harris et al., The Biological and Therapeutic Importance of Gastrin Gene Expression in Pancreatic Adenocarcinomas. Cancer Res. Aug. 15, 2004;64(16):5624-5631.
Harty and Badovinac, Shaping and reshaping CD8+ T-cell memory. Nat Rev Immunol. Feb. 2008;8(2):107-19-119.
Hashido et al., Evaluation of an Enzyme-Linked Immunosorbent Assay Based on Binding Inhibition for Type-Specific Quantification of Poliovirus Neutralization-Relevant Antibodies. Microbiol Immunol. 1999;43(1):73-77.
Hassan et al., Mesothelin: A New Target for Immunotherapy. Clin Cancer Res. Jun. 15, 2004;10(12 Pt 1):3937-3942.
Havlasova et al., Mapping of immunoreactive antigens of Francisella tularensis live vaccine strain. Proteomics. Jul. 2002;2(7):857-867.
Ablasser et al., cGAS produces 2'-5'-linked cdn second messenger that activates STING. Nature. Jun. 20, 2013;498 (7454):380-384.
Antonarakis and Drake, Combining immunological and androgen-directed approaches: an emerging concept in prostate cancer immunotherapy. Curr Opin Oncol. May 2012;24(3):258-265.
Ausmees et al., Genetic data indicate that proteins containing the GGDEF domain possess diguanylate cyclase activity. FEMS Microbiol Lett. Oct. 16, 2001;204(1):163-167.
Bahjat et al., Activation of Immature Hepatic NK Cells as Immunotherapy for Liver Metastatic Disease. J Immunol. Dec. 1, 2007;179(11):7376-7384.
Barker et al., STING-Dependent Recognition of Cyclic di-AMP Mediates Type I Interferon Responses during chlamydia trachomatis Infection. MBio. Apr. 30, 2013;4(3):e00018-e00013.
Blankenstein et al., The determinants of tumour immunogenicity. Nat Rev Cancer. Mar. 1, 2012;12(4):307-313.
Bowie et al., Innate Sensing of bacterial cdns: more than just STING. Nat Immunol. Dec. 2012;13(12):1137-1139.
Brahmer et al., Phase I Study of Single-Agent Anti-Programmed Death-1 (MDX-1106) in Refractory Solid Tumors: Safety, Clinical Activity, Pharmacodynamics, and Immunologic Correlates. J Clin Oncol. Jul. 1, 2010;28(19):3167-3175.
Brockstedt et al., Listeria-based cancer vaccines that segregate immunogenicity from toxicity. Proc Natl Acad Sci U S A. Sep. 21, 2004;101(38):13832-13837.
Burger's Medicinal Chemistry and Drug Discovery, Fifth Edition, published 1994 by Wiley-Interscience, edited by Manfred E Wolff, pp. 975-977.
Chan et al., Structural basis of activity and allosteric control of diguanylate cyclase. Proc Natl Acad Sci U S A. Dec. 7, 2004;101(49):17084-17089.
Chen et al., The potential of 3',5'-cyclic diguanylic acid (c-di-GMP) as an effective vaccine adjuvant. Vaccine. Apr. 19, 2010;28(18):3080-3085.
Civril et al., Structural mechanism of cytosolic DNA sensing by cGAS. Nature. Jun. 20, 2013;498(7454):332-337.
Conlon et al., Mouse, but not Human STING, Binds and Signals in Response to the Vascular Disrupting Agent 5,6-Dimethylxanthenone-4-Acetic Acid. J Immunol. May 15, 2013;190(10):5216-5225.
Crittenden et al., Expression of Inflammatory Chemokines Combined with Local Tumor Destruction Enhances Tumor Regression and Long-term Immunity. Cancer Res. Sep. 1, 2003;63(17):5505-5512.
Curran and Allison, Tumor Vaccines Expressing Flt3 Ligand Synergize with CTLA-4 Blockade to Reject Preimplanted Tumors. Cancer Res. Oct. 1, 2009;69(19):7747-7755.

(56) References Cited

OTHER PUBLICATIONS

Dalby et al., Advanced transfection with Lipofectamine 2000 reagent: primary neurons, siRNA, and high-throughput applications. Methods. Jun. 2004;33(2):95-103.

De Grujil et al., Whole-cell cancer vaccination: from autologous to allogeneic tumor—and dendritic cell-based vaccines. Cancer Immunol Immunother. Oct. 2008;57(10):1569-1577.

Di Lorenzo et al., Immunotherapy for the treatment of prostate cancer. Nat Rev Clin Oncol. May 24, 2011;8(9):551-561.

Drake et al., Androgen ablation mitigates tolerance to a prostate/prostate cancer-restricted antigen. Cancer Cell. Mar. 2005;7(3):239-249.

Dranoff et al., Vaccination with irradiated tumor cells engineered to secrete murine granulocyte-macrophage colony-stimulating factor stimulates potent, specific, and long-lasting anti-tumor immunity. Proc Natl Acad Sci U S A. Apr. 15, 1993;90(8):3539-3543.

Driessens et al., Highly Successful Therapeutic Vaccinations Combining Factor Dendritic Cells and Tumo Cells Secreting Granulocyte Macrophage Colony-stimulating Factor Cancer Res. Nov. 15, 2004;64(22):8435-8442.

Dubensky et al., Abstract 4573: A novel tumor vaccine with cyclic dinucleotides—can induce potent anti-tumor responses in vivo. Cancer Res. Apr. 15, 2013;73(8 Suppl):4573-4573.

Dubensky et al., Rationale, progress, and development of vaccines utilizing STING-activating cyclic dinucleotide adjuvants. Ther Adv Vaccines. Nov. 2013;1(4):131-143.

Ettmayer et al., Lessons Learned from Marketed and Investigational Prodrugs. J Med Chem. May 6, 2004;47(10)2393-2404.

Ertem and Ferris, Synthesis of RNA oligomers on heterogeneous templates. Nature. Jan. 18, 1996;379(6562):238-240.

Fasso et al., SPAS-1 (stimulator of prostatic adenocarcinoma-specific T cells)/SH3GLB2: A prostate tumor antigen identified by CTLA-4 blockade. Proc Natl Acad Sci U S A. Mar. 4, 2008;105(9):3509-3514.

Gao et al., GM-CSF-surface-modified B16.F10 melanoma cell vaccine. Vaccine. Jun. 19, 2006;24(25):5265-5268.

Goldberg et al., Role of PD-1 and its ligand, B7-H1, in early fate decisions of CD8 T cells. Blood. Jul. 1, 2007;110(1):186-192.

Gulley et al., Immunologic and Prognostic Factors Associated with Overall Survival Employing a Poxviral-based PSA Vaccine in Metastatic Castrate-resistant Prostate Cancer. Cancer Immunol Immunother. May 2010;59(5):663-674.

Hernandez et al., Novel Kidney Cancer Immunotherapy Based on the Granulocyte-Macrophage Colony-stimulating Factor and Carbonic Anhydrase IX Fusion Gene. Clin Cancer Res. May 2003;9(5):1906-1916.

Hodi et al., Improved Survival with Ipilimumab in Patients with Metastatic Melanoma. N Engl J Med. Aug. 19, 2010;363(8):711-723.

Huang et al., The structural basis for the sensing and binding of CDG by STING. Nat Struct Mol Biol. Jun. 24, 2012;19(7):728-730.

Hurwitz et al., The TRAMP Mouse as a Model for Prostate Cancer. Curr Protoc Immunol. Nov. 2001;Chapter 20:Unit 20.5.

Ishikawa and Barber, The STING pathway and regulation of innate immune signaling in response to DNA pathogens. Cell Mol Life Sci. Apr. 2011;68(7):1157-1165.

Jemal et al., Cancer statistics, 2010. CA Cancer J Clin. Sep.-Oct. 2010;60(5):277-300.

Kantoff et al., Sipuleucel-T Immunotherapy for Castration-Resistant Prostate Cancer. N Engl J Med. Jul. 29, 2010;363(5):411-422.

Kantoff et al., Overall Survival Analysis of a Phase II Randomized Controlled Trial of a Poxviral-Based PSA-Targeted Immunotherapy in Metastatic Castration-Resistant Prostate Cancer. J Clin Oncol. Mar. 1, 2010;28(7):1099-1105.

Krishnamachari et al., Nanoparticle Delivery Systems in Cancer Vaccines. Pharm Res 2011;28:215-236.

Lam et al, Adenovirus Detection by the cGAS/STING/TBK1 DNA Sensing Cascade. J Virol. Jan. 2014;88(2):974-981.

Le et al., A Live-Attenuated Listeria Vaccine (ANZ-100) and a Live-Attenuated Listeria Vaccine Expressing Mesothelin (CRS-207) for Advanced Cancers: Phase I Studies of Safety and Immune Induction. Clin Cancer Res. Feb. 1, 2012;18(3):858-868.

Le et al., Cellular Vaccine Approaches. Cancer J. Jul.-Aug. 2010;16(4):304-10.

Li et al, Cyclic GMP-AMP Synthase is Activated by Double-Stranded DNA-Induced Oligomerization. Immunity. Dec. 12, 2013;39(6):1019-1031.

Libanova, Cyclic di-nucleotides: new era for small molecules as adjuvants. Microb Biotechnol. Mar. 2012;5(2):168-176.

Luo et al, Selective binding of 2'F-c-di-GMP to Ct-E88 and Cb-E43, new class I riboswitches from Clostridium tetani and Clostridium botulinum respectively. Mol Biosyst. Jun. 2013;9(6):1535-1539.

Lutz et al., A Lethally Irradiated Allogeneic Granulocyte-Macrophage Colony Stimulating Factor-Secreting Tumor Vaccine for Pancreatic Adenocarcinoma: A Phase II Trial of Safety, Efficacy, and Immune Activation. Ann Surg. Feb. 2011;253(2):328-335.

Mathew et al, Cytosolic delivery of antisense oligonucleotides by listeriolysin O-containing liposomes. Gene Ther. Jul. 2003;10(13):1105-1115.

Mellman et al., Cancer immunotherapy comes of age. Nature. Dec. 21, 2011;480(7378):480-489.

Miyabe et al., A new adjuvant delivery system 'cyclic di-GMP/YSK05 liposome' for cancer immunotherapy. J Control Release. Jun. 28, 2014;184:20-27 (author's version).

Olson et al., Liposomal gD Ectodomain (gD1-306) Vaccine Protects Against HSV2 Genital or Rectal Infection of Female and Male Mice. Vaccine. Dec. 11, 2009;28(2):548-560.

O'Neill, Immunology. Sensing the dark side of DNA. Science. Feb. 15, 2013;339(6121):763-764.

Ora et al., Hydrolytic reactions of cyclic bis(3'-5')diadenylic acid (c-di-AMP). J Physical Organic Chem. 2013; 26(3):218-225.

Pardoll and Drake, Immunotherapy earns its spot in the ranks of cancer therapy. J Exp Med. Feb. 13, 2012;209(2):201-209.

Pardoll, The blockade of immune checkpoints in cancer immunotherapy. Nat Rev Cancer. Mar. 22, 2012;12(4):252-264.

Parvatiyar et al., DDX41 recognizes the bacterial secondary messengers cyclic di-GMP and cyclic di-AMP to activate a type I interferon immune response. Nat Immunol. Dec. 2012;13(12):1155-1161.

Prantner et al., 5,6-Dimethylxanthenone-4-acetic Acid (DMXAA) Activates Stimulator of Interferon Gene (STING)-dependent Innate Immune Pathways and is Regulated by Mitochondrial Membrane Potential. J Biol Chem. Nov. 16, 2012;287(47):39776-39788.

Roembke et al., A cyclic dinucleotide containing 2-aminopurine is a general fluorescent sensor for c-di-GMP and 3',3'-cGAMP. Mol Biosyst. 2014;10(6):1568-1575.

Sawai et al., Preparation and Properties of Oligocytidylates with 2'-5' Internucleotide Linkage. Bull Chem Soc Jpn 1985;58(1):361-366.

Sawai et al., Synthesis of 2'-5' Linked Oligouridylates in Aqueous Medium Using the Pd2+ Ion. Chem Pharm Bull. 1981;29(8):2237-2245.

Shanahan et al., Identification of c-di-GMP Derivatives Resistant to an EAL Domain Phosphodiesterase. Biochemistry. Jan. 15, 2013;52(2):365-377.

Silverman, The Organic Chemistry of Drug Design and Drug Action, Published 1992 by Academic Press, pp. 352-397.

Stella, Prodrugs and Therapeutics. Expert Opinion on Therapeutic Patents 2004;14(3):277-280.

Sun and Bevan, Defective CD8 T Cell Memory Following Acute Infection Without CD4 T Cell Help. Science. Apr. 11, 2003;300(5617):339-342.

Tannock et al., Docetaxel plus Prednisone or Mitoxantrone plus Prednisone for Advanced Prostate Cancer. N Engl J Med. Oct. 7, 2004;351(15):1502-1512.

Testa et al., Prodrug Research: futile or fertile? Biochem Pharmacol. Dec. 1, 2004;68(11):2097-2106.

Tezuka et al., Synthesis of 2'-Modified Cyclic Bis(3'-5')diadenylic Acids (c-di-AMPs) and Their Promotion of Cell Division in a Freshwater Green Alga. Chem Lett. 41: 1723-25, 2012.

Tijono et al., Identification of human-selective analogues of the vascular-disrupting agent 5,6-dimethylxanthenone-4-acetic acid (DMXAA). Br J Cancer. Apr. 2, 2013;108(6):1306-1315.

(56) References Cited

OTHER PUBLICATIONS

Topalian et al., Cancer Immunotherapy Comes of Age. J Clin Oncol 2011, vol. 29,(36), pp. 4828-4836.
Urata et al., Regio- and Diastereo-Selectivity of Montmorillonite-Catalyzed Oligomerization of Racemic Adenosine 5'-Phosphorimidazolide. Nucleosides Nucleotides Nucleic Acids. Apr. 2008;27(4):421-430.
Van Elsas et al., Elucidating the Autoimmune and Antitumor Effector Mechnaisms of a Treatment Based on Cytotoxic T Lymphocyte Antigen-4 Blockade in Combination with a B16 Melanoma Vaccine: Comparison of Prophylaxis and Therapy. J Exp Med. Aug. 20, 2001;194(4):481-489.
Waitz et al., Potent Induction of Tumor Immunity by Combining Tumor Cryoablation with Anti-CTLA-4 Therapy. Cancer Res. Jan. 15, 2012;72(2):430-439.
Woodward et al., Supporting Online Material for c-di-AMP Secreted by Intracellular Listeria monocytogenes Activates a Host Type I Interferon Response. May 27, 2010 on Science Express May 27, 2010;DOI:10.1126/science.1189801 (15 pages).
Wu et al., Cyclic GMP-AMP is an Endogenous Second Messenger in Innate Immune Signaling by Cytosolic DNA. Science. Feb. 15, 2013;339(6121):826-830.
Yan and Aguilar, Synthesis of 3',5'-cyclic diguanylic acid (cdiGMP) using 1-(4-chlorophenyl)-4-ethoxypiperidin-4-yl as a protecting group for 2'-hydroxy functions of ribonucleosides. Nucleosides Nucleotides Nucleic Acids. 2007;26(2):189-204.
Zhang et al., Cyclic GMP-AMP Containing Mixed Phosphodiester Linkages is an Endogenous High-Affinity Ligand for STING. Mol Cell. Jul. 25, 2013;51(2):226-235.
International Search Report and Written Opinion issued in PCT/US2013/044744 dated Nov. 7, 2013.
Extended European Search Report and Written Opinion issued in PCT/US2013/044744 (EP 13799826) dated Nov. 20, 2015.
Burdette et al., STING is a direct innate immune sensor of cyclic-di-GMP. Nature. Sep. 25, 2011;478(7370):515-518.
Search Report and Written Opinion issued by IPOS in Singapore patent application No. 11201407875U dated Sep. 15, 2015.
Non Final Office Action issued in U.S. Appl. No. 13/912,960 dated Jul. 15, 2015.
Non Final Office Action issued in U.S. Appl. No. 14/106,687 dated Nov. 20, 2015.
Non Final Office Action issued in U.S. Appl. No. 14/280,668 dated Dec. 3, 2015.
Non Final Office Action issued in U.S. Appl. No. 14/268,967 dated Nov. 9, 2015.
Dubensky, oral slide presentation "Development of Cyclic Dinucleotides as STING-Targeted Molecular Adjuvants.". Immunological Mechanisms of Vaccination seminar, Fairmont Château Laurier, Ottawa, Ontario Canada Dec. 14, 2012:13 pages.
The Extended European Search Report issued in EP 14800848 dated Dec. 7, 2016.
Sawai and Ohno, Synthesis of Oligoinosinates with 2'-5' Internucleotide Linkage in Aqueous Solution Using Pb2+ Ion. Bull Chem Soc Jpn. 1981;54(9)2759-2762.
Sun et al., Eris, an endoplasmic reticulum IFN stimulator, activates innate immune signaling through dimerization. Proc Natl Acad Sci U S A. May 26, 2009;106(21):8653-8658—plus 6 pages Supporting Information—(12 pp ttl).
Venes et al., Taber's Cyclopedic Medical Dictionary, Ed. 21. F.A. Davis Co., Philadelphia, Copyright: © 2009:1163.
Wolkowicz and Cook, NF45 dimerizes with NF90, Zfr and SPNR via a conserved domain that has a nucleotidyltransferase fold. Nucleic Acids Res. Oct 2012;40(18):9356-9368.
Xiao and Fitzgerald, The cGAS-STING Pathway for DNA Sensing. Mol Cell. Jul. 25, 2013;51(2):135-139.
Yang et al., The cytosolic nucleic acid sensor LRRFIP1 mediates the production of type I interferon via a beta-catenin-dependent pathway. Nat Immunol. Jun. 2010;11(6):487-494.

Zhang et al., The helicase DDX41 senses intracellular DNA mediated by the adaptor STING in dendritic cells. Nat Immunol. Sep. 4, 2011;12(10):959-965.
Zhong et al., The Adaptor Protein MITA Links Virus-Sensing Receptors to IRF3 Transcription Factor Activation. Immunity. Oct. 17, 2008;29(4):538-550.
Adams et al., Phenix: a comprehensive Python-based system for macromolecular structure solution. Acta Crystallogr D Biol Crystallogr. Feb. 2010;66(Pt 2):213-221.
Baguley and Ching, DMXAA: An antivascular agent with multiple host responses. Int J Radiat Oncol Biol Phys. Dec. 1, 2002;54(5)1503-1511.
Burckstummer et al., An orthogonal proteomic-genomic screen identifies AIM2 as a cytoplasmic DNA sensor for the inflammasome. Nat Immunol. Mar. 2009;10(3):266-272.
Cai et al., The cGAS-cGAMP-STING Pathway of Cytosolic DNA Sensing and Signaling. Mol Cell. Apr. 24, 2014;54 (2):289-296.
Cavlar et al., Species-specific detection of the antiviral small-molecule compound CMA by STING. Embo J. May 15, 2013;32(10):1440-1450.
The International Search Report and Written Opinion issued in PCTUS2014035909 dated Sep. 12, 2014.
The International Search Report and Written Opinion issued in PCTUS2014049140 dated Dec. 22, 2014.
Dai et al., Modified Vaccinia Virus Ankara Triggers Type I IFN Production in Murine Conventional Dendritic Cells via a cGas/STING-Mediated Cytosolic DNA-Sensing Pathway. PLoS Pathog. Apr. 17, 2014;10(4):e1003989.
Donovan et al., Structural basis for cytosolic double-stranded RNA surveillance by human oligoadenylate synthetase 1. Proc Natl Acad Sci U S A. Jan. 29, 2013;110(5):1652-1657 plus 12 pages Supporting Information—(18 pages ttl).
Egli et al., Atomic-resolution structure of the cellulose synthase regulator cyclic diguanylic acid. Proc Natl Acad Sci U S A. Apr. 1990;87(8):3235-3239.
Ekins et al., In silico pharmacology for drug discovery: methods for virtual ligand screening and profiling. Br J Pharmacol. Sep. 2007;152(1):9-20.
Emsley et al., Features and development of Coot. Acta Crystallogr D Biol Crystallogr. Apr. 2010;66(Pt 4):486-501.
Fernandes-Alnemri et al., AIM2 activates the inflammasome and cell death in response to cytoplasmic DNA. Nature. Mar. 26, 2009;458(7237):509-513.
Gaffney and Jones, One-flask syntheses of cyclic diguanosine monophosphate (c-di-GMP). Curr Protoc Nucleic Acid Chem. Mar. 2012;Chapter 14:Unit 14.8.1-7.
Gall et al., Autoimmunity Initiates in Nonhematopoietic Cells and Progresses via Lymphocytes in an Interferon-Dependent Autoimmune Disease. Immunity. Jan. 27, 2012;36(1):120-131.
Gao et al., Binding-Pocket and Lid-Region Substitutions Render Human STING Sensitive to the Species-Specific Drug DMXAA. Cell Rep. Sep. 25, 2014;8(6):1668-1676 plus 12 pages Supporting Information—(23 pages ttl).
Gehrke et al., Oxidative Damage of DNA Confers Resistance to Cytosolic Nuclease TREX1 Degradation and Potentiates STING-Dependent Immune Sensing. Immunity. Sep. 19, 2013;39(3):482-495.
Hartmann et al., Crystal Structure of the 2' Specific and Double-Stranded RNA-Activated Interferon-Induced Antiviral Protein 2'-5'-Oligoadenylate Synthetase. Mol Cell. Nov. 2003;12(5):1173-1185.
Head and Jameson, The development of the tumor vascular-disrupting agent ASA404 (vadimezan, DMXAA): current status and future opportunities. Expert Opin Investig Drugs. Feb. 2010;19(2):295-304.
Higashida et al., Measurement of adenylyl cyclase by separating cyclic AMP on silica gel thin-layer chromatography. Anal Biochem. Sep. 1, 2002;308(1):106-111.
Hornung and Latz, Intracellular DNA recognition. Nat Rev Immunol. Feb. 2010;10(2):123-130.
Hornung et al., AIM2 recognizes cytosolic dsDNA and forms a caspase-1-activating inflammasome with ASC. Nature. Mar. 26, 2009;458(7237):514-518.

(56) References Cited

OTHER PUBLICATIONS

Huang et al., The structural basis for the sensing and binding of cyclic di-GMP by STING. Nat Struct Mol Biol. Jun. 24, 2012;19(7):728-30—Supplementary Information only (5 pages).
Huffman and Brennan, Prokaryotic transcription regulators: more than just the helix-turn-helix motif. Curr Opin Struct Biol. Feb. 2002;12(1):98-106.
Jin et al., MPYS, a Novel Membrane Tetraspanner, Is Associated with Major Histocompatibility Complex Class II and Mediates Transduction of Apoptotic Signals. Mol Cell Biol. Aug. 2008;28(16):5014-5026 plus 9 pages Supporting Information—(22 pages ttl).
Jin et al., Structures of the HIN Domain: DNA Complexes Reveal Ligand Binding and Activation Mechanisms of the AIM2 Inflammasome and IFI16 Receptor. Immunity. Apr. 20, 2012;36(4):561-571.
Kasturi et al., Programming the magnitude and persistence of antibody responses with innate immunity. Nature 2011;470:543-547.
Keating et al., Cytosolic DNA sensors regulating type I interferon induction. Trends Immunol. Dec. 2011;32 (12):574-581.
Kerur et al., IFI16 Acts as a Nuclear Pathogen Sensor to Induce the Inflammasome in Response to Kaposi Sarcoma-Associated Herpesvirus Infection. Cell Host Microbe. May 19, 2011;9(5):363-375.
Kodym et al., 2'-5'-Oligoadenylate synthetase is activated by a specific RNA sequence motif. Biochem Biophys Res Commun. Oct. 16, 2009;388(2):317-322.
Krasteva et al., Sensing the messenger: The diverse ways that bacteria signal through c-di-GMP. Protein Sci. Jul. 2012;21(7):929-948.
Kubota et al., Identification of 2'-Phosphodiesterase, Which Plays a Role in the 2-5A System Regulated by Interferon. J Biol Chem. Sep. 3, 2004;279(36):37832-37841.
Kulshina et al., Recognition of the bacterial second messenger cyclic diguanylate by its cognate riboswitch. Nat Struct Mol Biol. Dec. 2009;16(12):1212-1217.
Lara Jr. et al., Randomized Phase III Placebo-Controlled Trial of Carboplatin and Paclitaxel With or Without the Vascular Disrupting Agent Vadimezan (ASA404) in Advanced Non-Small-Cell Lung Cancer. J Clin Oncol. Aug. 1, 2011;29(22):2965-2971.
Lee et al., An Allosteric Self-Splicing Ribozyme Triggered by a Bacterial Second Messenger. Science. Aug. 13, 2010;329(5993):845-848.
Lunde et al., RNA-binding proteins: modular design for efficient function. Nat Rev Mol Cell Biol. Jun. 2007;8 (6):479-490.
McCoy et al., Phaser crystallographic software. J Appl Crystallogr. Aug. 1, 2007;40(Pt 4):658-674.
Murshudov et al., Refinement of Macromolecular Structures by the Maximum-Likelihood Method. Acta Crystallogr D Biol Crystallogr. May 1, 1997;53(Pt 3):240-255.
Otwinowski and Minor, Processing of X-ray Diffraction Data Collected in Oscillation Mode. Methods Enzymol. 1997;276:307-326.
Paludan and Bowie, Immune Sensing of DNA. Immunity. May 23, 2013;38(5):870-880.
Porter et al., Merck Manual of Diagnosis and Therapy, 19th Edition. Merck Sharp & Dohme Corp., A Subsidiary of Merck & Co., Inc. Copyright: © Merck Manuals Aug. 1, 2011:1059-1062.
Rasmussen et al., Activation of Autophagy by α-Herpesviruses in Myeloid Cells Is Mediated by Cytoplasmic Viral DNA through a Mechanism Dependent on Stimulator of IFN Genes. J Immunol. Nov. 15, 2011;187(10):5268-5276.
Roberts et al., IFN-β-Dependent Inhibition of Tumor Growth by the Vascular Disrupting Agent 5,6-Dimethylxanthenone-4-Acetic Acid (DMXAA). J Interferon Cytokine Res. Mar. 2008;28(3):133-139.
Ross et al., Regulation of cellulose synthesis in Acetobacter xylinum by cyclic diguanylic acid. Nature. Jan. 15-21, 1987;325(6101):279-281.
Sadler and Williams, Interferon-inducible antiviral effectors. Nat Rev Immunol. Jul. 2008;8(7):559-568.
Schirmer and Jenal, Structural and mechanistic determinants of c-di-GMP signalling. Nat Rev Microbial. Oct. 2009;7(10):724-735.
Schoggins et al., A diverse range of gene products are effectors of the type I interferon antiviral response. Nature. Apr. 28, 2011;472(7344):481-485.
Shang et al., Crystal structures of STING protein reveal basis for recognition of cyclic di-GMP. Nat Struct Mol Biol. Jun. 24, 2012;19(7):725-727.
Smith et al., Structural basis of ligand binding by a c-di-GMP riboswitch. Nat Struct Mol Biol. Dec. 2009;16 (12):1218-1223.
Sudarsan et al., Riboswitches in Eubacteria Sense the Second Messenger Cyclic Di-GMP. Science. Jul. 18, 2008;321(5887):411-413.
Aguilar et al., Endemic Venezuelan Equine Encephalitis in Northern Peru. Emerg Infect Dis. May 2004;10 (5):880-888.
Battistini et al., Stereoselective Synthesis of Cyclic Dinucleotide Phosphorothioates. Tetrahedron, 1993;49 (5)1115-1132.
Brockstedt et al., Killed but metabolically active microbes: a new vaccine paradigm for eliciting effector T-cell responses and protective immunity. Nat Med. Aug. 2005;11(8):853-860.
Clements et al., Adenomatous Polyposis Coli/β-Catenin Interaction and Downstream Targets: Altered Gene Expression in Gastrointestinal Tumors. Clin Colorectal Cancer. Aug. 2003;3(2):113-120.
Havlasova et al., Proteomic analysis of anti-Francisella tularensis LVS antibody response in murine model of tularemia. Proteomics. May 2005;5(8):2090-2103.
Hayakawa, A facile synthesis of cyclic bis(30!50)diguanylic acid. Tetrahedron 2003;59:6465-6471.
He et al., Complexes of Poliovirus Serotypes with Their Common Cellular Receptor, CD155. J Virol. Apr. 2003;77 (8):4827-4835.
Hirose et al., Incidence of Diffuse Large B-Cell Lymphoma of Germinal Center B-Cell Origin in Whole Diffuse Large B-Cell Lymphoma: Tissue Fluorescence In Situ Hybridization Using t(14;18) Compared with Immunohistochemistry. Int J Hematol. Jan. 2005;81(1):48-57.
Hoffman et al., Strategy for development of a pre-erythrocytic Plasmodium falciparum DNA vaccine for human use. Vaccine. Jun. 1997;15(8):842-845.
Hoke, History of U.S. Military Contributions to the Study of Viral Encephalitis. Mil Med. Apr. 2005;170(4 Suppl):92-105.
Hu et al., c-di-GMP as a vaccine adjuvant enhances protection against systemic methicillin-resistant Staphylococcus aureus (MRSA) infection. Vaccine. Jul. 30, 2009;27(35):4867-4873.
Hughes, Nanostructure-mediated drug delivery. Nanomedicine. Mar. 2005;1(1):22-30.
Hussain and Paterson, What is needed for effective antitumor immunotherapy? Lessons learned using Listeria monocytogenes as a live vector for HPV-associated tumors. Cancer Immunol Immunother. Jun. 2005;54(6):577-586.
Hutchinson et al., Multiplex Analysis of Cytokines in the Blood of Cynomolgus Macaques Naturally Infected With Ebola Virus (Reston Serotype). J Med Virol. Nov. 2001;65(3):561-566.
Hyodo et al., Synthesis of cyclic bis(3'-5'1')diguanylic acid (c-di-GMP) analogs. Tetrahedron 2006;62:3089-3094.
Jacobuzio-Donahue et al., Highly Expressed Genes in Pancreatic Ductal Adenocarcinomas: A Comprehensive Characterization and Comparison of the Transcription Profiles Obtained from Three Major Technologies. Cancer Res. Dec. 15, 2003;63(24):8614-8622.
Iqbal et al., BCL2 Translocation Defines a Unique Tumor Subset within the Germinal Center B-Cell-Like Diffuse Large B-Cell Lymphoma. Am J Pathol. Jul. 2004;165(1):159-166.
Isherwood et al., Vaccination strategies for Francisella tularensis. Adv Drug Deliv Rev. Jun. 17, 2005;57 (9):1403-1414.
Ishikawa and Barber, STING an Endoplasmic Reticulum Adaptor that Facilitates Innate Immune Signaling. Nature. Oct. 2, 2008;455(7213):674-678.
Ito et al., Prostate Carcinoma Detection and Increased Prostate-Specific Antigen Levels after 4 Years in Dutch and Japanese Males Who Had No Evidence of Disease at Initial Screening. Cancer. Jan. 15, 2005;103(2):242-250.
Iwasaki and Medzhitov, Regulation of adaptive immunity by the innate immune system. Science. Jan. 15, 2010;327 (5963):291-295.

(56) References Cited

OTHER PUBLICATIONS

Jainkittivong and Langlais, Herpes B virus infection. Oral Surg Oral Med Oral Pathol Oral Radiol Endod. Apr. 1998;85(4):399-403.
Jamieson et al., Human Torovirus: A New Nosocomial Gastrointestinal Pathogen. J Infect Dis. Nov. 1998;178 (5):1263-1269.
Jansen and Shaw, Human Papillomavirus Vaccines and Prevention of Cervical Cancer. Annu Rev Med. 2004;55:319-331.
Jin et al., Identification and characterization of a loss-of-function human MPYS variant. Genes Immun. Jun. 2011;12 (4):263-269.
Jin et al., MPYS Is Required for IFN Response Factor 3 Activation and Type I IFN Production in the Response of Cultured Phagocytes to Bacterial Second Messengers Cyclic-di-AMP and Cyclic-di-GMP. J Immunol. Sep. 1, 2011;187 (5):2595-2601.
Jung et al., Strategies Against Human Papillomavirus Infection and Cervical Cancer. J Microbiol. Dec. 2004;42 (4):255-266.
Jungck et al., E-cadherin expression is homogeneously reduced in adenoma from patients with familial adenomatous polyposis: an immunohistochemical study of E-cadherin, beta-catenin and cyclooxygenase-2 expression. Int J Colorectal Dis. Sep. 2004;19(5):438-445.
Karaolis et al., Bacterial c-di-GMP Is an Immunostimulatory Molecule. J Immunol. Feb. 15, 2007;178(4):2171-2181.
Karaolis et al., Cyclic Di-GMP Stimulates Protective Innate Immunity in Bacterial Pneumonia. Infect Immun. Oct. 2007;75(10):4942-4950.
Kastenmuller et al., Protective T cell immunity in mice following protein-TLR7/8 agonist-conjugate immunization requires aggregation, type I IFN, and multiple DC subsets. J Clin Invest. May 2011;121(5):1782-1796.
Kaufman et al., Parvovirus B19 does not bind to membrane-associated globoside in vitro. Virology. Feb. 5, 2009;332 (1)189-198.
Kawai and Akira, The role of pattern-recognition receptors in innate immunity: update on Toll-like receptors. Nat Immunol. May 2010;11(5):373-384.
Kedl et al., Comparative Sequence Analysis of the Reovirus S4 Genes from 13 Serotype 1 and Serotype 3 Field Isolates. J Virol. Jan. 1995;69(1):552-559.
Kim et al., Co-Crystal Structures of PKG Iβ (92-227) with cGMP and cAMP Reveal the Molecular Details of Cyclic-Nucleotide Binding. PLoS One. Apr. 19, 2011;6(4):e18413.
Kim et al., Comparison of HPV DNA vaccines employing intracellular targeting strategies. Gene Ther. Jun. 2004;11 (12)1011-1018.
Krzych et al., T lymphocytes from volunteers immunized with irradiated Plasmodium falciparum sporozoites recognize liver and blood stage malaria antigens. J Immunol. Oct. 15, 1995;155(8):4072-4077.
Kubuschok et al., Expression of cancer testis antigens in pancreatic carcinoma cell lines, pancreatic adenocarcinoma and chronic pancreatitis. Int J Cancer. Apr. 20, 2004;109(4):568-575.
Kumamuru et al., T-cell receptor Vbeta gene usage by T cells reactive with the tumor-rejection antigen SART-1 in oral squamous cell carcinoma. Int J Cancer. Feb. 20, 2004;108(5):686-695.
Laheru and Jaffee, Immunotherapy for pancreatic cancer—science driving clinical progress. Nat Rev Cancer. Jun. 2005;5(6):459-467.
Lauvau et al., Priming of Memory But Not Effector CD8 T Cells by a Killed Bacterial Vaccine. Science. Nov. 23, 2001;294(5547):1735-1739.
Leber et al., Distinct TLR- and NLR-Mediated Transcriptional Responses to an Intracellular Pathogen. PLoS Pathog. Jan. 2008;4(1):e6.
Lee et al., A clinical grade cocktail of cytokines and PGE2 results in uniform maturation of human monocyte-derived dendritic cells: implications for immunotherapy. Vaccine. Dec. 19, 2002;20 Suppl 4:A8-A22.
Lee et al., Immunomic analysis of human sarcoma. Proc Natl Acad Sci U S A. Mar. 4, 2003;100(5)2651-2656.

Li et al., Advanced Glycation End Products Induce Tubular Epithelial-Myofibroblast Transition through the RAGE-ERK1/2 MAP Kinase Signaling Pathway. Am J Pathol. Apr. 2004;164(4):1389-1397.
Li et al., Expression Profile of Cancer-Testis Genes in 121 Human Colorectal Cancer Tissue and Adjacent Normal Tissue. Clin Cancer Res. Mar. 1, 2005;11(5):1809-1814.
Liang et al., Microvessel density, cyclo-oxygenase 2 expression, K-ras mutation and p53 overexpression in colonic cancer. Br J Surg. Mar. 2004;91(3):355-361.
Libanova et al., The member of the cyclic di-nucleotide family bis-(3', 5')-cyclic dimeric inosine monophosphate exerts potent activity as mucosal adjuvant. Vaccine. Mar. 2, 2010;28(10):2249-2258.
Lim et al., Molecular and phenotypic spectrum of de novo Philadelphia positive acute leukemia. Int J Mol Med. Dec. 1999;4(6):665-667.
Lin et al., Melanoma-Associated Antigens in Esophageal Adenocarcinoma Identification of Novel MAGE-A10 Splice Variants. Clin Cancer Res. Sep. 1, 2004;10(17):5708-5716.
Ross et al., The Cyclic Diguanylic Acid Regulatory System of Cellulose Synthesis in Acetobacter xylinum. Chemical synthesis and biological activity of cyclic nucleotide dimer, trimer, and phosphothioate derivatives. J Biol Chem. Nov. 5, 1990;265(31):18933-18943.
Salazar-Onfray et al., Synthetic peptides derived from the melanocyte-stimulating hormone receptor MC1R can stimulate HLA-A2-restricted cytotoxic T lymphocytes that recognize naturally processed peptides on human melanoma cells. Cancer Res. Oct. 1, 1997;57(19):4348-4355.
Santin et al., The serine protease stratum corneum chymotryptic enzyme (kallikrein 7) is highly overexpressed in squamous cervical cancer cells. Gynecol Oncol. Aug. 2004;94(2):283-288.
Sarcevic et al., Expression of Cancer/Testis Tumor Associated Antigens in Cervical Squamous Cell Carcinoma. Oncology. 2003;64(4):443-449.
Sarobe et al., Carcinoembryonic Antigen as a Target to Induce Anti-Tumor Immune Responses. Curr Cancer Drug Targets. Aug. 2004;4(5):443-454.
Sasaki et al., SAGE mRNA expression in advanced-stage lung cancers. Eur J Surg Oncol. Dec. 2003;29(10):900-903.
Sasatomi et al., Expression of tumor rejection antigens in colorectal carcinomas. Cancer. Mar. 15, 2002;94 (6):1636-1641.
Sauer et al., The N-Ethyl-N-Nitrosourea-Induced Goldenticket Mouse Mutant Reveals an Essential Function of Sting in the In Vivo Interferon Response to Listeria monocytogenes and Cyclic Dinucleotides. Infect Immun. Feb. 2011;79 (2):688-694.
Scanlan et al., Antigens recognized by autologous antibody in patients with renal-cell carcinoma. Int J Cancer. Nov. 12, 1999;83(4):456-464.
Scanlan et al., Cancer-related serological recognition of human colon cancer: identification of potential diagnostic and immunotherapeutic targets. Cancer Res. Jul. 15, 2002;62(14):4041-4047.
Scanlan et al., Expression of cancer-testis antigens in lung cancer: definition of bromodomain testis-specific gene (BRDT) as a new CT gene, CT9. Cancer Lett. Mar. 31, 2000;150(2)155-164.
Scanlan et al., Humoral immunity to human breast cancer: antigen definition and quantitative analysis of mRNA expression. Cancer Immun. Mar. 30, 2001;1:4.
Scanlan et al., The cancer/testis genes: review, standardization, and commentary. Cancer Immun. Jan. 23, 2004;4:1.
Scarcella et al., Expression of MAGE and GAGE in high-grade brain tumors: a potential target for specific immunotherapy and diagnostic markers. Clin Cancer Res. Feb. 1999;5(2):335-341.
Schmidt et al., Memory CD8 T cell responses exceeding a large but definable threshold provide long-term immunity to malaria. Proc Natl Acad Sci U S A. Sep. 16, 2008;105(37):14017-14022.
Schmittgen et al., Expression of prostate specific membrane antigen and three alternatively spliced variants of PSMA in prostate cancer patients. Int J Cancer. Nov. 1, 2003;107(2):323-329.

(56) References Cited

OTHER PUBLICATIONS

Schwartz et al., Hyperinduction of Host Beta Interferon by a Listeria monocytogenes Strain Naturally Overexpressing the Multidrug Efflux Pump MdrT. Infect Immun. Apr. 2012;80(4):1537-1545.

Schwartz et al., Novel targeted and immunotherapeutic strategies in chronic myeloid leukemia. Semin Hematol. Jan. 2003;40(1):87-96.

Seder et al., T-cell quality in memory and protection: implications for vaccine design. Nat Rev Immunol. Apr. 2008;8 (4):247-258.

Sepehr et al., Distinct pattern of TP53 mutations in squamous cell carcinoma of the esophagus in Iran. Oncogene. Nov. 1, 2001;20(50):7368-7374.

Shanahan et al., Differential analog binding by two classes of c-di-GMP riboswitches. J Am Chem Soc. Oct. 5, 2011;133(39):15578-15592.

Shigemasa et al., Expression of the protease inhibitor antileukoprotease and the serine protease stratum corneum chymotryptic enzyme (SCCE) is coordinated in ovarian tumors. Int J Gynecol Cancer. Nov.-Dec. 2001;11(6):454-461.

Shirakawa et al., A Cox-2 Promoter-Based Replication-Selective Adenoviral Vector to Target the Cox-2-Expressing Human Bladder Cancer Cells. Clin Cancer Res. Jul. 1, 2004;10(13):4342-4348.

Shirasawa et al., Receptor for advanced glycation end-products is a marker of type I lung alveolar cells. Genes Cells. Feb. 2004;9(2):165-174.

Shu et al., Structure of STING bound to c-di-GMP Reveals the Mechanism of Cyclic Dinucleotide Recognition by the Immune System. Nat Struct Mol Biol. Jun. 24, 2012;19(7):722-724.

Singh et al., Avian influenza viral nucleocapsid and hemagglutinin proteins induce chicken CD8+ memory T lymphocytes. Virology 2010;399:231-238.

Slager et al., Identification of multiple HLA-DR-restricted epitopes of the tumor-associated antigen CAMEL by CD4+ Th1/Th2 lymphocytes. J Immunol. Apr. 15, 2004;172(8):5095-5102.

Smith et al., Neutralization of HIV-1 Subtypes: Implications for Vaccine Formulations. J Med Virol. Nov. 1998;56 (3):264-268.

Suzuki et al., Practical Synthesis of Cyclic Bis(3'-5')diadenylic Acid (c-di-AMP). Chem Lett. 2011;40(10):1113-1114.

Tanaka and Chen, STING Specifies IRF3 Phosphorylation by TBK1 in the Cytosolic DNA Signaling Pathway. Sci Signal. Mar. 6, 2012;5(214):ra20.

Tewari et al., Poly(I:C) is an effective adjuvant for antibody and multi-functional CD4+ T cell responses to Plasmodium falciparum circumsporozoite protein (CSP) and αDEC-CSP in Non Human Primates. Vaccine. Oct. 21, 2010;28(45):7256-7266.

Trincado et al., Human Cytomegalovirus Strains Associated With Congenital and Perinatal Infections. J Med Virol. Aug. 2000;61(4):481-487.

Tsao and Sober, Melanoma Treatment Update. Dermatol Clin. Apr. 2005;23(2):323-333.

Van Den Eynde et al., A New Antigen Recognized by Cytolytic T Lymphocytes on a Human Kidney Tumor Results From Reverse Strand Transcription. J Exp Med. Dec. 20, 1999;190(12):1793-1800.

Vilas Boas et al., Cytomegalovirus Glycoprotein B Genotypes and Central Nervous System Disease in AIDS Patients. J Med Virol. Nov. 2003;71(3):404-407.

Vilchez and Butel, Emergent Human Pathogen Simian Virus 40 and Its Role in Cancer. Clin Microbiol Rev. Jul. 2004;17(3):495-508.

Wang et al., Cloning Genes Encoding MHV Class II—Restricted Antigens: Mutated CDC27 as a Tumor Antigen. Science. May 21, 1999;284(5418):1351-1354.

Ward et al., Binding activities of a repertoire of single immunoglobulin variable domains secreted from *Escherichia coli*. Nature. Oct. 12, 1989;341(6242):544-546.

Weaver et al., Genetic determinants of Venezuelan equine encephalitis emergence. Arch Virol Suppl. 2004; (18):43-64.

Weaver et al., Venezuelan Equine Encephalitis. Annu Rev Entomol. 2004;49:141-174.

Wells et al., Swine Influenza Virus Infections Transmission. From III Pigs to Humans at a Wisconsin Agricultural Fair and Subsequent Probable Person-to-Person Transmission. JAMA. Jan. 23-30, 1991;265(4):478-481.

Wille-Reece et al., HIV Gag protein conjugated to a Toll-like receptor 7/8 agonist improves the magnitude and quality of Th1 and CD8+ T cell responses in nonhuman primates. Proc Natl Acad Sci U S A. Oct. 18, 2005;102 (42):15190-15194.

Woycechowsky and Raines, Native Disulfide Bond Formation in Proteins. Curr Opin Chem Biol. Oct. 2000;4 (5):533-539.

Yan et al., Synthesis and immunostimulatory properties of the phosphorothioate analogues of cdiGMP. Bioorg Med Chem Lett. Oct. 15, 2008;18(20):5631-5634.

Yarmush et al., Coupling of antibody-binding fragments to solid-phase supports: site-directed binding of F(ab')2 fragments. J Biochem Biophys Methods. Dec. 1992;25(4):285-297.

Yi et al., Single Nucleotide Polymorphisms of Human STING Can Affect Innate Immune Response to Cyclic Dinucleotides. PLoS One. Oct. 21, 2013;8(10):e77846.

Yin et al., Cyclic di-GMP Sensing via the Innate Immune Signaling Protein STING. Mol Mol Cell. Jun. 29, 2012;46 (6):735-745.

Zaremba et al., Identification of an Enhancer Agonist Cytotoxic T Lymphocyte Peptide from Human Carcinoembryonic Antigen. Cancer Res. Oct. 15, 1997;57(20):4570-4577.

Zeier et al., New Ecological Aspects of Hantavirus Infection: A Change of a Paradigm and a Challenge of Prevention—A Review. Virus Genes. Mar. 2005;30(2):157-180.

Zhang et al., c-di-GMP Displays a Monovalent Metal Ion-Dependent Polymorphism. J Am Chem Soc. Dec. 29, 2004;126(51):16700-16701.

Zhao et al., Thiophosphate Analogs of c-di-GMP: Impact on Polymorphism. Nucleosides Nucleotides Nucleic Acids. May 2009;28(5):352-378.

Zhou et al., Endo-S-c-di-GMP Analogues-Polymorphism and Binding Studies with Class I Riboswitch. Molecules. Nov. 9, 2012;17(11):13376-13389.

Zhou et al., Potent suppression of c-di-GMP synthesis via I-site allosteric inhibition of diguanylate cyclases with 2'-F-c-di-GMP. Bioorg Med Chem. Jul. 15, 2013;21(14):4396-4404.

Zimmerman et al., Expression of annexin II in conventional renal cell carcinoma is correlated with Fuhrman grade and clinical outcome. Virchows Arch. Oct. 2004;445(4):368-374.

Ziyaeyan et al., The Seroprevalence of Parvovirus BI9 Infection among To-Be-Married Girls, Pregnant Women, and Their Neonates in Shiraz, Iran. Jpn J Infect Dis. Apr. 2005;58(2):95-97.

International Search Report and Written Opinion issued in PCT/US2014/038525 dated Sep. 9, 2014.

International Search Report and Written Opinion issued in PCT/US2014/038526 dated Sep. 19, 2014.

International Search Report issue in PCT/US2014/066436 dated Feb. 12, 2015.

Abe et al., STING Recognition of Cytoplasmic DNA Instigates Cellular Defense. Mol Cell. Apr. 11, 2013;50(1):5-15.

Ahn et al., STING manifests self DNA-dependent inflammatory disease. Proc Natl Acad Sci U S A. Nov. 20, 2012;109 (47):19386-19391.

Apetoh et al., Toll-like receptor 4—dependent contribution of the immune system to anticancer chemotherapy and radiotherapy. Nat Med. Sep. 2007;13(9):1050-1059.

Blank et al., PD-L1/B7H-1 Inhibits the Effector Phase of Tumor Rejection by T Cell Receptor(TCR) Transgenic CD8+ T Cells. Cancer Res. Feb. 1, 2004;64(3):1140-1145.

Corrales et al., Extremely potent immunotherapeutic activity of a STING agonist in the B16 melanoma model in vivo. J ImmunoTherapy, Nov. 10, 2013;1:1.

Danilchanka et al., Cyclic Dinucleotides and the Innate Immune Response. Cell. Aug. 29, 2013;154(5):962-970.

Diamond et al., Type I interferon is selectively required by dendritic cells for immune rejection of tumors. J Exp Med. Sep. 26, 2011;208(10):1989-2003.

Fridman et al., The immune contexture in human tumours: impact on clinical outcome. Nat Rev Cancer. Mar. 15, 2012;12(4):298-306.

(56) References Cited

OTHER PUBLICATIONS

Fuertes et al., Host type I IFN signals are required for antitumor CD8+ T cell responses through CD8{alpha}+ dendritic cells. J Exp Med. Sep. 26, 2011;208(10):2005-2016.

Fuertes et al., Type I IFN response and innate immune sensing of cancer. Trends Immunol. Feb. 2013;34(2):67-73.

Gajewski et al., Cancer immunotherapy strategies based on overcoming barriers within the tumor microenvironment. Curr Opin Immunol. Apr. 2013;25(2):268-276.

Gajewski et al., Gene Signature in Melanoma Associated With Clinical Activity: A Potential Clue to Unlock Cancer Immunotherapy. Cancer J. Jul.-Aug. 2010;16(4):399-403.

Gajewski, Identifying and Overcoming Immune Resistance Mechanismsin the Melanoma Tumor Microenvironment. Clin Cancer Res. Apr. 1, 2006;12(7 Pt 2):2326s-2330s.

Galon et al., Type, density, and location of immune cells within human colorectal tumors predict clinical outcome. Science. Sep. 29, 2006;313(5795):1960-1964.

Ghiringhelli et al., Activation of the NLRP3 inflammasome in dendritic cells induces IL-1beta—dependent adaptive immunity against tumors. Nat Med. Oct. 2009;15(10):1170-1178.

Gray et al., Evidence for cyclic diguanylate as a vaccine adjuvant with novel immunostimulatory activities. Cell Immunol. Jul.-Aug. 2012;278(1-2):113-119.

Hamid et al., A prospective phase II trial exploring the association between tumor microenvironment biomarkers and clinical activity of ipilimumab in advanced melanoma. J Transl Med. Nov. 28, 2011;9:204.

Harlin et al., Chemokine Expression in Melanoma Metastases Associated with CD8+ T-Cell Recruitment. Cancer Res. Apr. 1, 2009;69(7):3077-3085.

Henry et al., Type I interferon signaling is required for activation of the inflammasome during Francisella infection. J Exp Med. May 14, 2007;204(5):987-994.

Hoebe et al., Upregulation of costimulatory molecules induced by lipopolysaccharide and double-stranded RNA occurs by Trif-dependent and Trif-independent pathways. Nat Immunol. Dec. 2003;4(12):1223-1229.

Hwang et al., Prognostic Significance of Tumor-infiltrating T-cells in Ovarian Cancer: a Meta-analysis. Gynecol Oncol. Feb. 2012;124(2):192-198.

Ishii et al., A Toll-like receptor-independent antiviral response induced by double-stranded B-form DNA. Nat Immunol. Jan. 2006;7(1):40-48.

Ishikawa et al., STING regulates intracellular DNA-mediated, type I interferon-dependent innate immunity. Nature. Oct. 8, 2009;461(7265):788-792.

Jounai et al., Recognition of damage-associated molecular patterns related to nucleic acids during inflammation and vaccination. Front Cell Infect Microbiol. Jan. 8, 2013;2:168.

Kawarada et al., NK- and CD8+T Cell-Mediated Eradication of Established Tumors by Peritumoral Injection of CpG-Containing Oligodeoxynucleotides. J Immunol. Nov. 1, 2001;167(9):5247-5253.

Kim et al., Anti-cancer flavonoids are mouse selective STING agonists. ACS Chem Biol. Jul. 19, 2013;8(7):1396-1401.

Konno et al., Cyclic Di Nucleotides Trigger ULK1 (ATG1) Phosphorylation of STING to Prevent Sustained Innate Immune Signaling. Cell. Oct. 24, 2013;155(3):688-698.

Kono and Rock, How dying cells alert the immune system to danger. Nat Rev Immunol. Apr. 2008;8(4):279-289.

Kroemer et al., Immunogenic Cell Death in Cancer Therapy. Annu Rev Immunol. 2013;31:51-72.

Lande et al., Plasmacytoid dendritic cells sense self-DNA coupled with antimicrobial peptide. Nature. Oct. 4, 2007;449 (7162):564-569.

Li et al., Efficient Cross-presentation Depends on Autophagy in Tumor Cells. Cancer Res. Sep. 1, 2008;68 (17):6889-6895.

Mahmoud et al., Tumor-Infiltrating CD8+ Lymphocytes Predict Clinical Outcome in Breast Cancer. J Clin Oncol. May 20, 2011;29(15):1949-1955.

Marichal et al., DNA released from dying host cells mediates aluminum adjuvant activity. Nat Med. Jul. 17, 2011;17 (8):996-1002.

McKee et al., Host DNA released in response to aluminum adjuvant enhances MHC class II-mediated antigen presentation and prolongs CD4 T-cell interactions with dendritic cells. Proc Natl Acad Sci U S A. Mar. 19, 2013;110(12): E1122- E1131.

Molinero et al., Epidermal Langerhans cells promote skin allograft rejection inmice with NF-KB-impaired T cells. Am J Transplant. Jan. 2008;8(1):21-31.

Obeid et al., Calreticulin exposure dictates the immunogenicityof cancer cell death. Nat Med. Jan. 2007;13(1):54-61.

Oka et al., Mitochondrial DNA That Escapes from Autophagy Causes Inflammation and Heart Failure. Nature. May 10, 2012;485(7397):251-255.

Pagès et al., In Situ Cytotoxic and Memory T Cells Predict Outcome inPatients With Early-Stage Colorectal Cancer. J Clin Oncol. Dec. 10, 2009;27(35):5944-5951.

Roberson and Walker, Immortalization of Cloned Mouse Splenic Macrophages with a Retrovirus Containing the v-raf/mil and v-myc Oncogenes. Cell Immunol. Oct. 15, 1988;116(2):341-351.

Römling et al., Cyclic di-GMP: the First 25 Years of a Universal BacterialSecond Messenger. Microbiol Mol Biol Rev. Mar. 2013;77(1):1-52.

Sancho et al., Identification of a dendritic cell receptor that couples sensing of necrosis to immunity. Nature. Apr. 16, 2009;458(7240):899-903.

Sharma et al., Innate immune recognition of an AT-rich stem-loop DNA motif in the Plasmodium falciparum genome. Immunity. Aug. 26, 2011;35(2):194-207.

Slansky et al., Enhanced Antigen-Specific Antitumor Immunity with Altered Peptide Ligands that Stabilize the MHC-Peptide-TCR Complex. Immunity. Oct. 2000;13(4):529-538.

Spranger et al., Up-Regulation of PD-L 1, IDO, and Tregs in the Melanoma Tumor Microenvironment Is Driven by CD8+ T Cells. Sci Transl Med. Aug. 28, 2013;5(200):200ra116.

Stetson and Medzhitov, Recognition of Cytosolic DNA Activates an IRF3-Dependent Innate Immune Response. Immunity. Jan. 2006;24(1):93-103.

Takaoka et al., DAI (DLM-1/ZBP1) is a cytosolic DNA sensor and anactivator of innate immune response. Nature. Jul. 26, 2007;448(7152):501-505.

Twitty et al., Tumor-Derived Autophagosome Vaccine: Induction of Cross Protective Immune Responses Against Short-Lived Proteins Through a P62-Dependent Mechanism. Clin Cancer Res. Oct. 15, 2011;17(20):6467-6481.

Unterholzner et al., IFI16 is an innate immune sensor for intracellular DNA. Nat Immunol. Nov. 2010;11 (11):997-1004.

Wolchok et al., Nivolumab plus Ipilimumab in Advanced Melanoma. N Engl J Med. Jul. 11, 2013;369(2):122-133.

Wu et al., Cyclic-GMP-AMP is an Endogenous Second Messenger in Innate Immune Signaling by Cytosolic DNA. Science. Feb. 15, 2013;339(6121):826-830 supplemental material to already cited article.

Yanai et al., HMGB proteins function as universal sentinels for nucleic-acid-mediated innate immune responses. Nature. Nov. 5, 2009;462(7269):99-103.

Zhou et al., MyD88 Intrinsically Regulates CD4 T-Cell Responses. J Virol. Feb. 2009;83(4):1625-1634.

Zhou et al., MyD88 is critical for the development of innate and adaptive immunity during acute lymphocytic choriomeningitis virus infection. Eur J Immunol. Mar. 2005;35(3):822-830.

Lubong Sabado et al., In Vitro Priming Recapitulates in Vivo HIV-1 Specific T Cell Responses, Revealing Rapid Loss of Virus Reactive CD4+ T Cells in Acute HIV-1 Infection. PLoS One. 2009;4(1):e4256 (13 pages).

Lucas et al., MAGE-B5, MAGE-B6, MAGE-C2, and MAGE-C3: four new members of the MAGE family with tumor-specific expression. Int J Cancer. Jul. 1, 2000;87(1):55-60.

(56) References Cited

OTHER PUBLICATIONS

Machlenkin et al., Human CTL Epitopes Prostatic Acid Phosphatase-3 and Six-Transmembrane Epithelial Antigen of Prostate-3 as Candidates for Prostate Cancer Immunotherapy. Cancer Res. Jul. 15, 2005;65(14):6435-6442.
Madhun et al., Intranasal c-di-GMP-adjuvanted plant-derived H5 influenza vaccine induces multifunctional Thi CD4+ cells and strong mucosal and systemic antibody responses in mice. Vaccine. Jul. 12, 2011;29(31):4973-4982.
Mandruzzato et al., A CASP-8 Mutation Recognized by Cytolytic T Lymphocytes on a Human Head and Neck Carcinoma. J Exp Med. Aug. 29, 1997;186(5):785-793.
Matsumoto et al., Expression of the SART-1 antigens in uterine cancers. Jpn J Cancer Res. Dec. 1998;89 (12):1292-1295.
Matsushita et al., Preferentially Expressed Antigen of Melanoma (PRAME) in the Development of Diagnostic and Therapeutic Methods for Hematological Malignancies. Leuk Lymphoma. Mar. 2003;44(3):439-444.
Mayo et al., Mdm-2 Phosphorylation by DNA-dependent Protein Kinase Prevents Interaction with p53. Cancer Res. Nov. 15, 1997;57(22):5013-5016.
McCool et al., Roles of calreticulin and calnexin during mucin synthesis in LS180 and HT29/A1 human colonic adenocarcinoma cells. Biochem J. Aug. 1, 1999;341 (Pt 3):593-600.
McCune et al., Active specific immunotherapy with tumor cells and Corynebacterium parvum: A phase I study. Cancer. May 1979;43(5):1619-1623.
McWhirter et al., A host type I interferon response is induced by cytosolic sensing of the bacterial second messenger cyclic-di-GMP. J Exp Med. Aug. 31, 2009;206(9):1899-1911.
Millon et al., Detection of Prostate-Specific Antigen- or Prostate-Specific Membrane Antigen-Positive Circulating Cells in Prostatic Cancer Patients: Clinical Implications. Eur Urol. Oct. 1999;36(4):278-285.
Molijn et al., Molecular diagnosis of human papillomavirus (HPV) infections. J Clin Virol. Mar. 2005;32 Suppl 1: S43-51.
Moreau-Aubry et al., A Processed Pseudogene Codes for a New Antigen Recognized by a Cd8+ T Cell Clone on Melanoma. J Exp Med. May 1, 2000;191(9):1617-1624.
Morse et al., A Phase I Study of Active Immunotherapy with Carcinoembryonic Antigen Peptide (CAP-1)-pulsed, Autologous Human Cultured Dendritic Cells in Patients with Metastatic Malignancies Expressing Carcinoembryonic Antigen. Clin Cancer Res. Jun. 1999;5(6):1331-1338.
Muderhwa et al., Oil-in-water liposomal emulsions: Characterization and potential use in vaccine delivery. J Pharm Sci. Dec. 1999;88(12):1332-1339.
Mukhopadhyay et al., A structural perspective of the flavivirus life cycle. Nat Rev Microbial. Jan. 2005;3(1):13-22.
Mulders et al., Tumor antigens and markers in renal cell carcinoma. Urol Clin North Am. Aug. 2003;30(3):455-465.
Muller et al., MeCP2 and MBD2 expression in human neoplastic and non-neoplastic breast tissue and its association with oestrogen receptor status. Br J Cancer. Nov. 17, 2003;89(10):1934-1939.
Muminova et al., Characterization of human mesothelin transcripts in ovarian and pancreatic cancer. BMC Cancer. May 12, 2004;4:19.
Nair et al., Induction of cytotoxic T cell responses and tumor immunity against unrelated tumors using telomerase reverse transcriptase RNA transfected dendritic cells. Nat Med. Sep. 2000;6(9):1011-1017.
Nakatsura et al., Cellular and humoral immune responses to a human pancreatic cancer antigen, coactosin-like protein, originally defined by the SEREX method. Eur J Immunol. Mar. 2002;32(3):826-836.
Nakatsura et al., Glypican-3, overexpressed specifically in human hepatocellular carcinoma, is a novel tumor marker. Biochem Biophys Res Commun. Jun. 20, 2003;306(1):16-25.
Nakatsura et al., Identification of Glypican-3 as a Novel Tumor Marker for Melanoma. Clin Cancer Res. Oct. 1, 2004;10(19):6612-6621.

Nelson and Griswold, A computer program for calculating antibody affinity constants. Comput Methods Programs Biomed. Jul.-Aug. 1988;27(1):65-68.
Neumann et al., Identification of an HLA-DR-restricted peptide epitope with a promiscuous binding pattern derived from the cancer testis antigen HOM-MEL-40/SSX2. Int J Cancer. Nov. 20, 2004;112(4):661-668.
Nicoletto et al., BRCA-1 and BRCA-2 mutations as prognostic factors in clinical practice and genetic counselling. Cancer Treat Rev. Oct. 2001;27(5):295-304.
Oberste et al., Evidence for Frequent Recombination within Species Human Enterovirus B Based on Complete Genomic Sequences of All Thirty-Seven Serotypes. J Virol. Jan. 2004;78(2):855-867.
Oberthuer et al., The Tumor-Associated Antigen PRAME Is Universally Expressed in High-Stage Neuroblastoma and Associated with Poor Outcome. Clin Cancer Res. Jul. 1, 2004;10(13):4307-4313.
Ogunniyi et al., c-di-GMP is an Effective Immunomodulator and Vaccine Adjuvant Against Pneumococcal Infection. Vaccine. Aug. 26, 2008;26(36):4676-4685.
Oliveira-Ferreira and Daniel-Ribeiro, Protective CD8+ T Cell Responses against the Pre-erythrocytic Stages of Malaria Parasites: an Overview. Mem Inst Oswaldo Cruz. Feb. 2001;96(2):221-227.
O'Riordan et al., Innate recognition of bacteria by a macrophage cytosolic surveillance pathway. Proc Natl Acad Sci U S A. Oct. 15, 2002;99(21):13861-13866.
Orvell et al., Antigenic relationships between six genotypes of the small hydrophobic protein gene of mumps virus. J Gen Virol. Oct. 2002;83(Pt 10):2489-2496.
Otte et al., MAGE-A Gene Expression Pattern in Primary Breast Cancer. Cancer Res. Sep. 15, 2001;61 (18):6682-6687.
Ouyang et al., Structural Analysis of the STING Adaptor Protein Reveals a Hydrophobic Dimer Interface and Mode of Cyclic di-GMP Binding Immunity. Jun. 29, 2012;36(6):1073-1086.
Oyston and Quarry, Tularemia vaccine: past, present and future. Antonie Van Leeuwenhoek. May 2005;87 (4):277-281.
Padilla et al., Imaging of the varicella zoster virion in the viral highways: Comparison with herpes simplex viruses 1 and 2, cytomegalovirus, pseudorabies virus, and human herpes viruses 6 and 7. J Med Virol. 2003;70 Suppl 1:S103-S110.
Patel et al., Development of a simple restriction fragment length polymorphism assay for subtyping of coxsackie B viruses. J Virol Methods. Sep. 15, 2004;120(2):167-172.
Peh et al., Frequent presence of subtype A virus in Epstein-Barr virus-associated malignancies. Pathology. Oct. 2002;34(5):446-450.
Pham et al., Exploiting cross-priming to generate protective CD8 T-cell immunity rapidly. Proc Natl Acad Sci U S A. Jul. 6, 2010;107(27):12198-12203.
Pisarev et al., Full-length dominant-negative survivin for cancer immunotherapy. Clin Cancer Res. Dec. 15, 2003;9 (17):6523-6533.
Porsch-Ozcurumez et al., Comparison of Enzyme-Linked Immunosorbent Assay, Western Blotting, Microagglutination, Indirect Immunofluorescence Assay, and Flow Cytometry for Serological Diagnosis of Tularemia. Clin Diagn Lab Immunol. Nov. 2004;11(6):1008-1015.
Rappuoli et al., Vaccines for the twenty-first century society. Nat Rev Immunol. Nov. 4, 2011;11(12):865-872.
Reed et al., New horizons in adjuvants for vaccine development. Trends Immunol. Jan. 2009;30(1):23-32.
Renkvist et al., A listing of human tumor antigens recognized by T cells. Cancer Immunol Immunother. Mar. 2001;50 (1):3-15.
Reynolds et al., HLA-Independent Heterogeneity of CD8+ T Cell Responses to MAGE-3, Melan-A/MART-1, gp100, Tyrosinase, MC1R, and TRP-2 in Vaccine-Treated Melanoma Patients. J Immunol. Dec. 15, 1998;161(12):6970-6976.
Rezig et al., Molecular Characterization of Coxsackievirus B5 Isolates. J Med Virol. Feb. 2004;72(2):268-274.
Ries et al., Investigation of the expression of melanoma antigen-encoding genes (MAGE-A1 to -A6) in oral squamous cell carcinomas to determine potential targets for gene-based cancer immunotherapy. Int J Oncol. Mar. 2005;26 (3):817-824.

(56) References Cited

OTHER PUBLICATIONS

Roden and Wu, Preventative and therapeutic vaccines for cervical cancer. Expert Rev Vaccines. Aug. 2003;2 (4):495-516.
Roner et al., Identification of signals required for the insertion of heterologous genome segments into the reovirus genome. Proc Natl Acad Sci U S A. Dec. 19, 1995;92(26):12362-12366.

* cited by examiner

10) $X_1=X_2=O$; $X_3=G$; $X_4=G$; $X_5=CO(CH_2)_{12}CH_3$; $X_6=2TEAH$
20) $X_1=X_2=S$ [Rp,Rp]; $X_3=G$; $X_4=A$; $X_5=H$; $X_6=2TEAH$
21) $X_1=X_2=S$ [Rp,Rp]; $X_3=A$; $X_4=A$; $X_5=H$; $X_6=2Na$
22) $X_1=X_2=S$ [Rp,Rp]; $X_3=A$; $X_4=A$; $X_5=H$; $X_6=2NH_4$
23) $X_1=X_2=O$; $X_3=G$; $X_4=A$; $X_5=H$; $X_6=2TEAH$

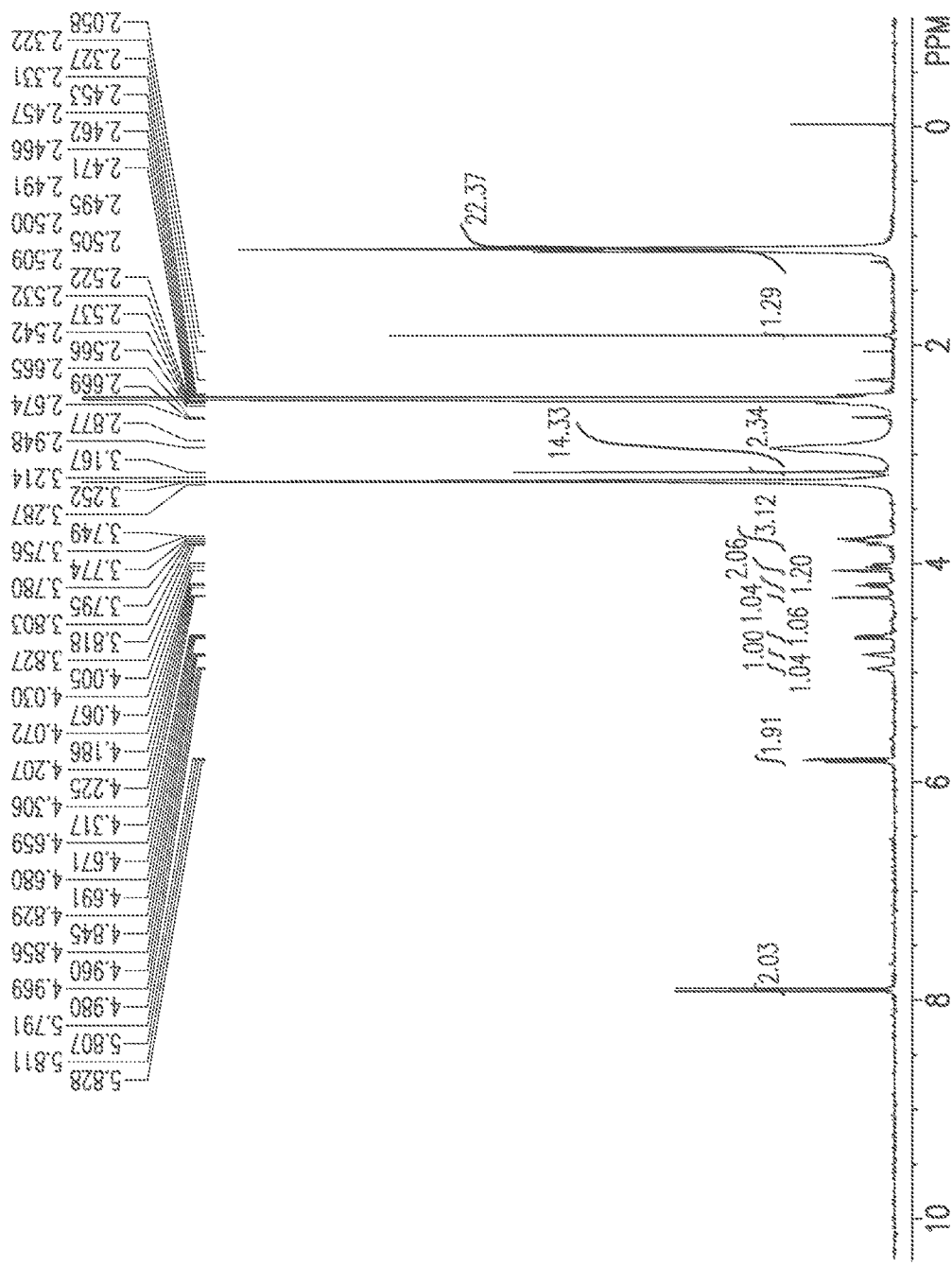

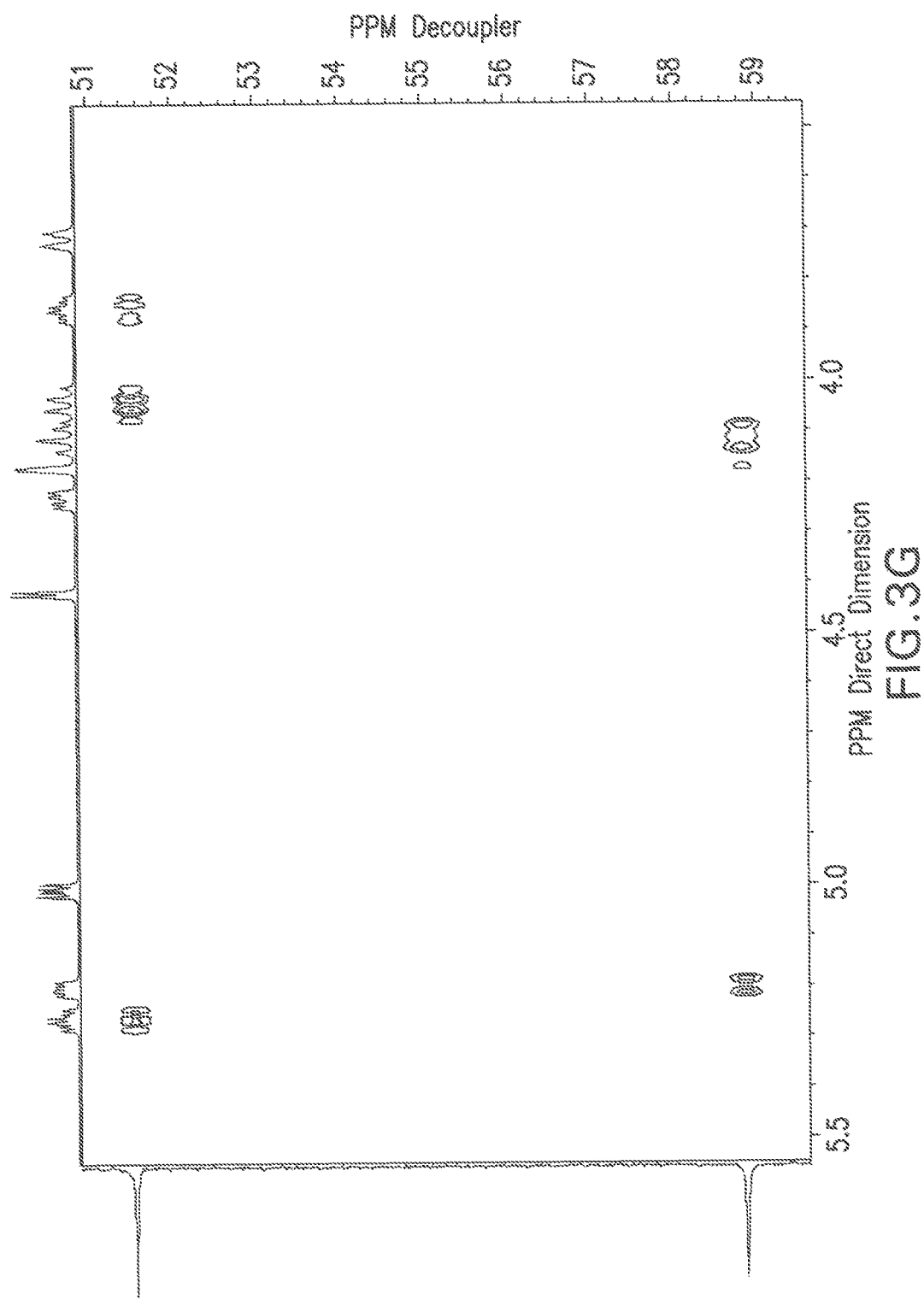

HBSS

ML RR-CDA

COMPOSITIONS AND METHODS FOR ACTIVATING STIMULATOR OF INTERFERON GENE-DEPENDENT SIGNALLING

The present application claims priority to U.S. Provisional Application 61/825,005 filed May 18, 2013, and to U.S. Provisional Application 61/902,125 filed Nov. 8, 2013, each of which is hereby incorporated by reference in its entirety.

BACKGROUND OF THE INVENTION

The following discussion of the background of the invention is merely provided to aid the reader in understanding the invention and is not admitted to describe or constitute prior art to the present invention.

The human immune system may generally be divided into two arms, referred to as "innate immunity" and "adaptive immunity." The innate arm of the immune system is predominantly responsible for an initial inflammatory response via a number of soluble factors, including the complement system and the chemokine/cytokine system; and a number of specialized cell types including mast cells, macrophages, dendritic cells (DCs), and natural killer cells. In contrast, the adaptive immune arm involves a delayed and a longer lasting antibody response together with CD8+ and CD4+ T cell responses that play a critical role in immunological memory against an antigen. A third arm of the immune system may be identified as involving γδ T cells and T cells with limited T cell receptor repertoires such as NKT cells and MAIT cells.

For an effective immune response to an antigen, antigen presenting cells (APCs) must process and display the antigen in a proper MHC context to a T cell, which then will result in either T cell stimulation of cytotoxic and helper T cells. Following antigen presentation successful interaction of co-stimulatory molecules on both APCs and T cells must occur or activation will be aborted. GM-CSF and IL-12 serve as effective pro-inflammatory molecules in many tumor models. For example, GM-CSF induces myeloid precursor cells to proliferate and differentiate into dendritic cells (DCs) although additional signals are necessary to activate their maturation to effective antigen-presenting cells necessary for activation of T cells. Barriers to effective immune therapies include tolerance to the targeted antigen that can limit induction of cytotoxic CD8 T cells of appropriate magnitude and function, poor trafficking of the generated T cells to sites of malignant cells, and poor persistence of the induced T cell response.

DCs that phagocytose tumor-cell debris process the material for major histocompatibility complex (MHC) presentation, upregulate expression of costimulatory molecules, and migrate to regional lymph nodes to stimulate tumor-specific lymphocytes. This pathway results in the proliferation and activation of CD4+ and CD8+ T cells that react to tumor-associated antigens. Indeed, such cells can be detected frequently in the blood, lymphoid tissues, and malignant lesions of patients.

New insights into the mechanisms underlying immune-evasion, together with combination treatment regimens that potentiate the potency of therapeutic vaccination—either directly or indirectly—through combination with immune checkpoint inhibitors or other therapies, have served as a basis for the development of vaccines that induce effective antitumor immunity. The CDNs cyclic-di-AMP (produced by *Listeria monocytogenes*) and its analog cyclic-di-GMP (produced by *Legionella pneumophila*) are recognized by the host cell as a PAMP (Pathogen Associated Molecular Pattern), which bind to the PRR (Pathogen Recognition Receptor) known as STING. STING is an adaptor protein in the cytoplasm of host mammalian cells which activates the TANK binding kinase (TBK1)—IRF3 signaling axis, resulting in the induction of IFN-β and other IRF-3 dependent gene products that strongly activate innate immunity. It is now recognized that STING is a component of the host cytosolic surveillance pathway, that senses infection with intracellular pathogens and in response induces the production of IFN-β, leading to the development of an adaptive protective pathogen-specific immune response consisting of both antigen-specific CD4 and CD8 T cells as well as pathogen-specific antibodies. Examples of cyclic purine dinucleotides are described in some detail in, e.g., U.S. Pat. Nos. 7,709,458 and 7,592,326; WO2007/054279; and Yan et al., Bioorg. Med. Chem Lett. 18: 5631 (2008), each of which is hereby incorporated by reference.

There remains a need for improved compositions and methods for immunologic strategies to treating diseases such as cancer that can be refractory to traditional therapeutic approaches.

SUMMARY OF THE INVENTION

It is an object of the present invention to provide compositions which modulate immune responses to diseases.

In a first aspect, the present invention provides compositions comprising: one or more cyclic purine dinucleotides ("CDNs") which that induce STimulator of INterferon Genes ("STING")-dependent type I interferon production. As described hereinafter, a number of CDNs find use in the present invention. Preferred cyclic purine dinucleotides include, but are not limited to, one or more of c-di-AMP, c-di-GMP, c-di-IMP, c-AMP-GMP, c-AMP-IMP, c-GMP-IMP, and analogs thereof. This list is not meant to be limiting.

The general structure of a cyclic purine dinucleotide according to the present invention is as follows:

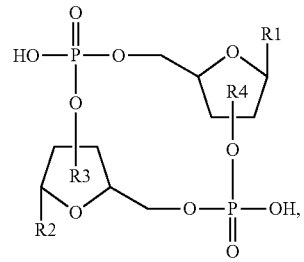

where each R1 and R2 is a purine, and the structure

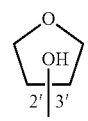

is intended to reflect that the phosphate linkage may be to either the 2' or 3'position on the ribose, and the other of the 2' or 3' position which is not participating in the cyclic linkage is an —OH. The present invention contemplates 2',5',2',5' CDNs and 2',5',3',5' CDNs. By way of example, c-di-GMP having 2'-5' linkages refers to the molecule indicated above where each of R1 and R2 are guanine, and each phosphate linkage is 2'-to-5'.

For purposes of the present invention, this general structure is further modified to introduce substituents which confer the ability to bind to STING and induce a STING-dependent signaling cascade (and most preferably induce a human STING-dependent signaling cascade), and thereby induce STING-dependent type I interferon production and other co-regulated genes. By way of example, the present invention provides compositions comprising the following compounds:

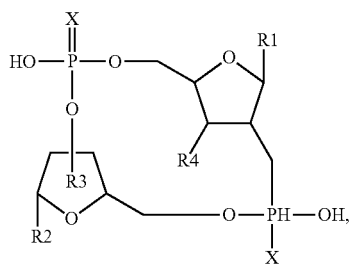

wherein each X is independently O or S, and R3 and R4 are each independently H or an optionally substituted straight chain alkyl of from 1 to 18 carbons and from 0 to 3 heteroatoms, an optionally substituted alkenyl of from 1-9 carbons, an optionally substituted alkynyl of from 1-9 carbons, or an optionally substituted aryl, wherein substitution(s), when present, may be independently selected from the group consisting of $C_{1-6}$ alkyl straight or branched chain, benzyl, halogen, trihalomethyl, $C_{1-6}$ alkoxy, —$NO_2$, —$NH_2$, —OH, =O, —COOR' where R' is H or lower alkyl, —$CH_2OH$, and —$CONH_2$, wherein R3 and R4 are not both H.

In preferred embodiments, one or both of R3 and R4 independently comprise a prodrug leaving group removed by cellular esterases. In certain embodiments, one or both of R3 and R4 are a C6 to C18 fatty acid ester. In certain embodiments, one or both of R3 and R4 are selected from the group consisting of myristoyl, pentanoyl, hexanoyl, heptanoyl, etc.

In certain embodiments, each X is S. In preferred embodiments when each X is S, the compositions comprise one or more substantially pure Sp,Sp, Rp,Rp, Sp,Rp, or Rp,Sp stereoisomers.

In certain embodiments, each of R1 and R2 are independently selected from the group consisting of adenine, guanine, inosine, and xanthine or analogs thereof. Preferably, each of R1 and R2 are independently adenine or guanine.

As described hereinafter, a cyclic purine dinucleotide composition according to the present invention can induce STING-dependent type I interferon production at least 2-fold, and more preferably 5-fold or 10-fold, or more, as compared to c-di-GMP having 3'-5' linkages. As noted herein, most preferably, the STING is human STING. In preferred embodiments, a substantially pure cyclic purine dinucleotide composition according to the present invention activates human STING but the corresponding cyclic purine dinucleotide having only bis-(3',5') linkages does not.

In their role as adjuvants, in certain embodiments the present compositions may be used as adjuvants in a therapeutic or prophylactic strategy employing vaccine(s). Thus, the substantially pure CDNs of the present invention, or prodrugs or pharmaceutically acceptable salts thereof, may be used together with one or more vaccines selected to stimulate an immune response to one or more predetermined antigens. The substantially pure CDNs of the present invention, or prodrugs or pharmaceutically acceptable salts thereof, may be provided together with, or in addition to, such vaccines.

Such vaccine(s) can comprise inactivated or attenuated bacteria or viruses comprising the antigens of interest, purified antigens, live viral or bacterial delivery vectors recombinantly engineered to express and/or secrete the antigens, antigen presenting cell (APC) vectors comprising cells that are loaded with the antigens or transfected with a composition comprising a nucleic acid encoding the antigens, liposomal antigen delivery vehicles, or naked nucleic acid vectors encoding the antigens. This list is not meant to be limiting. By way of example, such vaccine(s) may also comprise an inactivated tumor cell that expresses and secretes one or more of GM-CSF, CCL20, CCL3, IL-12p70, FLT-3 ligand.

The substantially pure CDNs of the present invention, or prodrugs or pharmaceutically acceptable salts thereof, may be administered to individuals in need thereof by a variety of parenteral and nonparenteral routes in formulations containing pharmaceutically acceptable carriers, adjuvants and vehicles. Preferred routes are parenteral, and include but, are not limited to, one or more of subcutaneous, intravenous, intramuscular, intraarterial, intradermal, intrathecal and epidural administrations. Intra-tumor routes are also preferred. Particularly preferred is administration by subcutaneous administration. Preferred pharmaceutical compositions are formulated as aqueous or oil-in-water emulsions.

The compositions of the present invention may comprise, or be administered together with, one or more additional pharmaceutically active components such as adjuvants, lipids, interbilayer crosslinked multilamellar vesicles, biodegradable poly(D,L-lactic-co-glycolic acid) [PLGA]-based or poly anhydride-based nanoparticles or microparticles, and nanoporous particle-supported lipid bilayers, CTLA-4 and PD-1 pathway Antagonists, PD-1 pathway blocking agents, inactivated bacteria which induce innate immunity (e.g., inactivated or attenuated *Listeria monocytogenes*), compositions which mediate innate immune activation via Toll-like Receptors (TLRs), (NOD)-like receptors (NLRs), Retinoic acid inducible gene-based (RIG)-I-like receptors (RLRs), C-type lectin receptors (CLRs), pathogen-associated molecular patterns ("PAMPs"), chemotherapeutic agents, etc.

In a related aspect, the present invention relates to methods of inducing, stimulating, or adjuvanting an immune response in an individual. These methods comprise administering the substantially pure CDNs of the present invention, or prodrugs or pharmaceutically acceptable salts thereof, to the individual. Preferred routes of administration are parenteral. As noted above, particularly preferred are thiophosphate derivatives of such cyclic purine dinucleotides.

In certain embodiments, the method is a method of cancer treatment. By way of example, the substantially pure CDNs of the present invention, or prodrugs or pharmaceutically acceptable salts thereof, may be provided alone, or together with or in addition to one or more cancer vaccine compositions that are known in the art. The patient receiving such treatment may be suffering from a cancer selected from the group consisting of a colorectal cancer cell, an aero-digestive squamous cancer, a lung cancer, a brain cancer, a liver cancer, a stomach cancer, a sarcoma, a leukemia, a lymphoma, a multiple myeloma, an ovarian cancer, a uterine cancer, a breast cancer, a melanoma, a prostate cancer, a pancreatic carcinoma, and a renal carcinoma. In other embodiments, the method is a method of inducing, stimulating, or adjuvanting an immune response a pathogen.

With regard to treatment of a mammal suffering from cancer, the methods described herein can comprise administering to the mammal an effective amount of the substantially pure CDNs of the present invention, or prodrugs or pharmaceutically acceptable salts thereof, optionally prior to or following a primary therapy administered to the mammal to remove or kill cancer cells expressing the cancer antigen. The compositions of the present invention may be provided as a neoadjuvant therapy; however in preferred embodiments, the compositions of the present invention are administered following the primary therapy. In various embodiments, the primary therapy comprises surgery to remove the cancer cells from the mammal, radiation therapy to kill the cancer cells in the mammal, or both surgery and radiation therapy.

In other embodiments, the methods described herein can comprise administering to the mammal an effective amount of the substantially pure CDNs of the present invention for the treatment of disorders in which shifting of Th1 to Th2 immunity confers clinical benefit. Cell-mediated immunity (CMI) is associated with TH1 CD4+ T lymphocytes producing cytokines IL-2, interferon (IFN)-γ and tumor necrosis factor (TNF)-α. In contrast, humoral immunity is associated with TH2 CD4+ T lymphocytes producing IL-4, IL-6 and IL-10. Immune deviation towards TH1 responses typically produces activation of cytotoxic T-cell lymphocytes (CTL), natural killer (NK) cells, macrophages and monocytes. Generally, Th1 responses are more effective against intracellular pathogens (viruses and bacteria that are inside host cells) and tumors, while Th2 responses are more effective against extracellular bacteria, parasites including helminths and toxins. In addition, the activation of innate immunity is expected to normalize the T-helper type 1 and 2 (Th1/Th2) immune system balance and to suppress the excessive reaction of Th2 type responses that cause immunoglobulin (Ig) E-dependent allergies and allergic asthma.

BRIEF DESCRIPTION OF THE FIGURES

FIG. 3A depicts $^1$H-NMR results for compound 9a.

FIG. 3B depicts COSY (3.5-6.0 ppm $^1$H-axis) results for compound 9a.

FIG. 3C depicts HMBC (3.0-5.5 ppm $^1$H-axis) results for compound 9a.

FIG. 3G depicts HMBC (3.5-5.5 ppm $^1$H-axis) results for compound 21.

DETAILED DESCRIPTION OF THE INVENTION

Figure 1:
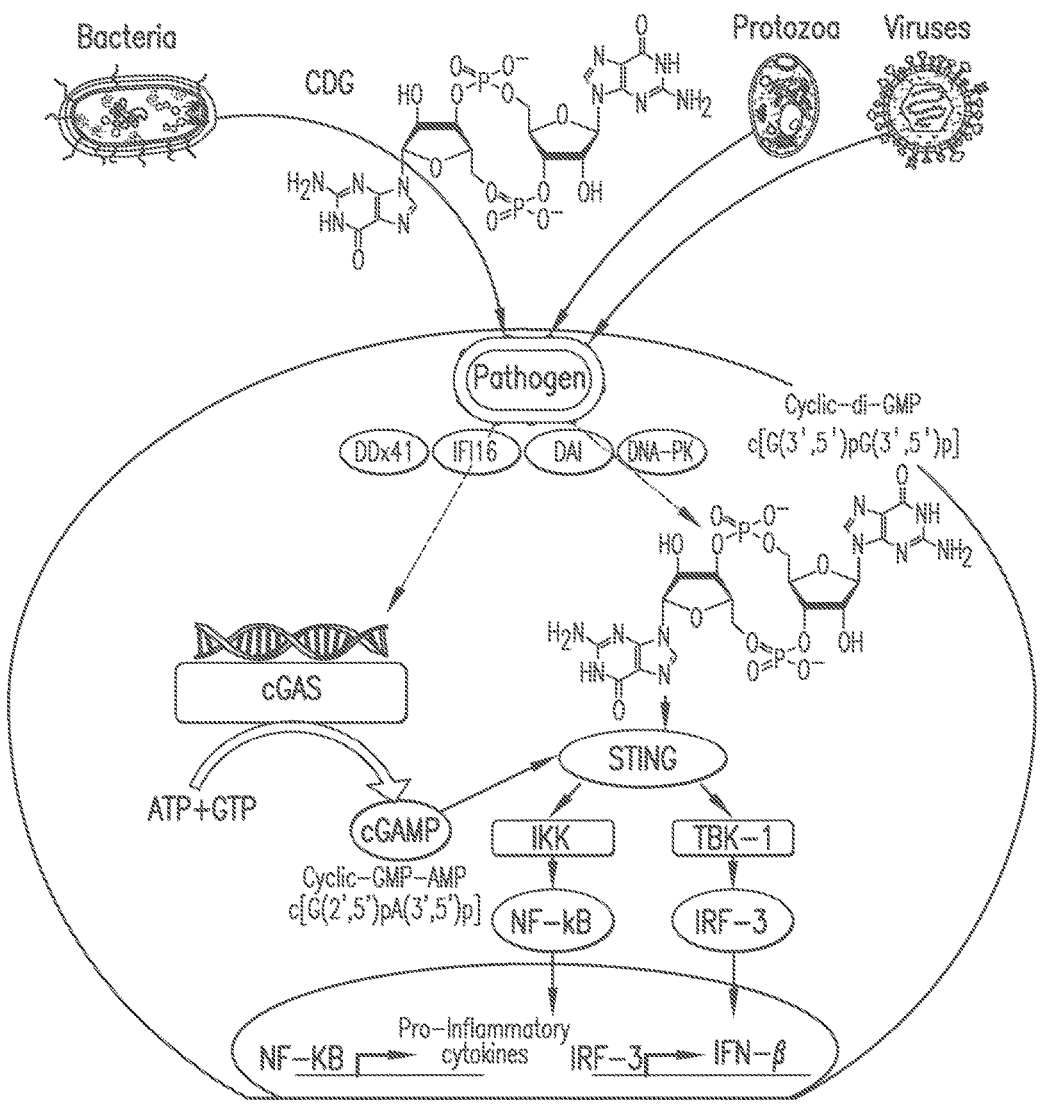
FIG. 1 depicts cyclic purine dinucleotide ("CDN")-mediated signaling. A CDN (e.g., c-di-AMP or c-di-GMP) induces production of IFN-β by binding to the cytosolic receptor STING (Stimulator of Interferon Genes), and inducing signaling through the TBK-1/IRF-3 pathway, resulting in both autocrine and paracrine activation of DCs through binding to the IFN receptor and subsequent signaling.

The present invention relates to the use of novel and highly active cyclic-di-nucleotide (CDN) immune stimulators that activate DCs via a recently discovered cytoplasmic receptor known as STING (Stimulator of Interferon Genes). In particular, the CDNs of the present invention are provided in the form of a composition comprising one or more cyclic purine dinucleotides induce STING-dependent type I interferon production, wherein the cyclic purine dinucleotides present in the composition are substantially pure 2',5',2',5' and 2',5',3',5' CDNs.

Recent insights into the design and development of adjuvants are informed by a fundamental understanding that conserved microbial structures known as Pathogen-Associated Molecular Patterns (PAMPs) are sensed by host cell Pattern Recognition Receptors (PRRs), triggering a downstream signaling cascade resulting in the induction of cytokines and chemokines, and initiation of a specific adaptive immune response. How the innate immune system is engaged by the PAMP complement of a microbe shapes the development of an adaptive response that is appropriate to combat the invading pathogen from causing disease. An objective of adjuvant design is to select defined PAMPs or synthetic molecules specific for designated PRRs to initiate a desired response. Adjuvants such as monophosphoryl lipid A (MPL) and CpG are PAMPs recognized by Toll-like receptors (TLRs), a class of transmembrane PRRs that signal through MyD88 and Trif adaptor molecules and mediate induction of NF-kB dependent proinflammatory cytokines. MPL (TLR-4 agonist) and CpG (TLR-9 agonist) are clinically advanced adjuvants, and are components of vaccines that are approved or pending approval by the FDA. While TLRs present on the cell surface (e.g., TLR-4) and endosomes (e.g., CpG) sense extracellular and vacuolar pathogens, the productive growth cycle of multiple pathogens including viruses and intracellular bacteria occurs in the cytosol. The compartmentalization of extracellular, vacuolar, and cytosolic PRRs has led to the hypothesis that the innate immune system distinguishes between pathogenic and non-pathogenic microbes by monitoring the cytosol. It should be apparent to one skilled in the art that agonists specific for PRRs comprising the cytosolic surveillance pathway that initiate development of protective immunity against intracellular pathogens, and is relevant to vaccine design. These same targeting ligands will also be essential in the development of effective vaccines targeting malignancies, know to require tumor-specific CD4+ and CD8+ T cells.

Activation of the Cytosolic Surveillance Pathway (CSP) is Integral to Development of Protective Immunity to Intracellular Pathogens. The CSP detects bacterial, viral, and protozoan pathogens, leading to activation of the TANK binding kinase (TBK-1)/IRF-3 signaling axis and induction of IFN-β and other co-regulated genes. Both viral and bacterial nucleic acids activate this pathway, and induction of IFN-β is MyD88 and Trif independent. While Type I interferon is often thought of primarily as a host anti-viral response, induction of IFN-β is a signature of cytosolic growth in macrophages infected with the intracellular bacterium, *Listeria monocytogenes* (Lm). A well-known dichotomy in the mouse listeriosis model is that, whereas wild-type Lm primes potent CD4 and CD8 T-cell immunity that protects mice against bacterial challenge, vaccination with listeriolysin O (LLO)-deleted Lm does not elicit functional T cells or induce protective immunity. This difference is evidence of the requirement for expression of host cell genes and cytosolic access by Lm to elicit functional T-cell mediated protective immunity. The level of IFN-β in infected host cells is regulated by Lm multidrug efflux pumps (MDRs), which that secrete structurally unrelated small molecules, including antibiotics. IFN-β is not induced in host cells infected with Lm LLO mutants that are confined to the phagolysosome. Normal levels of IFN-β are induced in infected MyD88$^{-/-}$ Trif$^{-/-}$ macrophages deficient in all TLR-mediated signaling. These data demonstrate that although Lm engages TLRs, in response to infection with wild-type Lm, the host cell CSP is required for development of protective immunity, correlated with induction of IFN-β.

Cyclic-di-Nucleotides (CDNs) activate the cytosolic surveillance pathway through direct binding of to the cytosolic PRR, STING. The Type I interferon response to infection by Lm and other intracellular bacteria results from the secretion of c-di-AMP or its related cyclic dinucleotide (CDN), c-di-GMP, and its direct binding to DDX41 and DEAD (aspartate-glutamate-alanine-aspartate) box helicase and STING (Stimulator of Interferon Genes), a recently defined receptor of the cytosolic surveillance pathway. CDNs are second messengers expressed by most bacteria and regulate diverse processes, including motility and formation of biofilms. In addition to activating the TBK-1/IRF-3 signaling pathway, in response to binding CDNs STING also activates the IkB kinase, resulting in translocation of the NF-kB transcription factor to the nucleus, activating the expression of multiple pro-inflammatory genes.

Until recently, how STING senses cytoplasmic DNA remained elusive. Unlike AIM2 which directly binds dsDNA, STING lacks any obvious DNA-binding domains.

Whether other candidate DNA sensors such as DDX41, DNA-PK and DAI kinase were essential mediators of dsDNA signaling through STING remained unclear. This conundrum was solved with the discovery of cyclic GMP-AMP synthase (cGAS), a host cell nucleotidyl transferase that in response to binding dsDNA synthesizes a second messenger, cyclic di-GMP-AMP, which binds directly to STING and initiates a signaling cascade through the TBK-1/IRF-3 axis, resulting in the induction of IFNs. Additionally, the cGAS innate immune DNA sensor produces a non-canonical cyclic di-nucleotide that activates STING signaling. Unlike the cyclic dinucleotide second messenger produced by bacteria, in which the internucleotide phosphate bridge is joined by bis-(3',5') linkages, the internucleotide phosphate bridge in the cyclic-GMP-AMP synthesized by cGAS is joined by non-canonical 2',5' and 3',5' linkages, represented c[G(2',5')pA(3',5')p]. Thus, STING (Stimulator of Interferon Genes) has emerged as a central pathway for sensing cytosolic pathogen nucleic acids, either through direct binding of cyclic dinucleotides (CDNs) secreted by intracellular bacterium[6], or via binding of a c-GMP-AMP second messenger, synthesized by host cell cyclic GMP-AMP synthase (cGAS) in response to binding cytosolic pathogen nucleic acids.

Native CDN molecules are sensitive to degradation by phosphodiesterases that are present in host cells, for example in antigen presenting cells, that take up vaccine formulations that contain said native CDN molecules. The potency of a defined adjuvant may be diminished by such degradation, as the adjuvant would be unable to bind and activate its defined PRR target. Lower adjuvant potency could be measured, for example by a lower amount of induced expression of a signature molecule of innate immunity (e.g., IFN-$\beta$), correlated with weaker vaccine potency, as defined by the magnitude of a measured antigen-specific immune response.

In the present invention, substantially pure 2',5',2',5' and 2',5',3',5' CDNs, and particularly dithio-diphosphate derivatives of 2',5',2',5' and 2',5',3',5' c-di-AMP and c-di-GMP are provided. The synthesis process for said dithio-diphosphate derivatives of c-di-AMP and c-di-GMP molecules results in a mixture of diastereomers, including Rp,Rp, Sp,Sp, SpRp, and Rp,Sp dithio-diphosphate derivatives of c-di-AMP and c-di-GMP molecules. These individual species may be separated, and exhibit substantial differences in their pharmaceutical characteristics.

Definitions

"Administration" as it is used herein with regard to a human, mammal, mammalian subject, animal, veterinary subject, placebo subject, research subject, experimental subject, cell, tissue, organ, or biological fluid, refers without limitation to contact of an exogenous ligand, reagent, placebo, small molecule, pharmaceutical agent, therapeutic agent, diagnostic agent, or composition to the subject, cell, tissue, organ, or biological fluid, and the like. "Administration" can refer, e.g., to therapeutic, pharmacokinetic, diagnostic, research, placebo, and experimental methods. Treatment of a cell encompasses contact of a reagent to the cell, as well as contact of a reagent to a fluid, where the fluid is in contact with the cell. "Administration" also encompasses in vitro and ex vivo treatments, e.g., of a cell, by a reagent, diagnostic, binding composition, or by another cell. By "administered together" it is not meant to be implied that two or more agents be administered as a single composition. Although administration as a single composition is contemplated by the present invention, such agents may be delivered to a single subject as separate administrations, which may be at the same or different time, and which may be by the same route or different routes of administration.

An "agonist," as it relates to a ligand and receptor, comprises a molecule, combination of molecules, a complex, or a combination of reagents, that stimulates the receptor. For example, an agonist of granulocyte-macrophage colony stimulating factor (GM-CSF) can encompass GM-CSF, a mutein or derivative of GM-CSF, a peptide mimetic of GM-CSF, a small molecule that mimics the biological function of GM-CSF, or an antibody that stimulates GM-CSF receptor.

An "antagonist," as it relates to a ligand and receptor, comprises a molecule, combination of molecules, or a complex, that inhibits, counteracts, downregulates, and/or desensitizes the receptor. "Antagonist" encompasses any reagent that inhibits a constitutive activity of the receptor. A constitutive activity is one that is manifest in the absence of a ligand/receptor interaction. "Antagonist" also encompasses any reagent that inhibits or prevents a stimulated (or regulated) activity of a receptor. By way of example, an antagonist of GM-CSF receptor includes, without implying any limitation, an antibody that binds to the ligand (GM-CSF) and prevents it from binding to the receptor, or an antibody that binds to the receptor and prevents the ligand from binding to the receptor, or where the antibody locks the receptor in an inactive conformation.

By "substantially purified" with regard to CDNs of the invention is meant that a specified species accounts for at least 50%, more often accounts for at least 60%, typically accounts for at least 70%, more typically accounts for at least 75%, most typically accounts for at least 80%, usually accounts for at least 85%, more usually accounts for at least 90%, most usually accounts for at least 95%, and conventionally accounts for at least 98% by weight, or greater, of the CDN activity present in a composition. The weights of water, buffers, salts, detergents, reductants, protease inhibitors, stabilizers (including an added protein such as albumin), and excipients are generally not used in the determination of purity.

"Specifically" or "selectively" binds, when referring to a ligand/receptor, nucleic acid/complementary nucleic acid, antibody/antigen, or other binding pair (e.g., a cytokine to a cytokine receptor) (each generally referred to herein as a "target biomolecule" or a "target") indicates a binding reaction which is related to the presence of the target in a heterogeneous population of proteins and other biologics. Specific binding can mean, e.g., that the binding compound, nucleic acid ligand, antibody, or binding composition derived from the antigen-binding site of an antibody, of the contemplated method binds to its target with an affinity that is often at least 25% greater, more often at least 50% greater, most often at least 100% (2-fold) greater, normally at least ten times greater, more normally at least 20-times greater, and most normally at least 100-times greater than the affinity with a non-target molecule.

"Ligand" refers to a small molecule, nucleic acid, peptide, polypeptide, saccharide, polysaccharide, glycan, glycoprotein, glycolipid, or combinations thereof that binds to a target biomolecule. While such ligands may be agonists or antagonists of a receptor, a ligand also encompasses a binding agent that is not an agonist or antagonist, and has no agonist or antagonist properties. Specific binding of a ligand for its cognate target is often expressed in terms of an "Affinity." In preferred embodiments, the ligands of the present invention bind with affinities of between about $10^4$ $M^{-1}$ and about $10^8 M^{-1}$. Affinity is calculated as $K_d = k_{off}/k_{on}$ ($k_{off}$ is the dissociation rate constant, $K_{on}$ is the association rate constant and $K_d$ is the equilibrium constant).

Affinity can be determined at equilibrium by measuring the fraction bound (r) of labeled ligand at various concentrations (c). The data are graphed using the Scatchard equation: r/c=K(n-r): where r=moles of bound ligand/mole of receptor at equilibrium; c=free ligand concentration at equilibrium; K=equilibrium association constant; and n=number of ligand binding sites per receptor molecule. By graphical analysis, r/c is plotted on the Y-axis versus r on the X-axis, thus producing a Scatchard plot. Affinity measurement by Scatchard analysis is well known in the art. See, e.g., van Erp et al., *J. Immunoassay* 12: 425-43, 1991; Nelson and Griswold, *Comput. Methods Programs Biomed.* 27: 65-8, 1988. In an alternative, affinity can be measured by isothermal titration calorimetry (ITC). In a typical ITC experiment, a solution of ligand is titrated into a solution of its cognate target. The heat released upon their interaction (ΔH) is monitored over time. As successive amounts of the ligand are titrated into the ITC cell, the quantity of heat absorbed or released is in direct proportion to the amount of binding. As the system reaches saturation, the heat signal diminishes until only heats of dilution are observed. A binding curve is then obtained from a plot of the heats from each injection against the ratio of ligand and binding partner in the cell. The binding curve is analyzed with the appropriate binding model to determine $K_B$, n and ΔH. Note that $K_B=1/K_d$.

The term "subject" as used herein refers to a human or non-human organism. Thus, the methods and compositions described herein are applicable to both human and veterinary disease. In certain embodiments, subjects are "patients," i.e., living humans that are receiving medical care for a disease or condition. This includes persons with no defined illness who are being investigated for signs of pathology. Preferred are subjects who have an existing diagnosis of a particular cancer which is being targeted by the compositions and methods of the present invention. Preferred cancers for treatment with the compositions described herein include, but are not limited to prostate cancer, renal carcinoma, melanoma, pancreatic cancer, cervical cancer, ovarian cancer, colon cancer, head & neck cancer, lung cancer and breast cancer.

"Therapeutically effective amount" is defined as an amount of a reagent or pharmaceutical composition that is sufficient to show a patient benefit, i.e., to cause a decrease, prevention, or amelioration of the symptoms of the condition being treated. When the agent or pharmaceutical composition comprises a diagnostic agent, a "diagnostically effective amount" is defined as an amount that is sufficient to produce a signal, image, or other diagnostic parameter. Effective amounts of the pharmaceutical formulation will vary according to factors such as the degree of susceptibility of the individual, the age, gender, and weight of the individual, and idiosyncratic responses of the individual. "Effective amount" encompasses, without limitation, an amount that can ameliorate, reverse, mitigate, prevent, or diagnose a symptom or sign of a medical condition or disorder or a causative process thereof. Unless dictated otherwise, explicitly or by context, an "effective amount" is not limited to a minimal amount sufficient to ameliorate a condition.

"Treatment" or "treating" (with respect to a condition or a disease) is an approach for obtaining beneficial or desired results including and preferably clinical results. For purposes of this invention, beneficial or desired results with respect to a disease include, but are not limited to, one or more of the following: preventing a disease, improving a condition associated with a disease, curing a disease, lessening severity of a disease, delaying progression of a disease, alleviating one or more symptoms associated with a disease, increasing the quality of life of one suffering from a disease, and/or prolonging survival. Likewise, for purposes of this invention, beneficial or desired results with respect to a condition include, but are not limited to, one or more of the following: preventing a condition, improving a condition, curing a condition, lessening severity of a condition, delaying progression of a condition, alleviating one or more symptoms associated with a condition, increasing the quality of life of one suffering from a condition, and/or prolonging survival. For instance, in embodiments where the compositions described herein are used for treatment of cancer, the beneficial or desired results include, but are not limited to, one or more of the following: reducing the proliferation of (or destroying) neoplastic or cancerous cells, reducing metastasis of neoplastic cells found in cancers, shrinking the size of a tumor, decreasing symptoms resulting from the cancer, increasing the quality of life of those suffering from the cancer, decreasing the dose of other medications required to treat the disease, delaying the progression of the cancer, and/or prolonging survival of patients having cancer. Depending on the context, "treatment" of a subject can imply that the subject is in need of treatment, e.g., in the situation where the subject comprises a disorder expected to be ameliorated by administration of a reagent.

"Vaccine" encompasses preventative vaccines. Vaccine also encompasses therapeutic vaccines, e.g., a vaccine administered to a mammal that comprises a condition or disorder associated with the antigen or epitope provided by the vaccine.

Cyclic Purine Dinucleotides

Prokaryotic as well as eukaryotic cells use various small molecules for cell signaling and intra- and intercellular communication. Cyclic nucleotides like cGMP, cAMP, etc. are known to have regulatory and initiating activity in pro- and eukaryotic cells. Unlike eukaryotic cells, prokaryotic cells also use cyclic purine dinucleotides as regulatory molecules. In prokaryotes, the condensation of two GTP molecules is catalyst by the enzyme diguanylate cyclase (DGC) to give c-diGMP, which represents an important regulator in bacteria.

Recent work suggests that cyclic diGMP or analogs thereof can also stimulate or enhance immune or inflammatory response in a patient or can enhance the immune response to a vaccine by serving as an adjuvant in mammals. Cytosolic detection of pathogen-derived DNA requires signaling through TANK binding kinase 1 (TBK1) and its downstream transcription factor, IFN-regulatory factor 3 (IRF3). A transmembrane protein called STING (stimulator of IFN genes; also known as MITA, ERIS, MPYS and TMEM173) functions as the signaling receptor for these cyclic purine dinucleotides, causing stimulation of the TBK1-IRF3 signalling axis and a STING-dependent type I interferon response. See, e.g., FIG. 1. Burdette et al., Nature 478: 515-18, 2011 demonstrated that STING binds directly to cyclic diguanylate monophosphate, but not to other unrelated nucleotides or nucleic acids.

Cyclic purine dinucleotides for use as precursors to derive the CDNs of the present invention are described in some detail in, e.g., Gao et al., Cell (2013) 153: doi: 10.1016/j.cell.2013.04.046; U.S. Pat. Nos. 7,709,458 and 7,592,326; WO2007/054279; and Yan et al., Bioorg. Med. Chem Lett. 18: 5631 (2008), each of which is hereby incorporated by reference. These CDNs may be modified using standard organic chemistry techniques in order to produce the CDNs of the present invention.

Preferred purines include, but are not limited to, adenine, guanine, inosine, hypoxanthine, xanthine, isoguanine, etc. The CDNs of the present invention are preferably phosphorothioate analogues, and most preferably substantially pure Sp,Sp, Rp,Rp, SpRp, or Rp,Sp stereoisomers thereof.

As denoted in the structures, each ribose comprises a 2' or 3' hydroxyl which may be substituted. As described hereinafter, the CDNs of the present invention can comprise a substitution at one or both of these 2' or 3' hydroxyls (which is not part of the cyclic linkage) which provide a prodrug leaving group or other modification which affects activity, solubility, bioavailability, etc. The term "prodrug" as used herein refers to a modification of contemplated compounds, wherein the modified compound exhibits less pharmacological activity (as compared to the modified compound) and wherein the modified compound is converted within the body (e.g., in a target cell or target organ) back into the unmodified form through enzymatic or non-enzymatic reactions. In certain embodiments, the hydroxyl on one ribose comprises a prodrug leaving group. Prodrugs can modify the physicochemical, biopharmaceutic, and pharmacokinetic properties of drugs. Traditional prodrugs are classified as drugs that are activated by undergoing transformation in vivo to form the active drug. Reasons for prodrug development are typically poor aqueous solubility, chemical instability, low oral bioavailability, lack of blood brain barrier penetration, and high first pass metabolism associated with the parent drug. Suitable prodrug moieties are described in, for example, "Prodrugs and Targeted Delivery," J. Rautico, Ed., John Wiley & Sons, 2011.

Preferred cyclic purine dinucleotides are phosphorothioate analogues, referred to herein as "thiophosphates". Phosphorothioates are a variant of normal nucleotides in which one of the nonbridging oxygens is replaced by a sulfur. The sulfurization of the internucleotide bond dramatically reduces the action of endo- and exonucleases, including 5' to 3' and 3' to 5' DNA POL 1 exonuclease, nucleases S1 and P1, RNases, serum nucleases and snake venom phosphodiesterase. In addition, the potential for crossing the lipid bilayer increases.

A phosphorothioate linkage in inherently chiral. The skilled artisan will recognize that the phosphates in this structure may each exist in R or S forms. Thus, Rp,Rp, Sp,Sp, Sp,Rp, and Rp,Sp forms are possible.

As noted above, cyclic purine dinucleotides of the present invention comprise 2'-O- and 3'-O-substituent forms of CDNs, and in particular CDN thiophosphates. Additional stability and bioavailability can be provided by the substitution of the 2'-OH of the ribose moiety. Substituent groups amenable herein include without limitation, halogen, hydroxyl, alkyl, alkenyl, alkynyl, acyl (—C(O)$R_{aa}$), carboxyl (—C(O)O—$R_{aa}$), aliphatic groups, alicyclic groups, alkoxy, substituted oxy (—O—$R_{aa}$), aryl, aralkyl, heterocyclic radical, heteroaryl, heteroarylalkyl, amino (—N($R_{bb}$)($R_{cc}$)), imino(=N$R_{bb}$), amido (—C(O)N($R_{bb}$)(Rc$_C$) or —N($R_{bb}$)C(O)$R_{aa}$), azido (—$N_3$), nitro (—$NO_2$), cyano (—CN), carbamido (—OC(O)N($R_{bb}$)($R_{cc}$) or —N($R_{bb}$)C(O)O$R_{aa}$), ureido (—N($R_{bb}$)C(O)—N(Rbb)(Rcc)), thioureido (—N($R_{bb}$)C(S)N($R_{bb}$)($R_{cc}$)), guanidinyl (—N($R_{bb}$)C(=N$R_{bb}$)N($R_{bb}$)($R_{cc}$)), amidinyl (—C(=N$R_{bb}$)N($R_{bb}$)(Rc$_C$) or —N($R_{bb}$)C(=N$R_{bb}$)($R_{aa}$)), thiol (—S$R_{bb}$), sulfinyl (—S(O)$R_{bb}$), sulfonyl (—S(O)$_2R_b$) and sulfonamidyl (—S(O)$_2$N($R_{bb}$)(Rc$_C$) or —N($R_{bb}$)S(O)$_2R_{bb}$). Wherein each $R_{aa}$, $R_{bb}$ and $R_{cc}$ is, independently, H, an optionally linked chemical functional group or a further substituent group with a preferred list including without limitation, H, alkyl, alkenyl, alkynyl, aliphatic, alkoxy, acyl, aryl, aralkyl, heteroaryl, alicyclic, heterocyclic and heteroarylalkyl. Selected substituents within the compounds described herein are present to a recursive degree.

The term "alkyl," as used herein, refers to a saturated straight or branched hydrocarbon radical containing up to twenty four carbon atoms. Examples of alkyl groups include without limitation, methyl, ethyl, propyl, butyl, isopropyl, n-hexyl, octyl, decyl, dodecyl and the like. Alkyl groups typically include from 1 to about 24 carbon atoms, more typically from 1 to about 12 carbon atoms with from 1 to about 6 carbon atoms being more preferred. The term "lower alkyl" as used herein includes from 1 to about 6 carbon atoms. Alkyl groups as used herein may optionally include one or more further substituent groups.

The term "alkenyl," as used herein, refers to a straight or branched hydrocarbon chain radical containing up to twenty four carbon atoms and having at least one carbon-carbon double bond. Examples of alkenyl groups include without limitation, ethenyl, propenyl, butenyl, 1-methyl-2-buten-1-yl, dienes such as 1,3-butadiene and the like. Alkenyl groups typically include from 2 to about 24 carbon atoms, more typically from 2 to about 12 carbon atoms with from 2 to about 6 carbon atoms being more preferred. Alkenyl groups as used herein may optionally include one or more further substituent groups.

The term "alkynyl," as used herein, refers to a straight or branched hydrocarbon radical containing up to twenty four carbon atoms and having at least one carbon-carbon triple bond. Examples of alkynyl groups include, without limitation, ethynyl, 1-propynyl, 1-butynyl, and the like. Alkynyl groups typically include from 2 to about 24 carbon atoms, more typically from 2 to about 12 carbon atoms with from 2 to about 6 carbon atoms being more preferred. Alkynyl groups as used herein may optionally include one or more further substituent groups.

The term "acyl," as used herein, refers to a radical formed by removal of a hydroxyl group from an organic acid and has the general Formula —C(O)—X where X is typically aliphatic, alicyclic or aromatic. Examples include aliphatic carbonyls, aromatic carbonyls, aliphatic sulfonyls, aromatic sulfinyls, aliphatic sulfinyls, aromatic phosphates, aliphatic phosphates and the like. Acyl groups as used herein may optionally include further substituent groups.

The term "alicyclic" refers to a cyclic ring system wherein the ring is aliphatic. The ring system can comprise one or more rings wherein at least one ring is aliphatic. Preferred alicyclics include rings having from about 5 to about 9 carbon atoms in the ring. Alicyclic as used herein may optionally include further substituent groups.

The term "aliphatic," as used herein, refers to a straight or branched hydrocarbon radical containing up to twenty four carbon atoms wherein the saturation between any two carbon atoms is a single, double or triple bond. An aliphatic group preferably contains from 1 to about 24 carbon atoms, more typically from 1 to about 12 carbon atoms with from 1 to about 6 carbon atoms being more preferred. The straight or branched chain of an aliphatic group may be interrupted with one or more heteroatoms that include nitrogen, oxygen, sulfur and phosphorus. Such aliphatic groups interrupted by heteroatoms include without limitation, polyalkoxys, such as polyalkylene glycols, polyamines, and polyimines. Aliphatic groups as used herein may optionally include further substituent groups.

The term "alkoxy," as used herein, refers to a radical formed between an alkyl group and an oxygen atom wherein the oxygen atom is used to attach the alkoxy group to a parent molecule. Examples of alkoxy groups include without limitation, methoxy, ethoxy, propoxy, isopropoxy, n-butoxy, sec-butoxy, tert-butoxy, n-pentoxy, neopentoxy, n-hexoxy and the like. Alkoxy groups as used herein may optionally include further substituent groups.

The term "aminoalkyl" as used herein, refers to an amino substituted C\-Cn alkyl radical. The alkyl portion of the radical forms a covalent bond with a parent molecule. The amino group can be located at any position and the aminoalkyl group can be substituted with a further substituent group at the alkyl and/or amino portions.

The terms "aralkyl" and "arylalkyl," as used herein, refer to an aromatic group that is covalently linked to a C\-Cn alkyl radical. The alkyl radical portion of the resulting aralkyl (or arylalkyl) group forms a covalent bond with a parent molecule. Examples include without limitation, benzyl, phenethyl and the like. Aralkyl groups as used herein may optionally include further substituent groups attached to the alkyl, the aryl or both groups that form the radical group.

The terms "aryl" and "aromatic," as used herein, refer to a mono- or polycyclic carbocyclic ring system radicals having one or more aromatic rings. Examples of aryl groups include without limitation, phenyl, naphthyl, tetrahydronaphthyl, indanyl, idenyl and the like. Preferred aryl ring systems have from about 5 to about 20 carbon atoms in one or more rings. Aryl groups as used herein may optionally include further substituent groups.

The terms "halo" and "halogen," as used herein, refer to an atom selected from fluorine, chlorine, bromine and iodine.

The terms "heteroaryl," and "heteroaromatic," as used herein, refer to a radical comprising a mono- or poly-cyclic aromatic ring, ring system or fused ring system wherein at least one of the rings is aromatic and includes one or more heteroatoms. Heteroaryl is also meant to include fused ring systems including systems where one or more of the fused rings contain no heteroatoms. Heteroaryl groups typically include one ring atom selected from sulfur, nitrogen or oxygen. Examples of heteroaryl groups include without limitation, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl and the like. Heteroaryl radicals can be attached to a parent molecule directly or through a linking moiety such as an aliphatic group or hetero atom. Heteroaryl groups as used herein may optionally include further substituent groups.

The term "heteroarylalkyl," as used herein, refers to a heteroaryl group as previously defined that further includes a covalently attached $C_1$-$C_{12}$ alkyl radical. The alkyl radical portion of the resulting heteroarylalkyl group is capable of forming a covalent bond with a parent molecule. Examples include without limitation, pyridinylmethyl, pyrimidinylethyl, napthyridinylpropyl and the like. Heteroarylalkyl groups as used herein may optionally include further substituent groups on one or both of the heteroaryl or alkyl portions.

As noted above, preferred cyclic purine dinucleotides also include prodrug forms of CDNs, and in particular CDN thiophosphates. Prodrugs can modify the physicochemical, biopharmaceutic, and pharmacokinetic properties of drugs. Traditional prodrugs are classified as drugs that are activated by undergoing transformation in vivo to form the active drug. Reasons for prodrug development are typically poor aqueous solubility, chemical instability, low oral bioavailability, lack of blood brain barrier penetration, and high first pass metabolism associated with the parent drug. Suitable prodrug moieties are described in, for example, "Prodrugs and Targeted Delivery," J. Rautico, Ed., John Wiley & Sons, 2011.

The term "substantially pure" as used herein with regard to cyclic purine dinucleotides refers to an Rp,Rp or Rp,Sp form which is at least 75% pure relative to other possible stereochemistries at the chiral centers indicated in the figure above. By way of example, a "substantially pure Rp,Rp c-di-GMP thiophosphate" would be at least 75% pure with regard to the Rp,Sp and Sp,Sp forms of c-di-GMP thiophosphate. In preferred embodiments, a substantially pure cyclic purine dinucleotide is at least 85% pure, at least 90% pure, at least 95% pure, at least 97% pure, and at least 99% pure. While a substantially pure cyclic purine dinucleotide preparation of the invention is "stereochemically pure," this is not meant to indicate that all CDNs within the preparation having a particular stereochemistry at these chiral centers are otherwise identical. For example, a substantially pure cyclic purine dinucleotide preparation may contain a combination of Rp,Rp c-di-GMP thiophosphate and Rp,Rp c-di-AMP thiophosphate and still be a substantially pure cyclic purine dinucleotide preparation. Such a preparation may also include other components as described hereinafter that are advantageous for patient treatment, provided that all CDNs within the preparation having a particular stereochemistry at these chiral centers.

The CDN compositions described herein can be administered to a host, either alone or in combination with a pharmaceutically acceptable excipient, in an amount sufficient to induce, modify, or stimulate an appropriate immune response. The immune response can comprise, without limitation, specific immune response, non-specific immune response, both specific and non-specific response, innate response, primary immune response, adaptive immunity, secondary immune response, memory immune response, immune cell activation, immune cell proliferation, immune cell differentiation, and cytokine expression. In certain embodiments, the CDN compositions are administered in conjunction with one or more additional compositions including vaccines intended to stimulate an immune response to one or more predetermined antigens; adjuvants; CTLA-4 and PD-1 pathway antagonists, lipids, liposomes, chemotherapeutic agents, immunomodulatory cell lines, etc.

The CDN compositions may be administered before, after, and/or together with an additional therapeutic or prophylactic composition or modality. These include, without limitation, B7 costimulatory molecule, interleukin-2, interferon-γ, GM-CSF, CTLA-4 antagonists, OX-40/OX-40 ligand, CD40/CD40 ligand, sargramostim, levamisol, vaccinia virus, Bacille Calmette-Guerin (BCG), liposomes, alum, Freund's complete or incomplete adjuvant, detoxified endotoxins, mineral oils, surface active substances such as lipolecithin, pluronic polyols, polyanions, peptides, and oil or hydrocarbon emulsions. Carriers for inducing a T cell immune response which preferentially stimulate a cytolytic T cell response versus an antibody response are preferred, although those that stimulate both types of response can be used as well. In cases where the agent is a polypeptide, the polypeptide itself or a polynucleotide encoding the polypeptide can be administered. The carrier can be a cell, such as an antigen presenting cell (APC) or a dendritic cell. Antigen presenting cells include such cell types as macrophages, dendritic cells and B cells. Other professional antigen-presenting cells include monocytes, marginal zone Kupffer cells, microglia, Langerhans' cells, interdigitating dendritic cells, follicular dendritic cells, and T cells. Facultative antigen-presenting cells can also be used. Examples of facultative antigen-presenting cells include astrocytes, follicular cells, endothelium and fibroblasts. The carrier can be a bacterial cell that is transformed to express the polypeptide or to deliver a polynucleotide which is subsequently expressed in cells of the vaccinated individual. Adjuvants, such as aluminum hydroxide or aluminum phosphate, can be added to increase the ability of the vaccine to trigger, enhance, or prolong an immune response. Additional materials, such as cytokines, chemokines, and bacterial nucleic acid sequences, like CpG, a toll-like receptor (TLR) 9 agonist as well as additional agonists for TLR 2, TLR 4, TLR 5, TLR 7, TLR 8, TLR9, including lipoprotein, LPS, monophosphoryl lipid A, lipoteichoic acid, imiquimod, resiquimod, and in addition retinoic acid-inducible gene I (RIG-I) agonists such as poly I:C, used separately or in combination with the described compositions are also potential adjuvants. Other representative examples of adjuvants include the synthetic adjuvant QS-21 comprising a homogeneous saponin purified from the bark of *Quillaja saponaria* and *Corynebacterium parvum* (McCune et al., Cancer, 1979; 43:1619). It will be understood that the adjuvant is subject to optimization. In other words, the skilled artisan can engage in routine experimentation to determine the best adjuvant to use.

Methods for co-administration with an additional therapeutic agent are well known in the art (Hardman, et al. (eds.) (2001) Goodman and Gilman's The Pharmacological Basis of Therapeutics, 10th ed., McGraw-Hill, New York, N.Y.; Poole and Peterson (eds.) (2001) Pharmacotherapeutics for Advanced Practice: A Practical Approach, Lippincott, Williams & Wilkins, Phila., Pa.; Chabner and Longo (eds.) (2001) Cancer Chemotherapy and Biotherapy, Lippincott, Williams & Wilkins, Phila., Pa.).

Because of the adjuvant properties of the compounds of the present invention, their use may also combined with other therapeutic modalities including other vaccines, adjuvants, antigen, antibodies, and immune modulators. Examples are provided below.

Adjuvants

In addition to the cyclic purine dinucleotide(s) described above, the compositions of the present invention may further comprise one or more additional substances which, because of their nature, can act to stimulate or otherwise utilize the immune system to respond to the cancer antigens present on the inactivated tumor cell(s). Such adjuvants include, but are not limited to, lipids, liposomes, inactivated bacteria which induce innate immunity (e.g., inactivated or attenuated *Listeria monocytogenes*), compositions which mediate innate immune activation via Toll-like Receptors (TLRs), (NOD)-like receptors (NLRB), Retinoic acid inducible gene-based (RIG)-I-like receptors (RLRs), and/or C-type lectin receptors (CLRs). Examples of PAMPs include lipoproteins, lipopolypeptides, peptidoglycans, zymosan, lipopolysaccharide, neisserial porins, flagellin, profillin, galactoceramide, muramyl dipeptide. Peptidoglycans, lipoproteins, and lipoteichoic acids are cell wall components of Gram-positive. Lipopolysaccharides are expressed by most bacteria, with MPL being one example. Flagellin refers to the structural component of bacterial flagella that is secreted by pathogenic and commensal bacterial. α-Galactosylceramide (α-GalCer) is an activator of natural killer T (NKT) cells. Muramyl dipeptide is a bioactive peptidoglycan motif common to all bacteria. This list is not meant to be limiting. Preferred adjuvant compositions are described below.

CTLA-4 and PD-1 Pathway Antagonists

CTLA-4 is thought to be an important negative regulator of the adaptive immune response. Activated T cells upregulate CTLA-4, which binds CD80 and CD86 on antigen-presenting cells with higher affinity than CD28, thus inhibiting T-cell stimulation, IL-2 gene expression and T-cell proliferation. Anti-tumor effects of CTLA4 blockade have been observed in murine models of colon carcinoma, metastatic prostate cancer, and metastatic melanoma.

Ipilimumab (Yervoy™) and tremelimumab are humanized monoclonal antibodies that bind to human CTLA4 and prevent its interaction with CD80 and CD86. Phase I and II studies using ipilimumab and tremelimumab have demonstrated clinical activity in cancer patients. Other negative immune regulators which may be targeted by a similar strategy include programmed cell death 1, B and T lymphocyte attenuator, transforming growth factor beta β, interleukin-10, and vascular endothelial growth factor.

PD-1 is another negative regulator of adaptive immune response that is expressed on activated T-cells. PD-1 binds to B7-H1 and B7-DC, and the engagement of PD-1 suppresses T-cell activation. Anti-tumor effects have been demonstrated with PD-1 pathway blockade. BMS-936558, MK3475, CT-011, AMP-224 and MDX-1106 have been reported in the literature to be examples of PD-1 pathway blockers which may find use in the present invention.

TLR Agonists

The term "Toll like receptor" (or "TLR") as used herein refers to a member of the Toll-like receptor family of proteins or a fragment thereof that senses a microbial product and/or initiates an adaptive immune response. In one embodiment, a TLR activates a dendritic cell (DC). Toll like receptors (TLRs) are a family of pattern recognition receptors that were initially identified as sensors of the innate immune system that recognize microbial pathogens. TLRs comprise a family of conserved membrane spanning molecules containing an ectodomain of leucine-rich repeats, a transmembrane domain and an intracellular TIR (Toll/IL-1R) domain. TLRs recognize distinct structures in microbes, often referred to as "PAMPs" (pathogen associated molecular patterns). Ligand binding to TLRs invokes a cascade of intra-cellular signaling pathways that induce the production of factors involved in inflammation and immunity.

In humans, ten TLR have been identified. TLRs that are expressed on the surface of cells include TLR-1, -2, -4, -5, and -6, while TLR-3, -7/8, and -9 are expressed with the ER compartment. Human dendritic cell subsets can be identified on the basis of distinct TLR expression patterns. By way of example, the myeloid or "conventional" subset of DC (mDC) expresses TLRs 1-8 when stimulated, and a cascade of activation markers (e.g. CD80, CD86, MHC class I and II, CCR7), pro-inflammatory cytokines, and chemokines are produced. A result of this stimulation and resulting expression is antigen-specific CD4+ and CD8+ T cell priming. These DCs acquire an enhanced capacity to take up antigens and present them in an appropriate form to T cells. In contrast, the plasmacytoid subset of DC (pDC) expresses only TLR7 and TLR9 upon activation, with a resulting activation of NK cells as well as T-cells. As dying tumor cells may adversely affect DC function, it has been suggested that activating DC with TLR agonists may be beneficial for priming anti-tumor immunity in an immunotherapy approach to the treatment of cancer. It has also been suggested that successful treatment of breast cancer using radiation and chemotherapy requires TLR4 activation.

TLR agonists known in the art and finding use in the present invention include, but are not limited to, the following:

Pam3Cys, a TLR-1/2 agonist;
CFA, a TLR-2 agonist;
MALP2, a TLR-2 agonist;
Pam2Cys, a TLR-2 agonist;
FSL-1, a TLR-2 agonist;
Hib-OMPC, a TLR-2 agonist;
polyribosinic:polyribocytidic acid (Poly I:C), a TLR-3 agonist;
polyadenosine-polyuridylic acid (poly AU), a TLR-3 agonist;
Polyinosinic-Polycytidylic acid stabilized with poly-L-lysine and carboxymethylcellulose (Hiltonol®), a TLR-3 agonist;
monophosphoryl lipid A (MPL), a TLR-4 agonist;
LPS, a TLR-4 agonist;
bacterial flagellin, a TLR-5 agonist;
sialyl-Tn (STn), a carbohydrate associated with the MUC1 mucin on a number of human
cancer cells and a TLR-4 agonist;
imiquimod, a TLR-7 agonist;
resiquimod, a TLR-7/8 agonist;
loxoribine, a TLR-7/8 agonist; and
unmethylated CpG dinucleotide (CpG-ODN), a TLR-9 agonist.

Because of their adjuvant qualities, TLR agonists are preferably used in combinations with other vaccines, adjuvants and/or immune modulators, and may be combined in various combinations. Thus, in certain embodiments, the cyclic purine dinucleotides that bind to STING and induces STING-dependent TBK1 activation and an inactivated tumor cell which expresses and secretes one or more cytokines which stimulate dendritic cell induction, recruitment and/or maturation, as described herein can be administered together with one or more TLR agonists for therapeutic purposes.

Antibody Therapeutics

Antibody-Dependent Cell-Mediated Cytotoxicity (ADCC) is a mechanism of cell-mediated immune defense whereby an effector cell of the immune system actively lyses a target cell, whose membrane-surface antigens have been bound by specific antibodies. It is one of the mechanisms through which antibodies, as part of the humoral immune response, can act to limit and contain infection. Classical ADCC is mediated by natural killer (NK) cells; macrophages, neutrophils and eosinophils can also mediate ADCC. ADCC is an important mechanism of action of therapeutic monoclonal antibodies, including trastuzumab and rituximab, against tumors. Compounds of the present invention may act to potentiate ADCC.

The following are an exemplary list of antibodies which may be used together with the compounds of the present invention.

Muromonab-CD3: Used to prevent acute rejection of organ, e.g., kidney, transplants. The humanized versions show promise in inhibiting the autoimmune destruction of beta cells in Type 1 diabetes mellitus.

Infliximab (Remicade®) and adalimumab (Humira®): Bind to tumor necrosis factor-alpha (TNF-α). Used in some inflammatory diseases such as rheumatoid arthritis, psoriasis, Crohns disease.

Omalizumab (Xolair®). Binds to IgE thus preventing IgE from binding to mast cells. Used against allergic asthma.

Daclizumab (Zenapax®). Binds to part of the IL-2 receptor exposed at the surface of activated T cells. Used to prevent acute rejection of transplanted kidneys.

Rituximab (trade name=Rituxan®). Binds to the CD20 molecule found on most B-cells and is used to treat B-cell lymphomas.

Ibritumomab (trade name=Zevalin®). This is a monoclonal antibody against the CD20 molecule on B cells (and lymphomas) conjugated to isotopes. Given to the lymphoma patient supplemented with Rituxan.

Tositumomab (Bexxar®). This is a conjugate of a monoclonal antibody against CD20 and the radioactive isotope iodine-131 (131I).

Cetuximab (Erbitux®). Blocks HER1, a receptor for epidermal growth factor (EGF) that is found on some tumor cells (some breast cancers, lymphomas).

Trastuzumab (Herceptin®). Blocks HER2, a growth factor receptor over-expressed in some 20% of breast cancers.

Adcetris®. A conjugate of a monoclonal antibody that binds CD30, a cell-surface molecule expressed by the cells of some lymphomas but not found on the normal stem cells needed to repopulate the bone marrow.

Alemtuzumab (Campath-1H®). Binds to CD52, a molecule found on lymphocytes and depletes both T cells and B cells. Has produced complete remission of chronic lymphocytic leukemia and shows promise in preventing rejection of kidney transplants.

Lym-1 (Oncolym®). Binds to the HLA-DR-encoded histocompatibility antigen that can be expressed at high levels on lymphoma cells.

Ipilimumab (Yervoy®) that acts to enhance the body's own immune response to tumors.

Vitaxin. Binds to a vascular integrin (alpha-v/beta-3) found on the blood vessels of tumors but not on the blood vessels supplying normal tissues. In Phase II clinical trials, Vitaxin has shown some promise in shrinking solid tumors without harmful side effects.

Bevacizumab (Avastin®). Binds to vascular endothelial growth factor (VEGF) preventing it from binding to its receptor. Used for the treatment of colorectal cancers.

Abciximab (ReoPro®). Inhibits the clumping of platelets by binding the receptors on their surface that normally are linked by fibrinogen. Helpful in preventing reclogging of the coronary arteries in patients who have undergone angioplasty.

Delivery Agents

Liposomes are vesicles formed from one ("unilamellar") or more ("multilamellar") layers of phospholipid. Because of the amphipathic character of the phospholipid building blocks, liposomes typically comprise a hydrophilic layer presenting a hydrophilic external face and enclosing a hydrophilic core. The versatility of liposomes in the incorporation of hydrophilic/hydrophobic components, their non-toxic nature, biodegradability, biocompatibility, adjuvanticity, induction of cellular immunity, property of sustained release and prompt uptake by macrophages, makes them attractive candidates for the delivery of antigens.

WO2010/104833, which is incorporated by reference herein in its entirety, describes suitable liposomal preparations. Such liposomal formulations, referred to herein as VesiVax® (Molecular Express, Inc.), with our without the "immunogenic polypeptide(s) or carbohydrate(s)" referred to above, can contain one or more additional components such as peptidoglycan, lipopeptide, lipopolysaccharide, monophosphoryl lipid A, lipoteichoic acid, resiquimod, imiquimod, flagellin, oligonucleotides containing unmethylated CpG motifs, beta-galactosylceramide, muramyl dipeptide, all-trans retinoic acid, double-stranded viral RNA, heat shock proteins, dioctadecyldimethylammonium bromide, cationic surfactants, toll-like receptor agonists, dimyristoyl-trimethylammoniumpropane, and nod-like receptor agonists. Advantageously, these liposomal formulations can be used to deliver one or more cyclic purine dinucleotides in accordance with the present invention.

Moreover, while the liposomal formulations discussed above employ a "steroid derivative" as an anchor for attaching an immunogenic polypeptide or carbohydrate to a liposome, the steroid may simply be provided as an unconjugated steroid such as cholesterol.

Suitable methods for preparing liposomes from lipid mixtures are well known in the art. See, e.g., Basu & Basu, *Liposome Methods and Protocols* (*Methods in Molecular Biology*), Humana Press, 2002; Gregoriadis, *Liposome Technology*, 3$^{rd}$ *Edition*, Informa HealthCare, 2006. Preferred methods include extrusion, homogenization, and sonication methods described therein. An exemplary method for preparing liposomes for use in the present invention, which comprises drying a lipid mixture, followed by hydration in an aqueous vehicle and sonication to form liposomes, is described in WO2010/104833.

In certain embodiments, the liposomes are provided within a particular average size range. Liposome size can be selected, for example, by extrusion of an aqueous vehicle comprising liposomes through membranes having a preselected pore size and collecting the material flowing through the membrane. In preferred embodiments, the liposomes are selected to be substantially between 50 and 500 nm in diameter, more preferably substantially between 50 and 200 nm in diameter, and most preferably substantially between 50 and 150 nm in diameter. The term "substantially" as used herein in this context means that at least 75%, more preferably 80%, and most preferably at least 90% of the liposomes are within the designated range.

Other lipid and lipid-like adjuvants which may find use in the present invention include oil-in-water (o/w) emulsions (see, e.g., Muderhwa et al., J. Pharmaceut. Sci. 88: 1332-9, 1999)), VesiVax® TLR (Molecular Express, Inc.), digitonin (see, e.g., U.S. Pat. No. 5,698,432), and glucopyranosyl lipids (see, e.g., United States Patent Application 20100310602).

Nanoparticles also represent drug delivery systems suitable for most administration routes. Over the years, a variety of natural and synthetic polymers have been explored for the preparation of nanoparticles, of which Poly(lactic acid) (PLA), Poly(glycolic acid) (PGA), and their copolymers (PLGA) have been extensively investigated because of their biocompatibility and biodegradability. Nanoparticles and other nanocarriers act as potential carries for several classes of drugs such as anticancer agents, antihypertensive agents, immunomodulators, and hormones; and macromolecules such as nucleic acids, proteins, peptides, and antibodies. See, e.g., Crit. Rev. Ther. Drug Carrier Syst. 21:387-422, 2004; Nanomedicine: Nanotechnology, Biology and Medicine 1:22-30, 2005.

Chemotherapeutic Agents

In additional embodiments the methods further involve administering to the subject an effective amount of one or more chemotherapeutics as an additional treatment. In certain embodiments the one or more chemotherapeutics is selected from abiraterone acetate, altretamine, anhydrovinblastine, auristatin, bexarotene, bicalutamide, BMS 184476, 2,3,4,5,6-pentafluoro-N-(3-fluoro-4-methoxyphenyl)benzene sulfonamide, bleomycin, N,N-dimethyl-L-valyl-L-valyl-N-methyl-L-valyl-L-poly-1-Lproline-t-butylamide, cachectin, cemadotin, chlorambucil, cyclophosphamide, 3',4'-didehydro-4'-deoxy-8'-norvin-caleukoblastine, docetaxol, doxetaxel, cyclophosphamide, carboplatin, carmustine, cisplatin, cryptophycin, cyclophosphamide, cytarabine, dacarbazine (DTIC), dactinomycin, daunorubicin, decitabine dolastatin, doxorubicin (adriamycin), etoposide, 5-fluorouracil, finasteride, flutamide, hydroxyurea and hydroxyureataxanes, ifosfamide, liarozole, lonidamine, lomustine (CCNU), MDV3100, mechlorethamine (nitrogen mustard), melphalan, mivobulin isethionate, rhizoxin, sertenef, streptozocin, mitomycin, methotrexate, taxanes, nilutamide, onapristone, paclitaxel, prednimustine, procarbazine, RPR109881, stramustine phosphate, tamoxifen, tasonermin, taxol, tretinoin, vinblastine, vincristine, vindesine sulfate, and vinflunine.

Immunomodulatory Cell Lines

By "inactivated tumor cell" is meant a tumor cell (either "autologous" or "allogeneic" to the patient) which has which been treated to prevent division of the cells. For purposes of the present invention, such cells preserve their immunogenicity and their metabolic activity. Such tumor cells are genetically modified to express a transgene which is expressed within a patient as part of cancer therapy. Thus, a composition or vaccine of the invention comprises neoplastic (e.g., tumor) cells that are autologous or allogeneic to the patient undergoing treatment and is most preferably the same general type of tumor cell as is afflicting the patient. For example, a patient suffering from melanoma will typically be administered a genetically modified cell derived from a melanoma. Methods for inactivating tumor cells for use in the present invention, such as the use of irradiation, are well known in the art.

The inactivated tumor cells of the present invention are administered to the patient together with one or more costimulatory molecules or agents. A preferred costimulatory agent comprises one or more cytokines which stimulate dendritic cell induction, recruitment, and/or maturation. Methods for assessing such costimulatory agents are well known in the literature. Induction and maturation of DCs is typically assessed by increased expression of certain membrane molecules such as CD80 and CD86, and/or secretion of pro-inflammatory cytokines, such as IL-12 and type I interferons following stimulation.

In preferred embodiments, the inactivated tumor cells themselves are modified to express and secrete one or more cytokines which stimulate dendritic cell induction, recruitment, and/or maturation. The present invention is described in exemplary terms with regard to the use of GM-CSF. Thus, by way of example, the tumor cell may express a transgene encoding GM-CSF as described in U.S. Pat. Nos. 5,637,483, 5,904,920, 6,277,368 and 6,350,445, as well as in US Patent Publication No. 20100150946, each of which is expressly incorporated by reference herein. A form of GM-CSF-expressing genetically modified cancer cells or a "cytokine-expressing cellular vaccine" for the treatment of pancreatic cancer is described in U.S. Pat. Nos. 6,033,674 and 5,985, 290, both of which are expressly incorporated by reference herein.

Other suitable cytokines which may be expressed by such inactivated tumor cells and/or bystander cells instead of, or together with, GM-CSF include, but are not limited to, one or more of CD40 ligand, IL-12, CCL3, CCL20, and CCL21. This list is not meant to be limiting.

While it is preferred that the inactivated tumor cells administered to the subject express one or more cytokines of interest, the tumor cell line may be accompanied by an inactivated bystander cell line which expresses and secretes one or more cytokines which stimulate dendritic cell induction, recruitment, and/or maturation. The bystander cell line may provide all of the cytokines which stimulate dendritic cell induction, recruitment, and/or maturation, or may supplement cytokines which stimulate dendritic cell induction, recruitment, and/or maturation expressed and secreted by the inactivated tumor cells. By way of example, immunomodulatory cytokine-expressing bystander cell lines are disclosed in U.S. Pat. Nos. 6,464,973, and 8,012,469, Dessureault et al., Ann. Surg. Oncol. 14: 869-84, 2007, and Eager and Nemunaitis, Mol. Ther. 12: 18-27, 2005, each of which is expressly incorporated by reference herein.

By "Granulocyte-macrophage colony stimulating factor (GM-CSF) polypeptide" is meant a cytokine or fragment thereof having immunomodulatory activity and having at least about 85% amino acid sequence identity to GenBank Accession No. AAA52122.1.

Vaccines

In certain embodiments, the CDN compositions are administered in conjunction with one or more vaccines intended to stimulate an immune response to one or more predetermined antigens. Examples of target antigens that may find use in the invention are listed in the following table. The target antigen may also be a fragment or fusion polypeptide comprising an immunologically active portion of the antigens listed in the table. This list is not meant to be limiting.

Table 1. Antigens.

TABLE 1

| Antigen | Reference |
|---|---|
| Tumor antigens | |
| Mesothelin | GenBank Acc. No. NM_005823; U40434; NM_013404; BC003512 (see also, e.g., Hassan, et al. (2004) Clin. Cancer Res. 10: 3937-3942; Muminova, et al. (2004) BMC Cancer 4: 19; Iacobuzio-Donahue, et al. (2003) Cancer Res. 63: 8614-8622). |
| Wilms' tumor-1 associated protein (Wt-1), including isoform A; isoform B; isoform C; isoform D. | WT-1 isoform A (GenBank Acc. Nos. NM_000378; NP_000369). WT-1 isoform B (GenBank Acc. Nos. NM_024424; NP_077742). WT-1 isoform C (GenBank Acc. Nos. NM_024425; NP_077743). WT-1 isoform D (GenBank Acc. Nos. NM_024426; NP_077744). |
| Stratum corneum chymotryptic enzyme (SCCE), and variants thereof. | GenBank Acc. No. NM_005046; NM_139277; AF332583. See also, e.g., Bondurant, et al. (2005) Clin. Cancer Res. 11: 3446-3454; Santin, et al. (2004) Gynecol. Oncol. 94: 283-288; Shigemasa, et al. (2001) Int. J. Gynecol. Cancer 11: 454-461; Sepehr, et al. (2001) Oncogene 20: 7368-7374. |
| MHC class I chain-related protein A (MICA); MHC class I chain-related protein A (MICB). | See, e.g., Groh, et al. (2005) Proc. Natl. Acad. Sci. USA 102: 6461-6466; GenBank Acc. Nos. NM_000247; BC_016929; AY750850; NM_005931. |
| Gastrin and peptides derived from gastrin; gastrin/CCK-2 receptor (also known as CCK-B). | Harris, et al. (2004) Cancer Res. 64: 5624-5631; Gilliam, et al. (2004) Eur. J. Surg. Oncol. 30: 536-543; Laheru and Jaffee (2005) Nature Reviews Cancer 5: 459-467. |
| Glypican-3 (an antigen of, e.g., hepatocellular carcinoma and melanoma). | GenBank Acc. No. NM_004484. Nakatsura, et al. (2003) Biochem. Biophys. Res. Commun. 306: 16-25; Capurro, et al. (2003) Gasteroenterol. 125: 89-97; Nakatsura, et al. (2004) Clin. Cancer Res. 10: 6612-6621). |
| Coactosin-like protein. | Nakatsura, et al. (2002) Eur. J. Immunol. 32: 826-836; Laheru and Jaffee (2005) Nature Reviews Cancer 5: 459-467. |
| Prostate stem cell antigen (PSCA). | GenBank Acc. No. AF043498; AR026974; AR302232 (see also, e.g., Argani, et al. (2001) Cancer Res. 61: 4320-4324; Christiansen, et al. (2003) Prostate 55: 9-19; Fuessel, et al. (2003) 23: 221-228). |
| Prostate acid phosphatase (PAP); prostate-specific antigen (PSA); PSM; PSMA. | Small, et al. (2000) J. Clin. Oncol. 18: 3894-3903; Altwein and Luboldt (1999) Urol. Int. 63: 62-71; Chan, et al. (1999) Prostate 41: 99-109; Ito, et al. (2005) Cancer 103: 242-250; Schmittgen, et al. (2003) Int. J. Cancer 107: 323-329; Millon, et al. (1999) Eur. Urol. 36: 278-285. |
| Six-transmembrane epithelial antigen of prostate (STEAP). | See, e.g., Machlenkin, et al. (2005) Cancer Res. 65: 6435-6442; GenBank Acc. No. NM_018234; NM_001008410; NM_182915; NM_024636; NM_012449; BC011802. |
| Prostate carcinoma tumor antigen-1 (PCTA-1). | See, e.g., Machlenkin, et al. (2005) Cancer Res. 65: 6435-6442; GenBank Acc. No. L78132. |
| Prostate tumor-inducing gene-1 (PTI-1). | See, e.g., Machlenkin, et al. (2005) Cancer Res. 65: 6435-6442). |
| Prostate-specific gene with homology to G protein-coupled receptor. | See, e.g., Machlenkin, et al. (2005) Cancer Res. 65: 6435-6442). |
| Prostase (an antrogen regulated serine protease). | See, e.g., Machlenkin, et al. (2005) Cancer Res. 65: 6435-6442; GenBank Acc. No. BC096178; BC096176; BC096175. |
| Proteinase 3. | GenBank Acc. No. X55668. |
| Cancer-testis antigens, e.g., NY-ESO-1; SCP-1; SSX-1; SSX-2; SSX-4; GAGE, CT7; CT8; CT10; MAGE-1; MAGE-2; | GenBank Acc. No. NM_001327 (NY-ESO-1) (see also, e.g., Li, et al. (2005) Clin. Cancer Res. 11: 1809-1814; Chen, et al. (2004) Proc. Natl. Acad. Sci. USA. 101(25): 9363-9368; Kubuschok, et al. (2004) Int. J. Cancer. 109: 568-575; Scanlan, et al. (2004) Cancer Immun. 4: 1; Scanlan, et al. (2002) Cancer Res. 62: 4041-4047; Scanlan, et al. (2000) Cancer |

TABLE 1-continued

Antigens.

| Antigen | Reference |
|---|---|
| MAGE-3; MAGE-4; MAGE-6; LAGE-1. MAGE-A1, MAGE-A2; MAGE-A3; MAGE-A4; MAGE-A6; MAGE-A9; MAGE-A10; MAGE-A12; GAGE-3/6; NT-SAR-35; BAGE; CA125. | Lett. 150: 155-164; Dalerba, et al. (2001) Int. J. Cancer 93: 85-90; Ries, et al. (2005) Int. J. Oncol. 26: 817-824. Otte, et al. (2001) Cancer Res. 61: 6682-6687; Lee, et al. (2003) Proc. Natl. Acad. Sci. USA 100: 2651-2656; Sarcevic, et al. (2003) Oncology 64: 443-449; Lin, et al. (2004) Clin. Cancer Res. 10: 5708-5716. |
| GAGE-1; GAGE-2; GAGE-3; GAGE-4; GAGE-5; GAGE-6; GAGE-7; GAGE-8; GAGE-65; GAGE-11; GAGE-13; GAGE-7B. | De Backer, et al. (1999) Cancer Res. 59: 3157-3165; Scarcella, et al. (1999) Clin. Cancer Res. 5: 335-341. |
| HIP1R; LMNA; KIAA1416; Seb4D; KNSL6; TRIP4; MBD2; HCAC5; MAGEA3. | Scanlan, et al. (2002) Cancer Res. 62: 4041-4047. |
| DAM family of genes, e.g., DAM-1; DAM-6. | Fleishhauer, et al. (1998) Cancer Res. 58: 2969-2972. |
| RCAS1. | Enjoji, et al. (2004) Dig. Dis. Sci. 49: 1654-1656. |
| RU2. | Van Den Eynde, et al. (1999) J. Exp. Med. 190: 1793-1800. |
| CAMEL. | Slager, et al. (2004) J. Immunol. 172: 5095-5102; Slager, et al. (2004) Cancer Gene Ther. 11: 227-236. |
| Colon cancer associated antigens, e.g., NY-CO-8; NY-CO-9; NY-CO-13; NY-CO-16; NY-CO-20; NY-CO-38; NY-CO-45; NY-CO-9/HDAC5; NY-CO-41/MBD2; NY-CO-42/TRIP4; NY-CO-95/KIAA1416; KNSL6; seb4D. | Scanlan, et al. (2002) Cancer Res. 62: 4041-4047. |
| N-Acetylglucosaminyl-tranferase V (GnT-V). | Dosaka-Akita, et al. (2004) Clin. Cancer Res. 10: 1773-1779. |
| Elongation factor 2 mutated (ELF2M). | Renkvist, et al. (2001) Cancer Immunol Immunother. 50: 3-15. |
| HOM-MEL-40/SSX2 | Neumann, et al. (2004) Int. J. Cancer 112: 661-668; Scanlan, et al. (2000) Cancer Lett. 150: 155-164. |
| BRDT. | Scanlan, et al. (2000) Cancer Lett. 150: 155-164. |
| SAGE; HAGE. | Sasaki, et al. (2003) Eur. J. Surg. Oncol. 29: 900-903. |
| RAGE. | See, e.g., Li, et al. (2004) Am. J. Pathol. 164: 1389-1397; Shirasawa, et al. (2004) Genes to Cells 9: 165-174. |
| MUM-1 (melanoma ubiquitous mutated); MUM-2; MUM-2 Arg-Gly mutation; MUM-3. | Gueguen, et al. (1998) J. Immunol. 160: 6188-6194; Hirose, et al. (2005) Int. J. Hematol. 81: 48-57; Baurain, et al. (2000) J. Immunol. 164: 6057-6066; Chiari, et al. (1999) Cancer Res. 59: 5785-5792. |
| LDLR/FUT fusion protein antigen of melanoma. | Wang, et al. (1999) J. Exp. Med. 189: 1659-1667. |
| NY-REN series of renal cancer antigens. | Scanlan, et al. (2002) Cancer Res. 62: 4041-4047; Scanlan, et al. (1999) Cancer Res. 83: 456-464. |
| NY-BR series of breast cancer antigens, e.g., NY-BR-62; NY-BR-75; NY-BR-85; NY-BR-62; NY-BR-85. | Scanlan, et al. (2002) Cancer Res. 62: 4041-4047; Scanlan, et al. (2001) Cancer Immunity 1: 4. |
| BRCA-1; BRCA-2. | Stolier, et al. (2004) Breast J. 10: 475-480; Nicoletto, et al. (2001) Cancer Treat Rev. 27: 295-304. |
| DEK/CAN fusion protein. | Von Lindern, et al. (1992) Mol. Cell. Biol. 12: 1687-1697. |
| Ras, e.g., wild type ras, ras with mutations at codon 12, 13, 59, or 61, e.g., mutations G12C; G12D; G12R; G12S; G12V; G13D; A59T; Q61H. K-RAS; H-RAS; N-RAS. | GenBank Acc. Nos. P01112; P01116; M54969; M54968; P01111; P01112; K00654. See also, e.g., GenBank Acc. Nos. M26261; M34904; K01519; K01520; BC006499; NM_006270; NM_002890; NM_004985; NM_033360; NM_176795; NM_005343. |
| BRAF (an isoform of RAF). | Tannapfel, et al. (2005) Am. J. Clin. Pathol. 123: 256-2601; Tsao and Sober (2005) Dermatol. Clin. 23: 323-333. |
| Melanoma antigens, including HST-2 | GenBank Acc. No. NM_206956; NM_206955; NM_206954; NM_206953; NM_006115; NM_005367; NM_004988; AY148486; |

TABLE 1-continued

Antigens.

| Antigen | Reference |
|---|---|
| melanoma cell antigens. | U10340; U10339; M77481. See, eg., Suzuki, et al. (1999) J. Immunol. 163: 2783-2791. |
| Survivin | GenBank Acc. No. AB028869; U75285 (see also, e.g., Tsuruma, et al. (2004) J. Translational Med. 2: 19 (11 pages); Pisarev, et al. (2003) Clin. Cancer Res. 9: 6523-6533; Siegel, et al. (2003) Br. J. Haematol. 122: 911-914; Andersen, et al. (2002) Histol. Histopathol. 17: 669-675). |
| MDM-2 | NM_002392; NM_006878 (see also, e.g., Mayo, et al. (1997) Cancer Res. 57: 5013-5016; Demidenko and Blagosklonny (2004) Cancer Res. 64: 3653-3660). |
| Methyl-CpG-binding proteins (MeCP2; MBD2). | Muller, et al. (2003) Br. J. Cancer 89: 1934-1939; Fang, et al. (2004) World J. Gastreenterol. 10: 3394-3398. |
| NA88-A. | Moreau-Aubry, et al. (2000) J. Exp. Med. 191: 1617-1624. |
| Histone deacetylases (HDAC), e.g., HDAC5. | Waltregny, et al. (2004) Eur. J. Histochem. 48: 273-290; Scanlan, et al. (2002) Cancer Res. 62: 4041-4047. |
| Cyclophilin B (Cyp-B). | Tamura, et al. (2001) Jpn. J. Cancer Res. 92: 762-767. |
| CA 15-3; CA 27.29. | Clinton, et al. (2003) Biomed. Sci. Instrum. 39: 408-414. |
| Heat shock protein Hsp70. | Faure, et al. (2004) Int. J. Cancer 108: 863-870. |
| GAGE/PAGE family, e.g., PAGE-1; PAGE-2; PAGE-3; PAGE-4; XAGE-1; XAGE-2; XAGE-3. | Brinkmann, et al. (1999) Cancer Res. 59: 1445-1448. |
| MAGE-A, B, C, and D families. MAGE-B5; MAGE-B6; MAGE-C2; MAGE-C3; MAGE-3; MAGE-6. | Lucas, et al. (2000) Int. J. Cancer 87: 55-60; Scanlan, et al. (2001) Cancer Immun. 1: 4. |
| Kinesin 2; TATA element modulatory factor 1; tumor protein D53; NY | Scanlan, et al. (2001) Cancer Immun. 30: 1-4. |
| Alpha-fetoprotein (AFP) | Grimm, et al. (2000) Gastroenterol. 119: 1104-1112. |
| SART1; SART2; SART3; ART4. | Kumamuru, et al. (2004) Int. J. Cancer 108: 686-695; Sasatomi, et al. (2002) Cancer 94: 1636-1641; Matsumoto, et al. (1998) Jpn. J. Cancer Res. 89: 1292-1295; Tanaka, et al. (2000) Jpn. J. Cancer Res. 91: 1177-1184. |
| Preferentially expressed antigen of melanoma (PRAME). | Matsushita, et al. (2003) Leuk. Lymphoma 44: 439-444; Oberthuer, et al. (2004) Clin. Cancer Res. 10: 4307-4313. |
| Carcinoembryonic antigen (CEA), CAP1-6D enhancer agonist peptide. | GenBank Acc. No. M29540; E03352; X98311; M17303 (see also, e.g., Zaremba (1997) Cancer Res. 57: 4570-4577; Sarobe, et al. (2004) Curr. Cancer Drug Targets 4: 443-454; Tsang, et al. (1997) Clin. Cancer Res. 3: 2439-2449; Fong, et al. (2001) Proc. Natl. Acad. Sci. USA 98: 8809-8814). |
| HER-2/neu. | Disis, et al. (2004) J. Clin. Immunol. 24: 571-578; Disis and Cheever (1997) Adv. Cancer Res. 71: 343-371. |
| Cdk4; cdk6; p16 (INK4); Rb protein. | Ghazizadeh, et al. (2005) Respiration 72: 68-73; Ericson, et al. (2003) Mol. Cancer Res. 1: 654-664. |
| TEL; AML1; TEL/AML1. | Stams, et al. (2005) Clin. Cancer Res. 11: 2974-2980. |
| Telomerase (TERT). | Nair, et al. (2000) Nat. Med. 6: 1011-1017. |
| 707-AP. | Takahashi, et al. (1997) Clin. Cancer Res. 3: 1363-1370. |
| Annexin, e.g., Annexin II. | Zimmerman, et al. (2004) Virchows Arch. 445: 368-374. |
| BCR/ABL; BCR/ABL p210; BCR/ABL p190; CML-66; CML-28. | Cobaldda, et al. (2000) Blood 95: 1007-1013; Hakansson, et al. (2004) Leukemia 18: 538-547; Schwartz, et al. (2003) Semin. Hematol. 40: 87-96; Lim, et al. (1999) Int. J. Mol. Med. 4: 665-667. |
| BCL2; BLC6; CD10 protein. | Iqbal, et al. (2004) Am. J. Pathol. 165: 159-166. |
| CDC27 (this is a melanoma antigen). | Wang, et al. (1999) Science 284: 1351-1354. |
| Sperm protein 17 (SP17); 14-3-3-zeta; MEMD; KIAA0471; TC21. | Arora, et al. (2005) Mol. Carcinog. 42: 97-108. |
| Tyrosinase-related proteins 1 and 2 (TRP-1 and TRP-2). | GenBank Acc. No. NM_001922. (see also, e.g., Bronte, et al. (2000) Cancer Res. 60: 253-258). |
| Gp100/pmel-17. | GenBank Acc. Nos. AH003567; U31798; U31799; U31807; U31799 (see also, e.g., Bronte, et al. (2000) Cancer Res. 60: 253-258). |
| TARP. | See, e.g., Clifton, et al. (2004) Proc. Natl. Acad. Sci. USA 101: 10166-10171; Virok, et al. (2005) Infection Immunity 73: 1939-1946. |
| Tyrosinase-related proteins 1 and 2 (TRP-1 and TRP-2). | GenBank Acc. No. NM_001922. (see also, e.g., Bronte, et al. (2000) Cancer Res. 60: 253-258). |

TABLE 1-continued

| Antigens. | |
|---|---|
| Antigen | Reference |
| Melanocortin 1 receptor (MC1R); MAGE-3; gp100; tyrosinase; dopachrome tautomerase (TRP-2); MART-1. | Salazar-Onfray, et al. (1997) Cancer Res. 57: 4348-4355; Reynolds, et al. (1998) J. Immunol. 161: 6970-6976; Chang, et al. (2002) Clin. Cancer Res. 8: 1021-1032. |
| MUC-1; MUC-2. | See, e.g., Davies, et al. (1994) Cancer Lett. 82: 179-184; Gambus, et al. (1995) Int. J. Cancer 60: 146-148; McCool, et al. (1999) Biochem. J. 341: 593-600. |
| Spas-1. | U.S. Published patent application No. 20020150588 of Allison, et al. |
| CASP-8; FLICE; MACH. | Mandruzzato, et al. (1997) J. Exp. Med. 186: 785-793. |
| CEACAM6; CAP-1. | Duxbury, et al. (2004) Biochem. Biophys. Res. Commun. 317: 837-843; Morse, et al. (1999) Clin. Cancer Res. 5: 1331-1338. |
| HMGB1 (a DNA binding protein and cytokine). | Brezniceanu, et al. (2003) FASEB J. 17: 1295-1297. |
| ETV6/AML1. | Codrington, et al. (2000) Br. J. Haematol. 111: 1071-1079. |
| Mutant and wild type forms of adenomatous polyposis coli (APC); beta-catenin; c-met; p53; E-cadherin; cyclooxygenase-2 (COX-2). | Clements, et al. (2003) Clin. Colorectal Cancer 3: 113-120; Gulmann, et al. (2003) Appl. Immunohistochem. Mol. Morphol. 11: 230-237; Jungck, et al. (2004) Int. J. Colorectal. Dis. 19: 438-445; Wang, et al. (2004) J. Surg. Res. 120: 242-248; Abutaily, et al. (2003) J. Pathol. 201: 355-362; Liang, et al. (2004) Br. J. Surg. 91: 355-361; Shirakawa, et al. (2004) Clin. Cancer Res. 10: 4342-4348. |
| Renal cell carcinoma antigen bound by mAB G250. | Mulders, et al. (2003) Urol. Clin. North Am. 30: 455-465; Steffens, et al. (1999) Anticancer Res. 19: 1197-1200. |
| EphA2 | See. e.g., U.S. Patent Publication No. 2005/0281783 A1; Genbank Accession No. NM_004431 (human); Genbank Accession No. NM_010139 (Mouse); Genbank Accession No. AB038986 (Chicken, partial sequence); GenBank Accession Nos. NP_004422, AAH37166, and AAA53375 (human); GenBank Accession Nos. NP_034269 (mouse), AAH06954 (mouse), XP_345597 (rat), and BAB63910 (chicken). |
| *Francisella tularensis* antigens | |
| *Francisella tularensis* A and B. | Complete genome of subspecies Schu S4 (GenBank Acc. No. AJ749949); of subspecies Schu 4 (GenBank Acc. No. NC_006570). Outer membrane protein (43 kDa) Bevanger, et al. (1988) J. Clin. Microbiol. 27: 922-926; Porsch-Ozcurumez, et al. (2004) Clin. Diagnostic. Lab. Immunol. 11: 1008-1015). Antigenic components of *F. tularensis* include, e.g., 80 antigens, including 10 kDa and 60 kDa chaperonins (Havlasova, et al. (2002) Proteomics 2: 857-86), nucleoside diphosphate kinase, isocitrate dehydrogenase, RNA-binding protein Hfq, the chaperone ClpB (Havlasova, et al. (2005) Proteomics 5: 2090-2103). See also, e.g., Oyston and Quarry (2005) Antonie Van Leeuwenhoek 87: 277-281; Isherwood, et al. (2005) Adv. Drug Deliv. Rev. 57: 1403-1414; Biagini, et al. (2005) Anal. Bioanal. Chem. 382: 1027-1034. |
| Malarial antigens | |
| Circumsporozoite protein (CSP); SSP2; HEP17; Exp-1 orthologs found in *P. falciparum*; and LSA-1. | See, e.g., Haddad, et al. (2004) Infection Immunity 72: 1594-1602; Hoffman, et al. (1997) Vaccine 15: 842-845; Oliveira-Ferreira and Daniel-Ribeiro (2001) Mem. Inst. Oswaldo Cruz, Rio de Janeiro 96: 221-227. CSP (see, e.g., GenBank Acc. No. AB121024). SSP2 (see, e.g., GenBank Acc. No. AF249739). LSA-1 (see, e.g., GenBank Acc. No. Z30319). |
| Ring-infected erythrocyte survace protein (RESA); merozoite surface protein 2 (MSP2); Spf66; merozoite surface protein 1(MSP1); 195A; BVp42. | See, e.g., Stirnadel, et al. (2000) Int. J. Epidemiol. 29: 579-586; Krzych, et al. (1995) J. Immunol. 155: 4072-4077. See also, Good, et al. (2004) Immunol. Rev. 201: 254-267; Good, et al. (2004) Ann. Rev. Immunol. 23: 69-99. MSP2 (see, e.g., GenBank Acc. No. X96399; X96397). MSP1 (see, e.g., GenBank Acc. No. X03371). RESA (see, e.g., GenBank Acc. No. X05181; X05182). |
| Apical membrane antigen 1 (AMA1). | See, e.g., Gupta, et al. (2005) Protein Expr. Purif. 41: 186-198. AMA1 (see, e.g., GenBank Acc. No. A`13; AJ494905; AJ490565). |
| Viruses and viral antigens | |
| Hepatitis A | GenBank Acc. Nos., e.g., NC_001489; AY644670; X83302; K02990; M14707. |
| Hepatitis B | Complete genome (see, e.g., GenBank Acc. Nos. AB214516; NC_003977; AB205192; AB205191; AB205190; AJ748098; AB198079; AB198078; AB198076; AB074756). |
| Hepatitis C | Complete genome (see, e.g., GenBank Acc. Nos. NC_004102; AJ238800; AJ238799; AJ132997; AJ132996; AJ000009; D84263). |
| Hepatitis D | GenBank Acc. Nos, e.g. NC_001653; AB118847; AY261457. |
| Human papillomavirus, including all 200+ subtypes (classed in 16 groups), such as the | See, e.g., Trimble, et al. (2003) Vaccine 21: 4036-4042; Kim, et al. (2004) Gene Ther. 11: 1011-1018; Simon, et al. (2003) Eur. J. Obstet. Gynecol. Reprod. Biol. 109: 219-223; Jung, et al. (2004) J. Microbiol. 42: 255-266; Damasus-Awatai and Freeman-Wang (2003) Curr. Opin. |

TABLE 1-continued

Antigens.

| Antigen | Reference |
|---|---|
| high risk subtypes 16, 18, 30, 31, 33, 45. | Obstet. Gynecol. 15: 473-477; Jansen and Shaw (2004) Annu. Rev. Med. 55: 319-331; Roden and Wu (2003) Expert Rev. Vaccines 2: 495-516; de Villiers, et al. (2004) Virology 324: 17-24; Hussain and Paterson (2005) Cancer Immunol. Immunother. 54: 577-586; Molijn, et al. (2005) J. Clin. Virol. 32 (Suppl. 1) S43-S51. GenBank Acc. Nos. AY686584; AY686583; AY686582; NC_006169; NC_006168; NC_006164; NC_001355; NC_001349; NC_005351; NC_001596). |
| Human T-cell lymphotropic virus (HTLV) types I and II, including the HTLV type I subtypes Cosmopolitan, Central African, and Austro-Melanesian, and the HTLV type II subtypes Iia, Iib, Iic, and Iid. | See, e.g., Capdepont, et al. (2005) AIDS Res. Hum. Retrovirus 21: 28-42; Bhigjee, et al. (1999) AIDS Res. Hum. Restrovirus 15: 1229-1233; Vandamme, et al. (1998) J. Virol. 72: 4327-4340; Vallejo, et al. (1996) J. Acquir. Immune Defic. Syndr. Hum. Retrovirol. 13: 384-391. HTLV type I (see, e.g., GenBank Acc. Nos. AY563954; AY563953. HTLV type II (see, e.g., GenBank Acc. Nos. L03561; Y13051; AF139382). |
| Coronaviridae, including Coronaviruses, such as SARS-coronavirus (SARS-CoV), and Toroviruses. | See, e.g., Brian and Baric (2005) Curr. Top. Microbiol. Immunol. 287: 1-30; Gonzalez, et al. (2003) Arch. Virol. 148: 2207-2235; Smits, et al. (2003) J. Virol. 77: 9567-9577; Jamieson, et al. (1998) J. Infect. Dis. 178: 1263-1269 (GenBank Acc. Nos. AY348314; NC_004718; AY394850). |
| Rubella virus. | GenBank Acc. Nos. NC_001545; AF435866. |
| Mumps virus, including the genotypes A, C, D, G, H, and I. | See, e.g., Orvell, eta 1. (2002) J. Gen. Virol. 83: 2489-2496. See, e.g., GenBank Acc. Nos. AY681495; NC_002200; AY685921; AF201473. |
| Coxsackie virus A including the serotypes 1, 11, 13, 15, 17, 18, 19, 20, 21, 22, and 24 (also known as Human enterovirus C; HEV-C). | See, e.g., Brown, et al. (2003) J. Virol. 77: 8973-8984. GenBank Acc. Nos. AY421768; AY790926: X67706. |
| Coxsackie virus B, including subtypes 1-6. | See, e.g., Ahn, et al. (2005) J. Med. Virol. 75: 290-294; Patel, et al. (2004) J. Virol. Methods 120: 167-172; Rezig, et al. (2004) J. Med. Virol. 72: 268-274. GenBank Acc. No. X05690. |
| Human enteroviruses including, e.g., human enterovirus A (HEV-A, CAV2 to CAV8, CAV10, CAV12, CAV14, CAV16, and EV71) and also including HEV-B (CAV9, CBV1 to CBV6, E1 to E7, E9, E11 to E21, E24 to E27, E29 to E33, and EV69 and E73), as well as HEV. | See, e.g., Oberste, et al. (2004) J. Virol. 78: 855-867. Human enterovirus A (GenBank Acc. Nos. NC_001612); human enterovirus B (NC_001472); human enterovirus C (NC_001428); human enterovirus D (NC_001430). Simian enterovirus A (GenBank Acc. No. NC_003988). |
| Polioviruses including PV1, PV2, and PV3. | See, e.g., He, et al. (2003) J. Virol. 77: 4827-4835; Hahsido, et al. (1999) Microbiol. Immunol. 43: 73-77. GenBank Acc. No. AJ132961 (type 1); AY278550 (type 2); X04468 (type 3). |
| Viral encephalitides viruses, including equine encephalitis, Venezuelan equine encephalitis (VEE) (including subtypes IA, IB, IC, ID, IIIC, IIID), Eastern equine encephalitis (EEE), Western equine encephalitis (WEE), St. Louis encephalitis, Murray Valley (Australian) encephalitis, Japanese encephalitis, and tick-born encephalitis. | See, e.g., Hoke (2005) Mil. Med. 170: 92-105; Estrada-Franco, et al. (2004) Emerg. Infect. Dis. 10: 2113-2121; Das, et al. (2004) Antiviral Res. 64: 85-92; Aguilar, et al. (2004) Emerg. Infect. Dis. 10: 880-888; Weaver, et al. (2004) Arch. Virol. Suppl. 18: 43-64; Weaver, et al. (2004) Annu. Rev. Entomol. 49: 141-174. Eastern equine encephalitis (GenBank Acc. No. NC_003899; AY722102); Western equine encephalitis (NC_003908). |
| Human herpesviruses, including cytomegalovirus (CMV), Epstein-Barr | See, e.g., Studahl, et al. (2000) Scand. J. Infect. Dis. 32: 237-248; Padilla, et al. (2003) J. Med. Virol. 70 (Suppl. 1) S103-S110; Jainkittivong and Langlais (1998) Oral Surg. Oral Med. 85: 399-403. GenBank Nos. NC_001806 (herpesvirus 1); NC_001798 |

TABLE 1-continued

Antigens.

| Antigen | Reference |
|---|---|
| virus (EBV), human herpesvirus-1 (HHV-1), HHV-2, HHV-3, HHV-4, HHV-5, HHV-6, HHV-7, HHV-8, herpes B virus, herpes simplex virus types 1 and 2 (HSV-1, HSV-2), and varicella zoster virus (VZV). | (herpesvirus 2); X04370 and NC_001348 (herpesvirus 3); NC_001345 (herpesvirus 4); NC_001347 (herpesvirus 5); X83413 and NC_000898 (herpesvirus 6); NC_001716 (herpesvirus 7). Human herpesviruses types 6 and 7 (HHV-6; HHV-7) are disclosed by, e.g., Padilla, et al. (2003) J. Med. Virol. 70 (Suppl. 1)S103-S110. Human herpesvirus 8 (HHV-8), including subtypes A-E, are disclosed in, e.g., Treurnicht, et al. (2002) J. Med. Virol. 66: 235-240. |
| HIV-1 including group M (including subtypes A to J) and group O (including any distinguishable subtypes) (HIV-2, including subtypes A-E. | See, e.g., Smith, et al. (1998) J. Med. Virol. 56: 264-268. See also, e.g., GenBank Acc. Nos. DQ054367; NC_001802; AY968312; DQ011180; DQ011179; DQ011178; DQ011177; AY588971; AY588970; AY781127; AY781126; AY970950; AY970949; AY970948; X61240; AJ006287; AJ508597; and AJ508596. |
| Epstein-Barr virus (EBV), including subtypes A and B. | See, e.g., Peh, et al. (2002) Pathology 34: 446-450. Epstein-Barr virus strain B95-8 (GenBank Acc. No. V01555). |
| Reovirus, including serotypes and strains 1, 2, and 3, type 1 Lang, type 2 Jones, and type 3 Dearing. | See, e.g., Barthold, et al. (1993) Lab. Anim. Sci. 43: 425-430; Roner, et al. (1995) Proc. Natl. Acad. Sci. USA 92: 12362-12366; Kedl, et al. (1995) J. Virol. 69: 552-559. GenBank Acc. No. K02739 (sigma-3 gene surface protein). |
| Cytomegalovirus (CMV) subtypes include CMV subtypes I-VII. | See, e.g., Chern, et al. (1998) J. Infect. Dis. 178: 1149-1153; Vilas Boas, et al. (2003) J. Med. Virol. 71: 404-407; Trincado, et al. (2000) J. Med. Virol. 61: 481-487. GenBank Acc. No. X17403. |
| Rhinovirus, including all serotypes. | Human rhinovirus 2 (GenBank Acc. No. X02316); Human rhinovirus B (GenBank Acc. No. NC_001490); Human rhinovirus 89 (GenBank Acc. No. NC_001617); Human rhinovirus 39 (GenBank Acc. No. AY751783). |
| Adenovirus, including all serotypes. | AY803294; NC_004001; AC_000019; AC_000018; AC_000017; AC_000015; AC_000008; AC_000007; AC_000006; AC_000005; AY737798; AY737797; NC_003266; NC_002067; AY594256; AY594254; AY875648; AJ854486; AY163756; AY594255; AY594253; NC_001460; NC_001405; AY598970; AY458656; AY487947; NC_001454; AF534906; AY45969; AY128640; L19443; AY339865; AF532578. |
| Filoviruses, including Marburg virus and Ebola virus, and strains such as Ebola-Sudan (EBO-S), Ebola-Zaire (EBO-Z), and Ebola-Reston (EBO-R). | See, e.g., Geisbert and Jahrling (1995) Virus Res. 39: 129-150; Hutchinson, et al. (2001) J. Med. Virol. 65: 561-566. Marburg virus (see, e.g., GenBank Acc. No. NC_001608). Ebola virus (see, e.g., GenBank Acc. Nos. NC_006432; AY769362; NC_002549; AF272001; AF086833). |
| Arenaviruses, including lymphocytic choriomeningitis (LCM) virus, Lassa virus, Junin virus, and Machupo virus. | Junin virus, segment S (GenBank Acc. No. NC_005081); Junin virus, segment L (GenBank Acc. No. NC_005080). |
| Rabies virus. | See, e.g., GenBank Acc. Nos. NC_001542; AY956319; AY705373; AF499686; AB128149; AB085828; AB009663. |
| Arboviruses, including West Nile virus, Dengue viruses 1 to 4, Colorado tick fever virus, Sindbis virus, Togaviraidae, Flaviviridae, Bunyaviridae, Reoviridae, Rhabdoviridae, Orthomyxoviridae, and the like. | Dengue virus type 1 (see, e.g., GenBank Acc. Nos. AB195673; AY762084). Dengue virus type 2 (see, e.g., GenBank Acc. Nos. NC_001474; AY702040; AY702039; AY702037). Dengue virus type 3 (see, e.g., GenBank Acc. Nos. AY923865; AT858043). Dengue virus type 4 (see, e.g., GenBank Acc. Nos. AY947539; AY947539; AF326573). Sindbis virus (see, e.g., GenBank Acc. Nos. NC_001547; AF429428; J02363; AF103728). West Nile virus (see, e.g., GenBank Acc. Nos. NC_001563; AY603654). |
| Poxvirus including orthopoxvirus (variola virus, monkeypox virus, vaccinia virus, cowpox virus), yatapoxvirus (tanapox virus, Yaba monkey tumor virus), | Viriola virus (see, e.g., GenBank Acc. Nos. NC_001611; Y16780; X72086; X69198). |

TABLE 1-continued

Antigens.

| Antigen | Reference |
| --- | --- |
| parapoxvirus, and molluscipoxvirus. | |
| Yellow fever. | See, e.g., GenBank Acc. No. NC_002031; AY640589; X03700. |
| Hantaviruses, including serotypes Hantaan (HTN), Seoul (SEO), Dobrava (DOB), Sin Nombre (SN), Puumala (PUU), and Dobrava-like Saaremaa (SAAV). | See, e.g., Elgh, et al. (1997) J. Clin. Microbiol. 35: 1122-1130; Sjolander, et al. (2002) Epidemiol. Infect. 128: 99-103; Zeier, et al. (2005) Virus Genes 30: 157-180. GenBank Acc. No. NC_005222 and NC_005219 (Hantavirus). See also, e.g., GenBank Acc. Nos. NC_005218; NC_005222; NC_005219. |
| Flaviviruses, including Dengue virus, Japanese encephalitis virus, West Nile virus, and yellow fever virus. | See, e.g., Mukhopadhyay, et al. (2005) Nature Rev. Microbiol. 3: 13-22. GenBank Acc. Nos NC_001474 and AY702040 (Dengue). GenBank Acc. Nos. NC_001563 and AY603654. |
| Measles virus. | See, e.g., GenBank Acc. Nos. AB040874 and AY486084. |
| Human parainfluenzaviruses (HPV), including HPV types 1-56. | Human parainfluenza virus 2 (see, e.g., GenBank Acc. Nos. AB176531; NC003443). Human parainfluenza virus 3 (see, e.g., GenBank Acc. No. NC_001796). |
| Influenza virus, including influenza virus types A, B, and C. | Influenza nucleocapsid (see, e.g., GenBank Acc. No. AY626145). Influenza hemagglutinin (see, e.g., GenBank Acc. Nos. AY627885; AY555153). Influenza neuraminidase (see, e.g., GenBank Acc. Nos. AY555151; AY577316). Influenza matrix protein 2 (see, e.g., GenBank Acc. Nos. AY626144(.Influenza basic protein 1 (see, e.g., GenBank Acc. No. AY627897). Influenza polymerase acid protein (see, e.g., GenBank Acc. No. AY627896). Influenza nucleoprotein (see, e.g., GenBank Acc. Nno. AY627895). |
| Influenza A virus subtypes, e.g., swine viruses (SIV): H1N1 influenzaA and swine influenza virus. | Hemagglutinin of H1N1 (GenBank Acc. No. S67220). Influenza A virus matrix protein (GenBank Acc. No. AY700216). Influenza virus A H5H1 nucleoprotein (GenBank Acc. No. AY646426). H1N1 haemagglutinin (GenBank Acc. No. D00837). See also, GenBank Acc. Nos. BD006058; BD006055; BD006052. See also, e.g., Wenrworth, et al. (1994) J. Virol. 68: 2051-2058; Wells, et al. (1991) J.A.M.A. 265: 478-481. |
| Respiratory syncytial virus (RSV), including subgroup A and subgroup B. | Respiratory syncytial virus (RSV) (see, e.g., GenBank Acc. Nos. AY353550; NC_001803; NC001781). |
| Rotaviruses, including human rotaviruses A to E, bovine rotavirus, rhesus monkey rotavirus, and human-RVV reassortments. | Human rotavirus C segment 8 (GenBank Acc. No. AJ549087); Human rotavirus G9 strain outer capsid protein (see, e.g., GenBank Acc. No. DQ056300); Human rotavirus B strain non-structural protein 4 (see, e.g., GenBank Acc. No. AY548957); human rotavirus A strain major inner capsid protein (see, e.g., GenBank Acc. No. AY601554). |
| Polyomavirus, including simian virus 40 (SV40), JC virus (JCV) and BK virus (BKV). | See, e.g., Engels, et al. (2004) J. Infect. Dis. 190: 2065-2069; Vilchez and Butel (2004) Clin. Microbiol. Rev. 17: 495-508; Shivapurkar, et al. (2004) Cancer Res. 64: 3757-3760; Carbone, et al. (2003) Oncogene 2: 5173-5180; Barbanti-Brodano, et al. (2004) Virology 318: 1-9) (SV40 complete genome in, e.g., GenBank Acc. Nos. NC_001669; AF168994; AY271817; AY271816; AY120890; AF345344; AF332562). |
| Coltiviruses, including Colorado tick fever virus, Eyach virus. | Attoui, et al. (1998) J. Gen. Virol. 79: 2481-2489. Segments of Eyach virus (see, e.g., GenBank Acc. Nos. AF282475; AF282472; AF282473; AF282478; AF282476; NC_003707; NC_003702; NC_003703; NC_003704; NC_003705; NC_003696; NC_003697; NC_003698; NC_003699; NC_003701; NC_003706; NC_003700; AF282471; AF282477). |
| Calciviruses, including the genogroups Norwalk, Snow Mountain group (SMA), and Saaporo. | Snow Mountain virus (see, e.g., GenBank Acc. No. AY134748). |
| Parvoviridae, including dependovirus, parvovirus (including parvovirus B19), and erythrovirus. | See, e.g., Brown (2004) Dev. Biol. (Basel) 118: 71-77; Alvarez-Lafuente, et al. (2005) Ann. Rheum. Dis. 64: 780-782; Ziyaeyan, et al. (2005) Jpn. J. Infect. Dis. 58: 95-97; Kaufman, et al. (2005) Virology 332: 189-198. |

Other organisms for which suitable antigens are known in the art include, but are not limited to, *Chlamydia trachomatis*, *Streptococcus pyogenes* (Group A Strep), *Streptococcus agalactia* (Group B Strep), *Streptococcus pneumonia*, *Staphylococcus aureus*, *Escherichia coli*, *Haemophilus influenzae*, *Neisseria meningitidis*, *Neisseria gonorrheae*, *Vibrio cholerae*, *Salmonella* species (including *typhi*, *typhimurium*), *enterica* (including *Helicobactor pylori Shigella*

*flexneri* and other Group D *shigella* species), *Burkholderia mallei, Burkholderia pseudomallei, Klebsiella pneumonia, Clostridium* species (including *C. difficile*), *Vibrio parahaemolyticus* and *V. vulnificus*. This list is not meant to be limiting.

Pharmaceutical Compositions

The term "pharmaceutical" as used herein refers to a chemical substance intended for use in the cure, treatment, or prevention of disease and which is subject to an approval process by the U.S. Food and Drug Administration (or a non-U.S. equivalent thereof) as a prescription or over-the-counter drug product. Details on techniques for formulation and administration of such compositions may be found in Remington, The Science and Practice of Pharmacy 21$^{st}$ Edition (Mack Publishing Co., Easton, Pa.) and Nielloud and Marti-Mestres, Pharmaceutical Emulsions and Suspensions: 2$^{nd}$ Edition (Marcel Dekker, Inc, New York).

For the purposes of this disclosure, the pharmaceutical compositions may be administered by a variety of means including orally, parenterally, by inhalation spray, topically, or rectally in formulations containing pharmaceutically acceptable carriers, adjuvants and vehicles. The term parenteral as used here includes but is not limited to subcutaneous, intravenous, intramuscular, intraarterial, intradermal, intrathecal and epidural injections with a variety of infusion techniques. Intraarterial and intravenous injection as used herein includes administration through catheters. Administration via intracoronary stents and intracoronary reservoirs is also contemplated. Intra-tumoral administration of the compounds of the present invention may directly activate locally infiltrating DC, directly promote tumor cell apoptosis or sensitize tumor cells to cytotoxic agents. The term oral as used herein includes, but is not limited to oral ingestion, or delivery by a sublingual or buccal route. Oral administration includes fluid drinks, energy bars, as well as pill formulations.

Pharmaceutical compositions may be in any form suitable for the intended method of administration. When used for oral use for example, tablets, troches, lozenges, aqueous or oil suspensions, dispersible powders or granules, emulsions, hard or soft capsules, syrups or elixirs may be prepared. Compositions intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing a drug compound in admixture with non-toxic pharmaceutically acceptable excipient which are suitable for manufacture of tablets are acceptable. These excipients may be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents; such as magnesium stearate, stearic acid or talc. Tablets may be uncoated, or may be coated by known techniques including enteric coating, colonic coating, or microencapsulation to delay disintegration and adsorption in the gastrointestinal tract and/or provide a sustained action over a longer period. For example, a time delay material such as glyceryl monostearate or glyceryl distearate alone or with a wax may be employed.

Formulations for oral use may be also presented as hard gelatin capsules where the drug compound is mixed with an inert solid diluent, for example calcium phosphate or kaolin, or as soft gelatin capsules wherein the active ingredient is mixed with water or an oil medium, such as peanut oil, liquid paraffin or olive oil.

Pharmaceutical compositions may be formulated as aqueous suspensions in admixture with excipients suitable for the manufacture of aqueous-suspensions. Such excipients include a suspending agent, such as sodium carboxymethylcellulose, methylcellulose, hydroxypropyl methylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxybenzoate, one or more coloring agents, one or more flavoring agents and one or more sweetening agents, such as sucrose or saccharin.

Oil suspensions may be formulated by suspending the active ingredient in a vegetable oil, such as *arachis* oil, olive oil, sesame oil or coconut oil, or a mineral oil such as liquid paraffin. The oral suspensions may contain a thickening agent, such as beeswax, hard paraffin or cetyl alcohol. Sweetening agents, such as those set forth above, and flavoring agents may be added to provide a palatable oral preparation. These compositions may be preserved by the addition of an antioxidant such as ascorbic acid.

Dispersible powders and granules of the disclosure suitable for preparation of an aqueous suspension by the addition of water provide the active ingredient in admixture with a dispersing or wetting agent, a suspending agent, and one or more preservatives. Suitable dispersing or wetting agents and suspending agents are exemplified by those disclosed above. Additional excipients, for example sweetening, flavoring and coloring agents, may also be present.

The pharmaceutical compositions of the disclosure may also be in the form of oil-in-water emulsions. The oily phase may be a vegetable oil, such as olive oil or *arachis* oil, a mineral oil, such as liquid paraffin, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan monooleate, and condensation products of these partial esters with ethylene oxide, such as polyoxyethylene sorbitan monooleate. The emulsion may also contain sweetening and flavoring agents.

Syrups and elixirs may be formulated with sweetening agents, such as glycerol, sorbitol or sucrose. Such formulations may also contain a demulcent, a preservative, a flavoring or a coloring agent.

The pharmaceutical compositions of the disclosure may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent such as a solution in 1,3-butane-diol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The amount of active ingredient that may be combined with the carrier material to produce a single dosage form will vary depending upon the host treated and the particular mode of administration. For example, a time-release formulation intended for oral administration to humans may contain approximately 20 to 500 mg of active material compounded with an appropriate and convenient amount of carrier material which may vary from about 5 to about 95% of the total compositions. It is preferred that the pharmaceutical composition be prepared which provides easily measurable amounts for administration. Typically, an effective amount to be administered systemically is about 0.1 mg/kg to about 100 mg/kg and depends upon a number of factors including, for example, the age and weight of the subject (e.g., a mammal such as a human), the precise condition requiring treatment and its severity, the route of administration, and will ultimately be at the discretion of the attendant physician or veterinarian. It will be understood, however, that the specific dose level for any particular patient will depend on a variety of factors including the activity of the specific compound employed, the age, body weight, general health, sex and diet of the individual being treated; the time and route of administration; the rate of excretion; other drugs which have previously been administered; and the severity of the particular condition undergoing therapy, as is well understood by those skilled in the art.

As noted above, formulations of the disclosure suitable for oral administration may be presented as discrete units such as capsules, cachets or tablets each containing a predetermined amount of the active ingredient, as a powder or granules; as a solution or a suspension in an aqueous or non-aqueous liquid, or as an oil-in-water liquid emulsion or a water-in-oil liquid emulsion. The pharmaceutical compositions may also be administered as a bolus, electuary or paste.

A tablet may be made by compression or molding, optionally with one or more accessory ingredients. Compressed tablets may be prepared by compressing in a suitable machine the active ingredient in a free flowing form such as a powder or granules, optionally mixed with a binder (e.g., povidone, gelatin, hydroxypropyl ethyl cellulose), lubricant, inert diluent, preservative, disintegrant (e.g., sodium starch glycolate, cross-linked povidone, cross-linked sodium carboxymethyl cellulose) surface active or dispersing agent. Molded tablets may be made in a suitable machine using a mixture of the powdered compound moistened with an inert liquid diluent. The tablets may optionally be coated or scored and may be formulated so as to provide slow or controlled release of the active ingredient therein using, for example, hydroxypropyl methylcellulose in varying proportions to provide the desired release profile. Tablets may optionally be provided with an enteric or colonic coating to provide release in parts of the gut other than the stomach. This is particularly advantageous with the compounds of formula 1 when such compounds are susceptible to acid hydrolysis.

Formulations suitable for topical administration in the mouth include lozenges comprising the active ingredient in a flavored base, usually sucrose and acacia or tragacanth; pastilles comprising the active ingredient in an inert base such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous isotonic sterile injection solutions which may contain antioxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose sealed containers, for example, ampoules and vials, and may be stored in a freeze-dried (lyophilized) condition requiring only the addition of the sterile liquid carrier, for example water for injections, immediately prior to use. Injection solutions and suspensions may be prepared from sterile powders, granules and tablets of the kind previously described.

As used herein, pharmaceutically acceptable salts include, but are not limited to: acetate, pyridine, ammonium, piperazine, diethylamine, nicotinamide, formic, urea, sodium, potassium, calcium, magnesium, zinc, lithium, cinnamic, methylamino, methanesulfonic, picric, tartaric, triethylamino, dimethylamino, and tris(hydroxymethyl)aminomethane. Additional pharmaceutically acceptable salts are known to those skilled in the art.

An effective amount for a particular patient may vary depending on factors such as the condition being treated, the overall health of the patient, the route and dose of administration and the severity of side effects. Guidance for methods of treatment and diagnosis is available (see, e.g., Maynard, et al. (1996) A Handbook of SOPs for Good Clinical Practice, Interpharm Press, Boca Raton, Fla.; Dent (2001) Good Laboratory and Good Clinical Practice, Urch Publ., London, UK).

An effective amount may be given in one dose, but is not restricted to one dose. Thus, the administration can be two, three, four, five, six, seven, eight, nine, ten, eleven, twelve, thirteen, fourteen, fifteen, sixteen, seventeen, eighteen, nineteen, twenty, or more, administrations of pharmaceutical composition. Where there is more than one administration of a pharmaceutical composition in the present methods, the administrations can be spaced by time intervals of one minute, two minutes, three, four, five, six, seven, eight, nine, ten, or more minutes, by intervals of about one hour, two hours, three, four, five, six, seven, eight, nine, ten, 11, 12, 13, 14, 15, 16, 17, 18, 19, 20, 21, 22, 23, 24 hours, and so on. In the context of hours, the term "about" means plus or minus any time interval within 30 minutes. The administrations can also be spaced by time intervals of one day, two days, three days, four days, five days, six days, seven days, eight days, nine days, ten days, 11 days, 12 days, 13 days, 14 days, 15 days, 16 days, 17 days, 18 days, 19 days, 20 days, 21 days, and combinations thereof. The invention is not limited to dosing intervals that are spaced equally in time, but encompass doses at non-equal intervals.

A dosing schedule of, for example, once/week, twice/week, three times/week, four times/week, five times/week, six times/week, seven times/week, once every two weeks, once every three weeks, once every four weeks, once every five weeks, and the like, is available for the invention. The dosing schedules encompass dosing for a total period of time of, for example, one week, two weeks, three weeks, four weeks, five weeks, six weeks, two months, three months, four months, five months, six months, seven months, eight months, nine months, ten months, eleven months, and twelve months.

Provided are cycles of the above dosing schedules. The cycle can be repeated about, e.g., every seven days; every 14 days; every 21 days; every 28 days; every 35 days; 42 days; every 49 days; every 56 days; every 63 days; every 70 days; and the like. An interval of non dosing can occur between a cycle, where the interval can be about, e.g., seven days; 14 days; 21 days; 28 days; 35 days; 42 days; 49 days; 56 days; 63 days; 70 days; and the like. In this context, the term "about" means plus or minus one day, plus or minus two days, plus or minus three days, plus or minus four days, plus or minus five days, plus or minus six days, or plus or minus seven days.

Methods for co-administration with an additional therapeutic agent are well known in the art (Hardman, et al. (eds.) (2001) Goodman and Gilman's The Pharmacological Basis of Therapeutics, 10th ed., McGraw-Hill, New York, N.Y.; Poole and Peterson (eds.) (2001) Pharmacotherapeutics for Advanced Practice: A Practical Approach, Lippincott, Williams & Wilkins, Phila., Pa.; Chabner and Longo (eds.) (2001) Cancer Chemotherapy and Biotherapy, Lippincott, Williams & Wilkins, Phila., Pa.).

As noted, the compositions of the present invention are preferably formulated as pharmaceutical compositions for parenteral or enteral delivery. A typical pharmaceutical composition for administration to an animal comprises a pharmaceutically acceptable vehicle such as aqueous solutions, non-toxic excipients, including salts, preservatives, buffers and the like. See, e.g., *Remington's Pharmaceutical Sciences*, 15th Ed., Easton ed., Mack Publishing Co., pp 1405-1412 and 1461-1487 (1975); *The National Formulary XIV*, 14th Ed., American Pharmaceutical Association, Washington, D.C. (1975). Examples of non-aqueous solvents are propylene glycol, polyethylene glycol, vegetable oil and injectable organic esters such as ethyloleate. Aqueous carriers include water, alcoholic/aqueous solutions, saline solutions, parenteral vehicles such as sodium chloride, Ringer's dextrose, etc. Intravenous vehicles include fluid and nutrient replenishers. Preservatives include antimicrobial agents, antioxidants, chelating agents and inert gases. The pH and exact concentration of the various components the pharmaceutical composition are adjusted according to routine skills in the art.

Repeated administrations of a particular vaccine (homologous boosting) have proven effective for boosting humoral responses. Such an approach may not be effective at boosting cellular immunity because prior immunity to the vector tends to impair robust antigen presentation and the generation of appropriate inflammatory signals. One approach to circumvent this problem has been the sequential administration of vaccines that use different antigen-delivery systems (heterologous boosting). In a heterologous boosting regimen, at least one prime or boost delivery comprises delivery of the inactivated tumor cell/cyclic purine dinucleotide compositions described herein. The heterologous arm of the regimen may comprise delivery of antigen using one or more of the following strategies:

inactivated or attenuated bacteria or viruses comprising the antigen of interest, which are particles that have been treated with some denaturing condition to render them ineffective or inefficient in mounting a pathogenic invasion;

purified antigens, which are typically naturally-produced antigens purified from a cell culture of the pathogen or a tissue sample containing the pathogen, or a recombinant version thereof;

live viral or bacterial delivery vectors recombinantly engineered to express and/or secrete antigens in the host cells of the subject. These strategies rely on attenuating (e.g., via genetic engineering) the viral or bacterial vectors to be non-pathogenic and non-toxic;

antigen presenting cell (APC) vectors, such as a dendritic cell (DC) vector, which comprise cells that are loaded with an antigen, or transfected with a composition comprising a nucleic acid encoding the antigen (e.g., Provenge® (Dendreon Corporation) for the treatment of castration-resistant metastatic prostate cancer);

liposomal antigen delivery vehicles; and naked DNA vectors and naked RNA vectors which may be administered by a gene gun, electroporation, bacterial ghosts, microspheres, microparticles, liposomes, polycationic nanoparticles, and the like.

A prime vaccine and a boost vaccine can be administered by any one or combination of the following routes. In one aspect, the prime vaccine and boost vaccine are administered by the same route. In another aspect, the prime vaccine and boost vaccine are administered by different routes. The term "different routes" encompasses, but is not limited to, different sites on the body, for example, a site that is oral, non-oral, enteral, parenteral, rectal, intranode (lymph node), intravenous, arterial, subcutaneous, intramuscular, intratumor, peritumor, intratumor, infusion, mucosal, nasal, in the cerebrospinal space or cerebrospinal fluid, and so on, as well as by different modes, for example, oral, intravenous, and intramuscular.

An effective amount of a prime or boost vaccine may be given in one dose, but is not restricted to one dose. Thus, the administration can be two, three, four, five, six, seven, eight, nine, ten, eleven, twelve, thirteen, fourteen, fifteen, sixteen, seventeen, eighteen, nineteen, twenty, or more, administrations of the vaccine. Where there is more than one administration of a vaccine the administrations can be spaced by time intervals of one minute, two minutes, three, four, five, six, seven, eight, nine, ten, or more minutes, by intervals of about one hour, two hours, three, four, five, six, seven, eight, nine, ten, 11, 12, 13, 14, 15, 16, 17, 18, 19, 20, 21, 22, 23, 24 hours, and so on. In the context of hours, the term "about" means plus or minus any time interval within 30 minutes. The administrations can also be spaced by time intervals of one day, two days, three days, four days, five days, six days, seven days, eight days, nine days, ten days, 11 days, 12 days, 13 days, 14 days, 15 days, 16 days, 17 days, 18 days, 19 days, 20 days, 21 days, and combinations thereof. The invention is not limited to dosing intervals that are spaced equally in time, but encompass doses at non-equal intervals, such as a priming schedule consisting of administration at 1 day, 4 days, 7 days, and 25 days, just to provide a non-limiting example.

EXAMPLES

The following examples serve to illustrate the present invention. These examples are in no way intended to limit the scope of the invention.

Example 1. General Methods

Anhydrous solvents and reagents suitable for solution phase oligonucleotide synthesis were purchased and handled under dry argon or nitrogen using anhydrous technique. Amidite coupling reactions and cyclizations were carried out in anhydrous acetonitrile or pyridine under dry argon or nitrogen. The starting materials for all reactions in dry pyridine were dried by concentration (three times) from pyridine. Preparative silica gel flash chromatography was carried out using Fluka 60A high-purity grade or Merck Grade 9385 silica using gradients of methanol in dichloromethane. Analytical HPLC was carried out on a Varian ProStar 210 HPLC system with a ProStar 330 photodiode array detector monitoring at 254 nm using a either a Varian Microsorb 10 micron C18 250×4.6 mm or a Varian 3micronC18 100×4.6 mm column and gradients of 10 mM TEAA and acetonitrile. Preparative HPLC was carried out on a Shimadzu preparative LC20-AP HPLC system, equipped with a SPD-20A UV/Vis detector monitoring at 254 nm on a Varian Microsorb 60-8 C-18 41.6×250 mm column using gradients of 10 mM TEAA and acetonitrile at a flow rate of 50 ml/min. Solid phase extractions using C-18 Sep-Pak (Waters) were carried out at loadings of 3% (wt/wt). LC/MS (ESI/APCI) was obtained on a single quadrapole Shimadzu 2010EV instrument with PDA, MS, and ELSD detection using a Shimadzu LC20D analytical HPLC. High resolution FT-ICR mass spec was obtained from both WM Keck Foundation Biotechnology Resource Laboratory at Yale University in New Haven, Conn., and the QB3/Chemistry Mass Spect Lab at UC Berkeley.

$^1$H, $^{31}$P, $^1$H-$^1$H COSY (2D NMR correlation spectroscopy), $^1$H-$^{31}$P HMBC (heteronuclear multiple-bond correlation spectroscopy) spectra were acquired in d6-DMSO with 10 uL D$_2$O (16 hr delay after D$_2$O addition) at 45° C. on a Varian INOVA-500 NMR spectrometer operating at 500 MHz for 1H and 202 MHz for 31P. The resulting FIDs were transferred to a PC and processed using NUTS NMR processing software from Acorn NMR Inc. The chemical shifts were referenced to the DMSO solvent, 2.50 ppm for 1H. Per IUPAC recommendations for referencing of NMR spectral, the 31P chemical shifts were referenced using the "unified scale" to the absolute 1H frequency of 0 ppm. Some of the 1H and 31P spectra were acquired on a JEOL ECX-400 NMR spectrometer operating at 400 MHz for 1H and 162 MHz for 31P.

The gradient COSY spectrum was acquired in absolute value mode using 2048 data points in the direct dimension and 256 time points in the indirect dimension. Both dimensions were apodized using sinebell squared functions. The indirect dimension was zero filled to give a final matrix size of 2048×2048 points and a resolution of 3.91 Hz/data point in both dimensions.

Assignment of regiochemistry at phosphodiester linkage: 1H-1H COSY in combination with $^1$H-$^{31}$P HMBC (and in some cases phosphorous decoupling) experiments were used to provide direct evidence that the regiochemistry of the phosphodiester linkages are 2',5'-3',5' (see discussion in experimental for 9a and FIG. 3A-G). Similar $^1$H-$^{31}$P HMBC experiments confirmed the non-canonical regiochemistry (2',5'-3',5') at the phoshodiester linkage of all the synthesized cyclic di-nucleotides after final silyl deprotection or ion exchange Assignment of the RR- and RS-diastereomers (main CDN products of the synthetic sequence) followed literature methods (Zhao et al. *Nucleosides, Nucleotides and Nucleic Acids* 289:352-378, 2009).

Figure 2A:
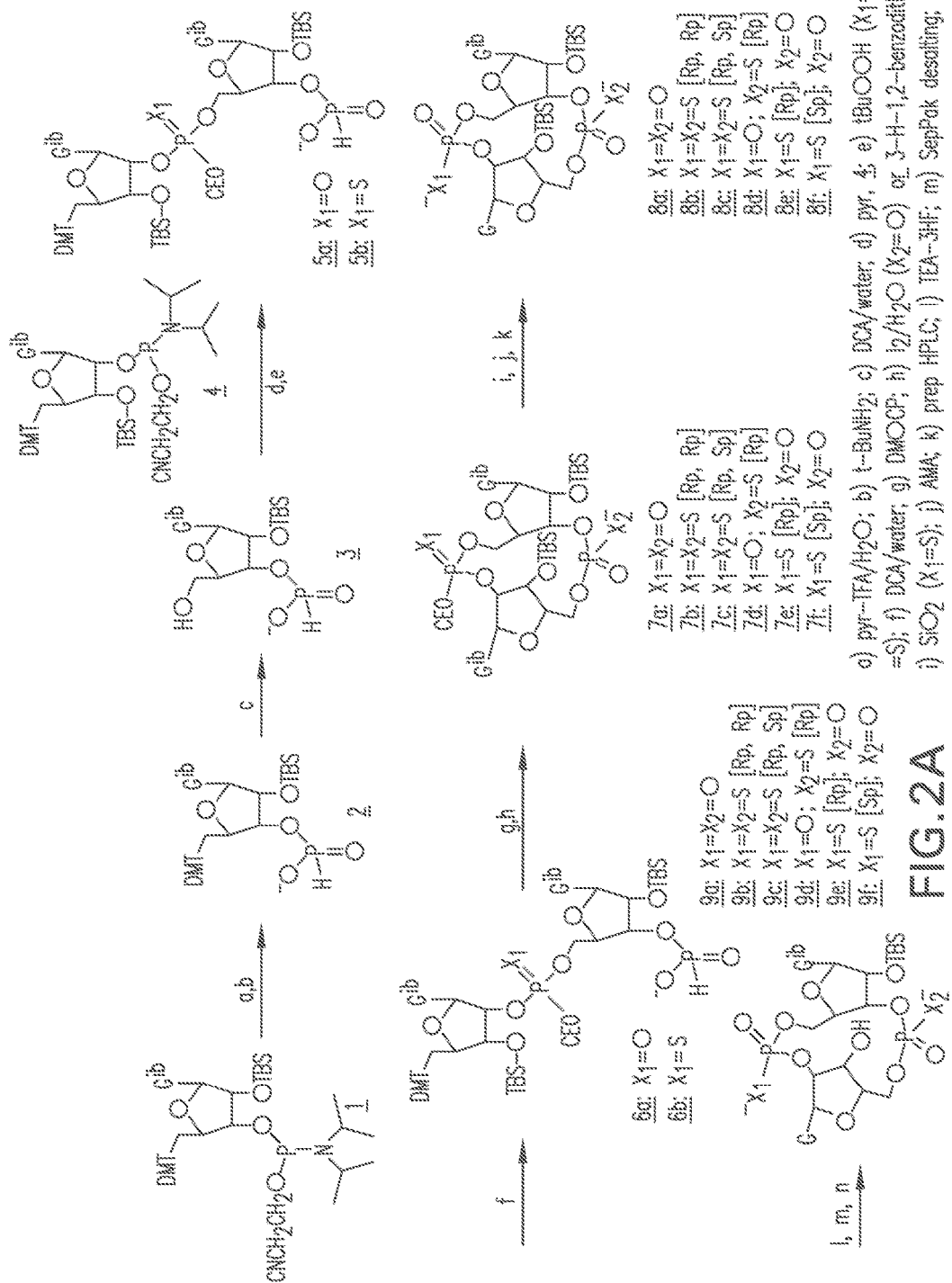
FIG. 2A depicts a synthesis scheme for c-[G(2',5')pG(3',5')p] and dithio derivatives.
Figure 2B:
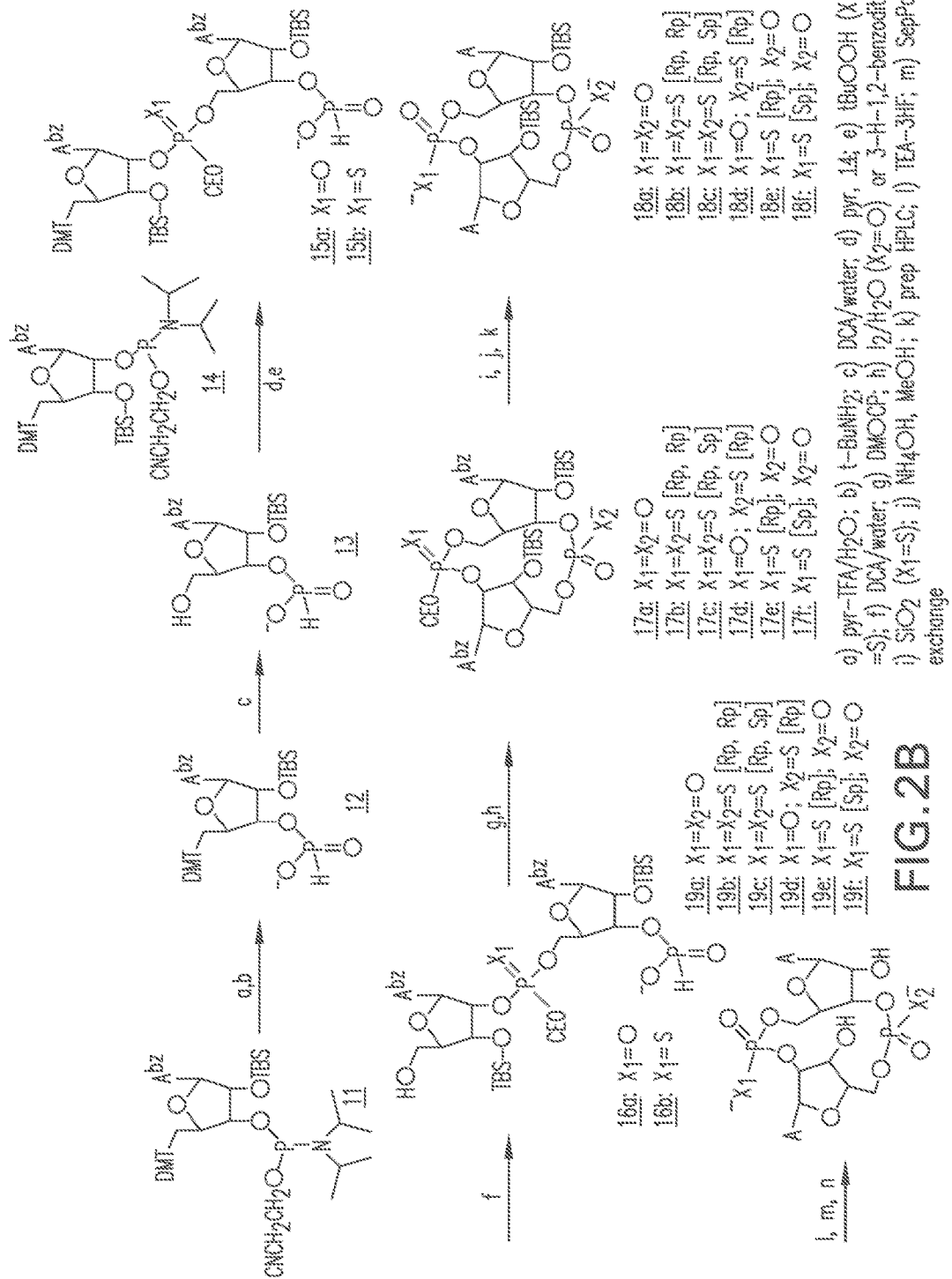
FIG. 2B depicts a synthesis scheme for c-[A(2',5')pA(3',5')p] and dithio derivatives.
Figure 2C:
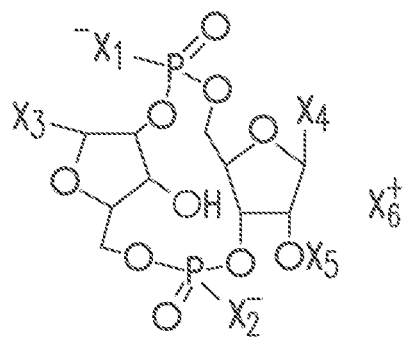
FIG. 2C depicts structures of compounds 10, 20, 21, 22, and 23.

All CDN products (FIG. 2A-2C) were ≥95% pure as indicated by C18 reverse phase HPLC analysis (UV detection at 254 nm)

Abbreviations and Acronyms: Guanine=G. isobutyryl guanine=G$^{ib}$. 4,4-dimethoxytrityl=DMT. OCH$_2$CH$_2$CN=CEO. tert-butyldimethylsilyl=TBS. adenine=A. benzoyl adenine=A$^{Bz}$. cyclic-[A(2',5')pA(3',5')p]=ML-CDA=19a(TEA salt). dithio-[R$_P$, R$_P$]-cyclic-[A(2',5')pA(3',5')p]=ML-RR-CDA=19b (TEA salt); 21 (sodium salt); 22 (ammonium salt). dithio-[R$_P$,S$_P$]-cyclic-[A(2',5')pA(3',5')p]=ML-RS-CDA=19c(TEA salt). cyclic-[G(2',5')pG(3',5')p]=ML-CDG=9a(TEA salt). dithio-[R$_P$,R$_P$]-cyclic-[G(2',5')pG(3',5')p]=ML-RR-CDG=9b (TEA salt). dithio-[R$_P$,S$_P$]-cyclic-[G(2',5')pG(3',5')p]=ML-RS-CDG=9c (TEA salt). cyclic[G(2',5')pA(3',5')p]=ML-cGAMP. dithio-[R$_P$,R$_P$]-cyclic-[G(2',5')pA(3',5')p]=ML-RR-cGAMP=20 (TEA salt). monothio-cyclic-[A(2',5')pA(3',5')Rp]=ML-3',5'-R-CDA=19d (TEA salt). 2'-O-myristoyl-cyclic-[G(2',5')pG(3',5')p]=C14-ML-CDG=10 (TEA salt). ML-cGAMP=2',3'-cGAMP=cyclic-[G(2',5')pA(3',5')p]=23 (TEA salt)

ML-cGAMP (structure 23 in FIG. 2c) was prepared enzymatically from cellular cGAS and purified by prep HPLC.

Example 2. General Experimental for the ML-CDG Series (FIG. 2a): Synthesis of Cyclic [G(2',5')pG(3',5')p] 9a 1) Preparation of 3. To a solution of 4.87 g (5.0 mmol) N$^2$-isobutyryl-5'-O-(4,4'-dimethoxytrityl)-2'-O-tert-butyldimethylsilyl-3'-O-[(2-cyanoethyl)-N,N-diisopropylaminophinyl]guanosine (1) in 25 ml acetonitrile was added 0.18 ml (10 mmole) water and 1.23 g (6 mmole) pyridinium trifluoroacetate. After 5 minutes stirring at room temperature 25 ml t-butylamine was added and the reaction stirred for 15 minutes at room temperature. The solvents were removed under reduced pressure to give 2 as a foam which was then co-evaporated with acetonitrile (2×50 ml). To a solution of 2 in 60 ml dichloromethane was added 0.9 ml (50 mmole) water and 60 ml 6% (v/v) dichloroacetic acid in dichloromethane (44 mmol). After 10 minutes at room temperature the reaction was quenched by the addition of pyridine (7.0 ml, 87 mmol). The reaction mixture was concentrated to an oil which was dried by three co-evaporations with 40 ml anhydrous acetonitrile, the last time leaving 3 in a volume of 12 ml.

2) Preparation of a dry solution of 4. N$^2$-isobutyryl-5'-O-(4,4'-dimethoxytrityl)-3'-O-tert-butyldimethylsilyl-2'-O-[(2-cyanoethyl)-N,N-diisopropylaminophinyl]guanosine (4, 6.33 g, 6.5 mmole) was dissolved in 40 ml anhydrous acetonitrile and dried by three co-evaporations with 40 ml anhydrous acetonitrile, the last time leaving 20 ml. Ten 3A molecular sieves were added and the solution stored under argon until use.

3) Coupling of 3 and 4 to give after oxidation and detritylation the 2',5'linear dimer 6a. Azeo dried 4 (6.5 mmole) in 20 ml acetonitrile was added via syringe to 3 (5.0 mmole). After 5 minutes stirring at room temperature, 2.37 ml (15 mmole) of 5.5 M t-butylhydroperoxide in decane was added and the reaction stirred for 30 minutes at room temperature. The reaction was then cooled to 0° C., and 1.25 g NaHSO$_3$ in 2.5 ml water was added, the ice bath removed, and the reaction stirred for 5 minutes. The reaction was concentrated to a foam, which was then taken up in 80 ml dichloromethane. 0.9 ml water and 80 ml 6% (v/v) dichloroacetic acid in dichloromethane was added, and the reaction stirred for 10 minutes at room temperature. 50 ml pyridine was added to quench the dichloroacetic acid. The solvents were removed under reduced pressure to give crude 6a as a solid.

4) Cyclization of 6a to give 7a. 6a was dissolved in 50 ml dry pyridine and 5 ml (1/10th of total reaction, approximately 0.5 mmole) was transferred via syringe to 150 ml dry pyridine. This was concentrated to a volume of approximately 100 ml. 2-chloro-5,5-dimethyl-1,3,2-dioxaphosphorinane-2-oxide (DMOCP, 0.35 g, 1.8 mmole) was then added and the reaction stirred for 30 minutes at room temperature. 0.32 ml water was added immediately followed by addition of 0.16 g iodine, and the reaction stirred for 5 minutes at room temperature. The reaction mix was then poured into 350 ml water containing 0.1 g NaHSO3 and stirred for 5 minutes at room temperature. 2 g of NaHCO3 was slowly added with stirring, then poured into a separatory funnel and extracted with 400 ml 1:1 ethyl acetate:diethylether. The aqueous layer was extracted again with 400 ml 1:1 ethyl acetate:diethylether, and the organic layers were combined, dried over sodium sulfate, and concentrated under reduced pressure to yield 0.75 g of a mixture containing 7a, the fully-protected cyclic-[G(2',5')pG(3',5')p].

5) Deprotection of crude 7a with methylamine to give crude 8a. To 750 mg of 7a was added 18 ml of methylamine in anhydrous ethanol (33% by weight) and the mixture was stirred for 90 min at which point analysis by HPLC indicated the reaction was complete. The reaction mixture was concentrated to give an oil which upon treatment with 10 ml of hexane/ethyl acetate (50:50) produced an off-white solid. The trituration/wash solvent was decanted and residual solvent was removed under reduced pressure to give 240 mg of an off-white solid.

Figure 3B:
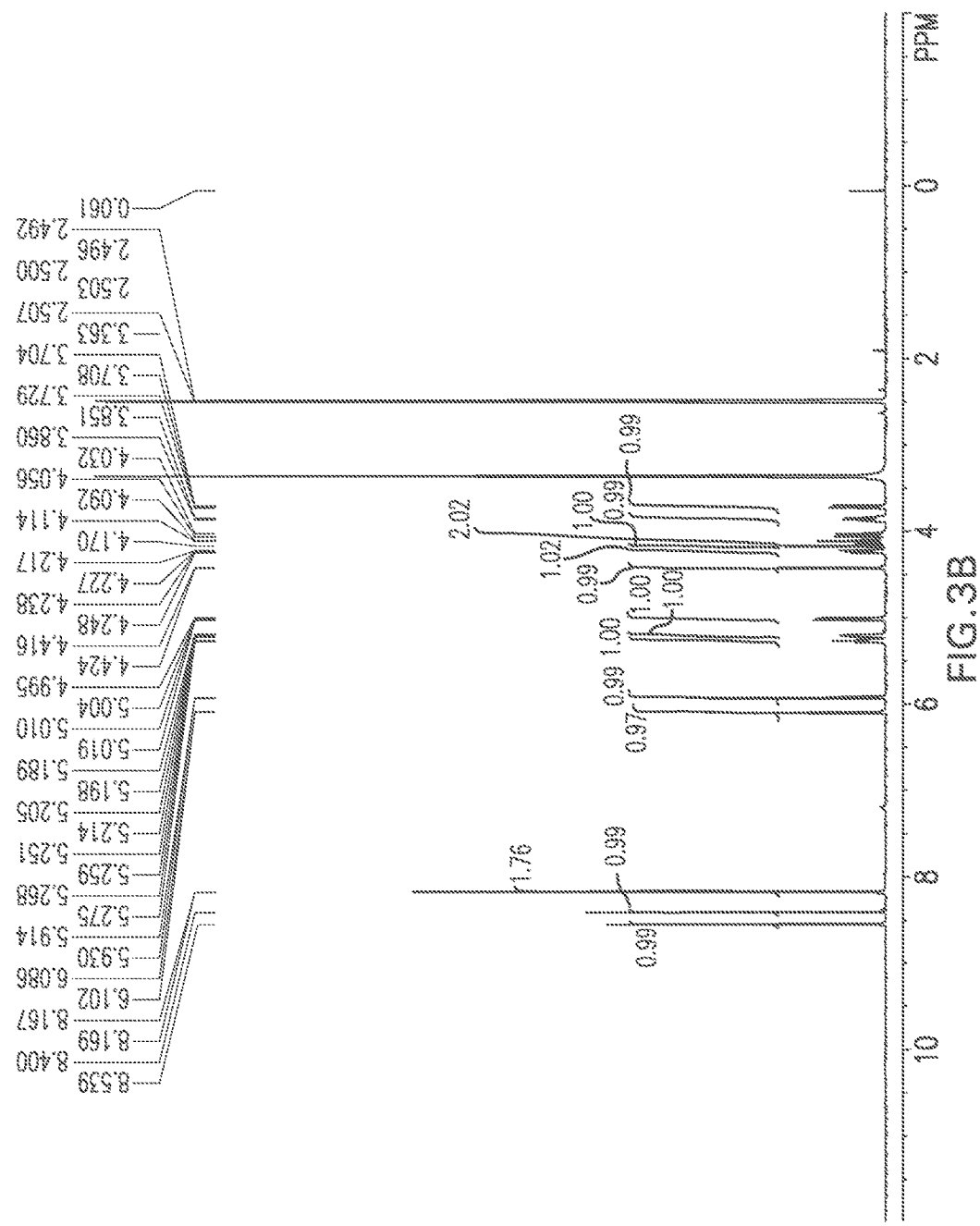
Figure 3C:
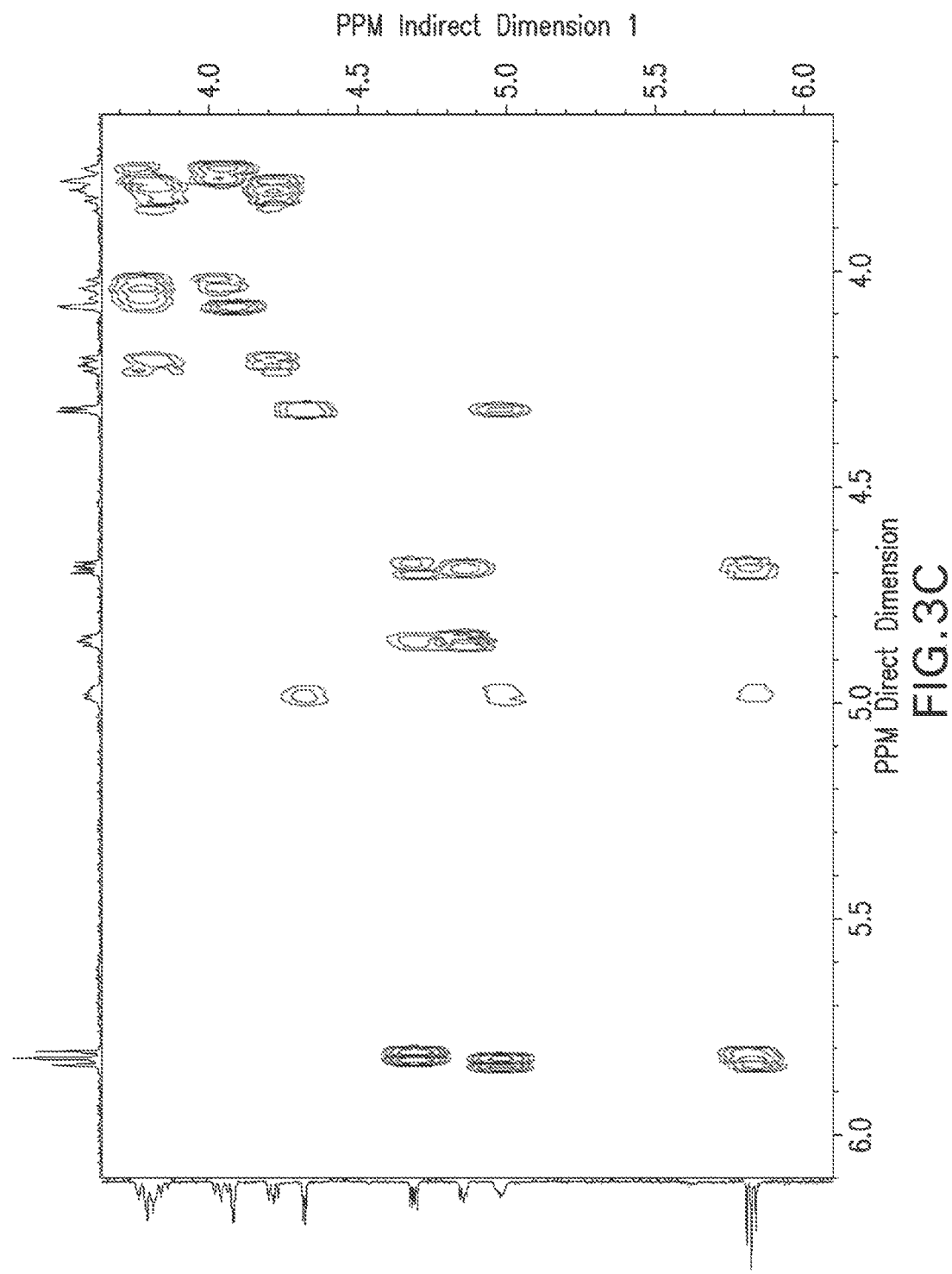
Figure 3D:
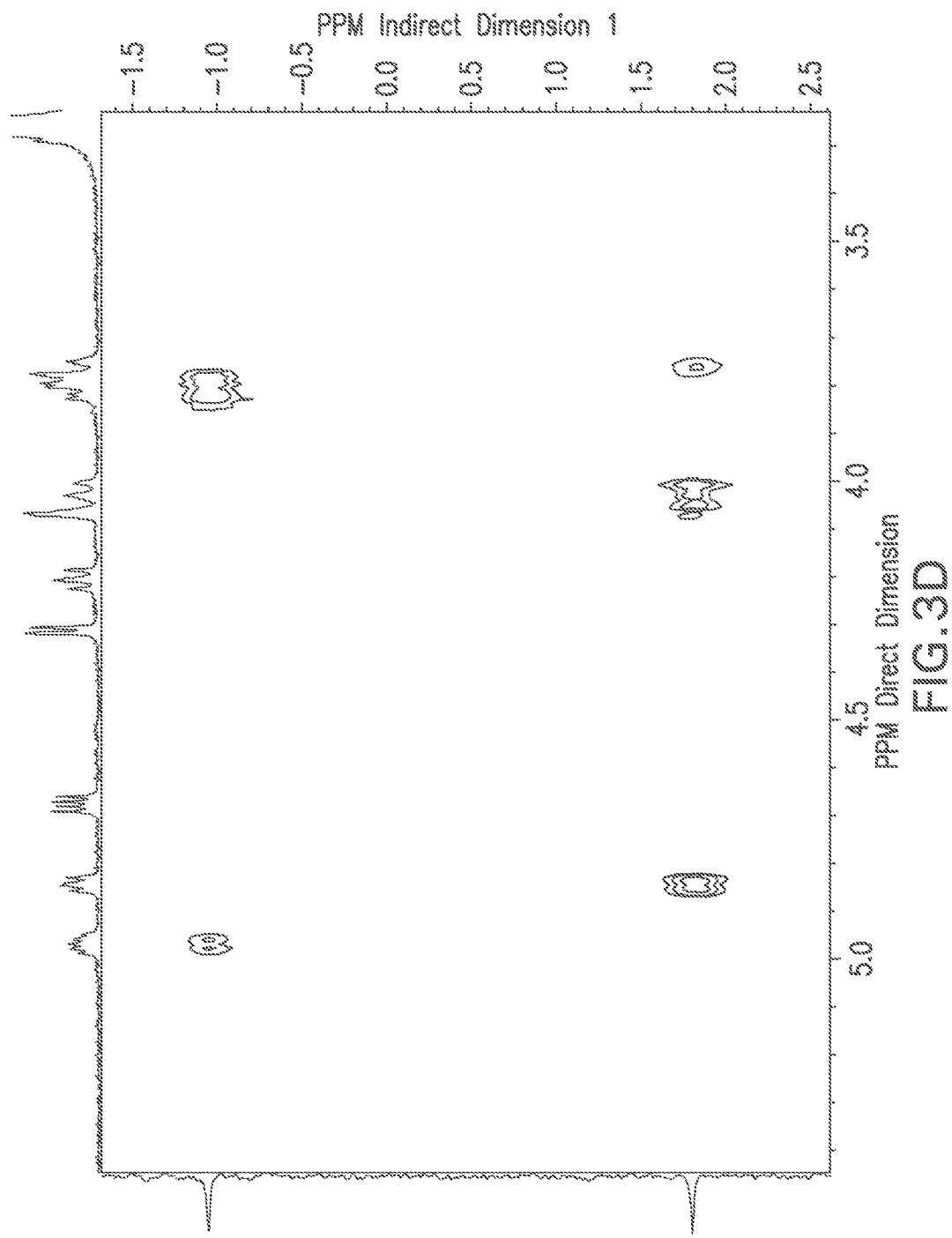
FIG. 3D depicts $^1$H-NMR results for compound 21.
Figure 3E:
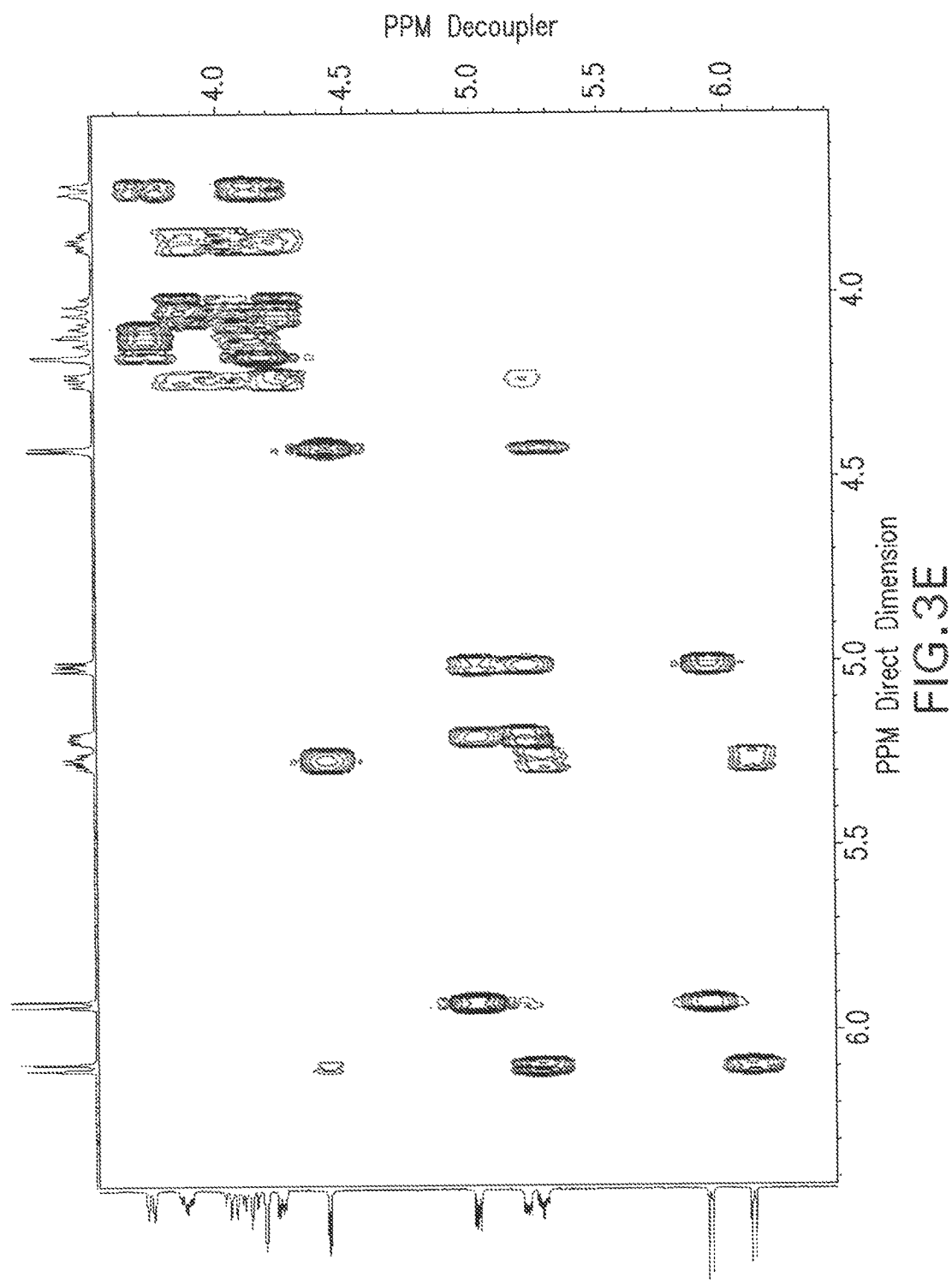
FIG. 3E depicts COSY (3.5-6.0 ppm $^1$H-axis) results for compound 21.
Figure 3F:
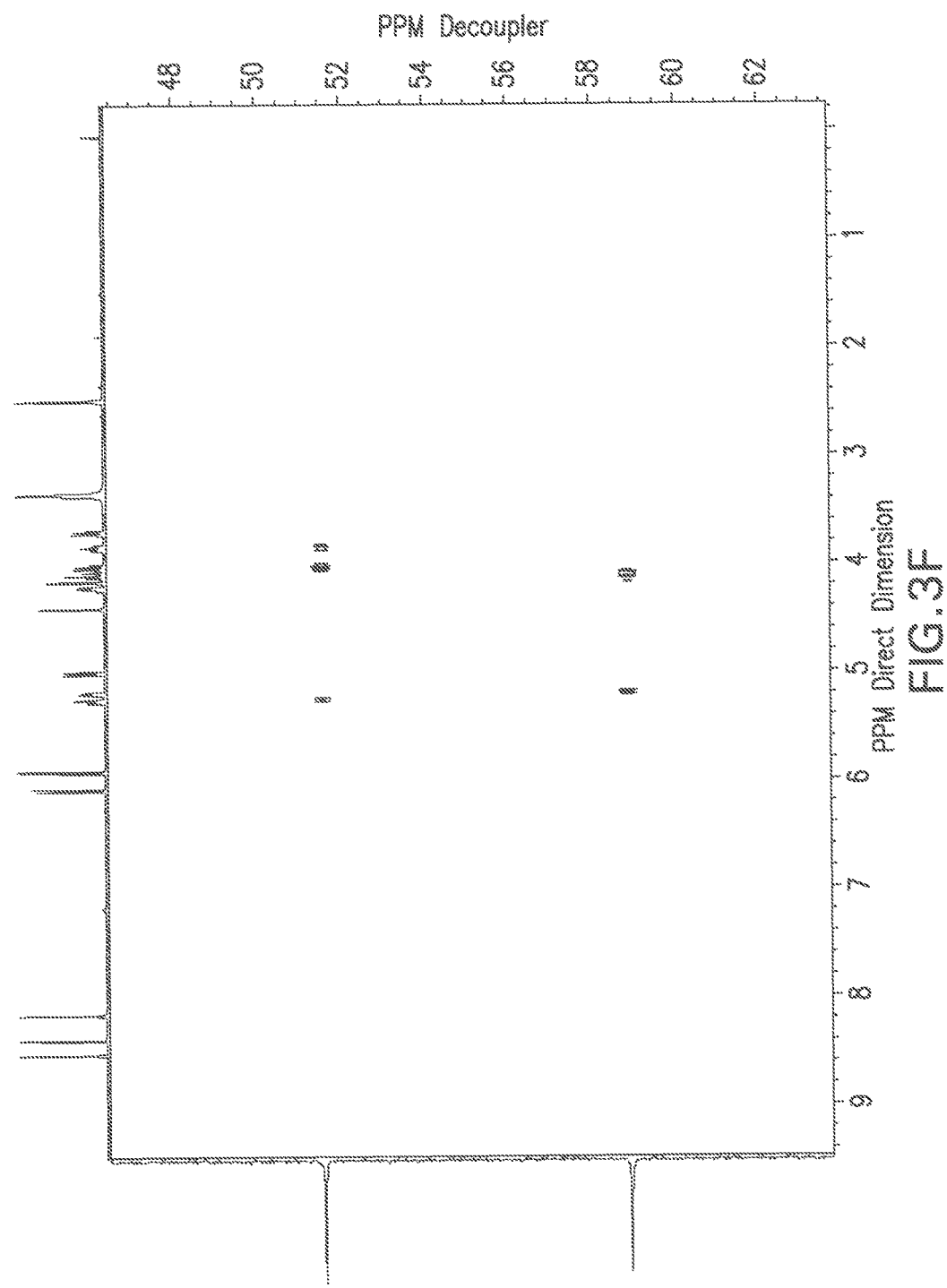
FIG. 3F depicts HMBC (0-9.5 ppm $^1$H-axis) results for compound 21.

6) Preparative HPLC of crude 8a. A 120 mg portion of crude 8a was taken up in 5 ml of CH3CN/10 mM aqueous triethylammonium acetate (20/80). After 0.45 micron PTFE filtration the injection sample was applied to a C-18 Dynamax column (40×250 mm). Elution was performed with a gradient of acetonitrile and 10 mM aqueous triethylammonium acetate (20% to 50% $CH_3CN$ over 20 minutes at 50 ml/min flow). HPLC fractions from the two HPLC runs containing pure 8a were pooled, evaporated to remove $CH_3CN$ and lyophilized to remove most of remaining water and volatile buffer to give after azeotropic drying with acetonitrile (3×4 ml) 42 mg of pure 8a as the bis-triethylammonium salt. (It is also possible to defer the prep HPLC purification until after the last step). HRMS (FT-ICR) m/z: [M-H]$^-$ calcd for $C_{32}H_{51}N_{10}O_{14}P_2Si_2$ 917.2606; found 917.2622. $^1$H NMR (DMSO-d$_6$+ trace D$_2$O) 45° C. δ 8.22 (1H, s), 7.85 (1H, s), 5.76-5.79 (2H, dd), 5.21 (1H, m), 4.85 (1H, m), 4.58 (1H, t), 4.49 (1H, d), 4.31 (1H, m), 4.21 (1H, m), 3.97 (1H, d), 3.83 (3H, m), 2.94 (12H, m), 1.12 (18H, t), 0.90 (9H, s), 0.72 (9H, s), 0.14 (6H, d), 0.09 (3H, s), −0.02 (3H, s). $^{31}$P NMR (DMSO-d$_6$+ trace D$_2$O) 45° C. δ −1.26, −2.02 (FIG. 3a-3c).

7) Deprotection of TBS groups of 8a with triethylamine trihydrofluoride, neutralization with TEAB, and solid phase extraction with a C-18 Sep-Pak to give pure 9a as the bis-triethylammonium salt. To 40 mg of 8a was added 1.0 ml of triethylamine trihydrofluoride. The mixture was stirred at room temperature for 30 h. After confirming completion of reaction by analytical HPLC, the sample was neutralized by dropwise addition into 12 ml of chilled 1M triethylammonium bicarbonate. The neutralized solution was desalted on a Waters C-18 Sep-Pak and the product eluted with CH3CN/10 mM aqueous triethylammonium acetate (1:1). The $CH_3CN$ was evaporated under reduced pressure and the remaining aqueous solution was frozen and lyophilized overnight. Multiple evaporations from methanol (3×3 ml) and a final evaporation from 50% acetonitrile in methanol (1×3 ml) gave 29.3 mg of cyclic-[G(2',5')pG(3',5')p] (9a) as the bis-triethylammonium salt. HRMS (FT-ICR) m/z: [M-H]$^-$ calcd for $C_{20}H_{23}N_{10}O_{14}P_2$ 689.0876; found 689.0874. $^1$H NMR (DMSO-d$_6$+ trace D$_2$O) 45° C. δ 7.92 (1H, s), 7.90 (1H, s), 5.82 (1H, d), 5.80 (1H, d), 4.97 (1H, m), 4.85 (1H, m), 4.68 (1H, m), 4.31 (1H, d), 4.21 (1H, t), 4.10 (2H, m), 3.79 (3H, m), 2.91 (14H, m), 1.13 (22H, t). $^{31}$P NMR (DMSO-d$_6$) 45° C. δ 1.80, -1.05.

The HPLC retention time of 9a is 7.25 min compared to 9.3 min for c-di-GMP using a gradient of 2 to 20% CH3CN in 10 mM triethylammonium acetate over 20 min on a C-18 column (3 micron, 100×4.6 mm, 0.6 ml/min.) The HRMS (FT-ICR) confirmed the expected elemental formula: [M-H]$^-$ calcd for $C_{20}H_{23}N_{10}O_{14}P_2$ 689.0876; found 689.0874. The 31-P NMR of 9a showed two peaks (integrating 1:1) at 2.03 and -0.95 ppm consistent with a 2',5'/3',5' mixed linkage (both c[G(3',5')pG(3',5')p] and c[G(2',5')pG(2',5')p], for example, would give only one 31-P NMR signal due to symmetry). Direct evidence for the regiochemistry of the phosphodiester linkages was obtained by 1H-1H COSY in combination with phosphorous decoupling experiments, and by $^1$H-$^{31}$P HMBC two-dimensional NMR (FIGS. 3b and 3c). The anomeric (H-1) protons appear as overlapping doublet of doublets (or triplet) at 5.82 ppm. The "A" designation was given to the downfield anomeric (H-1) proton and "B" to the anomeric proton slightly upfield of that. Starting with the anomeric proton in both the "A" and "B" ribose a 1H-1H COSY experiment (FIG. 3b) allowed assignment of H-2A (4.96 ppm), H-3A (4.31 ppm), as well as H-2B (4.67 ppm) and H-3B (4.84 ppm). Irradiation of the downfield phosphorous (2.03 ppm) converted the H-3B multiplet to a doublet, while irradiation of the upfield phosphorous (−0.95 ppm) resulted in a simplification of the complex multiplet of H-2A. In both decoupling experiments simplification of the 5' ribose methylene multiplet was also observed. Two-dimensional $^1$H-$^{31}$P HMBC confirmed the result of the decoupling experiments. The 1H-1H COSY results in combination with phosphorous decoupling and $^1$H-$^{31}$P HMBC experiments thus provide direct evidence that the regiochemistry of the phosphodiester linkages is 2',5'/3',5' and that 9a is cyclic [G(2',5')pG(3',5')p].

Example 3. General Experimental for the ML-CDA Series (FIG. 2b): Synthesis of Cyclic [a(2',5')pA(3', 5')p] Na Salt 21 (See Compound FIG. 2c)

1) Preparation of 13.

To a solution of 5 g (5.15 mmol) N$^6$-benzoyl-5'-O-(4,4'-dimethoxytrityl)-2'-O-tert-butyldimethylsilyl-3'-O-[(2-cyanoethyl)-N,N-diisopropylaminophinyl]adenosine (11) in 25 ml acetonitrile was added 0.18 ml (10 mmole) water and 1.20 g (6.2 mmole) pyridinium trifluoroacetate. After 5 minutes stirring at room temperature 25 ml tert-butylamine was added and the reaction stirred for 15 minutes at room temperature. The solvents were removed under reduced pressure to give 12 as a foam which was then co-evaporated with acetonitrile (2×50 ml), then dissolved in 60 ml dichloromethane. To this solution was added water (0.9 ml, 50 mmole) and 60 ml of 6% (v/v) dichloroacetic acid (44 mmol) in dichloromethane. After 10 minutes at room temperature the reaction was quenched by the addition of pyridine (7.0 ml, 87 mmol), and concentrated to an oil which was dried by three co-evaporations with 40 ml anhydrous acetonitrile, the last time leaving 13 in a volume of 12 ml.

2) Preparation of a Dry Solution of 14.

N$^6$-benzoyl-5'-O-(4,4'-dimethoxytrityl)-3'-O-tert-butyldimethylsilyl-2'-O-[(2-cyanoethyl)-N,N-diisopropylaminophinyl]adenosine (14, 6.4 g, 6.6 mmole) was dissolved in 40 ml anhydrous acetonitrile and dried by three co-evaporations with 40 ml anhydrous acetonitrile, the last time leaving 20 ml. Ten 3A molecular sieves were added and the solution stored under argon until use.

3) Preparation of 2',5'-Monothio-Linear Dimer 16.

Azeo dried 14 (6.4 g, 6.6 mmole) in 20 ml acetonitrile was added via syringe to a solution of 13 (5.15 mmol) in 12 ml of anhydrous acetonitrile. After 5 minutes stirring at room temperature, 1.14 g (5.6 mmol) of 3-((N,N-dimethylaminomethylidene)amino)-3H-1,2,4-dithiazole-5-thione (DDTT) was added and the reaction stirred for 30 minutes at room temperature. The reaction was concentrated and the residual oil dissolved in 80 ml dichloromethane. Water (0.9 ml, 50 mmol) and 80 ml of 6% (v/v) dichloroacetic acid (58 mmol) in dichloromethane was added, and the reaction stirred for 10 minutes at room temperature. 50 ml pyridine was added to quench the dichloroacetic acid. The solvents were removed under reduced pressure to give crude 16b as a solid.

4) Cyclization and Sulfurization of 16b to Give the Protected Cyclic-Dithio Diastereoisomers 17b and 17c.

16b was dissolved in 150 ml dry pyridine which was concentrated down to a volume of approximately 100 ml. 2-chloro-5,5-dimethyl-1,3,2-dioxaphosphorinane-2-oxide (DMOCP, 3.44 g, 18 mmole) was then added and the reaction stirred for 5 minutes at room temperature. 3.2 ml water was added immediately followed by addition of 3-H-1,2-benzodithiol-3-one (1.3 g, 7.7 mmole), and the reaction stirred for 5 minutes at room temperature. The reaction mix was then poured into 700 ml water containing 20 g $NaHCO_3$ and stirred for 5 minutes at room temperature, then poured into a separatory funnel and extracted with 800 ml 1:1 ethyl acetate:diethyl ether. The aqueous layer was extracted again with 600 ml 1:1 ethyl acetate:diethyl ether. The organic layers were combined and concentrated under reduced pressure to yield approximately 11 g of an oil containing diastereoisomers 17b and 17c.

5) Silica Gel Column Chromatography of the Crude Mixture Containing 17b and 17c.

The crude mixture above was dissolved in dichloromethane and applied to a 250 g silica column. The desired diastereoisomers were eluted from the column using a gradient of methanol in dichloromethane (0-10%). Fractions containing the desired diastereoisomers 17b and 17c were combined and concentrated, giving 2.26 g of approximately 50% 17b and 50% 17c.

6) Deprotection of the Fully-Protected Cyclic Diastereoisomers 17b and 17c to Crude 18b and 18c.

2.26 g of crude 17b and 17c from the silica gel column was transferred to a thick-walled glass pressure tube. 60 ml methanol and 60 ml concentrated aqueous ammonia was added and the tube was heated with stirring in an oil bath at 50° C. for 16 h (recent runs have been 12 h since starting material is consumed at this time). The reaction mixture was cooled to near ambient temperature, sparged with a stream of nitrogen gas for 30 minutes, and then transferred to a large round bottom flask. Most of the volatiles were removed under reduced pressure with caution so as to avoid foaming and bumping. If water was still present the residue was frozen and lyophilized to dryness.

7) Preparative HPLC Purification of Crude 18b and 18c to Give Pure 18b.

The lyophilized crude mixture containing 18b and 18c was taken up in approximately 50 ml of $CH_3CN$/10 mM aqueous triethylammonium acetate (60/40). After 0.45 micron PTFE filtration, 4-5 ml sample portions were applied to a C-18 Dynamax column (40×250 mm). Elution was performed with a gradient of acetonitrile and 10 mM aqueous triethylammonium acetate (30% to 50% $CH_3CN$ over 20 minutes at 50 ml/min flow). Fractions from the preparative HPLC runs containing pure 18b were pooled, evaporated to remove $CH_3CN$ and lyophilized to give 360 mg of pure 18b (the $R_PR_P$-diastereoisomer) as the bis-triethylammonium salt.

8) Deprotection of the two TBS groups of 18b with triethylamine trihydrofluoride, neutralization with TEAB, solid phase extraction with a C-18 Sep-Pak and lyophilization to give pure 19b as the bis-triethylammonium salt.

8a) To 270 mg (0.24 mmol) of 18b was added 5.0 ml of neat triethylamine trihydrofluoride. The mixture was stirred at room temperature for approximately 40 h. After confirming completion of reaction by analytical HPLC, the sample was neutralized by dropwise addition into 45 ml of chilled, stirred 1M triethylammonium bicarbonate. The neutralized solution was desalted on a Waters C-18 Sep-Pak and the product eluted with CH3CN/10 mM aqueous triethylammonium acetate (5:1). The $CH_3CN$ was evaporated under reduced pressure and the remaining aqueous solution was frozen and lyophilized. Multiple rounds of lyophilization from water gave 122 mg (57%) of dithio-(Rp,Rp)-[cyclic-A(2',5')pA(3',5')p] (19b) as the bis-triethylammonium salt.

8b) 90 mg (0.08 mmol) of 18b was coevaporated three times with 10 ml dry acetonitrile. The dried residue was taken up in 0.4 ml anhydrous pyridine. The flask with a vent needle was placed in a 50° C. oil bath, and 0.62 ml triethylamine trihydrofluoride and 1.0 ml triethylamine were added simultaneously to the stirring mixture. The mixture was stirred at 50° C. for two hours. After confirming completion of reaction by analytical HPLC, the sample was neutralized by dropwise addition into 25 ml of chilled, stirred 1M triethylammonium bicarbonate. The neutralized solution was desalted on a Waters C-18 Sep-Pak and the product eluted with CH3CN/10 mM aqueous triethylammonium acetate (1:4). The $CH_3CN$ was evaporated under reduced pressure and the remaining aqueous solution was frozen and lyophilized. Multiple rounds of lyophilization from water gave 54 mg (76%) of dithio-(Rp,Rp)-[cyclic-A (2',5')pA(3',5')p] (19b) as the bis-triethylammonium salt.

8c) A variant of TEA-HF deprotection by heating in neat TEA-HF at 45° C. followed by TEAB neutralization, Sep-Pak desalting and lyophilization.

Figure 3H:
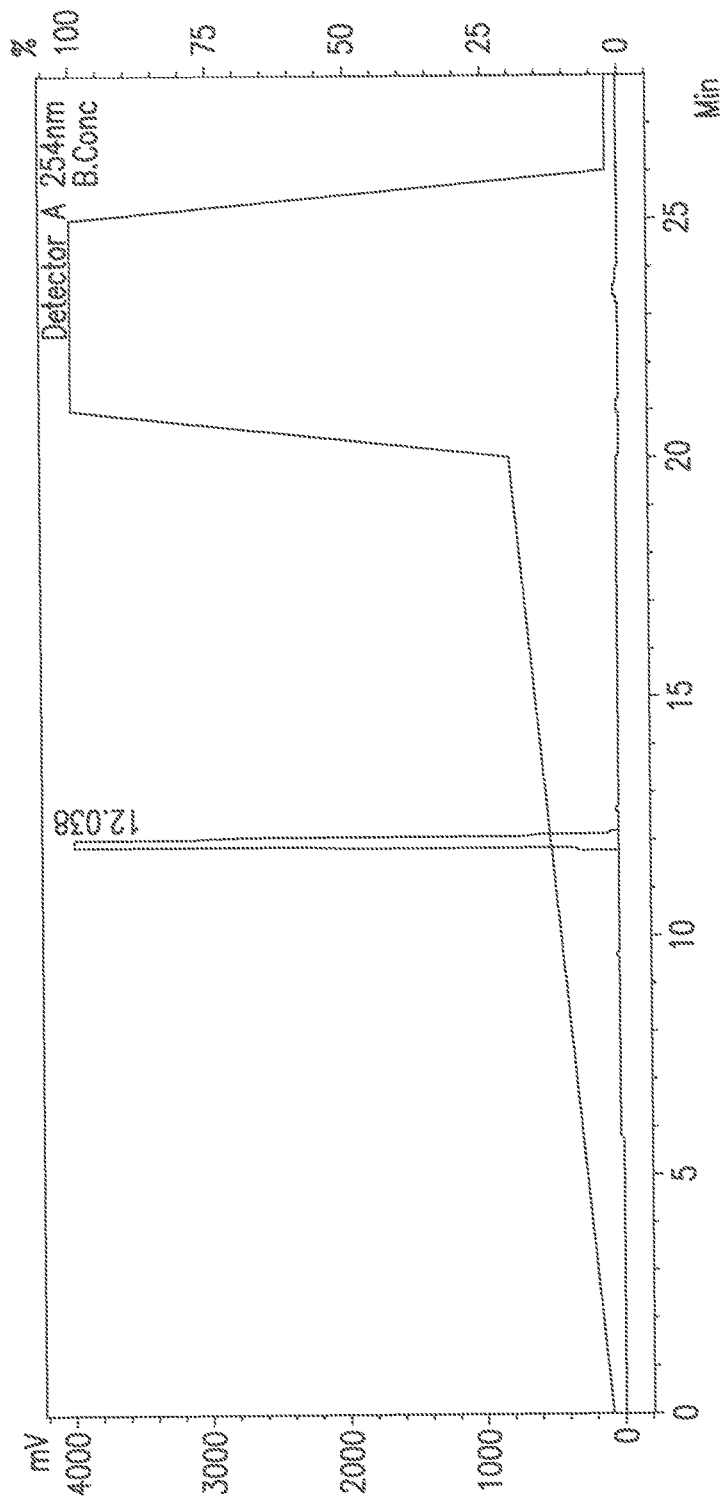
FIG. 3H depicts analytical HPLC (2-20% ACN/10 mM TEAA buffer—20 min) results for compound 19b.

TEA.3HF (1 mL, 6.1 mmol) was added to 18b (41 mg, 0.04 mmol) in a flask equipped with a vent needle and the mixture stirred at 45° C. The reaction progress was monitored by LC and upon consumption of the starting material and mono-TBS analogs (~2 hr) the mixture was cooled to room temperature. The mixture was slowly pipetted into a solution of 1 M TEAB (4.9 mL) and TEA (1.6 mL) at 0° C. and a slightly basic pH was confirmed by pH paper. The neutralized solution was desalted on a Waters C-18 Sep-Pak (10 g) and the product eluted with 15% $CH_3CN$/10 mM aqueous triethylammonium acetate. Lyophilization gave 21 mg (64%) of 19b (bis-triethylammonium salt) as a white solid. Analysis by analytical HPLC (2-20% Acetonitrile/10 nM TEAA buffer—20 min) showed >95% purity (FIG. 3h). $^1H$ NMR (500 MHz, 45° C., (CD3)$_2$SO-15 μL D$_2$O) δ 8.58 (s, 1H), 8.41 (s, 1H), 8.18 (s, 1H), 8.15 (s, 1H), 6.12 (d, J=8.0, 1H), 5.92 (d, J=7.0, 1H), 5.30 (td, J=8.5, 4.0, 1H), 5.24-5.21 (m, 1H), 5.03 (dd, J=7.5, 4.5, 1H), 4.39 (d, J=4, 1H), 4.23 (dd, J=10.5, 4.0, 1H), 4.18 (s, 1H), 4.14-4.08 (m, 2H), 3.85-3.83 (m, 1H), 3.73 (d, J=12.0, 1H), 3.06 (q, J=7.5, 12H), 1.15 (t, J=7.5, 1H); $^{31}P$ NMR (200 MHz, 45° C., (CD3)$_2$SO-15 μL D$_2$O) δ 58.81, 52.54; HRMS (FT-ICR) m/z calcd for $C_{20}H_{24}O_{10}N_{10}P_2S_2$ (M-H)$^-$ 689.0521, found 689.0514.

8d) the work-up of the TEA-HF reaction via acetone precipitation as described in Gaffney et al. 2010 is also possible, but we have obtained somewhat cleaner product using the modifications described in sections 8a-8c above.

10) Conversion to Sodium Salt

The ML-RR-CDA bis-TEA salt (19b) is readily converted to the pharmaceutically acceptable sodium salt (21) by ion exchange as described below.

ML-RR-CDA.2Na$^+$ (21). BT AG® 50W-X2 Resin 100-200 Mesh, hydrogen form (100 mg) was slurry packed with DI water into a Bio-spin® column. The excess DI water was drained via gravity. 3 bed volumes of 1 M NaOH (1 mL) was passed through the column via gravity followed by 5 bed volumes of DI water (2 mL). After draining the excess DI water via gravity a solution of ML-RR-CDA.2TEA (19b, 10 mg) in DI water (1 mL) was loaded onto the column. The column was eluted with 5 bed volumes of DI water (2 mL), fractions were collected and checked for UV activity via TLC plate and UV lamp. The fractions of interest were pooled, frozen, and lyophilized over night to give ML-RR-CDA.2Na$^+$ quantitatively. $^1$H NMR (500 MHz, 45° C., (CD$_3$)$_2$SO-30 µL D$_2$O) δ 8.54 (s, 1H), 8.40 (s, 1H), 8.17 (s, 1H), 8.167 (s, 1H), 6.09 (d, J=8.0, 1H), 5.92 (d, J=8.0, 1H), 5.26 (td, J=8.5, 4.5, 1H), 5.21-5.19 (m, 1H), 5.01 (dd, J=7.5, 4.5, 1H), 4.42 (d, J=4, 1H), 4.23 (dd, J=10.5, 5.0, 1H), 4.17 (s, 1H), 4.15-4.00 (m, 2H), 3.90-3.82 (m, 1H), 3.73-3.70 (m, 1H); $^{31}$P NMR (200 MHz, 45° C., (CD3)$_2$SO-30 µL D$_2$O) δ 58.85, 51.53 (FIG. 3d-3g); HRMS (FT-ICR) m/z calcd for C$_{20}$H$_{23}$O$_{10}$N$_{10}$P$_2$S$_2$(M-H)$^-$ 689.0521, found 689.0503.

Direct evidence for the regiochemistry of the phosphodiester linkages was obtained by 1H-1H COSY in combination with $^1$H-$^{31}$P HMBC two-dimensional NMR (FIG. 3e-3g) analogously to the ML-CDG series experimentals.

ML-RR-CDG (9b).

Compound 9b was synthesized analogously to ML-CDG following the procedures of ML-CDG series experimental with the following modifications (FIG. 2a): e) DDTT; h) 3-H-1,2-benzodithiol-3-one; n) obtained as the TEA salt, no ion exchange was needed.

$^1$H NMR (500 MHz, 45° C., (CD$_3$)$_2$SO-15 µL D$_2$O) δ 7.98 (s, 1H), 7.94 (s, 1H), 5.85 (d, J=9.0, 1H), 5.80 (d, J=7.5, 1H), 5.25-5.23 (m, 1H), 5.12 (dd, J=8.5, 4.5, 1H), 4.73 (dd, J=8.0, 4.5, 1H), 4.42 (d, J=4.0, 1H), 4.22 (t, J=7.5, 1H), 4.14-4.10 (m, 2H), 3.94-3.90 (m, 2H), 3.77-3.73 (m, 1H), 3.05 (q, J=7.0, 12H), 1.160 (t, J=7.0, 1H); $^{31}$P NMR (200 MHz, 45° C., (CD$_3$)$_2$SO-15 µL D$_2$O) δ 59.09, 50.37; HRMS (FT-ICR) m/z calcd for C$_{20}$H$_{23}$O$_{12}$N$_{10}$P$_2$S$_2$(M-H)$^-$ 721.0419, found 721.0410.

ML-RS-CDG (9c).

Compound 9c was synthesized analogously to ML-CDG following the procedures of ML-CDG series experimental with the following modifications (FIG. 2a): e) DDTT; h) 3-H-1,2-benzodithiol-3-one; k) the [Rp, S$_P$] diastereomer 8c was collected; n) obtained as the TEA salt, no ion exchange was needed.

$^1$H NMR (500 MHz, 45° C., (CD$_3$)$_2$SO-15 µL D$_2$O) δ 8.01 (s, 1H), 7.98 (s, 1H), 5.86 (d, J=8.5, 1H), 5.79 (d, J=8.0, 1H), 5.29 (dd, J=8.5, 4.0, 1H), 5.20-5.19 (m, 1H), 4.68 (dd, J=8.5, 4.0, 1H), 4.21-4.18 (m, 2H), 4.10-4.05 (m, 3H), 3.71-3.68 (m, 2H), 2.96 (q, J=7.0, 12H), 1.13 (t, J=7.0, 18H); $^{31}$P NMR (200 MHz, 45° C., (CD3)$_2$SO-15 µL D$_2$O) S 59.89, 57.17; HRMS (FT-ICR) m/z calcd for C$_{20}$H$_{24}$O$_{12}$N$_{10}$P$_2$S$_2$ (M-H)$^-$ 721.041904, found 721.04143.

C14-ML-CDG (10):

Compound 10 (FIG. 2c) was synthesized analogously to ML-CDG following the procedures of ML-CDG series experimental with the following modifications (FIG. 2a): n) myristic anhydride, DMF.

To the bis-triethylamine salt of 9a (0.260 g, 0.291 mmol) was added 3.7 ml DMF, 0.3 ml pyridine, and 128 mg (0.292 mmol) of myristic anhydride. The reaction mixture was heated for a total of 5 h at 60° C., cooled to room temperature and quenched with 100 ul of MeOH. The LC trace indicated 25% conversion to a major new product with the remainder of mass appearing in the retention time range of starting material. The mass of the major product was confirmed as the C14-acylated product by LC/MS in negative mode, with m/z (M-1) of 899 (calcd for C34H49N10O15P2$^-$: 889.3). After evaporation the residue was taken up in 2 ml CH3CN, 3 ml 0.1 M TEAA and enough MeOH to bring most of material into solution. After a brief spin down via centrifugation to remove a small amount of particulate matter the solution was purified via C18-prep HPLC using a gradient of 25%→50% CH3CN in 10 mM TEAA over 20 min. Fractions containing the desired product were combined and lyophilized to dryness to afford 36 mg of C14-ML-CDG 10 (triethylammonium salt) as a white solid.

$^1$H NMR (500 MHz, 45° C., (CD3)$_2$SO-15 µL D$_2$O) δ 8.00 (s, 1H), 7.90 (s, 1H), 5.98 (d, J=7.5, 1H), 5.83 (d, J=8.5, 1H), 5.76 (dd, J=7.5, 4.5, 1H), 5.15-5.10 (m, 1H), 4.90-4.85 (m, 1H), 4.36 (d, J=4.5, 1H), 4.30-4.27 (m, 1H), 4.07 (s, 1H), 3.94-3.90 (m, 3H), 3.82-3.78 (m, 1H), 3.04 (q, J=7.0, 12H), 2.37-2.23 (m, 2H), 1.51-1.43 (m, 2H), 1.28-1.14 (m, 38H). 0.85 (t, J=7.0, 3H); $^{31}$P NMR (200 MHz, 45° C., (CD3)$_2$SO-15 µL D$_2$O) 6-1.36, -2.12; HRMS (FT-ICR) m/z calcd for C$_{34}$H$_{49}$O$_{15}$N$_{10}$P$_2$ (M-H)$^-$ 899.2860, found 899.2834.

ML-CDA (19a).

Compound 19a was synthesized analogously to ML-RR-CDA following the procedures of ML-CDA series experimental with the following modifications (FIG. 2b): e) t-BuOOH; h) I$_2$/H$_2$O; n) obtained as the TEA salt, no ion exchange was needed.

$^1$H NMR (500 MHz, 45° C., (CD$_3$)$_2$SO-15 µL D$_2$O) δ 8.44 (s, 1H), 8.37 (s, 1H), 8.16 (s, 1H), 8.14 (s, 1H), 6.08 (d, J=8.0, 1H), 5.90 (d, J=7.5, 1H), 5.10-5.0 (m, 3H), 4.30 (d, J=4.5, 1H), 4.3-4.19 (m, 1H), 4.14 (d, J=1.5, 1H), 4.05 (q, J=11.5, 2H), 3.78-3.75 (m, 2H), 2.90 (q, J=7.5, 18H), 1.08 (t, J=7.0, 27H); $^{31}$P NMR (200 MHz, 45° C., (CD3)$_2$SO-150 µL D$_2$O) δ 1.67, −0.47; HRMS (FT-ICR) m/z calcd for C$_{20}$H$_{24}$O$_{12}$N$_{10}$P$_2$ (M-H)$^-$ 657.097763, found 657.09680.

ML-RS-CDA (19c).

Compound 19c was synthesized analogously to ML-RR-CDA following the procedures of ML-CDA series experimental with the following modifications (FIG. 2b): k) the [Rp, S$_P$] diastereomer 18c was collected; n) obtained as the TEA salt, no ion exchange was needed.

$^1$H NMR (500 MHz, 45° C., (CD3)$_2$SO-15 µL D$_2$O) δ 8.52 (s, 1H), 8.37 (s, 1H), 8.16 (s, 1H), 8.15 (s, 1H), 6.10 (d, J=8.5, 1H), 5.90 (d, J=7.5, 1H), 5.45 (dd, J=8.5, 4.5, 1H), 5.31-5.26 (m, 1H), 5.00 (dd, J=8.5, 4.5, 1H), 4.41-4.36 (m, 1H), 4.22 (d, J=5.0, 1H), 4.14-4.07 (m, 3H), 3.70-3.67 (m, 3H), 2.84 (q, J=7.0, 19H), 1.08 (t, J=7.5, 29H); $^{31}$P NMR (200 MHz, 45° C., (CD$_3$)$_2$SO-15 µL D$_2$O) δ 59.98, 57.35; HRMS (FT-ICR) m/z calcd for C$_{20}$H$_{24}$O$_{10}$N$_{10}$P$_2$S$_2$ (M-2H+Na)$^-$ 711.0340, found 711.0316.

ML-3'-5'-R-CDA (19e).

Compound 19e was synthesized analogously to ML-RR-CDA following the procedures of ML-CDA series experimental with the following modifications (FIG. 2b): e)

t-BuOOH; h) 3-H-1,2-benzodithiol-3-one; n) obtained as the TEA salt, no ion exchange was needed.

$^1$H NMR (500 MHz, 45° C., (CD3)$_2$SO-15 μL D$_2$O) δ 8.49 (s, 1H), 8.38 (s, 1H), 8.17 (s, 1H), 8.14 (s, 1H), 6.09 (d, J=8.5, 1H), 5.90 (d, J=7.5, 1H), 5.23 (dd, J=8.0, 5.0, 1H), 5.12-5.04 (m, 2H), 4.31 (d, J=4.5, 1H), 4.21-4.14 (m, 3H), 4.10 (q, J=11.0, 1H), 3.80-3.71 (m, 2H), 2.85 (q, J=7.0, 18H), 1.08 (t, J=7.5, 27H); $^{31}$P NMR (200 MHz, 45° C., (CD3)$_2$SO-15 μL D$_2$O) δ 59.32, −0.37; HRMS (FT-ICR) m/z calcd for C$_{20}$H$_{23}$O$_{11}$N$_{10}$P$_2$S (M−H)$^-$ 673.0749, found 673.0729.

ML-RR-CDA (22) as an Ammonia Salt.

Compound 22 was synthesized analogously to ML-RR-CDA following the procedures of ML-CDA series experimental with the following modifications (FIG. 2b): n) BT AG® 50W-X2 Resin 100-200 Mesh, hydrogen form, 1 M NH$_4$OH. $^1$H NMR (500 MHz, 45° C., (CD$_3$)$_2$SO-30 μL D$_2$O) δ 8.80 (s, 1H), 8.44 (s, 1H), 8.39 (s, 2H), 6.45 (d, J=10.0, 1H), 6.34 (s, 1H), 5.50 (td, J=10.5, 4.5, 1H), 5.21-5.15 (m, 1H), 5.02 (d, J=4.0, 1H), 4.92 (d, J=4.5, 1H), 4.61-4.49 (m, 2H), 4.30-4.27 (m, 2H); $^1$HRMS (FT-ICR) m/z calcd for C$_{20}$H$_{23}$O$_{10}$N$_{10}$P$_2$S$_2$ (M−H)$^-$ 689.0521, found 689.0504.

ML-RR-cGAMP (20).

Compound 20 (FIG. 2c) was synthesized analogously to ML-RR-CDA series experimental with the following modifications (FIG. 2b): d) pyr, 4; n) obtained as the TEA salt, no ion exchange was needed.

NMR (500 MHz, 45° C., (CD$_3$)$_2$SO-30 μL D$_2$O) δ 8.34 (s, 1H), 8.15 (s, 1H), 8.01 (s, 1H), 5.91 (d, J=7.5, 1H), 5.86 (d, J=8.5, 1H), 5.29-5.23 (m, 1H), 5.17-5.14 (m, 1H), 5.02 (dd, J=7.5, 4.0, 1H), 4.41 (d, J=4.5, 1H), 4.25 (dd, J=5.0, 10.5, 1H), 4.13-4.03 (m, 3H), 3.95-3.85 (m, 1H), 3.78-3.74 (m, 1H), 2.84 (q, J=7.5, 18H), 1.08 (t, J=7.5, 28H); $^{31}$P NMR (200 MHz, 45° C., (CD$_3$)$_2$SO-304 D$_2$O) δ 58.81, 50.91; HRMS (FT-ICR) m/z calcd for C$_{20}$H$_{23}$O$_{11}$N$_{10}$P$_2$S$_2$ (M−H)$^-$ 705.0470, found 705.0451.

Example 4. Ribose 2'- and 3-Substituted Derivatives

Figure 4:
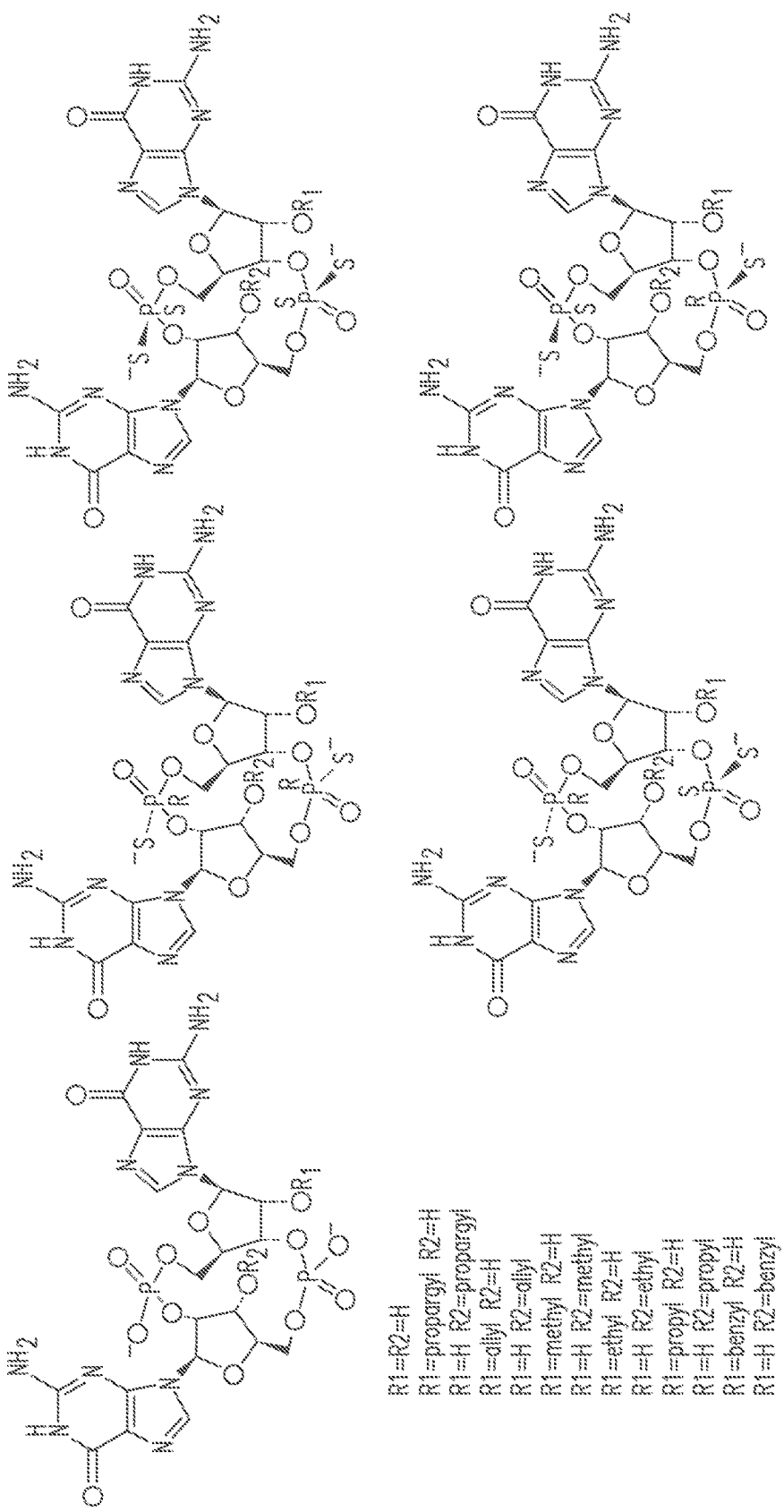
FIG. 4 depicts c-[G(2',5')pG(3',5')p] and dithio ribose O-substituted derivatives.
Figure 5:
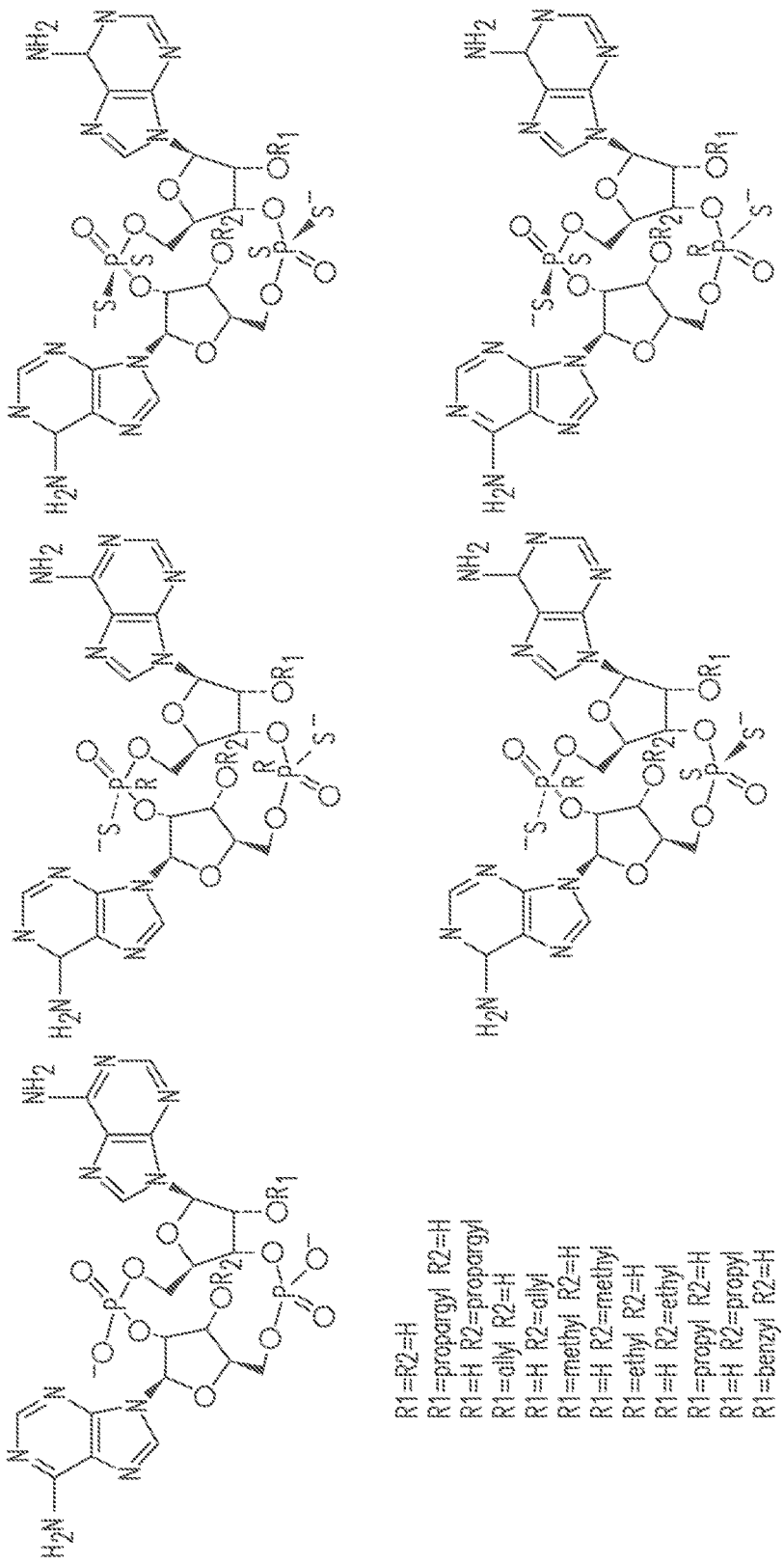
FIG. 5 depicts c-[A(2',5')pA(3',5')p] and dithio ribose O-substituted derivatives.
Figure 6:
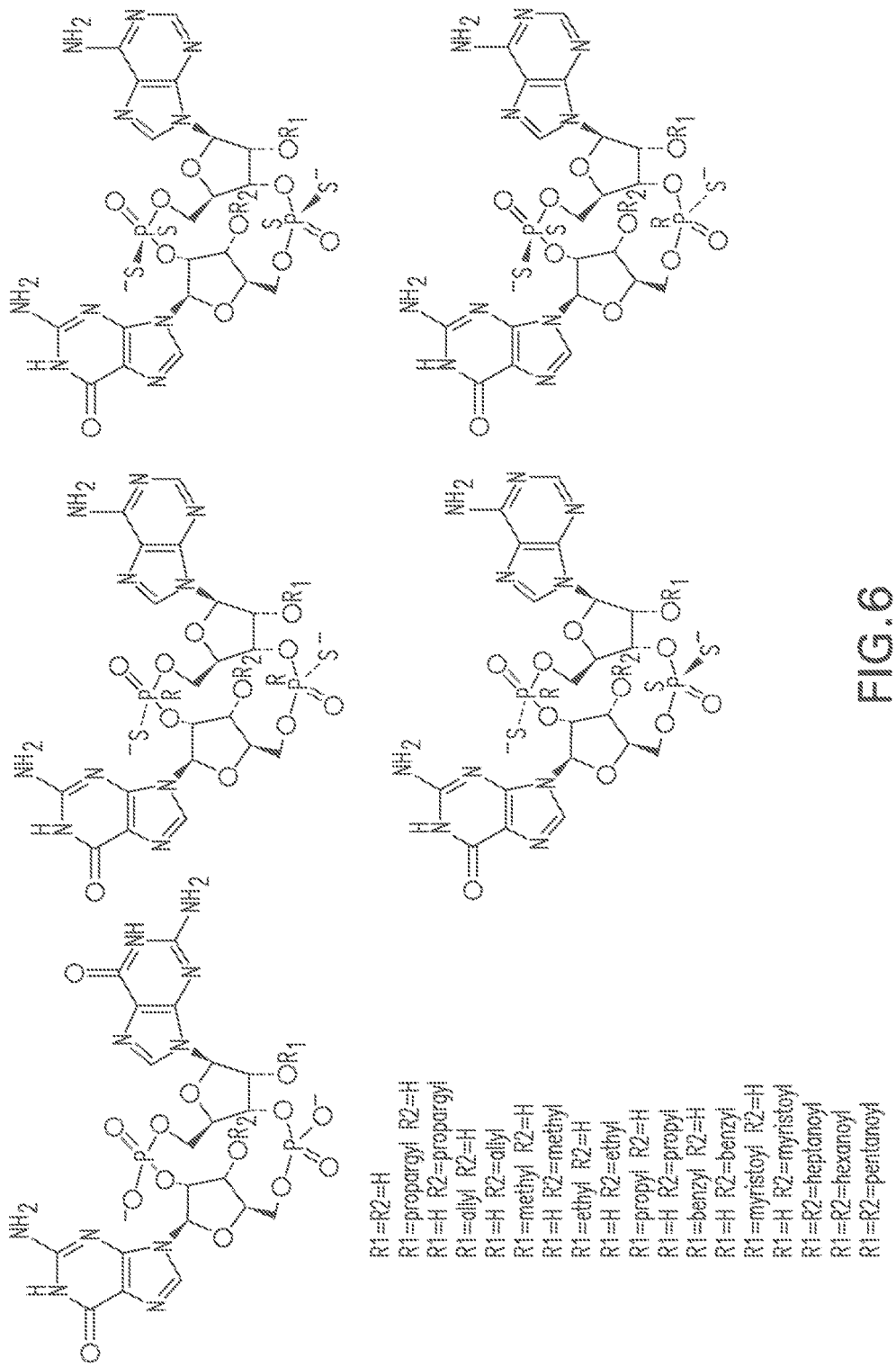
FIG. 6 depicts c-[G(2',5')pA(3',5')p] and dithio ribose O-substituted derivatives.

Examples of derivatives finding use in the present invention are depicted in FIG. 4-6.

Example 5. CDN-Induced Type I Interferon Expression

To determine the relative level of type I interferon induced in human cells by each of the native and derivative molecules as a signature of adjuvant potency, 4×10$^5$ THP1-Blue™ ISG cells (a human monocyte cell line transfected with an IRF-inducible secreted embryonic alkaline phosphatase reporter gene (Invivogen) which express alkaline phosphatase under the control of a promoter comprised of five IFN-stimulated response elements) were incubated with 100 μM of cyclic [G(3',5')pG(3',5')p] (CDG), cyclic [G(2',5')pG(3',5')p] (mixed linkage, or ML-CDG), or HBSS for 30 minutes at 37° C. with 5% CO$_2$. After 30 minutes, cells were washed and plated in 96-well dish in RPMI media containing 10% FBS, and incubated at 37° C. with 5% CO$_2$. Cell culture supernatants from each sample were collected after overnight incubation, and 20 μL of the cell culture supernatants was added to 180 μL QUANTI-Blue reagent (Invivogen) and incubated for 45 minutes to evaluate type I interferon protein levels. Readings at Absorbance 655 nm were taken every 3 minutes using a Versa Max kinetic spectrophotometer (Molecular Diagnostics).

Figure 7:
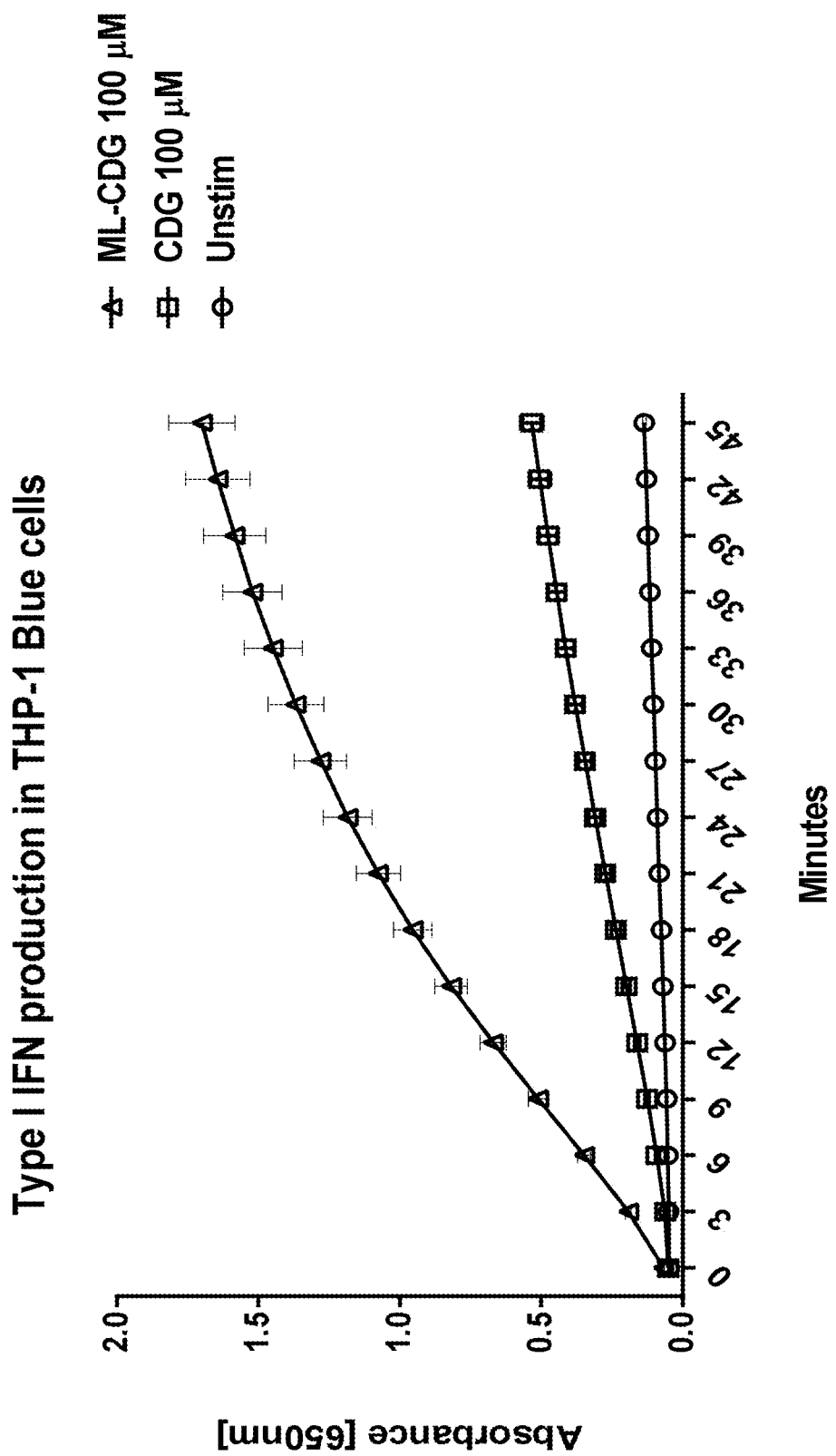
FIG. 7 Depicts Type 1 interferon production in THP-1 cells following stimulation with various cyclic dinucleotide molecules

As shown in FIG. 7, cyclic [G(2',5')pG(3',5')p] (ML-CDG) induced significantly higher levels of IFN-β than cyclic [G(3',5')pG(3',5')p] across a broad range of time points. These results demonstrate that a purified preparation of cyclic [G(2',5')pG(3',5')p] more profoundly activates the innate immune response than does cyclic [G(3',5')pG(3',5')p] in a human monocyte cell line.

To determine the levels of IFN-α, -β and -γ induced by cyclic [G(2',5')pG(3',5')p] (ML-CDG) compared to cyclic [G(3',5')pG(3',5')p] as a signature of potency to activate innate immunity, 1×10$^6$ primary human PBMCs isolated from four independent human donors were incubated in a 96 well U bottom plate for 30 min at 37° C., 5% CO$_2$ with 5 or 0.5 μM of cyclic [G(3',5')pG(3',5')p] (CDG) or cyclic [G(2',5')pG(3',5')p] (ML-CDG), 1 μg/mL of Interferon Stimulatory DNA (ISD), or 4 μg/mL of Poly (I:C) utilizing Effectene transfection reagent (Qiagen) to transfer the molecules into the PBMC. ISD (Interferon Stimulating DNA) is TLR independent (Stetston, D. B. et. al. Immunity 24, 93-103, January 2006) and signals through cGAS, and is thus STING-dependent, while Poly (I:C) can signal through both TLR3 and RIG-I pathways, and are thus STING-independent. After 30 minutes, the cells were washed and replaced with RPMI media containing 10% FBS and incubated at 37° C., 5% CO$_2$. After 6 hrs incubation, a portion of the cells were harvested and assessed by real-time quantitative RT-PCR for gene expression of the type I cytokines interferon alpha 2 (IFNA2) and interferon beta 1 (IFNB1), and the type II cytokine gene interferon gamma (IFNG). Gene expression was determined by real-time quantitative RT-PCR using the PrimePCR RNA purification and cDNA analysis system, and run on the CFX96 gene cycler (all BioRad). Normalized expression was determined for each, which accounts for the different efficiencies of PCR amplification for the target (E$_{target}$) and the reference (E$_{reference}$), and transforms the logarithmic scaled raw data unit Cycle Threshold (CT) into the linear unit of Normalized Expression. Reference genes used were GUSB and PGK1, genes confirmed to have a coefficient variable (CV) below 0.5 and M value below 1, and thus did not vary with different treatment conditions. To assess correlative secreted protein levels of these cytokines, supernatants were harvested from the remaining cells after 24 hours incubation and IFN-α and -γ levels were determined by Cytometric Bead Array (CBA, BD Biosciences), while IFN-β levels were determined by ELISA (PBL).

Figure 8:
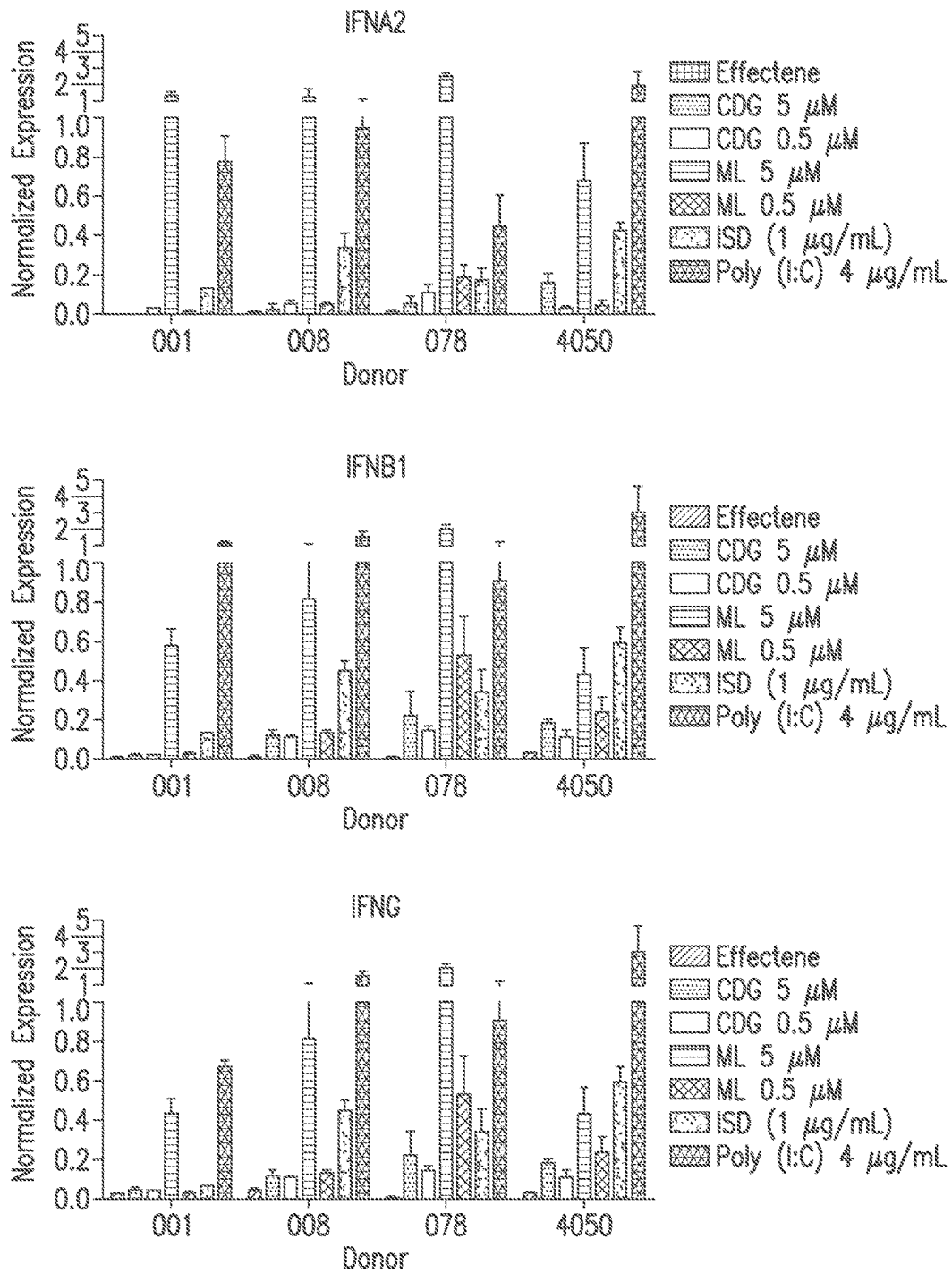
FIG. 8 depicts normalized RNA expression levels of Type 1 interferons and interferon gamma in human PBMCs from independent donors following stimulation with various cyclic dinucleotide molecules

As shown in FIG. 8, gene expression of interferon alpha 2 (IFNA2) was significantly higher for cyclic [G(2',5')pG(3',5')p] at 5 μM than for cyclic [G(3',5')pG(3',5')p] at 5 μM across all four donors. Similarly, gene expression of interferon beta 1 (IFNB1) was significantly higher for cyclic [G(2',5')pG(3',5')p] at 5 μM than for cyclic [G(3',5')pG(3',5')p] at 5 μM in all four donors. Gene expression for interferon gamma (IFNG) was induced to a significantly higher level for cyclic [G(2',5')pG(3',5')p] at 5 μM than for cyclic [G(3',5')pG(3',5')p] across all four donors. These data demonstrate the increased potency of cyclic [G(2',5')pG(3',5')p] compared to cyclic [G(3',5')pG(3',5')p] to induce gene expression of critical innate immune cytokines in a variety of human donors.

Figure 9A:
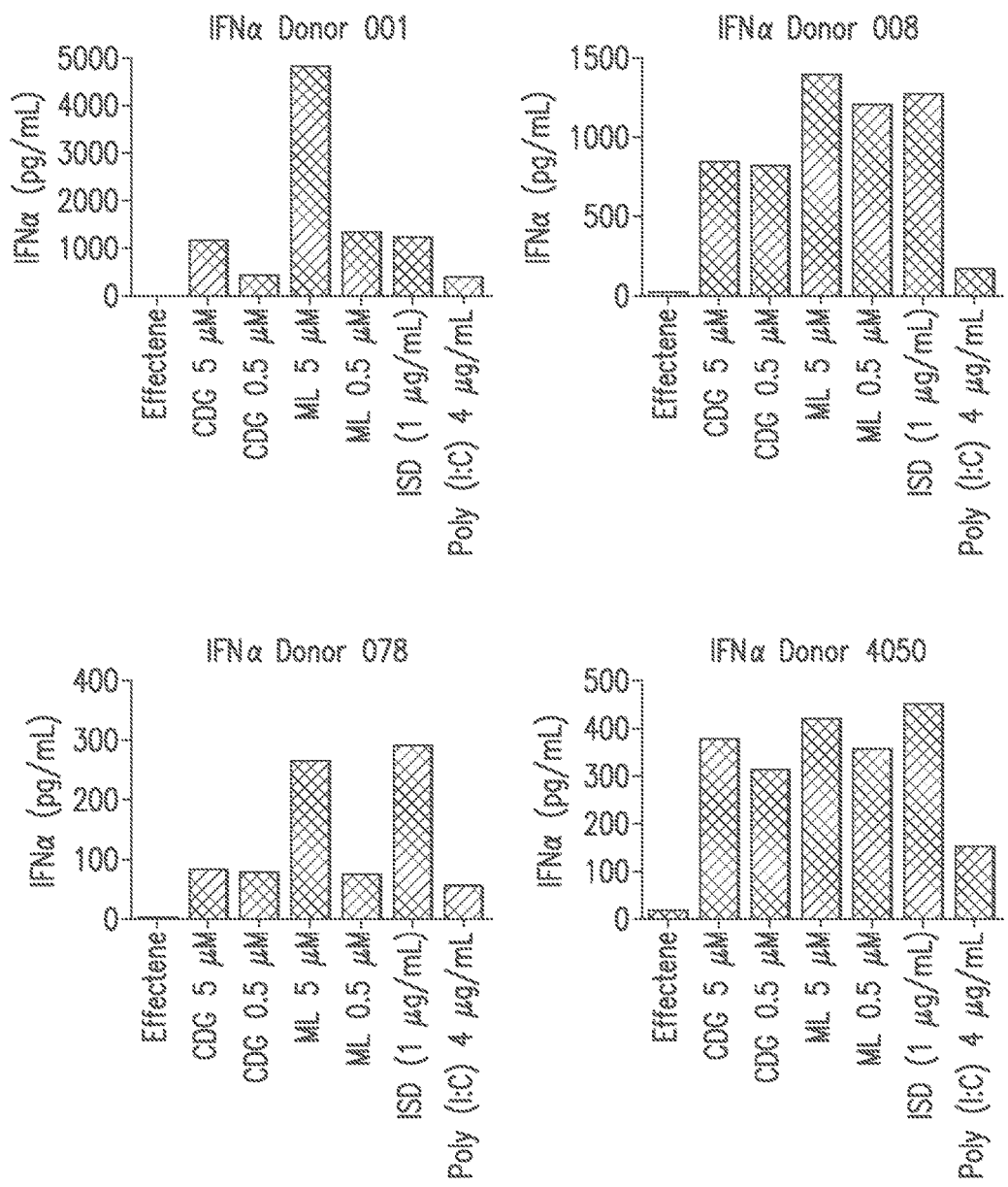
FIG. 9A depicts levels of Type 1 interferon alpha protein in human PBMCs from independent donors following stimulation with various cyclic dinucleotide molecules.
Figure 9B:
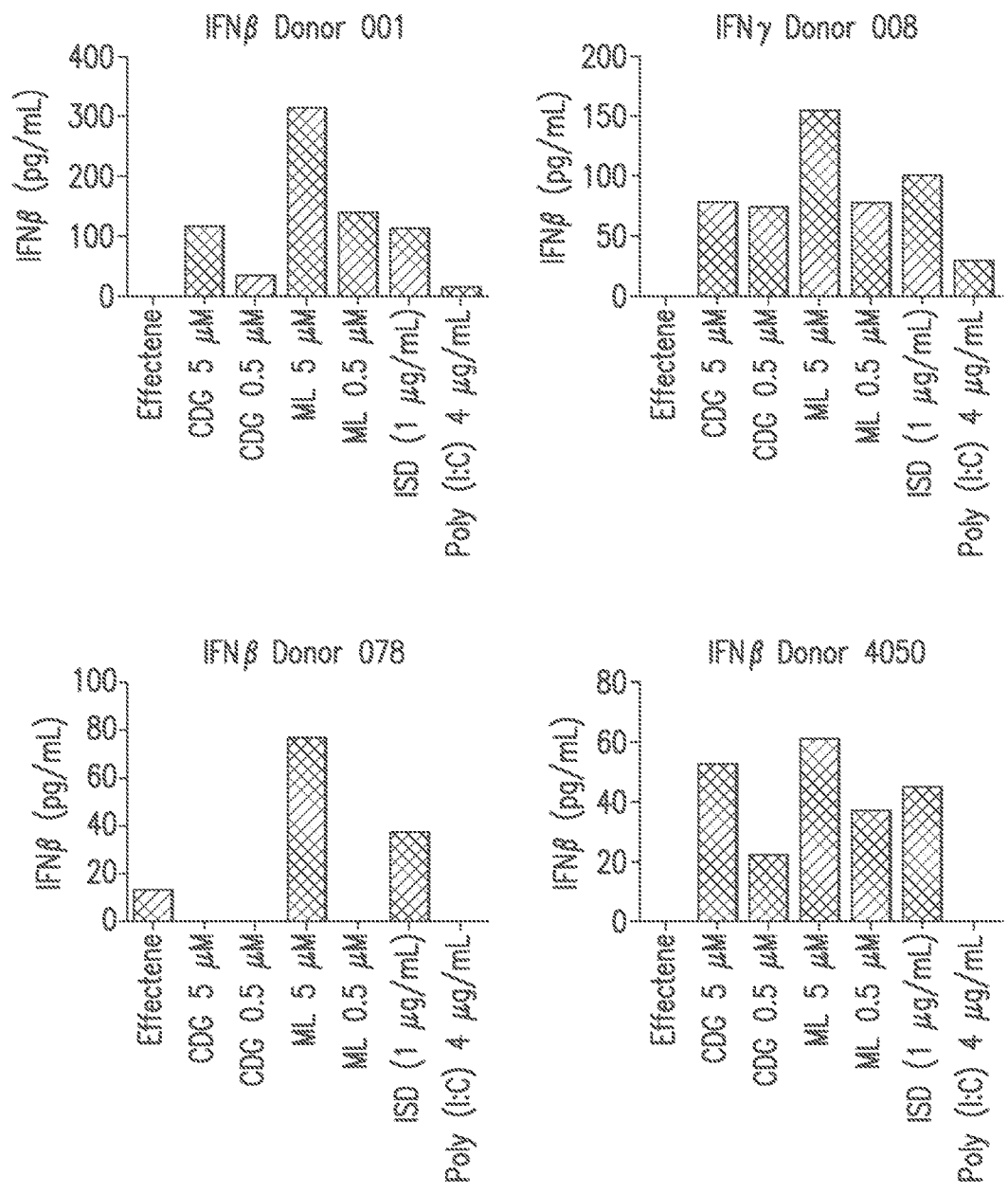
FIG. 9B depicts levels of Type 1 interferon beta protein in human PBMCs from independent donors following stimulation with various cyclic dinucleotide molecules.

As shown in FIG. 9(a), the levels of secreted IFN-α induced in primary human PBMCs by cyclic [G(2',5')pG(3',5')p] at 5 μM are higher than cyclic [G(3',5')pG(3',5')p] at the same or lower dose across all four donors. In FIG. 9(b), levels of IFN-β, as assessed by ELISA, for cyclic [G(2',5')pG(3',5')p] at 5 μM were also higher than with cyclic

Figure 9C:
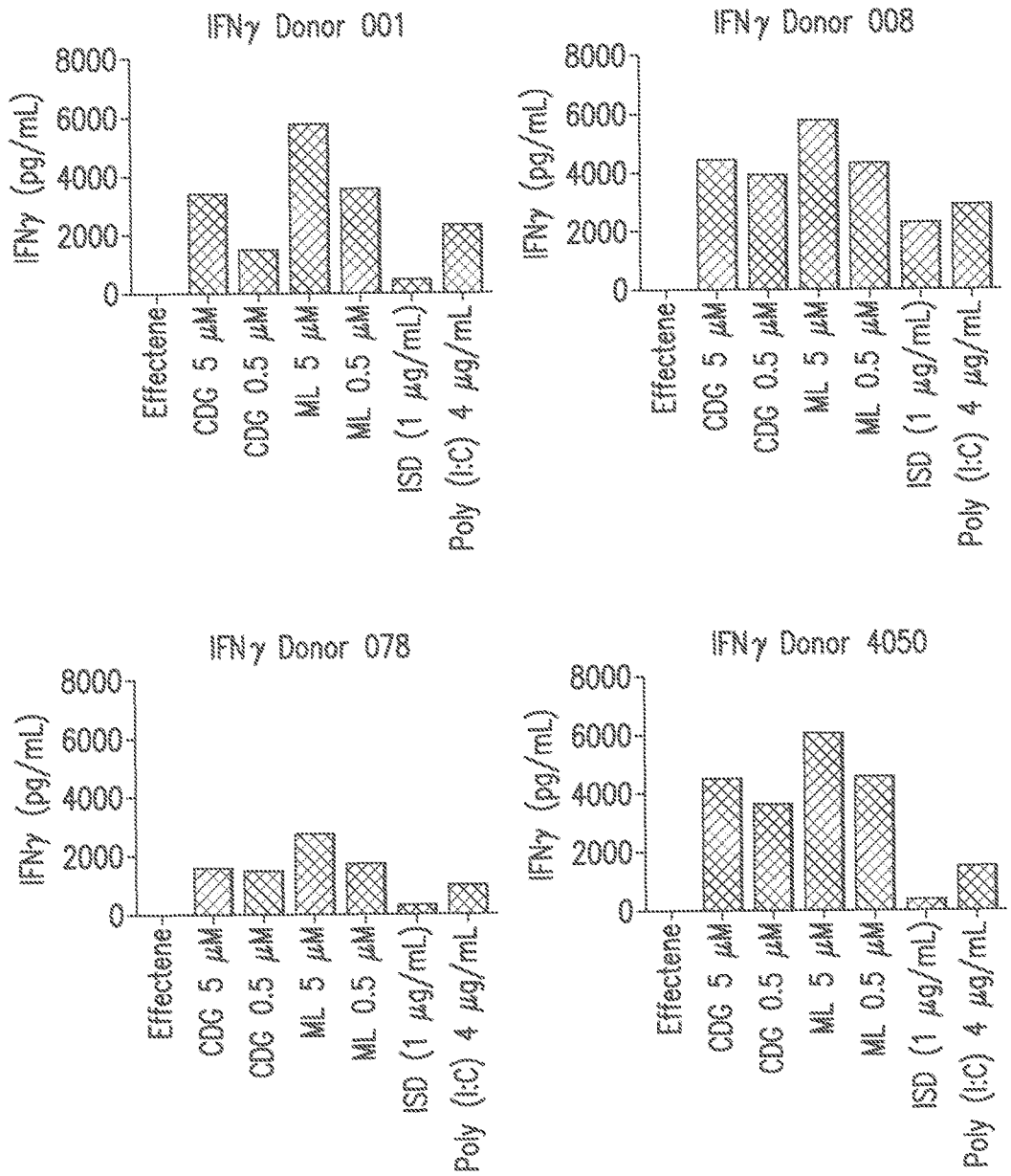
FIG. 9C depicts levels of interferon gamma protein in human PBMCs from independent donors following stimulation with various cyclic dinucleotide molecules.

[G(3',5')pG(3',5')p] induced levels, as well as for the ISD and Poly I:C controls in all four donors. FIG. 9(c) demonstrates a similar finding for secretion of IFN-γ, as assessed by CBA. At both 5 μM and 0.5 μM, cyclic [G(2',5')pG(3',5')p] induced higher levels of IFN-γ than cyclic [G(3',5')pG(3',5')p] at the same doses, and higher levels than the ISD and Poly I:C controls across all four donors. These data demonstrate the increased potency of cyclic [G(2',5')pG(3',5')p] compared to cyclic [G(3',5')pG(3',5')p] to stimulate type I and II IFN production, critical to the induction of innate immunity across a broad sampling of human donors.

To determine the relative level of IFN-β induced in human cells by each of the native and derivative molecules as a signature of adjuvant potency, $4\times10^5$ THP1-Blue cells, a human monocyte cell line transfected with an IRF-inducible secreted embryonic alkaline phosphatase reporter gene (Invivogen), were incubated with 50 μM of cyclic [G(3',5')pG(3',5')p] (CDG), cyclic [G(2',5')pG(3',5')p] (mixed linkage, or ML-CDG), Rp, Rp dithio cyclic [G(2',5')pG(3',5')p] (ML RR-CDG), compared to [A(3',5')pA(3',5')p] (CDA), cyclic [A(2',5')pA(3',5')p] (mixed linkage, or ML-CDA), Rp, Rp dithio cyclic [A(2',5')pA(3',5')p] (ML RR-CDA), or media control for 30 minutes at 37° C. with 5% $CO_2$. After 30 minutes, cells were washed and plated in 96-well dish in RPMI media containing 10% FBS, and incubated at 37° C. with 5% $CO_2$. Cell culture supernatants from each sample were collected after overnight incubation, and 20 μL of the cell culture supernatants was added to 180 μL QUANTI-Blue reagent (Invivogen) and incubated for 45 minutes. Readings at Absorbance 655 nm were taken at 15 minutes using a SpectraMax spectrophotometer (Molecular Diagnostics).

Figure 10:
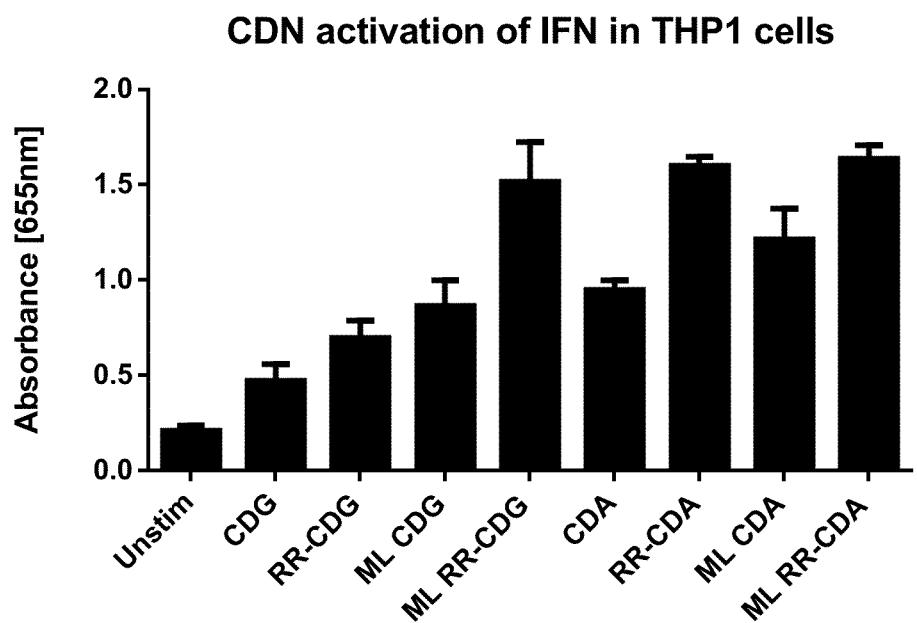
FIG. 10 depicts IFN-β induction in human cells as a signature of adjuvant potency following treatment with various cyclic dinucleotide molecules.

As shown in FIG. 10, the Rp, Rp dithio cyclic [G(2',5')pG(3',5')p] (ML RR-CDG) derivative induced significantly higher levels of IFN-β than the unmodified cyclic c-di-GMP (CDG) or modified CDG molecules. Similarly, the Rp, Rp dithio cyclic [A(2',5')pA(3',5')p] (ML RR-CDA) molecule induced significantly higher IFN-β levels that either the unmodified CDA or ML CDA molecules. These results demonstrate that purified preparations of the ML RR-CDN derivatives more profoundly activate the innate immune response than the parental CDN molecules in a human monocyte cell line.

To determine the relative ability of the derivative molecules to activate immune responses, CDN compounds were administered to 6-8 week old female BALB/c mice (in a total volume of 100 μL in HBSS) at doses of 50, 5 and 0.5 μM by subcutaneous injection into the base of the tail. Mice were assessed 24 hours later for lymphocyte immune cell activation by fluorescent activated cell sorting (FACS) for upregulation of surface CD69 expression on natural killer (NK) cells, CD4+ and CD8+ T cells, as compared to IgG1 isotype controls.

Figure 11A:
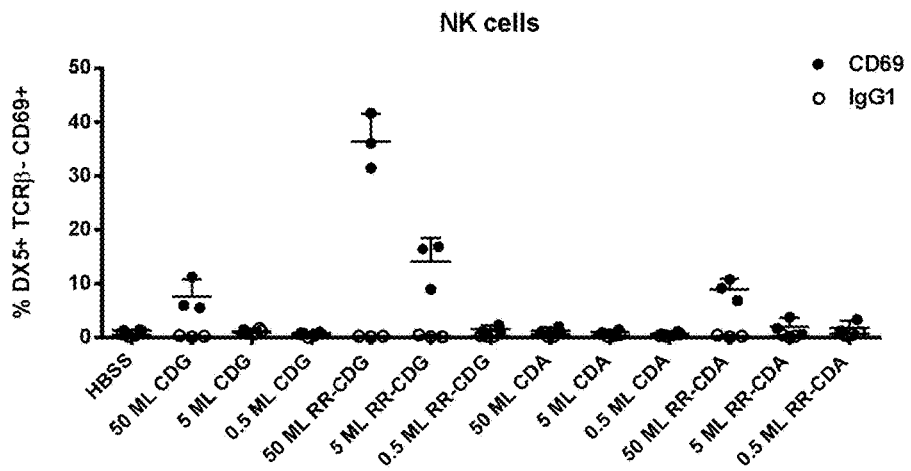
FIG. 11A depicts upregulation of surface CD69 expression on natural killer (NK) cells as a measure of immune activation following treatment with various cyclic dinucleotide molecules.
Figure 11B:
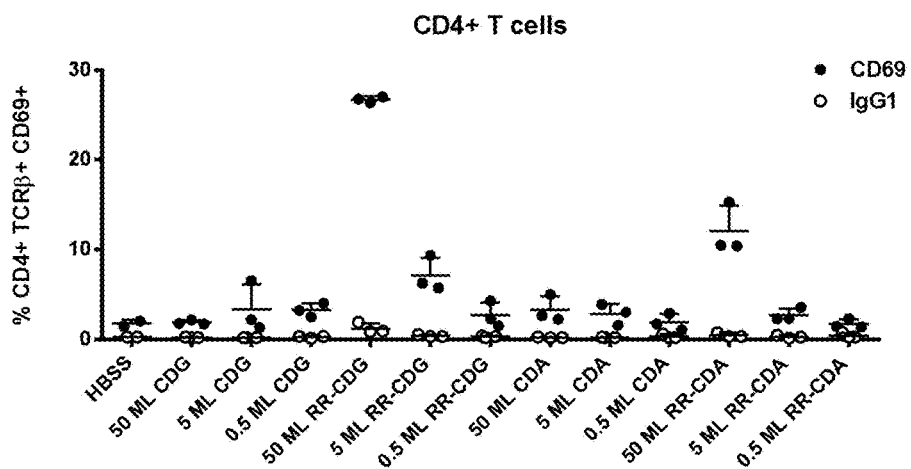
FIG. 11B depicts upregulation of surface CD69 expression on CD4$^+$ cells as a measure of immune activation following treatment with various cyclic dinucleotide molecules.
Figure 11C:
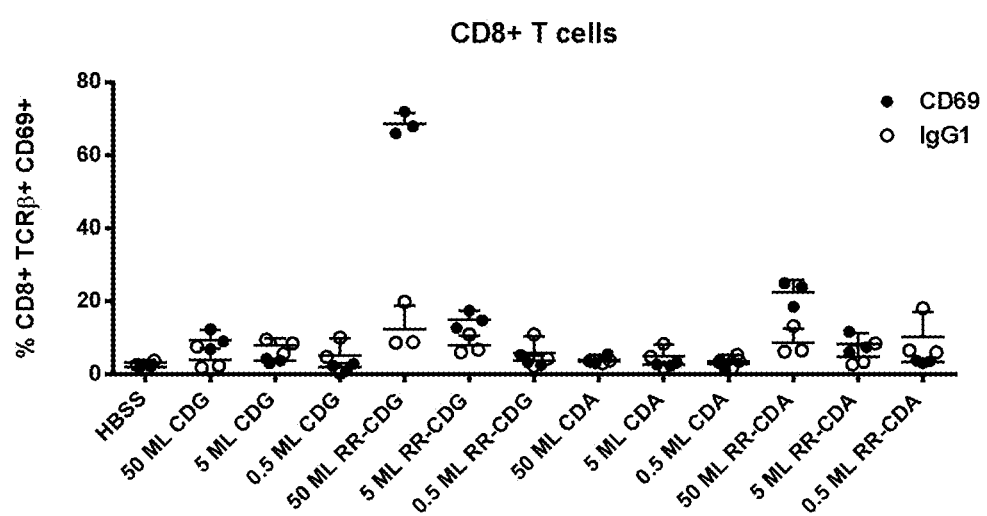
FIG. 11C depicts upregulation of surface CD69 expression on CD8+ T cells as a measure of immune activation following treatment with various cyclic dinucleotide molecules.

As shown in FIGS. 11(a-c), the Rp, Rp dithio cyclic [G(2',5')pG(3',5')p] (ML RR-CDG) molecule induced potent immune activation of NK and T cells in a dose-dependent manner. The Rp, Rp dithio cyclic [A(2',5')pA(3',5')p] (ML RR-CDA) molecule also induced NK and T cell activation, although to a lesser extent than the ML RR-CDG molecule. Both the ML RR-CDN molecules induced more immune cell activation that the ML CDN molecules at all doses. These data demonstrate the increased immune activation properties of the ML RR-CDN molecules as compared to the ML CDN molecules, and specifically, highlights the ability of the ML RR-CDG molecule to induce potent immune cell activation.

Example 6. Enhanced Resistance of Rp,Rp Dithio CDNs to Phosphodiesterases

The induction of type I interferon in human cells was measured to evaluate the potency of untreated and phosphodiesterase-treated oxo, Rp monothio and Rp, Rp dithio derivatives. Five compounds (cyclic[A(3',5')pA(3',5')p] (CDA), cyclic [A(2',5')pA(3',5')p] (ML-CDA), Rp monothio (Rp, monothio cyclic [A(2',5')pA(3',5')p] (ML R-CDA), Rp, Rp dithio (Rp, Rp dithio cyclic [A(3',5')pA(3',5')p] (RR-CDA), and Rp, Rp dithio cyclic [A(2',5')pA(3',5')p] (ML RR-CDA) were either treated with 160 μg of snake venom phosphodiesterase (SVPD) from *Crotalus adamanteus* (Sigma), 2.5 mU of Nuclease P1 (NP1) from *Penicillium citrinum* (Sigma) or mock treated. 7 μg of each compound was diluted in either SVPD buffer (1×PBS and 0.6 mM $MgCl_2$), NP1 buffer (30 mM Na Acetate, pH 5.3, 2 mM $ZnCl_2$) or left untreated and then incubated for 2 hr at 37° C., followed by boiling for 10 min to inactivate the nucleases. $4\times10^5$ THP1-Blue™ ISG cells (a human monocyte cell line transfected with an IRF-inducible secreted embryonic alkaline phosphatase reporter gene (Invivogen) which express alkaline phosphatase under the control of a promoter comprised of five IFN-stimulated response elements) were incubated with 50 μM of mock treated, SVPD treated or NP1-treated molecules. After 30 minutes, cells were washed and plated in a 96-well dish in RPMI media containing 10% FBS, and incubated at 37° C. with 5% $CO_2$. Cell culture supernatants from each sample were collected after 16 hr incubation, and 20 μL of the cell culture supernatants was added to 180 μL QUANTI-Blue reagent (Invivogen) and incubated for 25 minutes to evaluate type I interferon protein levels. Readings at Absorbance 655 nm were measured with a Versa Max spectrophotometer (Molecular Diagnostics).

Figure 12:
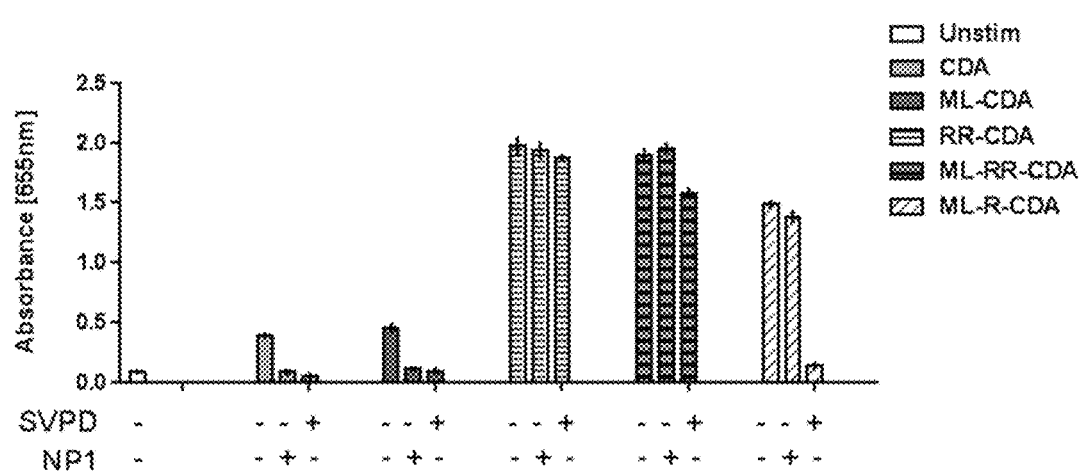
FIG. 12 depicts resistance of various CDN derivatives to phosphodiesterase treatment.

As shown in FIG. 12, the untreated Rp, Rp dithio compounds, Rp, Rp dithio cyclic [A(3',5')pA(3',5')p] (RR-CDA) and Rp, Rp dithio cyclic [A(2',5')pA(3',5')p] (ML RR-CDA) are more potent inducers of type I interferon than the oxo (cyclic[A(3',5')pA(3',5')p] (CDA) and cyclic [A(2',5')pA(3',5')p] (ML-CDA) and the Rp monothio. (Rp, monothio cyclic[A(2',5')pA(3',5')p] (ML R-CDA) CDN derivative molecules. We evaluated the activity of the CDN derivatives after treatment with either the phosphodiesterase SVPD, which cleaves both 2'-5' and 3'-5' phosphodiester linkages, or with NP1, which selectively digests 3'-5'phosphodiester linkages (Pino, et al, (2008) *Journal of Biological Chemistry*, 283, 36494-36503). FIG. 12 shows that the Rp, Rp dithio compounds, Rp, Rp dithio cyclic [A(3',5')pA(3',5')p] (RR-CDA) and Rp, Rp dithio cyclic [A(2',5')pA(3',5')p] (ML RR-CDA) retain their potency after SVPD and NP1 treatment, whereas the oxo (cyclic[A(3',5')pA(3',5')p] (CDA) and cyclic [A(2',5')pA(3',5')p] (ML-CDA) lost activity after digestion with both SVPD and NP1. The Rp monothio derivative (Rp, monothio cyclic [A(2',5')pA(3',5')p] (ML R-CDA) which contains a single thio substitution at the 3'-5 phosphodiester linkage retained activity after NP1 digestion, but was susceptible to SVPD treatment, which cleaves the 2'-5' phosphodieseter linkage. The differential susceptibility of the oxo, Rp monothio and Rp, Rp derivatives to SVPD or NP1 digestion confirms the structure of the Rp monothio and Rp, Rp dithio derivatives. These results also demonstrate the utility of the Rp, Rp dithio derivatives due to their resistance to digestion with phosphodiesterases, present in sera and/or in host cells, thus resulting in more potent activation of innate immune signaling, and increased therapeutic anti-tumor efficacy in vivo, as shown herein.

Figure 13:
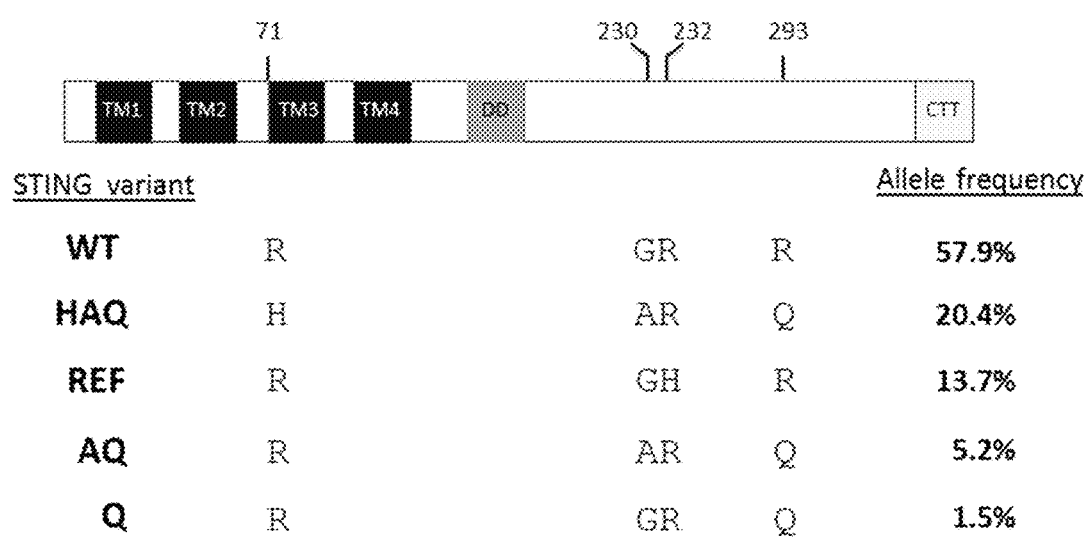
FIG. 13 depicts various known STING variants.

Example 7. Synthetic CDN Derivative Molecules Potently Activate Signaling of all Human STING Alleles To determine the responsiveness of the five known natural human STING variants (referred to as WT, REF, HAQ, AQ and Q) to the native and derivative molecules, a panel of human embryonic kidney (HEK) 293T cell lines that expressed the human STING alleles was generated. The parental HEK 293T cell line does not express endogenous STING, so the responsiveness of exogenously expressed STING alleles can be evaluated. MSCV2.2 plasmids encoding hSTING(REF)-GFP, hSTING(WT)-GFP, hSTING (HAQ)-GFP, hSTING(Q)-GFP and mSTING(WT)-GFP were obtained from the Vance Laboratory at UC Berkeley. hSTING(AQ)-GFP was derived from hSTING(Q)-GFP using a QuickChange Site-Directed Mutagenesis kit (Stratagene). The sequence of the hSTING(REF) allele is also known as the Barber allele (Ishikawa, H., and Barber, G. N. (2008). *Nature* 455, 674-678), and has the NCBI Reference Sequence NP_938023.1. The amino acid difference between hSTING(REF) and the other WT, HAQ, AQ and Q human STING alleles are shown in FIG. 13, which is adapted from Yi et al., Plos One 8: e77846 (2013). Stable HEK 293T-derived cell lines expressing each of the individual human STING alleles were generated by FACS sorting of GFP positive cells using a Mo Flo cell sorter at the Cancer Research Laboratory Flow Cytometry Facility at UC Berkeley. $1 \times 10^4$ HEK293T STING cells were seeded in 96-well plates and transiently transfected (using Lipofectamine 2000) with 50 ng of a human IFN-β reporter plasmid (pLuc-IFN-β) expressing the human IFN-β promoter upstream of a luciferase reporter and 10 ng of TK-*renilla* for normalization. 24 hours later, cells were stimulated with native and synthetic CDN derivative molecules using digitonin permeabalization to ensure uniform uptake. Each STING cell line was stimulated with 10 μM of cyclic [G(3',5')pA(3',5')p] (cGAMP), cyclic [G(2',5')pA(3',5')p] (ML-cGAMP), Rp, Rp dithio cyclic [G(2',5')pA(3',5')p] (ML RR-cGAMP), cyclic[A(3',5')pA(3',5')p] (CDA), Rp, Rp dithio cyclic [A(3',5')pA(3',5')p] (RR-CDA), cyclic [A(2',5')pA(3',5')p] (ML-CDA), Rp, Rp dithio cyclic [A(2',5')pA(3',5')p] (ML RR-CDA), cyclic [G(3',5')pG(3',5')p] (CDG), Rp, Rp dithio cyclic [G(3',5')pG(3',5')p] (RR-CDG), cyclic [G(2',5')pG(3',5')p] (ML-CDG) or Rp, Rp dithio cyclic [G(2',5')pG(3',5')p] (ML RR-CDG) in 25 ul digitonin buffer (50 mM HEPES, 100 mM KCL, 3 mM MgCl2, 0.1 mM DTT, 85 mM Sucrose, 0.2% BSA, 1 mM ATP, 0.1 mM GTP, 10 ug/ml digitonin). After 20 min, the stimulation mixtures were removed and 200 ul of standard RPMI media was added. After stimulation for 6 hrs, cell lysates were prepared and reporter gene activity measured using the Dual Luciferase Assay System (Promega) on a Spectramax M3 luminometer.

Figure 14:
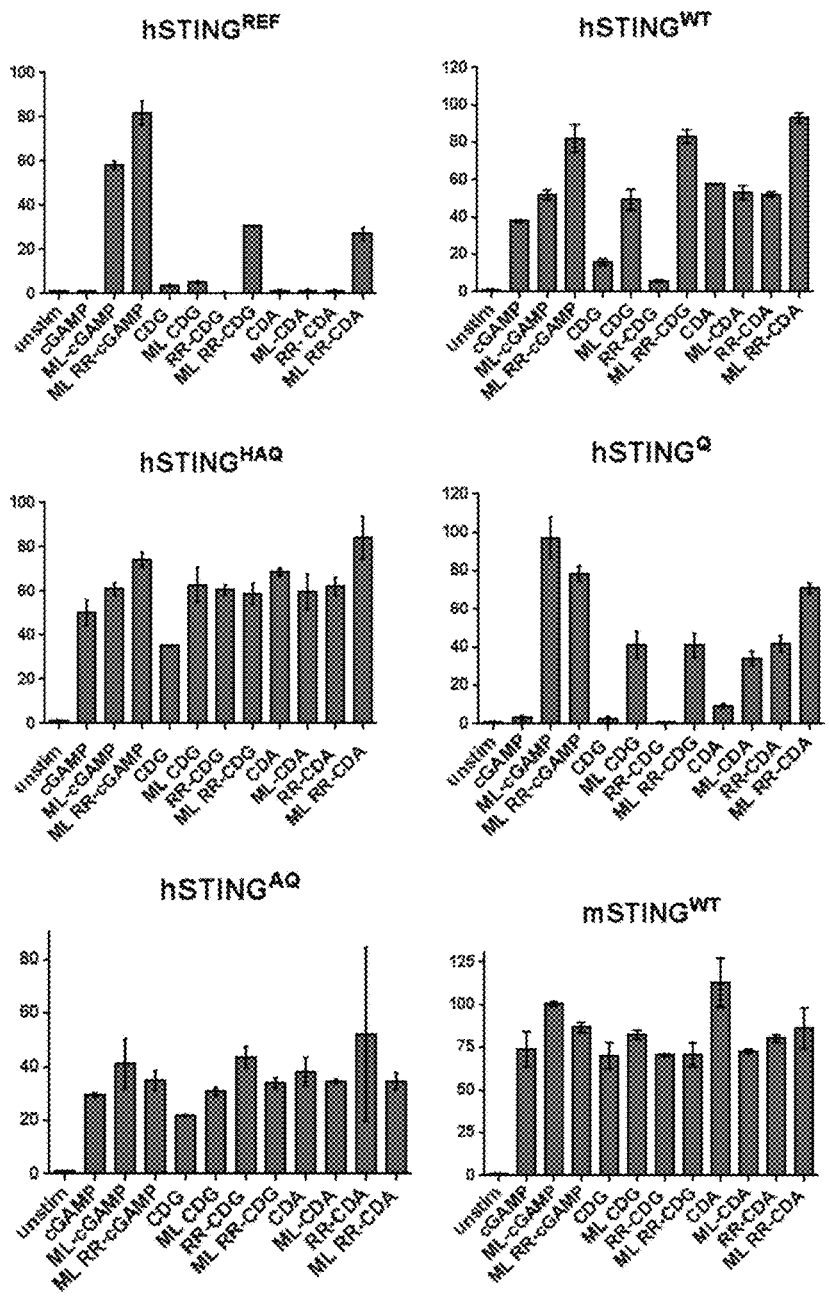
FIG. 14 depicts stimulation of HEK293 cell lines encoding human STING variant alleles by measuring the fold induction of the IFNβ-LUC reporter.

FIG. 14 depicts stimulation of HEK293 cell lines encoding human STING variant alleles by measuring the fold induction of the IFNβ-LUC reporter (RLU plotted on y-axis). As shown in FIG. 14, the Rp, Rp dithio mixed linkage compounds, Rp, Rp dithio cyclic [G(2',5')pA(3',5')p] (ML RR-cGAMP), Rp, Rp dithio cyclic [G(2',5')pG(3',5')p] (ML RR-CDG) and Rp, Rp dithio cyclic [A(2',5')pA(3',5')p] (ML RR-CDA) strongly induce IFNβ reporter activity by all human STING alleles. The refractory human STING alleles, hSTING (REF) and hSTING (Q), responded poorly to stimulation with the native molecules with canonical internucleotide phosphate bridge linkages: cyclic [G(3',5')pA(3',5')p] (cGAMP), cyclic[A(3',5')pA(3',5')p] (CDA); and, cyclic [G(3',5')pG(3',5')p] (CDG). In striking contrast, cell lines expressing the refractory human STING alleles were responsive to stimulation with the synthetic Rp, Rp dithio cyclic [A(2',5')pA(3',5')p] (ML RR-CDA): ML RR-CDA; ML RR-CDG; and, ML RR-cGAMP. Cells expressing mouse STING were responsive to all of the molecules tested, demonstrating that the modified synthetic CDN derivative molecules are relevant for activation of the human STING signaling pathway. These results demonstrate that the Rp, Rp dithio mixed linkage compounds, Rp, Rp dithio cyclic [G(2',5')pA(3',5')p] (ML RR-cGAMP), Rp, Rp dithio cyclic [G(2',5')pG(3',5')p] (ML RR-CDG) and Rp, Rp dithio cyclic [A(2',5')pA(3',5')p] (ML RR-CDA) potently activate all human STING alleles tested, indicating that these molecules will effectively induce innate immunity across a broad range of the human population.

Figure 15A:
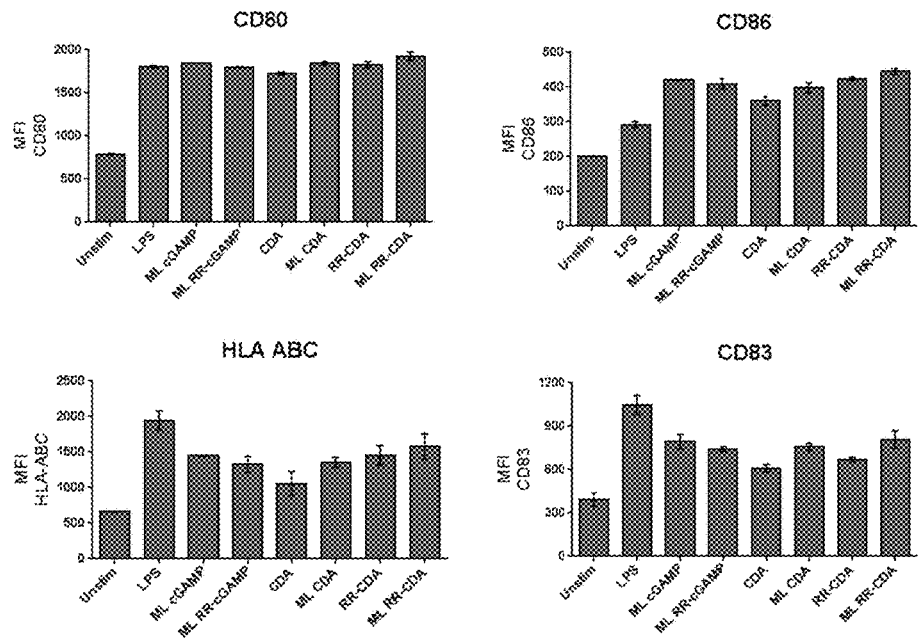
FIG. 15A depicts surface expression of MHC class I (HLA-ABC), CD80, CD83 and CD86 by stimulated human dendritic cells.
Figure 15B:
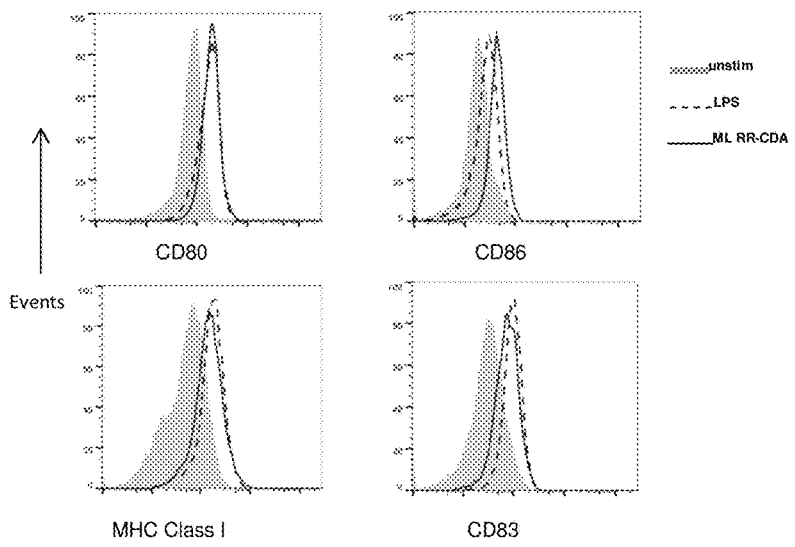
FIG. 15B representative histograms of CD80, CD86, CD83 and MHC Class I (HLA-ABC) expression in human DCs following LPS or CDN stimulation.

To demonstrate that the synthetic CDN derivative molecules induced the maturation of human dendritic cells (DCs), CD14+ monocytes from human PBMCs were treated for 6 days with 50 ng/ml GM-CSF and 25 ng/ml IL-4. Seven days later, the monocyte-derived DCs were stimulated with either LPS (1 μg/ml) or CDNs (50 μM) added directly to the media. After 48 hrs, surface expression of MHC class I (HLA-ABC), CD80, CD83 and CD86 was determined by FACS gated on the CD11c+ DC population. FIG. 15A depicts bar graphs indicating the average of the mean fluorescence intensity (MFI) following stimulation with the CDN molecules indicated in the figure. Also shown in FIG. 15B are representative histograms of CD80, CD86, CD83 and MHC Class I (HLA-ABC) expression in human DCs. Filled histograms correspond to unstimulated cells, the dotted line represents LPS stimulation, and the solid line represents Rp, Rp dithio cyclic [A(2',5')pA(3',5')p] (ML RR-CDA) stimulation. These results demonstrate that synthetic CDN molecules with structures comprising Rp, Rp dithio substitution of the nonbridging oxygen atoms of the internucleotide phosphate bridge in combination with 2'-5, 3'-5' noncanonical or mixed linkage (ML) phosphate bridge structure activate signaling in all human STING alleles, and potently activate the maturation of human DCs.

Example 8. CDN-Induced Antigen-Specific T-Cell Response

To determine the OVA-specific CD8 T cell response induced by the different cyclic dinucleotide molecules, C57BL/6 mice (n=5) were immunized subcutaneously with 0 μg (no CDN) or 5 μg or 25 μg [G(2',5')pG(3',5')p] (mixed linkage or ML-CDG) formulated in 2% squalene-and-water with 10 μg ovalbumin protein. Seven days following the vaccination, blood was collected from each animal, and PBMCs were prepared. $5 \times 10^4$ PBMCs were stimulated overnight in an IFNγ ELISpot assay with media alone (unstimulated) or with 1 μM $OVA_{257-264}$ peptide in the presence of $1 \times 10^5$ naïve splenocytes as feeder cells. IFNγ ELISpots were developed and quantified using a CTL plate reader and ImmunoSpot software.

Figure 16:
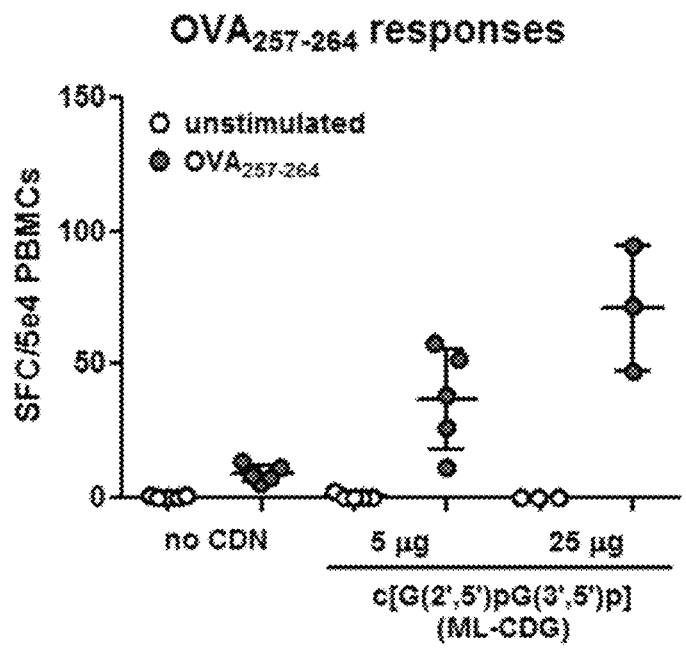
FIG. 16 depicts OVA-specific CD8 T cell immunity in PBMCs in C57BL/6 mice at 7 days post vaccination with cyclic dinucleotide adjuvanted OVA protein.

As shown in FIG. 16, both doses of cyclic [G(2',5')pG(3',5')p] (ML-CDG) induce OVA-specific CD8 immune responses in C57BL/6 mice. These responses are significantly higher than responses induced by unstimulated controls and by a no CDN control group. These results demonstrate that formulations of cyclic [G(2',5')pG(3',5')p]

(ML-CDG) with an antigen can stimulate antigen-specific CD8 T cell responses in vivo.

To determine whether STING signaling is required for c[G(2',5')pG(3',5')p] (ML-CDG) to induce an OVA-specific CD8 T cell response, C57BL/6 mice (n=3 or 5) and goldenticket mice (n=3) were immunized subcutaneously with either 0 μg (no CDN) or 25 μg c[G(2',5')pG(3',5')p] (ML-CDG) formulated in 2% squalene-and-water with 10 μg ovalbumin protein. Seven days following the vaccination, blood was collected from each animal, and PBMCs were prepared. $5 \times 10^4$ PBMCs were stimulated overnight in an IFNγ ELISpot assay with media alone (unstimulated) or with 1 μM $OVA_{257-264}$ peptide in the presence of $1 \times 10^5$ naïve splenocytes as feeder cells. IFNγ ELISpots were developed and quantified using a CTL plate reader and ImmunoSpot software.

Figure 17:
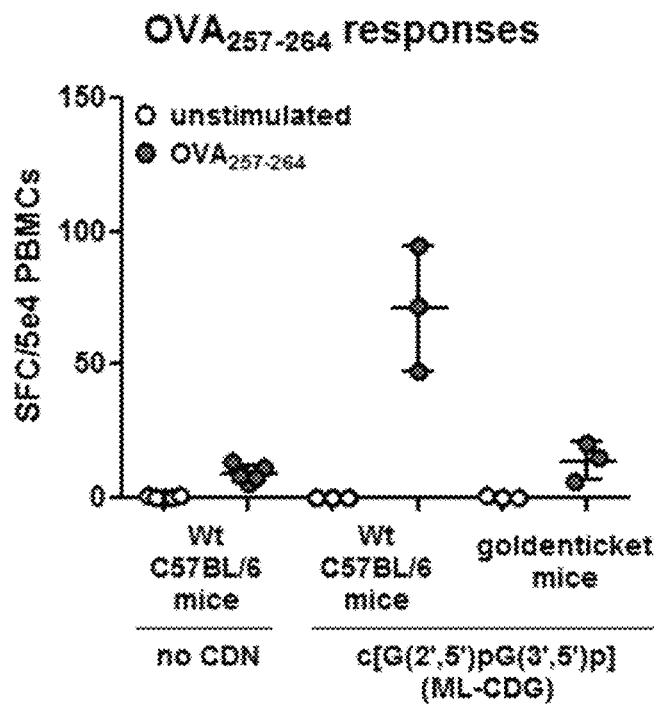
FIG. 17 depicts OVA-specific CD8 T cell immunity in PBMCs in C57BL/6 or goldenticket (STING$^{-/-}$) mice at 7 days post vaccination with cyclic dinucleotide adjuvanted OVA protein.

FIG. 17 shows that c[G(2',5')pG(3',5')p] (ML-CDG) induces an OVA-specific CD8 T cell response that is dependent on the presence of a functional STING molecule. In the wild-type C57BL/6 mice with a functional STING molecule, formulation of c[G(2',5')pG(3',5')p] (ML-CDG) and ovalbumin protein induces significant $OVA_{257-264}$ immune responses compared to unstimulated control and a no CDN control. In goldenticket mice, which do not express a functional STING molecule (Sauer, Infection and Immunity 2011), the OVA-specific responses induced by c[G(2',5')pG(3',5')p] (ML-CDG) are not significantly different than the OVA-specific responses induced by a control formulation that does not include CDN (no CDN). These results indicate that immune response induced by c[G(2',5')pG(3',5')p] (ML-CDG) requires a functional STING molecule.

Example 9. Comparative Data with Various CDN Derivatives

To assess the ability of the derivative molecules to promote anti-tumor immunity, B16 melanoma cells ($5 \times 10^4$ cells in 100 μL PBS) were implanted subcutaneously on the lower back of 6-8 week old female C57BL/6 mice (8 mice per group). Treatments began when tumors reached a volume of approximately 75 mm³, on day 14 post tumor implantation. The CDN compounds were administered (25 μg in a total volume of 40 μL HBSS) by subcutaneous injection into the center of the tumor using a 27 gauge needle. Injections were repeated every three days, for a total of three intratumoral injections. The CDNs tested were cyclic [G(3',5')pG(3',5')p] (CDG); cyclic [G(2',5')pG(3',5')p] (mixed linkage, or ML CDG); Rp, Rp dithio cyclic [G(2',5')pG(3',5')p] (ML RR-CDG); cyclic [A(3',5')pA(3',5')p] (CDA); cyclic [A(2',5')pA(3',5')p] (mixed linkage, or ML CDA); and Rp, Rp dithio cyclic [A(2',5')pA(3',5')p] (ML RR-CDA).

Figure 18:
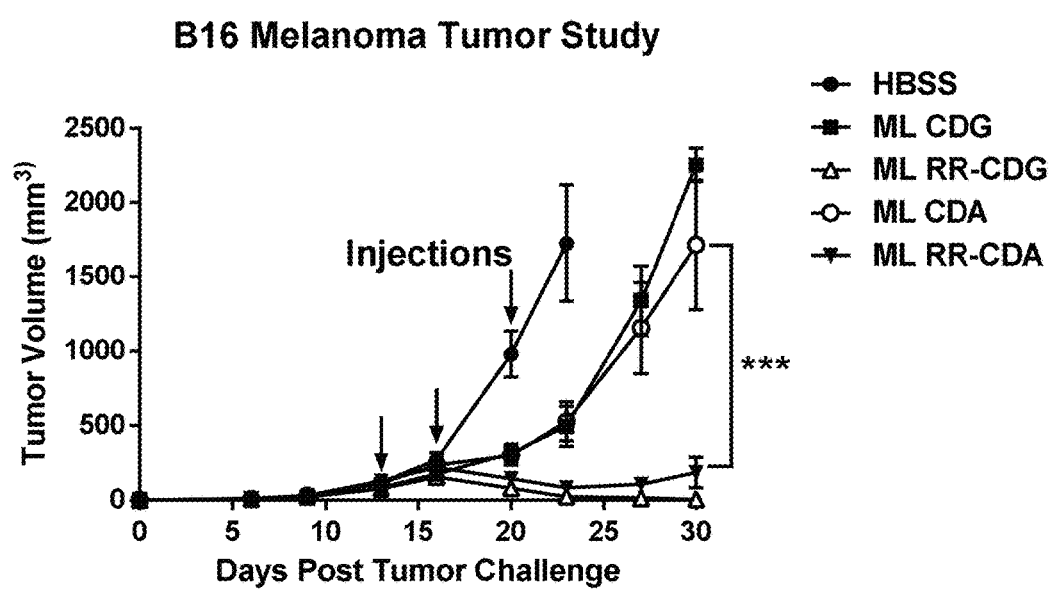
FIG. 18 depicts tumor volume in a B16 melanoma model following treatment with various cyclic dinucleotide molecules.

As shown in FIG. 18, the ML RR-CDG and ML RR-CDA derivatives induced potent anti-tumor efficacy, as compared to the cyclic ML CDG and cyclic ML CDA cyclic dinucleotide molecules. The ML RR-CDA molecule induced significantly more tumor rejection than the ML CDA derivative (P=0.0004, student's t-test), and mice remained nearly tumor-free in the ML RR-CDG tumor group by day 44 post tumor implantation. These data demonstrate the enhanced potency of the ML RR-CDN derivatives compared to the ML CDN derivative molecules, and the significant anti-tumor efficacy of the ML RR-CDN molecules in the B16 melanoma mouse model.

To further assess the ability of the derivative molecules to promote anti-tumor immunity, CT26 colon carcinoma cells ($2 \times 10^5$ cells in 100 μL PBS) were implanted by intravenous injection into 6-8 week old female BALB/c mice and assessed for overall survival. The CDN compounds (25 μg in a total volume of 100 μL HBSS) were administered one day post tumor implantation by subcutaneous injection into the base of the tail. Mice were boosted with an additional injection one week later for a total of two vaccinations.

Figure 19A:
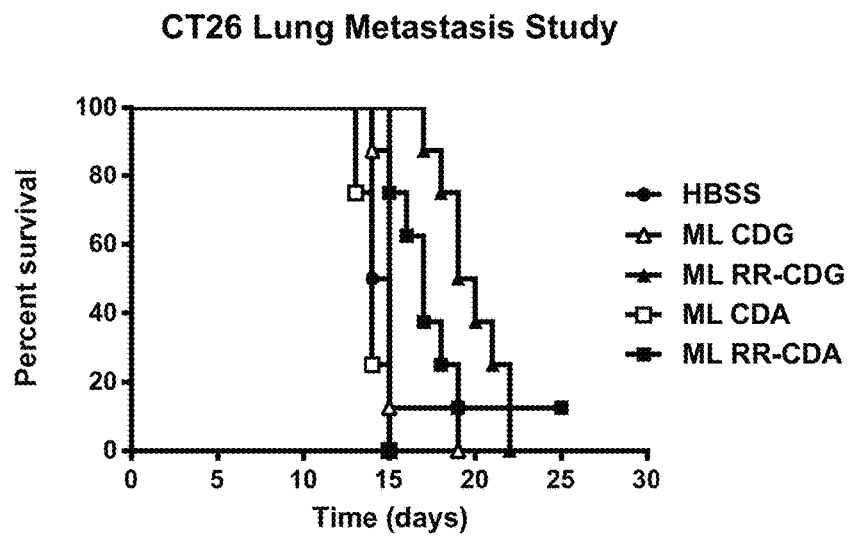
FIG. 19A depicts survival curves in a CT26 lung metastasis tumor model following treatment with various cyclic dinucleotide molecules.

As shown in FIG. 19A, the Rp, Rp dithio cyclic [G(2',5')pG(3',5')p] (ML RR-CDG) induced significantly higher survival rates compared to the cyclic [G(2',5')pG(3',5')p] (ML CDG) molecule (P=0.0018, log-rank test), and the Rp, Rp dithio cyclic [A(2',5')pA(3',5')p] (ML RR-CDA) induced significantly higher survival rates compared to the cyclic [A(2',5')pA(3',5')p] (ML CDA) molecule (P=0.0005, log-rank test). This demonstrates the significant anti-tumor efficacy of the ML RR-CDN derivatives compared to the ML CDN derivative molecules in a CT26 lung metastasis survival model. These results demonstrate that CDN derivative molecules can be successfully administered subcutaneously.

To demonstrate that activation of tumor-initiated T cell priming and anti-tumor efficacy induced by CDN derivative molecules was not limited to a single tumor type and mouse genetic background, the ability of the synthetic CDNs to promote anti-tumor immunity in other tumor models was tested. Either CT26 colon carcinoma cells ($1 \times 10^5$ cells in 100 μL PBS) or 4T1 mammary carcinoma cells ($1 \times 10^5$ cells in 100 μL PBS) were implanted subcutaneously on the flanks of 6-8 week old female BALB/c mice (8 mice per group). Treatments began when tumors reached a volume of approximately 75 mm³, which was approximately day 14 post tumor implantation. The compounds Rp, Rp dithio cyclic [A(2',5')pA(3',5')p] (ML RR-CDA) or Rp, Rp dithio cyclic [G(2',5')pG(3',5')p] (ML RR-CDG) compounds (25 μg in a total volume of 40 μL HBSS), or HBSS vehicle control, and Rp, Rp dithio cyclic [A(2',5')pA(3',5')p] (ML RR-CDA) (50 μg in a total volume of 40 μL HBSS) or HBSS vehicle control, were administered by subcutaneous injection into the center of the tumor using a 27 gauge needle. Injections were repeated every three days, for a total of three intratumoral injections.

Figure 19B:
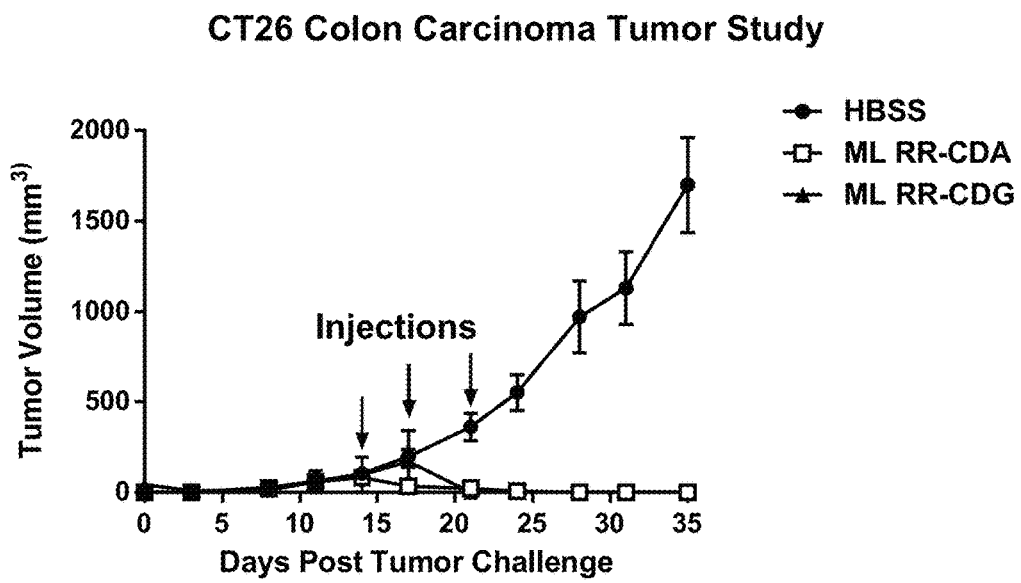
FIG. 19B depicts survival curves in a CT26 colon carcinoma tumor model following treatment with various cyclic dinucleotide molecules.
Figure 19C:
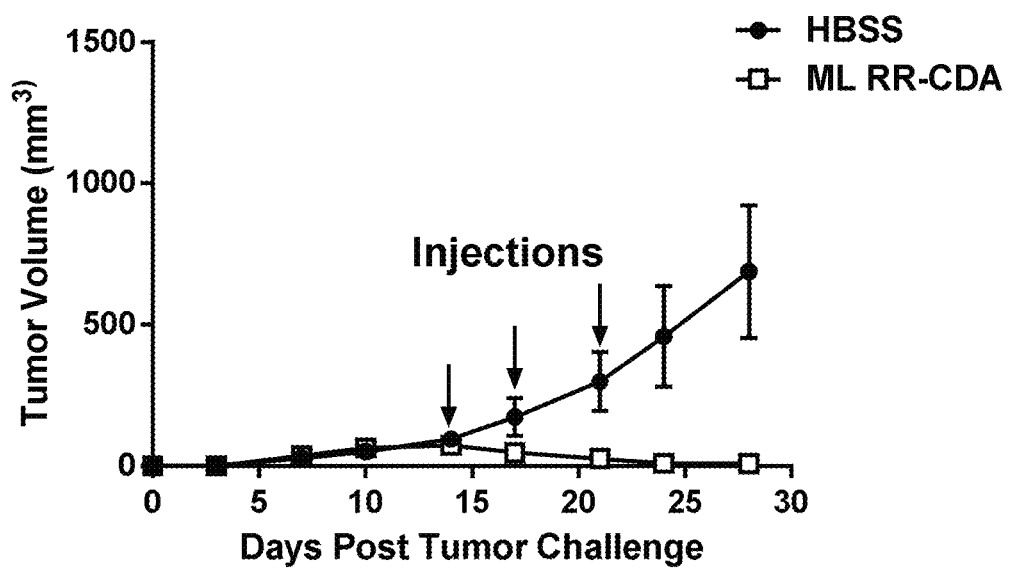
FIG. 19C depicts survival curves in a 4T1 mammary carcinoma tumor model following treatment with various cyclic dinucleotide molecules.

As shown in FIG. 19B, ML RR-CDG completely inhibited tumor growth in 7 out of 8 mice, while ML RR-CDA completely inhibited tumor growth of all established CT26 tumors. As shown in FIG. 19C, ML RR-CDA derivative completely inhibited tumor growth of all established 4T1 mammary tumors. These data demonstrate the striking potency and durable anti-tumor efficacy of the synthetic mixed linkage RpRp dithio cyclic dinucleotide (ML RR-CDN) derivatives in multiple tumor models.

Example 10. CDN Induced Anti-Tumor Efficacy is STING-Dependent

To determine whether the effects of the derivative molecules are STING-dependent, B16 melanoma cells ($5 \times 10^4$ cells in 100 μL PBS) were implanted on the right flanks of 6-8 week old female goldenticket STING$^{-/-}$ mice, or wild-type C57BL/6 control mice (5 mice per group). Treatments began when tumors reached a volume of approximately 75 mm³, on day 14 post tumor implantation. The compounds administered were Rp, Rp dithio cyclic [G(2',5')pG(3',5')p] (ML RR-CDG) (25 μg in a total volume of 40 μL HBSS), Rp, Rp dithio cyclic [A(2',5')pA(3',5')p] (ML RR-CDA) (50 μg in a total volume of 40 μL HBSS), the TLR9 agonist CpG 1668 (50 μg in a total volume of 40 μL HBSS), or HBSS vehicle control. Mice were treated by subcutaneous injection into the center of tumor only using a 27 gauge needle. Injections were repeated every three days, for a total of three intratumoral injections.

Figure 20A:
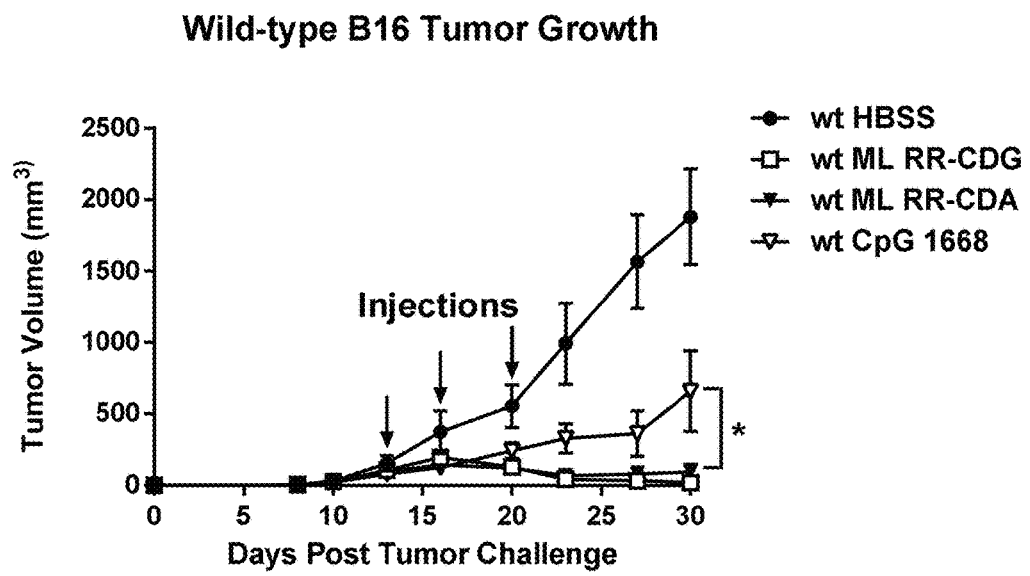
FIG. 20A depicts tumor inhibition in wild-type C57BL/6 mice following ML RR-CDN administration as compared to control mice receiving HBSS and CpG dinucleotide.
Figure 20B:
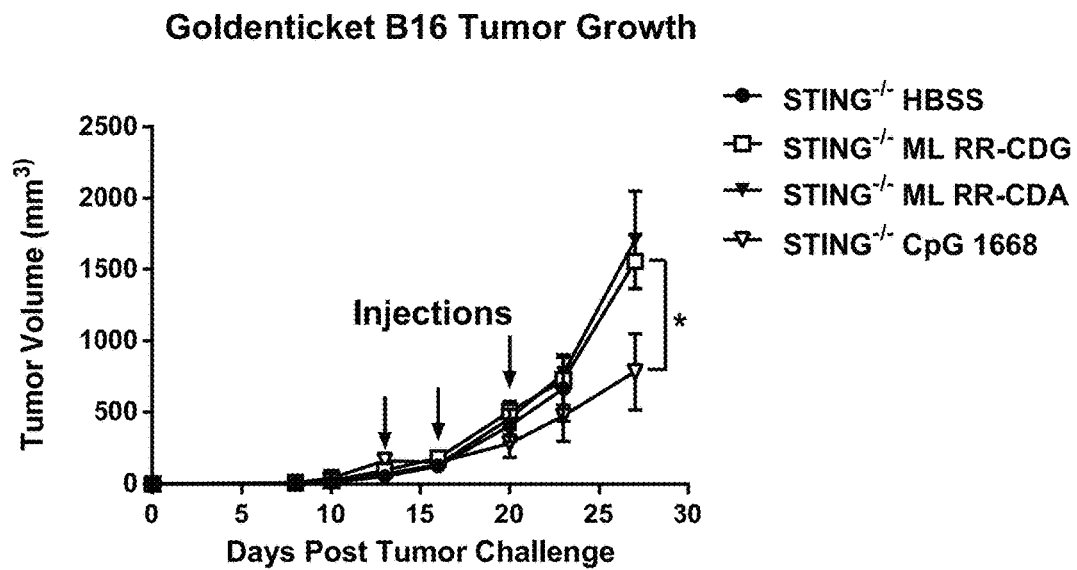
FIG. 20B depicts results obtained in STING deficient mice.

As shown in FIG. 20A, the derivative ML RR-CDNs induced dramatic tumor inhibition in wild-type C57BL/6 mice as compared to HBSS control, and significantly more tumor inhibition than the TLR9 agonist CpG 1668 (P=0.03, student's t-test). In FIG. 20B, tumor growth was not inhibited by either ML RR-CDG or ML RR-CDA, demonstrating that the anti-tumor efficacy observed in wild-type C57BL/6 mice (FIG. 20A) was entirely dependent on a functional STING signaling pathway. In contrast, tumor growth of CpG 1668 was similar in both wild-type and STING$^{-/-}$ mice, as compared to HBSS control (P=0.03, student's t-test), demonstrating that the action of this compound is STING-independent.

Example 11. CDN Derivatives Induce Durable and Effective Anti-Tumor Specific T-Cell Immunity To determine whether the synthetic derivative CDN molecules elicit durable and effective anti-tumor T-cell immunity, 6-8 week old female BALB/c mice (8 mice per group) were implanted with CT26 colon carcinoma cells ($1\times10^5$ cells in 100 µL PBS). Mice were treated with Rp, Rp dithio cyclic [A(2',5')pA(3',5')p] (ML RR-CDA) compound (50 mg in a total volume of 40 µL HBSS) or HBSS vehicle control, and tumor growth was monitored as per previous example. Mice were bled on day 18 post tumor implantation and PBMCs were isolated by Ficoll gradient (Miltenyi Biotech). $5\times10^4$ PBMCs were stimulated overnight in an IFNγ ELISpot assay with media alone (unstimulated), or with 1 µM of the endogenous H-2 L$^d$-restricted tumor rejection antigen AH1 peptide in the presence of $1\times10^5$ naïve splenocytes as feeder cells. IFN-γ ELISpot plates were developed and quantified using a CTL plate reader and Immuno-Spot software. On day 55 post tumor implantation, surviving mice and age-matched naïve control mice were implanted on the contralateral flank with either CT26 or 4T1 (both $1\times10^5$ cells in 100 µL PBS) tumor cells (4 mice per group), and monitored for tumor growth.

Figure 21A:
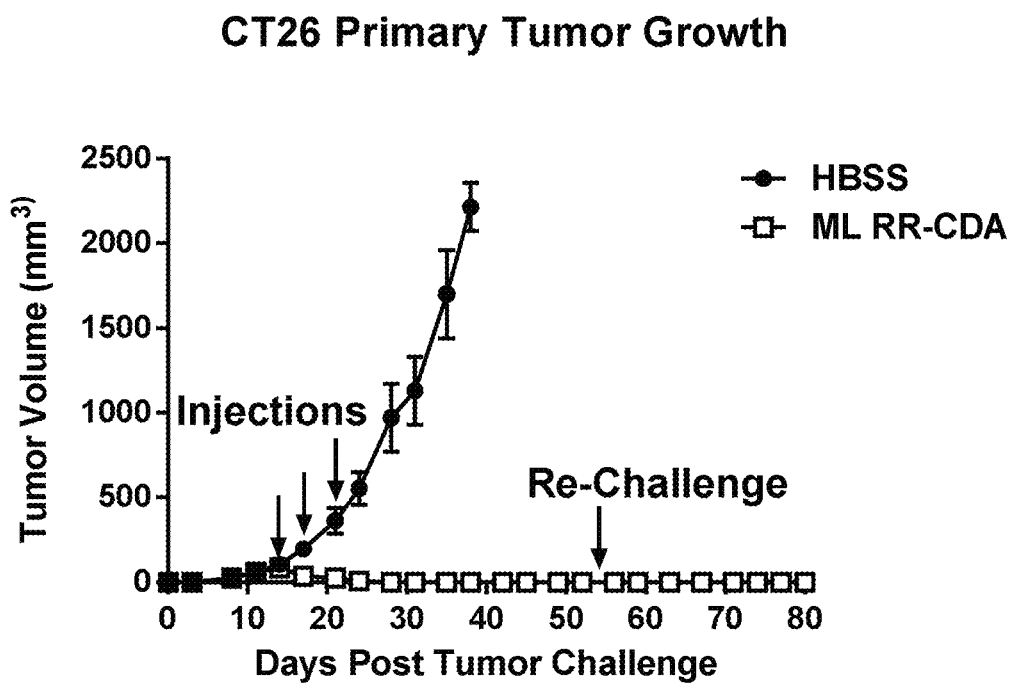
FIG. 21A depicts rejection of established CT26 colon carcinomas following ML
RR-CDN administration.
Figure 21B:
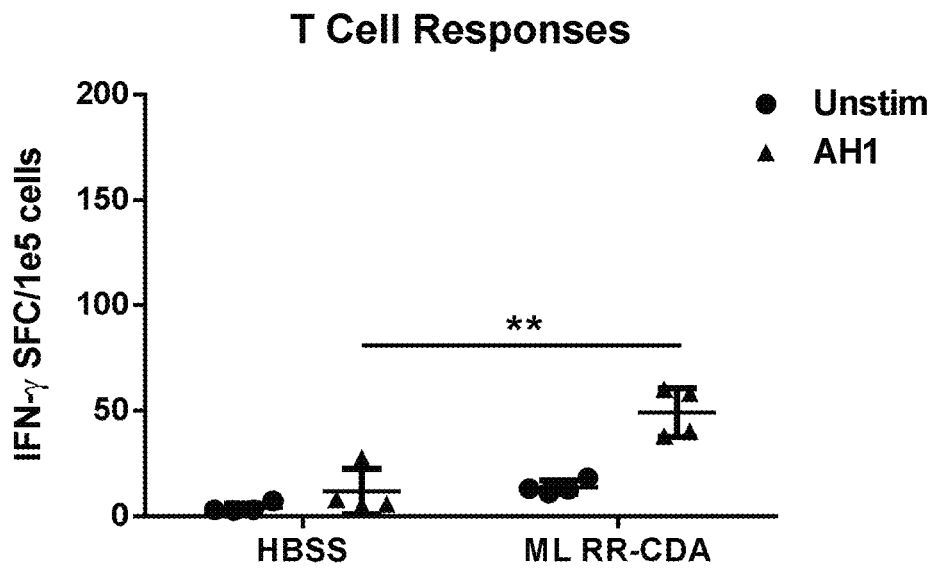
FIG. 21B depicts IFN-γ induction from mice treated with ML RR-CDA.
Figure 21C:
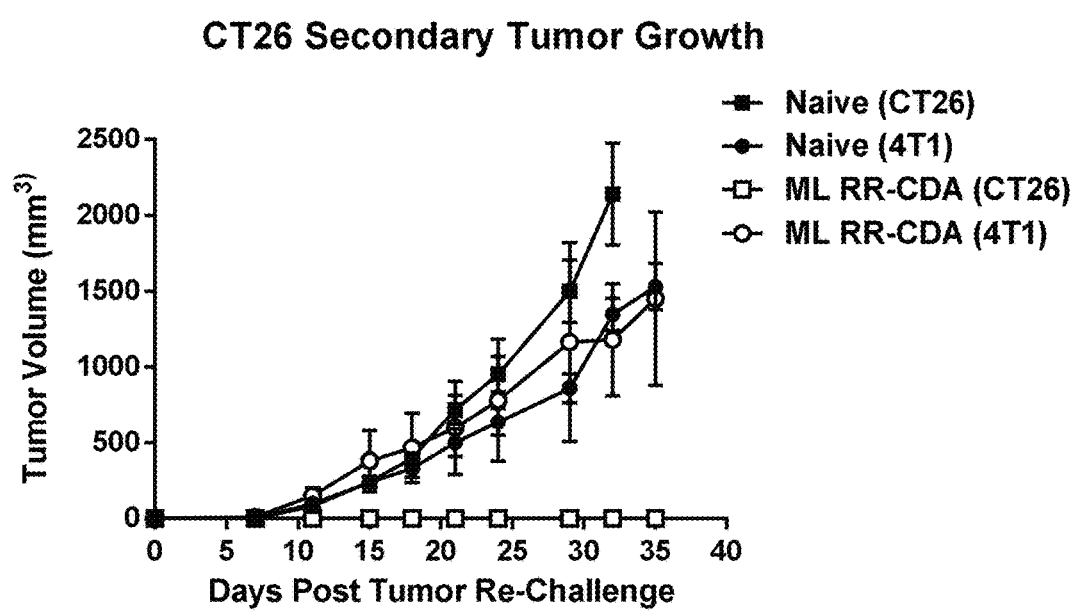
FIG. 21C depicts survival in mice following re-challenge with CT26 tumor cells.

As shown in FIG. 21A, all mice treated with ML RR-CDA rejected the growth of established CT26 colon carcinomas. To demonstrate that the effect was mediated by the CDN-mediated induction of an adaptive T cell immune response, PBMCs on day 18 post tumor induction were assessed for IFN-γ production by ELISpot assay, in response to stimulation with the endogenous tumor antigen AH1. As shown in FIG. 21B, PBMCs isolated from mice treated with ML RR-CDA generated significantly higher IFN-γ in response to AH1 peptide stimulation, as compared to the HBSS-treated control group (P=0.003, student's t-test). Further, in FIG. 21C, surviving mice re-challenged with a contralateral tumor exhibited complete protection against the same CT26 tumor type, while not inhibiting growth of the 4T1 tumor type. These data demonstrate the ability of ML RR-CDA to elicit durable and effective tumor-specific T cell-mediated anti-tumor immunity that results in both rejection of the treated tumor, and a stable tumor-antigen specific memory T cell population that can reject tumor challenge.

To determine whether CDN derivative molecules induce effective and durable anti-tumor immunity in an alternate tumor model, 6-8 week old female BALB/c mice (8 mice per group) were implanted with 4T1 mammary carcinoma cells ($1\times10^5$ cells in 100 µL PBS). Mice were treated with Rp, Rp dithio cyclic [A(2',5')pA(3',5')p] (ML RR-CDA) compound (50 µg in a total volume of 40 µL HBSS), or HBSS vehicle control, as per previous experiment. On day 35 post tumor implantation, surviving mice and age-matched naïve control mice were implanted on the contralateral flank with either CT26 or 4T1 (both $1\times10^5$ cells in 100 µL PBS) tumor cells (4 mice per group), and monitored for tumor growth.

Figure 22A:
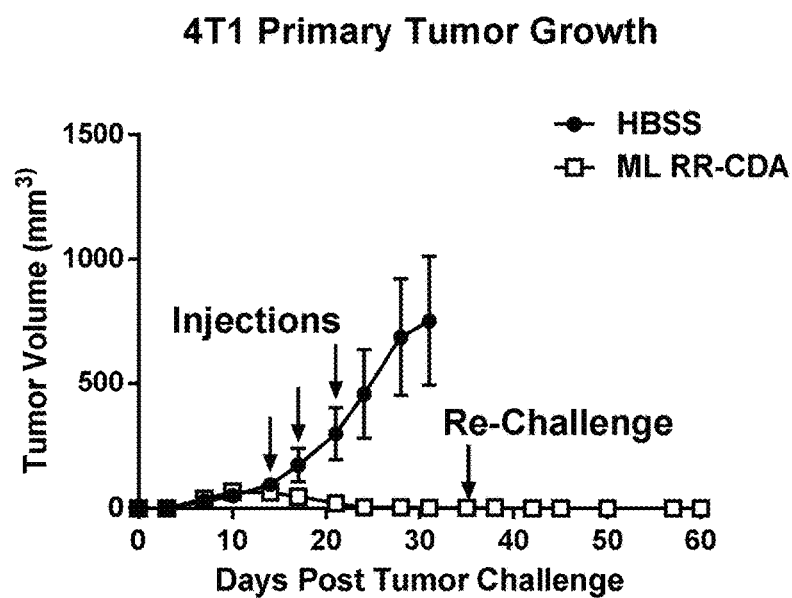
FIG. 22A depicts rejection of established 4T1 mammary carcinomas following ML RR-CDN administration.
Figure 22B:
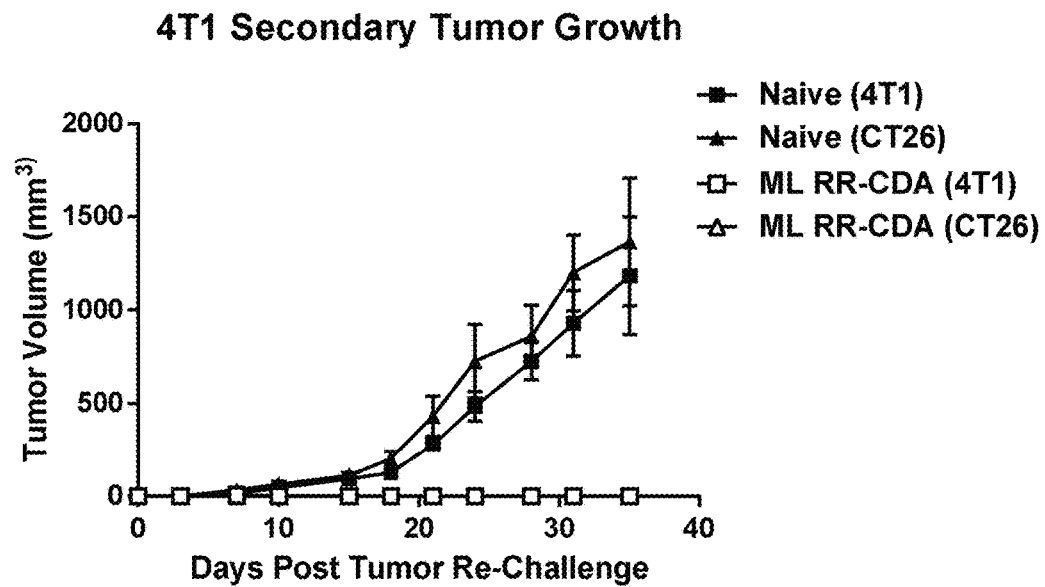
FIG. 22B depicts protection from re-challenge with CT26 tumor cells.

As shown in FIG. 22A, and demonstrated previously, treatment with ML RR-CDA completely inhibited tumor growth of established 4T1 mammary carcinomas. Further, in FIG. 22B, re-challenge with 4T1 tumor cells on the contralateral flank induced complete protection. Re-challenge with the more immunogenic CT26 tumor also elicited complete protection, indicating that these tumors share similar tumor antigens, providing yet further evidence of the potency of the synthetic CDN derivative molecules.

Example 12. Activation of Tumor-Initiated T Cell Priming by Intratumoral Injection with CDN Synthetic Derivatives Induces Abscopal Tumor Inhibition The examples shown herein demonstrate that intratumoral (IT) injection of synthetic CDN derivatives results in striking and durable tumor destruction, due to the STING-dependent activation of pro-inflammatory cytokines, to facilitate the development of effective tumor-specific T cell immunity. The STING-dependent induction of tumor-specific T cell immunity protects animals against subsequent challenge with the autologous tumor. It will be apparent to those skilled in the art that advanced cancer is metastatic, and that to be effective, therapies must inhibit outgrowth of distal masses. Treatment of one or selected lesions that inhibits tumor outgrowth of distal untreated tumor masses is known as an abscopal effect. To test whether IT injection of a selected tumor with synthetic CDN derivative molecules inhibited the tumor outgrowth of a distal untreated tumor, (A) CT26 colon carcinoma cells ($1\times10^5$ cells in 100 µL PBS) and (B) 4T1 mammary carcinoma cells ($1\times10^5$ cells in 100 µL PBS) were implanted subcutaneously on the contralateral flanks of 6-8 week old female BALB/c mice (8 mice per group). Treatments began when tumors reached a volume of approximately 75 mm$^3$, on day 13 post tumor implantation. The Rp, Rp dithio cyclic [A(2',5')pA(3',5')p] (ML RR-CDA) compound (50 µg in a total volume of 40 µL HBSS), or HBSS vehicle control, was administered by subcutaneous injection into the center of the primary (right side) tumor only using a 27 gauge needle. Injections were repeated every three days, for a total of three intratumoral injections.

Figure 23A:
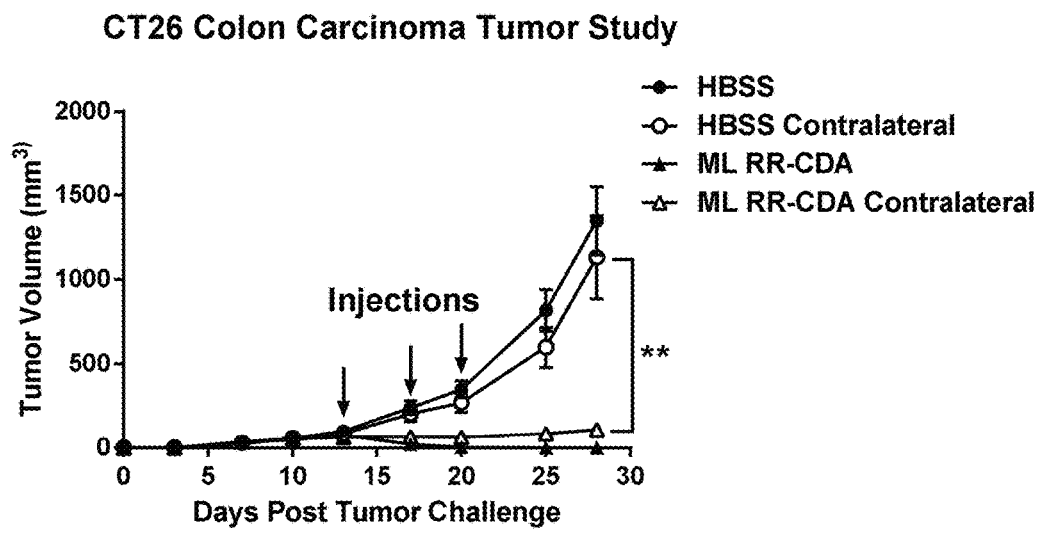
FIG. 23A depicts inhibition of the treated primary tumor in CT26 tumor-bearing animals following ML RR-CDA administration, as compared to HBSS vehicle control.
Figure 23B:
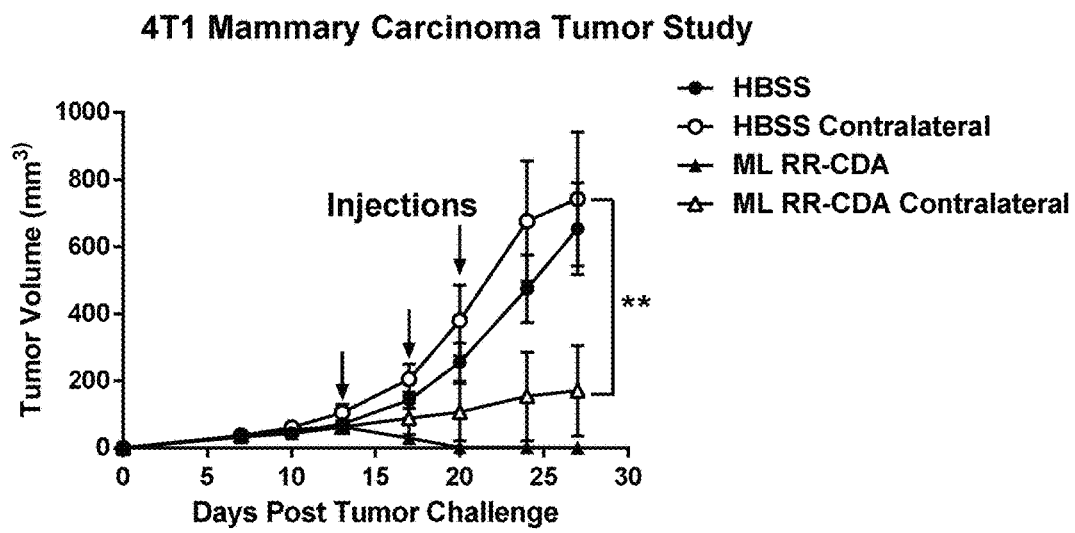
FIG. 23B depicts inhibition of the treated primary tumor in 4T1 tumor-bearing animals following ML RR-CDA administration, as compared to HBSS vehicle control.

As shown in FIG. 23, the Rp, Rp dithio cyclic [A(2',5') pA(3',5')p] (ML RR-CDA) compound induced complete inhibition of the treated primary tumor in both CT26 (FIG. 23A) and 4T1 (FIG. 23B) tumor-bearing animals, as compared to HBSS vehicle control. Further, outgrowth of the contralateral (untreated) tumor in both tumor models was also significantly inhibited, as compared to HBSS controls (FIG. 23A P=0.0011, FIG. 23B P=0.0019, student's t-test). These data demonstrate the significant anti-tumor efficacy of the ML RR-CDA derivative when injected into the primary tumor, as well as its significant abscopal anti-tumor immune effects.

To determine whether the synthetic CDN derivative molecules promote abscopal anti-tumor immunity in an alternative tumor model and mouse genetic background, 6-8 week old female C57BL/6 mice (8 mice per group) were implanted with B16 melanoma cells ($5\times10^4$ cells in 100 µL PBS) in the right flank. One week later mice were implanted intravenously with $1\times10^5$ B16 melanoma cells to colonize the lung, along with a group of naïve age-matched control mice. When the subcutaneous flank tumor reached approximately 75 mm$^3$ on day 13, mice were treated intratumorally with Rp, Rp dithio cyclic [A(2',5')pA(3',5')p] (ML RR- CDA) (50 μg in a total volume of 40 μL HBSS) or HBSS vehicle control, for three injections as per previous protocol. On day 28 post subcutaneous tumor implantation (day 21 post i.v. implantation), mice were euthanized and lungs were harvested and fixed (10% Neutral Buffered Formalin), and the number of lung tumor nodules counted using a dissecting microscope.

Figure 24A:
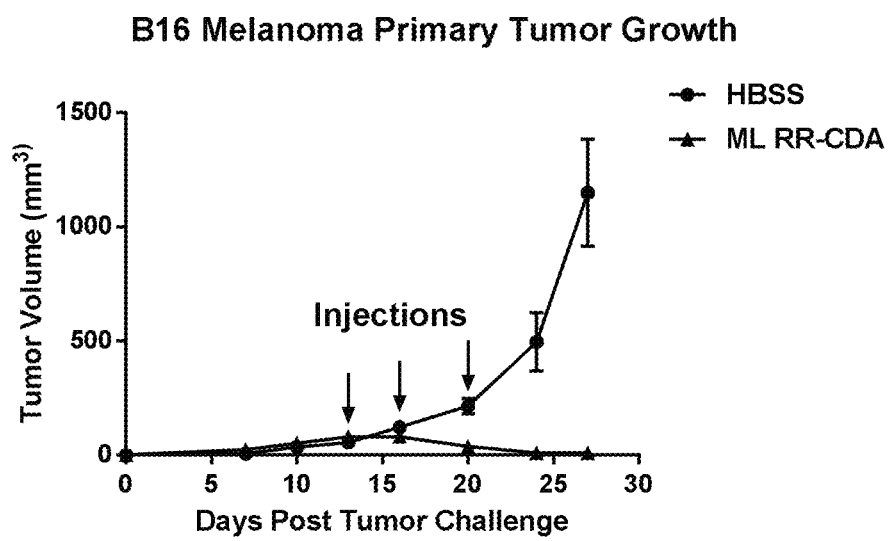
FIG. 24A depicts inhibition of the treated primary tumor in B16 melanoma following ML RR-CDA administration.
Figure 24B:
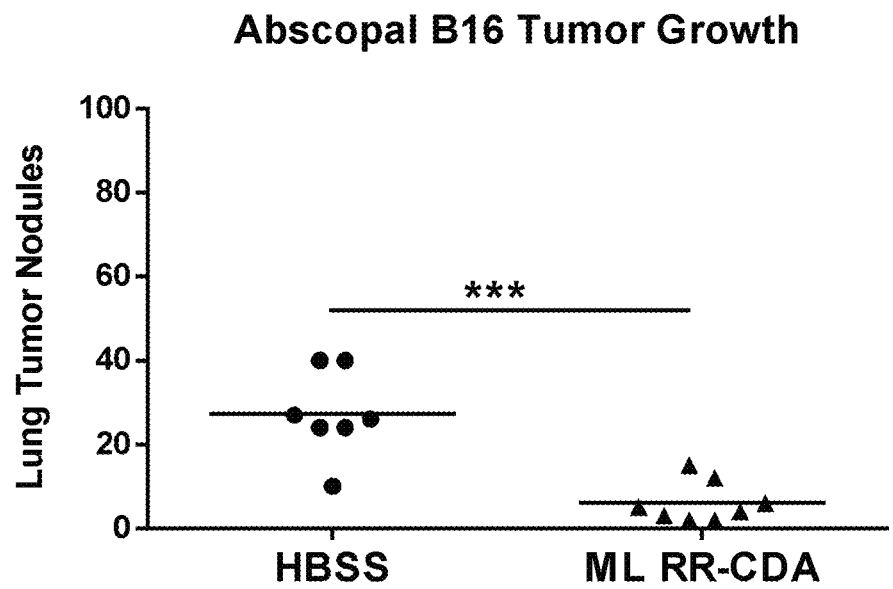
FIG. 24B depicts inhibition of growth of distal lung tumor nodules following ML RR-CDA administration, as compared to HBSS vehicle control in graphical form.
Figure 24C:
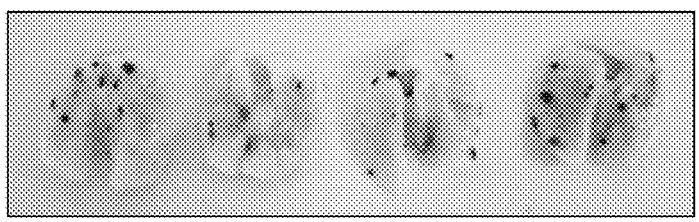
FIG. 24C depicts inhibition of growth of distal lung tumor nodules following ML RR-CDA administration, as compared to HBSS vehicle control in the lung tissue itself in photographic form.
Figure 24C:
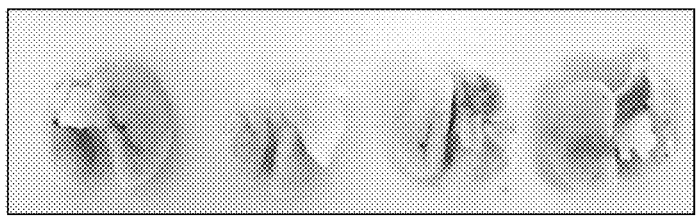

As shown in FIG. 24A, and in previous experiments, treatment with ML RR-CDA significantly inhibited tumor growth of the primary flank tumor, as compared to the HBSS control group (P<0.001, student's t-test). Further, in FIG. 24B and depicted in FIG. 24C, treatment with the CDN derivative significantly inhibited the growth of distal lung tumor nodules, compared to the HBSS and naïve (i.v. only) tumor groups. The results shown here demonstrate that intratumoral (IT) injection of synthetic CDN derivatives results in an abscopal anti-tumor effect, as demonstrated by the destruction of the treated tumor, due to the STING-dependent activation of pro-inflammatory cytokines and development of effective tumor-specific T cell immunity, which then inhibits outgrowth of untreated distal tumors.

One skilled in the art readily appreciates that the present invention is well adapted to carry out the objects and obtain the ends and advantages mentioned, as well as those inherent therein. The examples provided herein are representative of preferred embodiments, are exemplary, and are not intended as limitations on the scope of the invention.

It is to be understood that the invention is not limited in its application to the details of construction and to the arrangements of the components set forth in the following description or illustrated in the drawings. The invention is capable of embodiments in addition to those described and of being practiced and carried out in various ways. Also, it is to be understood that the phraseology and terminology employed herein, as well as the abstract, are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

While the invention has been described and exemplified in sufficient detail for those skilled in this art to make and use it, various alternatives, modifications, and improvements should be apparent without departing from the spirit and scope of the invention. The examples provided herein are representative of preferred embodiments, are exemplary, and are not intended as limitations on the scope of the invention. Modifications therein and other uses will occur to those skilled in the art. These modifications are encompassed within the spirit of the invention and are defined by the scope of the claims.

It will be readily apparent to a person skilled in the art that varying substitutions and modifications may be made to the invention disclosed herein without departing from the scope and spirit of the invention.

All patents and publications mentioned in the specification are indicative of the levels of those of ordinary skill in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

Other embodiments are set forth within the following claims.

We claim:

1. A compound of the formula

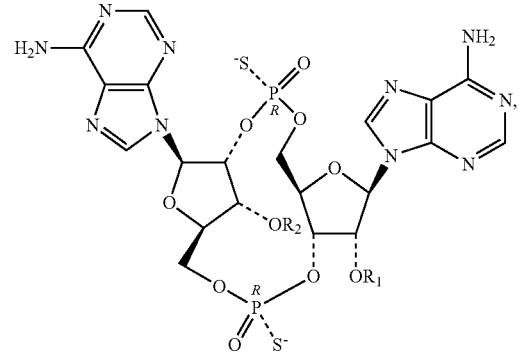

where $R_1$ and $R_2$ are each H,
or a pharmaceutically acceptable salt thereof.

2. A pharmaceutical composition:
   a compound according to claim 1 formulated with a pharmaceutically acceptable carrier.

3. The pharmaceutical composition according to claim 2, wherein the pharmaceutical acceptable carrier comprises one or more agents selected from the group consisting of lipids, interbilayer crosslinked multilamellar vesicles, biodegradeable poly(D,L-lactic-co-glycolic acid) [PLGA]-based or poly anhydride-based nanoparticles or microparticles, and nanoporous particle-supported lipid bilayers.

4. A composition comprising:
   a compound according to claim 1 and one or more antigens selected for purposes of inducing an immune response against the antigen(s) when the composition is administered to an individual.

5. A method of inducing stimulator of interferon genes protein (STING)-dependent type I interferon production in an individual in need thereof, comprising:
   administering a compound according to claim 1 to the individual in an amount sufficient to induce STING-dependent type I interferon production.

6. The method according to claim 5, wherein the administration is directly into a tumor mass.

* * * * *

UNITED STATES PATENT AND TRADEMARK OFFICE
CERTIFICATE OF CORRECTION

PATENT NO. : 9,724,408 B2  
APPLICATION NO. : 14/280667  
DATED : August 8, 2017  
INVENTOR(S) : Thomas W. Dubensky, Jr. et al.

Page 1 of 1

It is certified that error appears in the above-identified patent and that said Letters Patent is hereby corrected as shown below:

In the Claims

Column 62, Claim 2 Line 1, after the term "composition", Add the term "comprising".

Signed and Sealed this
Ninth Day of October, 2018

Andrei Iancu
*Director of the United States Patent and Trademark Office*